US012178831B2

(12) United States Patent
Dekosky et al.

(10) Patent No.: US 12,178,831 B2
(45) Date of Patent: Dec. 31, 2024

(54) TECHNIQUES FOR GENERATING CELL-BASED THERAPEUTICS USING RECOMBINANT T CELL RECEPTOR GENES

(71) Applicant: University of Kansas, Lawrence, KS (US)

(72) Inventors: Brandon Dekosky, Lawrence, KS (US); Cheng-Yu Chung, Lawrence, KS (US)

(73) Assignee: UNIVERSITY OF KANSAS, Lawrence, KS (US)

( * ) Notice: Subject to any disclaimer, the term of this patent is extended or adjusted under 35 U.S.C. 154(b) by 1095 days.

(21) Appl. No.: 16/976,983

(22) PCT Filed: Feb. 27, 2019

(86) PCT No.: PCT/US2019/019754
§ 371 (c)(1),
(2) Date: Aug. 31, 2020

(87) PCT Pub. No.: WO2019/168923
PCT Pub. Date: Sep. 6, 2019

(65) Prior Publication Data
US 2021/0000873 A1    Jan. 7, 2021

Related U.S. Application Data

(60) Provisional application No. 62/637,240, filed on Mar. 1, 2018.

(51) Int. Cl.
*A61K 35/17* (2015.01)
*A61P 35/00* (2006.01)
*C07K 14/725* (2006.01)

(52) U.S. Cl.
CPC .............. *A61K 35/17* (2013.01); *A61P 35/00* (2018.01); *C07K 14/7051* (2013.01)

(58) Field of Classification Search
None
See application file for complete search history.

(56) References Cited

U.S. PATENT DOCUMENTS

| 2011/0217736 A1 | 9/2011 | Hindson |
| 2016/0046700 A1 | 2/2016 | Foster et al. |
| 2017/0051036 A1 | 2/2017 | Jakobsen et al. |

FOREIGN PATENT DOCUMENTS

| WO | WO-2016/201394 | 12/2016 |
| WO | WO-2017/023801 | 2/2017 |
| WO | WO-2017/053902 | 3/2017 |
| WO | WO-2017/096239 | 6/2017 |
| WO | WO-2017/120428 A2 | 7/2017 |
| WO | WO-2017/180738 | 10/2017 |

OTHER PUBLICATIONS

Communication pursuant to Rules 161(2) and 162 EPC in EP Appl. Ser. No. 19761362.3 dated Oct. 9, 2020 (4 pages).
Extended European Search Report for EP Appl. Ser. No. 19761362.3 dated Nov. 15, 2021 (10 pages).
Sun et al., "Unbiased Analysis of TCRα/β Chains at the Single-Cell Level in Human CD8+ T-Cell Subsets," PLoS One, vol. 7, No. 7, Jul. 6, 2012, 11 pages.
Turchaninova et al., "Pairing of T-Cell Receptor Chains via Emulsion PCR," Eur. J. Immunol., vol. 43, 2013, pp. 2507-2515.
Kim, et al., "Analysis of the Paired TCR .alpha.- and .beta.-chains of Single Human T Cells," PLoS One, May 2012, vol. 7, No. 5,e37338, pp. 1-12.
International Search Report and Written Opinion in International Patent Application No. PCT/US2019/019754 dated May 17, 2019 (18 pages).
Notice of Reasons for Rejection issued JP Application No. 2020-545519 on Feb. 20, 2023, with English Translation (12 pages).
Boria et al., "Primer sets for cloning the human repertoire of T cell Receptor Variable regions", BMC Immunology, vol. 9, No. 50, Aug. 29, 2008, 9 pages.
Examination Report No. 1 issued in AU Application No. 2019227700 mailed Sep. 20, 2024.
Notice of Preliminary Rejection issued in KR Application No. 10-2020-7027921 mailed Sep. 20, 2024.

*Primary Examiner* — Ruixiang Li
(74) *Attorney, Agent, or Firm* — Foley & Lardner LLP

(57) ABSTRACT

The present technology relates generally to compositions and methods for creating recombinant T cell receptor (TCR) libraries and methods of their therapeutic use. The compositions and methods of the present technology are useful for rapid isolation of antigen-specific TCR repertoires as personalized, targeted therapies for cancer and viral infection.

5 Claims, 22 Drawing Sheets

Specification includes a Sequence Listing.

TECHNIQUES FOR GENERATING CELL-BASED THERAPEUTICS USING RECOMBINANT T CELL RECEPTOR GENES

CROSS-REFERENCE TO RELATED APPLICATIONS

This application is a National Stage Application of PCT/US2019/019754, filed Feb. 27, 2019, which claims the benefit of and priority to U.S. Provisional Patent Application No. 62/637,240, filed Mar. 1, 2018, the contents of each of which are incorporated herein by reference in their entireties.

U.S. GOVERNMENT SUPPORT

This invention was made with government support under GM103418 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Feb. 25, 2019, is named 104434-0179_SL.txt and is 206,931 bytes in size.

FIELD OF TECHNOLOGY

The present technology relates generally to methods of high-throughput isolation and manipulation of genes from single T cells that encode T cell receptors as cellular therapies, compositions of T cell libraries, and methods of their therapeutic use.

BACKGROUND

The following description is provided to assist the understanding of the reader. None of the information provided or references cited is admitted to be prior art to the present methods.

Humans have many thousands of T cell receptors that provide a major component of adaptive immune systems, and T cell receptor responses have been demonstrated to provide important contributions to protection from diseases including viral infections, cancer, and autoimmunity. However, molecularly defined T cell receptor therapies have had narrow impact on clinical care because the methods for translating T cell receptor responses into treatments have not fully been elucidated at a scale that is practical for translational therapies. Current methods rely on low-throughput T cell receptor identification technologies, cumbersome practices for cloning of T cell receptors, and a limited ability to direct the cell state of T cell libraries.

There is a need to establish methods for the rapid translation of T cell receptor responses as drugs for cellular therapeutics, particularly for the treatment of cancer. The present technology addresses this need, in part by leveraging the contributions of TCR repertoires to adaptive immunity for clinical treatment or prevention of cancer.

SUMMARY

The present technology relates generally to novel compositions and methods for creating recombinant TCR libraries, and methods of their therapeutic use. The compositions and methods of the present technology are useful for rapid isolation of antigen-specific TCR repertoires for development of personalized, targeted therapies for cancer and viral infections.

Accordingly, in one aspect, the present technology provides a recombinant T cell receptor (TCR) library vector comprising: (a) a vector backbone; and (b) a first polynucleotide encoding a TCRα polypeptide and a second polynucleotide encoding a TCRβ polypeptide; or (b) a first polynucleotide encoding a TCRγ polypeptide and a second polynucleotide encoding a TCRδ polypeptide; wherein the first and second polynucleotides are a cognate pair, and wherein the first polynucleotide and the second polynucleotide are derived from mRNA isolated from a single lysed T cell that is present in a compartment. In some embodiments, the mRNA of the single lysed T cell is isolated using an mRNA capture reagent or reverse transcription-PCR (RT-PCR). Additionally or alternatively, in some embodiments, the compartment containing the contents of the single lysed T cell is a microwell (e.g., a microwell within a 96-well plate) or a droplet.

In some embodiments of the vector, the first polynucleotide and the second polynucleotide are operably linked, optionally via a linker polynucleotide. In some embodiments of the vector, the first polynucleotide and the second polynucleotide have been operably linked by reverse transcription and PCR amplification of the captured T cell mRNA. In some embodiments of the vector, the first polynucleotide and the second polynucleotide have been cloned into the vector backbone by cleavage at a target restriction endonuclease site that is natively found in TCR genes. In certain embodiments, the target restriction endonuclease site occurs in TCR genes with low frequency. In some embodiments, the first polynucleotide and the second polynucleotide have been altered to incorporate at least one target restriction endonuclease site disclosed in Table 7 or 8. In certain embodiments, the target restriction endonuclease site comprises a silent mutation.

In certain embodiments of the vector, the mRNA capture reagent is selected from the group consisting of a poly(dT) coated bead, an oligonucleotide-coated bead, a hydrogel bead, and a printed oligo on the surface of a microarray well. In some embodiments, the compartment is an emulsion droplet or a well. In certain embodiments, the well is located in a printed polymer slide, a plastic plate, a microtiter plate, or a gel. In some embodiments, the volume of the compartment is 5 nL or less.

In certain embodiments of the vector, the vector further comprises at least one polynucleotide encoding an expression control element operably linked to the first polynucleotide and/or the second polynucleotide. In some embodiments, the expression control element is selected from the group consisting of: a promoter, a p2a sequence, and an IRES sequence. In particular embodiments, the promoter is an EF1α promoter or a CMV promoter. In certain embodiments, the polynucleotide encoding the expression control element is located between the first polynucleotide and the second polynucleotide.

In some embodiments of the vector, the vector is circularized. In some embodiments, the vector has been circularized prior to incorporation of the expression control element into the vector. In other embodiments, the vector has been circularized after incorporation of the expression control element into the vector. In some embodiments, the vector is linear (e.g., not circularized).

In certain embodiments of the vector, the expression control element has been incorporated near a protospacer adjacent motif (PAM). In other embodiments, the expression control element has been incorporated into the vector using a DNA-modifying enzyme selected from a restriction enzyme or a TALEN. In other embodiments, the vector further comprises one or more polynucleotides encoding a transposon operably linked to at least one of the first polynucleotide and the second polynucleotide.

In some embodiments of the vector, the vector further comprises one or more of: a polynucleotide encoding a detectable marker, a polynucleotide encoding a selectable marker, a polynucleotide encoding a switch mechanism for controlling expression and/or activation of the first polynucleotide and the second polynucleotide, and a polynucleotide encoding a Kozak consensus sequence or an enhancer.

In certain embodiments of the vector, the vector backbone is selected from a group consisting of a retroviral, a lentiviral, an adenoviral, and an adeno-associated viral vector backbone. In certain embodiments, the vector may comprise linear DNA for CRISPR/Cas9 integration. In certain embodiments, the vector may comprise DNA that can be incorporated into a host using a recombinase enzyme. In some embodiments, the vector may comprise DNA that can be incorporated into a host using a transposase enzyme.

In some embodiments of the vector, the encoded T cell receptor (e.g., TCRαβ or TCRγδ) is reactive against a disease antigen or target cell. In certain embodiments, the disease antigen is a viral antigen derived from a virus selected from the group consisting of adenovirus, CMV, coronavirus, coxsackievirus, Dengue virus, Epstein-Barr virus (EBV), enterovirus 71 (EV71), Ebola virus, hepatitis A (HAV), hepatitis B (HBV), cytomegalovirus (CMV), hepatitis C (HCV), hepatitis D (HDV), hepatitis E (HEV), human immunodeficiency virus (HIV), human papillomavirus (HPV), herpes simplex virus (HSV), human T-lymphotropic virus (HTLV), influenza A virus, influenza B virus, Japanese encephalitis, leukemia virus, measles virus, molluscum contagiosum, orf virus, parvovirus, rabies virus, respiratory syncytial virus, rift valley fever virus, rubella virus, rotavirus, tick-borne encephalitis (TBEV), simian immunodeficiency virus, tobacco etch virus (TEV), varicella zoster virus, variola, West Nile virus, Zika virus, and Chikungunya virus. In other embodiments, the disease antigen is a tumor antigen selected from the group consisting of CD45, glypican-3, IGF2B3, Kallikrein 4, KIF20A, Lengsin, Meloe, mucin 5AC (MUC5AC), survivin, cyclin-A1, MAGE-A1, MAGE-C1, MAGE-C2, SSX2, XAGE1b/GAGED2A, CD19, CD20, CD22, CD52, epidermal growth factor receptor (EGFR), human epidermal growth factor receptor 2 (HER2), tumor necrosis factor receptor superfamily, member 10a (TRAILR1), receptor activator of nuclear factor kappa-B ligand (RANKL), insulin-like growth factor 1 receptor (IGF1R), epithelial cell adhesion molecule (EpCAM), and carcinoembryonic antigen (CEA).

In another aspect, the present technology provides a recombinant cell comprising a vector, wherein the vector comprises (a) a vector backbone; and (b) a first polynucleotide encoding a TCRα polypeptide and a second polynucleotide encoding a TCRβ polypeptide; or (b) a first polynucleotide encoding a TCRγ polypeptide and a second polynucleotide encoding a TCRδ polypeptide; wherein the first and second polynucleotides are a cognate pair, and wherein the first polynucleotide and the second polynucleotide are derived from mRNA of a single lysed T cell in a compartment. In some embodiments, the mRNA of the single lysed T cell is isolated using an mRNA capture reagent in a compartment, optionally wherein the recombinant cell is a bacterial cell, mammalian cell, or a yeast cell.

In other embodiments, the polynucleotides encoding the paired T cell receptor polypeptides are derived from a single cell, without the use of an mRNA capture reagent. Additionally or alternatively, in some embodiments, the compartment containing the contents of the single lysed T cell is a microwell (e.g., a microwell within a 96-well plate) or a droplet.

In one aspect, the present technology provides a recombinant TCR vector library comprising a plurality of vectors each comprising (a) a vector backbone; and (b) a first polynucleotide encoding a TCRα polypeptide and a second polynucleotide encoding a TCRβ polypeptide; or (b) a first polynucleotide encoding a TCRγ polypeptide and a second polynucleotide encoding a TCRδ polypeptide; wherein the first and second polynucleotides are a cognate pair, and wherein the first polynucleotide and the second polynucleotide are derived from mRNA of a single lysed T cell that was captured by an mRNA capture reagent in a compartment. In some embodiments, the plurality of vectors comprises a TCR repertoire. In some embodiments, the individual vectors in the TCR vector library were selected for inclusion in the TCR library on the basis of one or more of the following characteristics: TCR clonal prevalence, TCR enrichment characteristics from in vitro assays, TCR binding specificity, TCR V segment sequence, TCR D segment sequence, TCR J segment sequence, TCR gene motifs, and/or CDR3 gene motifs. In some embodiments, the individual vectors in the library are mixed in a defined ratio to generate a synthetically-derived TCR library.

In another aspect, the present technology provides an isolated immune cell comprising (a) a vector backbone; and (b) a first polynucleotide encoding a TCRα polypeptide and a second polynucleotide encoding a TCRβ polypeptide; or (b) a first polynucleotide encoding a TCRγ polypeptide and a second polynucleotide encoding a TCRδ polypeptide; wherein the first and second polynucleotides are a cognate pair, and wherein the first polynucleotide and the second polynucleotide are derived from mRNA of a single lysed T cell that was captured by an mRNA capture reagent in a compartment. In some embodiments the immune cell is a hematopoietic stem cell, a hematopoietic progenitor cell, a T cell, or a natural killer (NK) cell.

In one aspect, the present technology provides a cell population comprising a recombinant TCR vector library comprising a plurality of vectors each comprising (a) a vector backbone; and (b) a first polynucleotide encoding a TCRα polypeptide and a second polynucleotide encoding a TCRβ polypeptide; or (b) a first polynucleotide encoding a TCRγ polypeptide and a second polynucleotide encoding a TCRδ polypeptide; wherein the first and second polynucleotides are a cognate pair, and wherein the first polynucleotide and the second polynucleotide are derived from mRNA of a single lysed T cell in a compartment. In some embodiments, the mRNA of the single lysed T cell is isolated using an mRNA capture reagent. In other embodiments, the polynucleotides encoding the paired T cell receptor polypeptides are derived from a single cell, without the use of an mRNA capture reagent. Additionally or alternatively, in some embodiments, the compartment containing the contents of the single lysed T cell is a microwell (e.g., a microwell within a 96-well plate) or a droplet. In some embodiments, the population comprises hematopoietic stem cells, hematopoietic progenitor cells, T cells, or NK cells.

In another aspect, also provided herein is a method for preparing a recombinant TCR library, the method comprising transforming a population of cells with a vector library comprising a plurality of vectors each comprising (a) a vector backbone; and (b) a first polynucleotide encoding a TCRα polypeptide and a second polynucleotide encoding a TCRβ polypeptide; or (b) a first polynucleotide encoding a TCRγ polypeptide and a second polynucleotide encoding a TCRδ polypeptide; wherein the first and second polynucleotides are a cognate pair, and wherein the first polynucleotide and the second polynucleotide are derived from mRNA of a single lysed T cell in a compartment. In some embodiments, the mRNA of the single lysed T cell is isolated using an mRNA capture reagent. In other embodiments, the polynucleotides encoding the paired T cell receptor polypeptides are derived from a single cell, without the use of an mRNA capture reagent. Additionally or alternatively, in some embodiments, the compartment containing the contents of the single lysed T cell is a microwell (e.g., a microwell within a 96-well plate) or a droplet. In some embodiments, the population comprises hematopoietic stem cells, hematopoietic progenitor cells, T cells, or NK cells. In some embodiments, the plurality of vectors is circularized at certain steps of the method, and linearized at other steps.

In some embodiments of the method, the library is screened for specific binding to a target cell. In certain embodiments, the cell is a cancer cell or a cell infected with a virus. In some embodiments, the target cell was isolated from a subject.

In other embodiments of the method, the library is screened for specific binding to an antigen:MHC complex. In some embodiments the antigen of the antigen:MHC complex is a viral antigen derived from a virus selected from the group consisting of adenovirus, CMV, coronavirus, coxsackievirus, Dengue virus, Epstein-Barr virus (EBV), enterovirus 71 (EV71), Ebola virus, hepatitis A (HAV), hepatitis B (HBV), cytomegalovirus (CMV), hepatitis C (HCV), hepatitis D (HDV), hepatitis E (HEV), human immunodeficiency virus (HIV), human papillomavirus (HPV), herpes simplex virus (HSV), human T-lymphotropic virus (HTLV), influenza A virus, influenza B virus, Japanese encephalitis, leukemia virus, measles virus, molluscum contagiosum, orf virus, parvovirus, rabies virus, respiratory syncytial virus, rift valley fever virus, rubella virus, rotavirus, tick-borne encephalitis (TBEV), simian immunodeficiency virus, tobacco etch virus (TEV), varicella zoster virus, variola, West Nile virus, Zika virus, and Chikungunya virus. In other embodiments, the antigen of the antigen:MHC complex is a tumor antigen selected from the group consisting of CD45, glypican-3, IGF2B3, Kallikrein 4, KIF20A, Lengsin, Meloe, mucin 5AC (MUC5AC), survivin, cyclin-A1, MAGE-A1, MAGE-C1, MAGE-C2, SSX2, XAGE1b/GAGED2A, CD19, CD20, CD22, CD52, EGFR, HER2, TRAILR1, RANKL, IGF1R, EpCAM, and CEA.

In some embodiments of the method, the library is screened for T cell phenotypic markers. In other embodiments of the method, the library is screened for hematopoietic stem cell phenotypic markers. In other embodiments of the method, the library is screened for natural killer cell phenotypic markers.

In certain embodiments of the method, the library is screened for activity in a co-culture system, wherein the co-culture system comprises at least one of the following: (a) a cancer cell line; (b) a plurality of cells infected with a known virus; (c) a plurality of tumor cells isolated from a cancer patient; (d) an immortalized cell line; or (e) a plurality of cells derived from a patient tissue biopsy.

In some embodiments of the method, the transformed cells are activated in vitro. In particular embodiments, activation is performed using one or more of the following stimulants: anti-CD3 antibody, anti-CD8 antibody, anti-CD27 antibody, IL-2, IL-4, IL-21, anti-PD1 antibody, anti-CTLA4 antibody, tumor cell lysate, cellular co-culture with virus-infected cells, and tumor cell lines.

In certain embodiments of the method, the population of cells is transformed with a transcription factor. The transcription factor may influence the behavior or phenotype of the transformed cells. In some embodiments, the transcription factor is selected from the group consisting of FOXP3, BLIMP-1, Helios, Ikaros, and TGF-beta.

In another aspect, provided herein is a recombinant TCR library prepared by a method comprising transforming a population of cells with a vector library comprising a plurality of vectors each comprising (a) a vector backbone; and (b) a first polynucleotide encoding a TCRα polypeptide and a second polynucleotide encoding a TCRβ polypeptide; or (b) a first polynucleotide encoding a TCRγ polypeptide and a second polynucleotide encoding a TCRδ polypeptide; wherein the first and second polynucleotides are a cognate pair, and wherein the first polynucleotide and the second polynucleotide are derived from mRNA of a single lysed T cell in a compartment. In some embodiments, the mRNA of the single lysed T cell is isolated using an mRNA capture reagent. In other embodiments, the polynucleotides encoding the paired T cell receptor polypeptides are derived from a single cell, without the use of an mRNA capture reagent. Additionally or alternatively, in some embodiments, the compartment containing the contents of the single lysed T cell is a microwell (e.g., a microwell within a 96-well plate) or a droplet. In some embodiments, the population comprises hematopoietic stem cells, hematopoietic progenitor cells, T cells, or NK cells.

In one aspect, the present technology provides a composition comprising a recombinant TCR library prepared by a method comprising transforming a population of cells with a vector library comprising a plurality of vectors each comprising (a) a vector backbone; and (b) a first polynucleotide encoding a TCRα polypeptide and a second polynucleotide encoding a TCRβ polypeptide; or (b) a first polynucleotide encoding a TCRγ polypeptide and a second polynucleotide encoding a TCRδ polypeptide; wherein the first and second polynucleotides are a cognate pair, and wherein the first polynucleotide and the second polynucleotide are derived from mRNA of a single lysed T cell in a compartment, and a carrier. In some embodiments, the carrier is a pharmaceutically acceptable carrier. In some embodiments, the mRNA of the single lysed T cell is isolated using an mRNA capture reagent. In other embodiments, the polynucleotides encoding the paired T cell receptor polypeptides are derived from a single cell, without the use of an mRNA capture reagent. Additionally or alternatively, in some embodiments, the compartment containing the contents of the single lysed T cell is a microwell (e.g., a microwell within a 96-well plate) or a droplet.

In one aspect, provided herein is a method of treating a subject in need thereof, the method comprising administering to the subject an effective amount of a recombinant TCR library or a composition comprising a recombinant TCR library, wherein the recombinant TCR library was prepared by a method comprising transforming a population of cells with a vector library comprising a plurality of vectors each comprising (a) a vector backbone; and (b) a first polynucleotide encoding a TCRα polypeptide and a second polynucleotide encoding a TCRβ polypeptide; or (b) a first polynucleotide encoding a TCRγ polypeptide and a second polynucleotide encoding a TCRδ polypeptide; wherein the first and second polynucleotides are a cognate pair, and wherein the first polynucleotide and the second polynucleotide are derived from mRNA of a single lysed T cell in a compartment. In some embodiments, the mRNA of the single lysed T cell is isolated using an mRNA capture reagent. In other embodiments, the polynucleotides encoding the paired T cell receptor polypeptides are derived from a single cell, without the use of an mRNA capture reagent. Additionally or alternatively, in some embodiments, the compartment containing the contents of the single lysed T cell is a microwell (e.g., a microwell within a 96-well plate) or a droplet.

In another aspect, provided herein is a method of treating cancer in a subject in need thereof, the method comprising administering to the subject an effective amount of a recombinant TCR library or a composition comprising a recombinant TCR library, wherein the recombinant TCR library was prepared by a method comprising transforming a population of cells with a vector library comprising a plurality of vectors each comprising (a) a vector backbone; and (b) a first polynucleotide encoding a TCRα polypeptide and a second polynucleotide encoding a TCRβ polypeptide; or (b) a first polynucleotide encoding a TCRγ polypeptide and a second polynucleotide encoding a TCRδ polypeptide; wherein the first and second polynucleotides are a cognate pair, and wherein the first polynucleotide and the second polynucleotide are derived from mRNA of a single lysed T cell in a compartment. In some embodiments, the mRNA of the single lysed T cell is isolated using an mRNA capture reagent. In other embodiments, the polynucleotides encoding the paired T cell receptor polypeptides are derived from a single cell, without the use of an mRNA capture reagent. Additionally or alternatively, in some embodiments, the compartment containing the contents of the single lysed T cell is a microwell (e.g., a microwell within a 96-well plate) or a droplet.

In some embodiments, the cancer is acute lymphoblastic leukemia (ALL); acute myeloid leukemia (AML); adrenocortical carcinoma; AIDS-related cancers; anal cancer; appendix cancer; astrocytoma; atypical teratoid/rhabdoid tumor, brain cancer; basal cell carcinoma of the skin; bile duct cancer; bladder cancer; bone cancer; breast cancer; bronchial tumors; Burkitt lymphoma; carcinoid tumor (gastrointestinal); germ cell tumor; primary CNS lymphoma; cervical cancer; cholangiocarcinoma; chordoma; chronic lymphocytic leukemia (CLL); chronic myelogenous leukemia (CML); chronic myeloproliferative neoplasms; colorectal cancer; craniopharyngioma; cutaneous T-cell lymphoma; ductal carcinoma in situ (DCIS); endometrial cancer; ependymoma; esophageal cancer; esthesioneuroblastoma; extracranial germ cell tumor; extragonadal germ cell tumor; eye cancer; intraocular melanoma; retinoblastoma; fallopian tube cancer; fibrous histiocytoma of bone, malignant, and osteosarcoma; gallbladder cancer; gastric cancer; gastrointestinal carcinoid tumor; gastrointestinal stromal tumors (GIST); germ cell tumors; gestational trophoblastic disease; hairy cell leukemia; head and neck cancer; heart tumors; hepatocellular cancer; histiocytosis, Langerhans cell; Hodgkin lymphoma; hypopharyngeal cancer; intraocular melanoma; islet cell tumors, pancreatic neuroendocrine tumors; kidney cancer; laryngeal cancer; leukemia; lip and oral cavity cancer; liver cancer; lung cancer; lymphoma; male breast cancer; malignant fibrous histiocytoma of bone and osteosarcoma; melanoma; Merkel cell carcinoma; mesothelioma; metastatic cancer; mouth cancer; multiple endocrine neoplasia syndrome; multiple myeloma/plasma cell neoplasms; mycosis fungoides; myelodysplastic syndrome, myeloproliferative neoplasm, chronic; nasopharyngeal cancer; neuroblastoma; Non-Hodgkin lymphoma; non-small cell lung cancer; oral cancer, oropharyngeal cancer; osteosarcoma; ovarian cancer; pancreatic cancer; pancreatic neuroendocrine tumors; papillomatosis; paraganglioma; paranasal sinus cancer; parathyroid cancer; pharyngeal cancer; pheochromocytoma; pituitary tumor; pleuropulmonary blastoma; prostate cancer; rectal cancer; recurrent cancer; renal cell cancer; retinoblastoma; rhabdomyosarcoma; salivary gland cancer; sarcoma; Ewing sarcoma; Kaposi sarcoma; osteosarcoma; uterine sarcoma; Sezary syndrome; skin cancer; small cell lung cancer; small intestine cancer; soft tissue sarcoma; squamous cell carcinoma of the skin; squamous neck cancer; stomach cancer; T cell lymphoma; testicular cancer; throat cancer; nasopharyngeal cancer; hypopharyngeal cancer; thymic carcinoma; thyroid cancer; urethral cancer; uterine cancer; vaginal cancer; vascular tumors; vulvar cancer; or Wilms tumor.

In one aspect, provided herein is a method of inhibiting tumor growth in a subject in need thereof, the method comprising administering to the subject an effective amount of a recombinant TCR library or a composition comprising a recombinant TCR library, wherein the recombinant TCR library was prepared by a method comprising transforming a population of cells with a vector library comprising a plurality of vectors each comprising (a) a vector backbone; and (b) a first polynucleotide encoding a TCRα polypeptide and a second polynucleotide encoding a TCRβ polypeptide; or (b) a first polynucleotide encoding a TCRγ polypeptide and a second polynucleotide encoding a TCRδ polypeptide; wherein the first and second polynucleotides are a cognate pair, and wherein the first polynucleotide and the second polynucleotide are derived from mRNA of a single lysed T cell in a compartment. In some embodiments, the mRNA of the single lysed T cell is isolated using an mRNA capture reagent. In other embodiments, the polynucleotides encoding the paired T cell receptor polypeptides are derived from a single cell, without the use of an mRNA capture reagent. Additionally or alternatively, in some embodiments, the compartment containing the contents of the single lysed T cell is a microwell (e.g., a microwell within a 96-well plate) or a droplet. In some embodiments, the tumor is a solid tumor.

In another aspect, provided herein is a method of treating a viral infection in a subject in need thereof, the method comprising administering to the subject an effective amount of a recombinant TCR library or a composition comprising a recombinant TCR library, wherein the recombinant TCR library was prepared by a method comprising transforming a population of cells with a vector library comprising a plurality of vectors each comprising (a) a vector backbone; and (b) a first polynucleotide encoding a TCRα polypeptide and a second polynucleotide encoding a TCRβ polypeptide; or (b) a first polynucleotide encoding a TCRγ polypeptide and a second polynucleotide encoding a TCRδ polypeptide; wherein the first and second polynucleotides are a cognate pair, and wherein the first polynucleotide and the second polynucleotide are derived from mRNA of a single lysed T cell in a compartment. In some embodiments, the mRNA of the single lysed T cell is isolated using an mRNA capture reagent. In other embodiments, the polynucleotides encoding the paired T cell receptor polypeptides are derived from a single cell, without the use of an mRNA capture reagent. Additionally or alternatively, in some embodiments, the compartment containing the contents of the single lysed T cell is a microwell (e.g., a microwell within a 96-well plate) or a droplet. In some embodiments, the viral infection is caused by a virus selected from the group consisting of adenovirus, CMV, coronavirus, coxsackievirus, Dengue virus, Epstein-Barr virus (EBV), enterovirus 71 (EV71), Ebola virus, hepatitis A (HAV), hepatitis B (HBV), cytomegalovirus (CMV), hepatitis C (HCV), hepatitis D (HDV), hepatitis E (HEV), human immunodeficiency virus (HIV), human papillomavirus (HPV), herpes simplex virus (HSV), human T-lymphotropic virus (HTLV), influenza A virus, influenza B virus, Japanese encephalitis, leukemia virus, measles virus, molluscum contagiosum, orf virus, parvovirus, rabies virus, respiratory syncytial virus, rift valley fever virus, rubella virus, rotavirus, tick-borne encephalitis (TBEV), simian immunodeficiency virus, tobacco etch virus (TEV), varicella zoster virus, variola, West Nile virus, Zika virus, and Chikungunya virus.

In some embodiments, the methods of treatment provided herein further comprise administering one or more additional doses of the recombinant TCR library or the composition to the subject.

In some embodiments, the recombinant TCR library comprises cells that are autologous or allogenic to the subject being treated.

In some embodiments, the subject is a human, an animal, a non-human primate, a dog, cat, a sheep, a mouse, a horse, or a cow. In a particular embodiment, the subject is a human.

DETAILED DESCRIPTION

Figure 1:
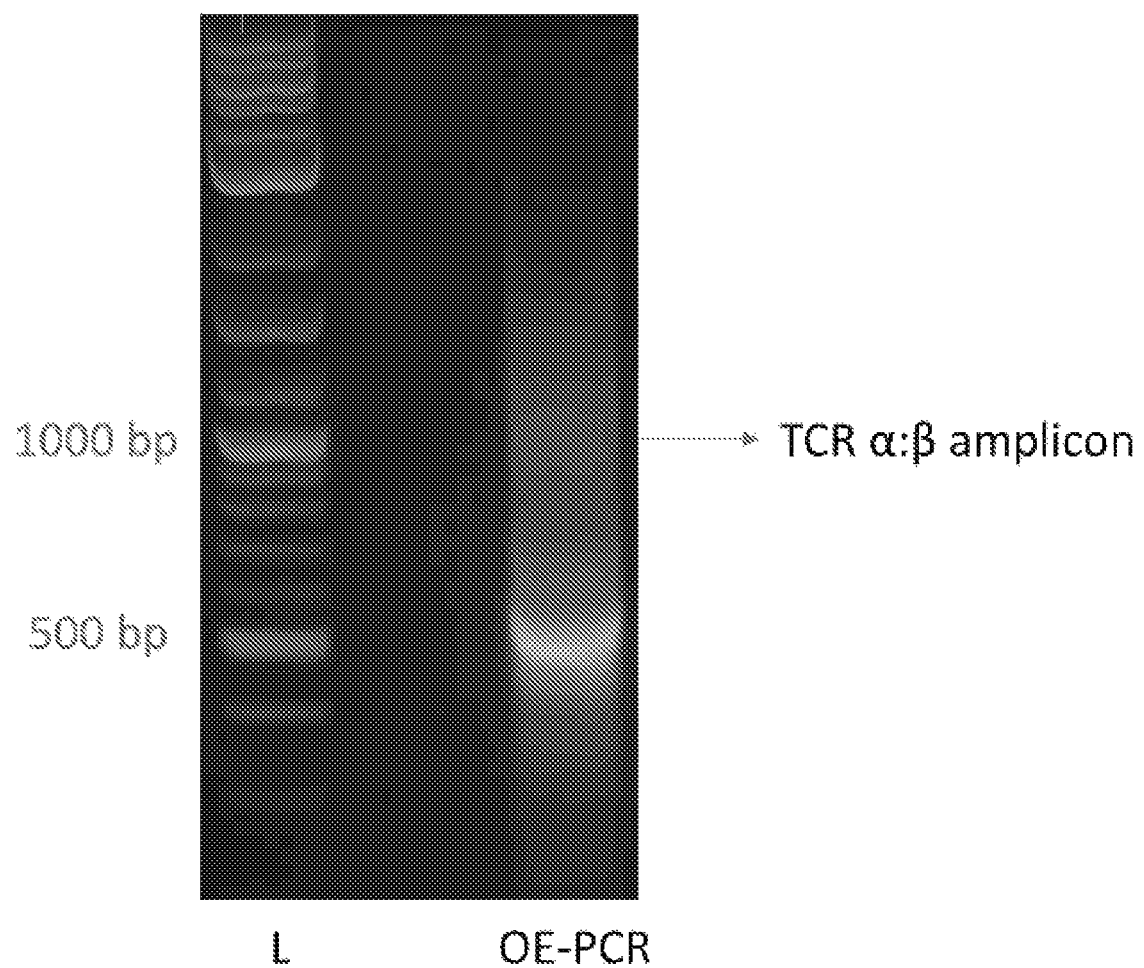
FIG. 1 shows a gel image of overlap extension (OE-PCR) to obtain the full-length TCR α:β variable region. After the OE-PCR, the PCR products were purified and analyzed by DNA gel electrophoresis. The TCR α:β amplicon (around 1000 b.p.) was visible, and was further enriched using nested PCR. After DNA gel electrophoresis, gel extraction was performed to obtain the TCR α:β amplicon. 5 ng of purified PCR product was used as a template for performing semi-nested PCR.

Immune checkpoint inhibitors have catalyzed tremendous progress in cancer therapy, highlighting the critical role of immune cells, particularly CD8+ T cells, in controlling tumor growth. However, while recent progress in immune receptor sequencing has provided insights regarding clonal rank-based features of adaptive immunity, the inability to sequence and functionally screen paired TCR alpha and beta chains has precluded the collection of broader functional data regarding tumor immunosuppression and complicated the discovery and rapid therapeutic use of anti-cancer T cell receptor genes for gene therapies (Bonter, K. et al., Regen. Med. 12, 623-636 (2017); Malherbe, L., Ann. Allergy. Asthma. Immunol. 103, 76-79 (2009); Ahmad, T. A. et al., Vaccine Rep. 6, 13-22 (2016); Maus, M. V. et al., Annu. Rev. Immunol. 32, 189-225 (2014); Yee, C. J. Transl. Med. 3, 17 (2005)). To date, cloning and functional analysis of tumor-specific T cells is practically limited to just a few common peptide-MHC combinations per sample due to requirements for sorting primary, viable T cells (Malherbe, L., Ann. Allergy. Asthma. Immunol. 103, 76-79 (2009); Ahmad, T. A. et al., Vaccine Rep. 6, 13-22 (2016); Sanchez-Trincado, J. L. et al., Journal of Immunology Research (2017)). The low number of peptide-MHCs that can be effectively screened is further complicated by the fact that repetitive screening is necessary for neoantigen discovery because each tumor sample has its own unique landscape of somatic mutations (Martincorena, I. & Campbell, P. J. Science 349, 1483-1489 (2015); Tran, E. et al., Science aad1253 (2015); Choudhury, N. J. et al., Eur. Urol. Focus 2, 445-452 (2016)). Alternative methods such as T cell proliferation and ELISPOT rely on live T cells, which are highly limited in many patient samples, as well as having limitations in terms of cell growth rates, time required for application as cell-based therapies, specificity and maintenance of appropriate T cell phenotype (Bonter, K. et al., Regen. Med. 12, 623-636 (2017); Maus, M. V. et al., Annu. Rev. Immunol. 32, 189-225 (2014); Yee, C. J. Transl. Med. 3, 17 (2005); Redeker, A. & Arens, R., Front. Immunol. 7, (2016)).

The methods and compositions described herein directly address these bottlenecks and provide the first comprehensive sequence- and function-based annotation of epitope-specific T cell responses in patients, providing new molecular-scale technologies to guide the development of targeted cancer therapeutics. The compositions and methods of the present technology are generally useful for rapid isolation of antigen-specific TCR repertoires that can be screened, modified, and used as personalized, targeted therapies for, e.g., cancer and viral infections. The targeted therapies described herein can be developed and administered more rapidly (in as few as five days to two weeks) than presently available cell-based therapies. In addition, these therapies comprise multiple, distinct TCRs that have a greater likelihood of avoiding immune escape, a mechanism wherein target cells can evade immune detection by suppression of a targeted epitope or antigen.

Furthermore, specific embodiments of the methods and compositions described herein provide the following distinct advantages over previously described approaches to creating TCR libraries: (1) in some embodiments, described herein is a method wherein the TCR library can be grown as colonies in bacteria and numerous colonies can be selected, sequenced, and mixed together an re-delivered as a defined product; (2) in some embodiments, described herein is a separation and characterization step that minimizes the likelihood of PCR error variants which may be included in the final drug product, thereby reducing the risk that the final therapeutic cell composition contains uncharacterizable and potentially very dangerous variants which may induce side effects; (3) in some embodiments, described herein is the inclusion of a suicide switch to reduce the risk of harm to the patient in the event of complications and off-target effects; (4) in some embodiments, the cells are pre-stimulated prior to administration to achieve or enhance the desired TCR function in vivo; (5) in some embodiments, the methods include the ability co-express transcription factors in the cells to influence T cell development into a potent anti-cancer phenotype; (6) in some embodiments, the in vitro activation techniques may be modified as needed depending on the patient's specific response to therapy administration; and (7) in some embodiments, the disclosed methods can be used to provide repeated doses of cell therapy to the patient if the disease condition persists or recurs.

It is to be appreciated that certain aspects, modes, embodiments, variations and features of the present methods are described below in various levels of detail in order to provide a substantial understanding of the present technology.

In practicing the present methods, many conventional techniques in molecular biology, protein biochemistry, cell biology, immunology, microbiology and recombinant DNA are used. See, e.g., Sambrook and Russell eds. (2001) *Molecular Cloning: A Laboratory Manual,* 3rd edition; the series Ausubel et al. eds. (2007) *Current Protocols in Molecular Biology*; the series Methods in Enzymology (Academic Press, Inc., N.Y.); MacPherson et al. (1991) *PCR 1: A Practical Approach* (IRL Press at Oxford University Press); MacPherson et al. (1995) *PCR 2: A Practical Approach*; Harlow and Lane eds. (1999) *Antibodies, A Laboratory Manual*; Freshney (2005) *Culture of Animal Cells: A Manual of Basic Technique,* 5th edition; Gait ed. (1984) Oligonucleotide Synthesis; U.S. Pat. No. 4,683,195; Hames and Higgins eds. (1984) *Nucleic Acid Hybridization*; Anderson (1999) *Nucleic Acid Hybridization*; Hames and Higgins eds. (1984) *Transcription and Translation; Immobilized Cells and Enzymes* (IRL Press (1986)); Perbal (1984) *A Practical Guide to Molecular Cloning*; Miller and Calos eds. (1987) *Gene Transfer Vectors for Mammalian Cells* (Cold Spring Harbor Laboratory); Makrides ed. (2003) *Gene Transfer and Expression in Mammalian Cells*; Mayer and Walker eds. (1987) *Immunochemical Methods in Cell and Molecular Biology* (Academic Press, London); and Herzenberg et al. eds (1996) *Weir's Handbook of Experimental Immunology*. Methods to detect and measure levels of polypeptide gene expression products (i.e., gene translation level) are well-known in the art and include the use of polypeptide detection methods such as antibody detection and quantification techniques. (See also, Strachan & Read, *Human Molecular Genetics*, Second Edition. (John Wiley and Sons, Inc., NY, 1999)).

Unless defined otherwise, all technical and scientific terms used herein generally have the same meaning as commonly understood by one of ordinary skill in the art to which this technology belongs. As used in this specification and the appended claims, the singular forms "a", "an" and "the" include plural referents unless the content clearly dictates otherwise. For example, reference to "a cell" includes a combination of two or more cells, and the like. Generally, the nomenclature used herein and the laboratory procedures in cell culture, molecular genetics, organic chemistry, analytical chemistry and nucleic acid chemistry and hybridization described below are those well-known and commonly employed in the art. All references cited herein are incorporated herein by reference in their entireties and for all purposes to the same extent as if each individual publication, patent, or patent application was specifically and individually incorporated by reference in its entirety for all purposes.

As used herein, the term "about" in reference to a number is generally taken to include numbers that fall within a range of 1%, 5%, or 10% in either direction (greater than or less than) of the number unless otherwise stated or otherwise evident from the context (except where such number would be less than 0% or exceed 100% of a possible value).

As used herein, the "administration" of an agent or drug to a subject includes any route of introducing or delivering to a subject a compound to perform its intended function. Administration can be carried out by any suitable route, including orally, intranasally, parenterally (intravenously, intramuscularly, intraperitoneally, or subcutaneously), rectally, or topically. Administration includes self-administration and the administration by another.

An "adjuvant" refers to one or more substances that cause stimulation of the immune system. In this context, an adjuvant is used to enhance an immune response to one or more vaccine antigens or antibodies. An adjuvant may be administered to a subject before, in combination with, or after administration of the vaccine. Examples of chemical compounds used as adjuvants include aluminum compounds, oils, block polymers, immune stimulating complexes, vitamins and minerals (e.g., vitamin E, vitamin A, selenium, and vitamin B12), Quil A (saponins), bacterial and fungal cell wall components (e.g., lipopolysaccarides, lipoproteins, and glycoproteins), hormones, cytokines, and co-stimulatory factors.

As used herein, the term "antibody" collectively refers to immunoglobulins or immunoglobulin-like molecules including by way of example and without limitation, IgA, IgD, IgE, IgG and IgM, combinations thereof, and similar molecules produced during an immune response in any vertebrate, for example, in mammals such as humans, goats, rabbits and mice, as well as non-mammalian species, such as shark immunoglobulins. The term "antibody" includes intact immunoglobulins and "antibody fragments" or "antigen binding fragments" that specifically bind to a molecule of interest (or a group of highly similar molecules of interest) to the substantial exclusion of binding to other molecules (for example, antibodies and antibody fragments that have a binding constant for the molecule of interest that is at least 103 $M^{-1}$ greater, at least $10^4$ $M^{-1}$ greater or at least $10^5$ $M^{-1}$ greater than a binding constant for other molecules in a biological sample). The term "antibody" also includes genetically engineered forms such as chimeric antibodies (for example, humanized murine antibodies), heteroconjugate antibodies (such as, bispecific antibodies). See also, Pierce Catalog and Handbook, 1994-1995 (Pierce Chemical Co., Rockford, Ill.); Kuby, J., Immunology, $3^{rd}$ Ed., W. H. Freeman & Co., New York, 1997.

More particularly, antibody refers to a polypeptide ligand comprising at least a light chain immunoglobulin variable region or heavy chain immunoglobulin variable region, which specifically recognizes and binds an epitope of an antigen. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody. Typically, an immunoglobulin has heavy (H) chains and light (L) chains interconnected by disulfide bonds. There are two types of light chain, lambda (λ) and kappa (κ). There are five main heavy chain classes (or isotypes), which determine the functional activity of an antibody molecule: IgM, IgD, IgG, IgA and IgE. Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs". The extent of the framework region and CDRs have been defined (see, Kabat et al., *Sequences of Proteins of Immunological Interest*, U.S. Department of Health and Human Services, 1991, which is hereby incorporated by reference). The Kabat database is now maintained online. The sequences of the framework regions of different light or heavy chains are relatively conserved within a species. The framework region of an antibody, that is the combined framework regions of the constituent light and heavy chains, largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions.

As used herein, "complementarity determining region" or "CDR" refers to a region of an antibody or TCR that is primarily responsible for binding to an epitope of an antigen or an antigen:MHC complex. CDRs are also referred to as hypervariable regions. The CDRs of each TCR or antibody chain are typically referred to as CDR1, CDR2, and CDR3, numbered sequentially starting from the N-terminus, and are also typically identified by the chain in which the particular CDR is located. Antibodies and TCRs with different specificities (i.e. different combining sites for different antigens) have different CDRs. Only a limited number of amino acid positions within the CDRs are directly involved in antigen binding. These positions within the CDRs are called specificity determining residues (SDRs).

As used herein, an "antigen" refers to a molecule to which an antibody can selectively bind. The target antigen may be a protein (e.g., an antigenic peptide), carbohydrate, nucleic acid, lipid, hapten, or other naturally occurring or synthetic compound. The target antigen may be a polypeptide or peptide mimic. An antigen may also be administered to an animal to generate an immune response in the animal. In some embodiments, the antigen comprises one or more epitopes. In some embodiments, the antigen or an epitope derived from the antigen, can be loaded into an MHC class I or MHC class II complex.

As used herein, the term "autologous," in reference to cells refers to cells that are isolated and administered back into the same subject (e.g., recipient, donor, or host). "Allogeneic" refers to non-autologous cells.

As used herein, "binding affinity" refers to the strength of the total noncovalent interactions between a single binding site of a molecule (e.g., an antibody) and its binding partner (e.g., an antigen or antigenic peptide). The affinity of a molecule X for its partner Y can generally be represented by the dissociation constant ($K_d$). Affinity can be measured by standard methods known in the art, including those described herein. A low-affinity complex contains an antibody that generally tends to dissociate readily from the antigen, whereas a high-affinity complex contains an antibody that generally tends to remain bound to the antigen for a longer duration.

As used herein, the term "B cell," refers to a type of lymphocyte in the humoral immunity of the adaptive immune system. B cells principally function to make antibodies, serve as antigen presenting cells, release cytokines, and develop memory B cells after activation by antigen interaction. B cells are distinguished from other lymphocytes, such as T cells, by the presence of a B-cell receptor on the cell surface. B cells may either be isolated or obtained from a commercially available source. Non-limiting examples of commercially available B cell lines include lines AHH-1 (ATCC® CRL-8146™), BC-1 (ATCC® CRL-2230™), BC-2 (ATCC® CRL-2231™), BC-3 (ATCC® CRL-2277™), CA46 (ATCC® CRL-1648™), DG-75 [D.G.-75] (ATCC® CRL-2625™), DS-1 (ATCC® CRL-11102™) EB-3 [EB3] (ATCC® CCL-85™), Z-138 (ATCC #CRL-3001), DB (ATCC CRL-2289), Toledo (ATCC CRL-2631), Pfiffer (ATCC CRL-2632), SR (ATCC CRL-2262), JM-1 (ATCC CRL-10421), NFS-5 C-1 (ATCC CRL-1693); NFS-70 C10 (ATCC CRL-1694), NFS-25 C-3 (ATCC CRL-1695), AND SUP-B15 (ATCC CRL-1929). Further examples include but are not limited to cell lines derived from anaplastic and large cell lymphomas, e.g., DEL, DL-40, FE-PD, JB6, Karpas 299, Ki-JK, Mac-2A Ply1, SR-786, SU-DHL-1, -2, -4, -5, -6, -7, -8, -9, -10, and -16, DOHH-2, NU-DHL-1, U-937, Granda 519, USC-DHL-1, RL; Hodgkin's lymphomas, e.g., DEV, HD-70, HDLM-2, HD-MyZ, HKB-1, KM-H2, L 428, L 540, L1236, SBH-1, SUP-HD1, SU/RH-HD-1. Non-limiting exemplary sources for such commercially available cell lines include the American Type Culture Collection, or ATCC, (www.atcc.org/) and the German Collection of Microorganisms and Cell Cultures (https.//www.dsmz.de/).

As used herein, the term "cognate" refers to a relationship signifying correspondence between two molecules (e.g., between a receptor and its ligand). In the context of a TCR, a "cognate pair" refers to the relationship of two distinct TCR polypeptides or polynucleotides encoding polypeptides derived from a single T cell (e.g., a TCR alpha chain and a TCR beta chain derived from a single T cell). "Cognate" may also refer the relationship between a TCR and the corresponding antigen:MHC complex to which it specifically binds.

As used herein, the term "CRISPR" refers to a technique of sequence specific genetic manipulation relying on the clustered regularly interspaced short palindromic repeats pathway (CRISPR). CRISPR can be used to perform gene editing and/or gene regulation, as well as to simply target proteins to a specific genomic location. Gene editing refers to a type of genetic engineering in which the nucleotide sequence of a target polynucleotide is changed through introduction of deletions, insertions, or base substitutions to the polynucleotide sequence. In some aspects, CRISPR-mediated gene editing utilizes the pathways of nonhomologous end-joining (NHEJ) or homologous recombination to perform the edits.

Gene regulation refers to increasing or decreasing the production of specific gene products such as protein or RNA.

The term "guide RNA" or "gRNA" as used herein refers to the guide RNA sequences used to target the CRISPR complex to a specific nucleotide sequence such as a specific region of a cell's genome. Techniques of designing gRNAs and donor therapeutic polynucleotides for target specificity are well known in the art. For example, Doench, J., et al.

Nature biotechnology 2014; 32(12):1262-7, Mohr, S. et al. (2016) FEBS Journal 283: 3232-38, and Graham, D., et al. Genome Biol. 2015; 16: 260. gRNA comprises or alternatively consists essentially of, or yet further consists of a fusion polynucleotide comprising CRISPR RNA (crRNA) and trans-activating CRIPSPR RNA (tracrRNA); or a polynucleotide comprising CRISPR RNA (crRNA) and trans-activating CRIPSPR RNA (tracrRNA). In some aspects, a gRNA is synthetic (Kelley, M. et al. (2016) J of Biotechnology 233 (2016) 74-83).

As used herein, the term "detectable marker" refers to at least one marker capable of directly or indirectly, producing a detectable signal. A non-exhaustive list of exemplary markers includes enzymes which produce a detectable signal, for example by colorimetry, fluorescence, luminescence, such as horseradish peroxidase, alkaline phosphatase, β-galactosidase, glucose-6-phosphate dehydrogenase, chromophores such as fluorescent, luminescent dyes, groups with electron density detected by electron microscopy or by their electrical property such as conductivity, amperometry, voltammetry, impedance, detectable groups, for example whose molecules are of sufficient size to induce detectable modifications in their physical and/or chemical properties, such detection may be accomplished by optical methods such as diffraction, surface plasmon resonance, surface variation, the contact angle change or physical methods such as atomic force spectroscopy, tunnel effect, or radioactive molecules such as $^{32}P$, $^{35}S$, or $^{125}I$.

As used herein, the term "purification marker" refers to at least one marker useful for purification or identification. A non-exhaustive list of this marker includes His, lacZ, GST, maltose-binding protein, NusA, BCCP, c-myc, CaM, FLAG, GFP, YFP, cherry, thioredoxin, poly(NANP), V5, Snap, HA, chitin-binding protein, Softag 1, Softag 3, Strep, or S-protein. Suitable direct or indirect fluorescence marker comprise FLAG, GFP, YFP, RFP, dTomato, cherry, Cy3, Cy 5, Cy 5.5, Cy 7, DNP, AMCA, Biotin, Digoxigenin, Tamra, Texas Red, rhodamine, Alexa fluors, FITC, TRITC or any other fluorescent dye or hapten.

As used herein, the term "effective amount" or "therapeutically effective amount" of a composition, is a quantity sufficient to achieve a desired therapeutic effect, e.g., an amount which results in the decrease in the symptoms associated with a disease that is being treated, e.g., the diseases or medical conditions associated with cancer or viral infection. The amount of a composition of the present technology administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions of the present technology can also be administered in combination with one or more additional therapeutic compounds. In some embodiments, effective amount refers to the quantity of cells of the present technology that is partially or fully effective in neutralizing the cancer or viral infection.

As used herein, the term "epitope" means a protein determinant capable of specific binding to an antibody or TCR. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

As used herein, "expression" includes one or more of the following: transcription of the gene into precursor mRNA; splicing and other processing of the precursor mRNA to produce mature mRNA; mRNA stability; translation of the mature mRNA into protein (including codon usage and tRNA availability); and glycosylation and/or other modifications of the translation product, if required for proper expression and function.

As used herein, "elevated expression" refers to an increase in gene expression or protein expression, as compared to a control or a reference sample (e.g., an increase of at least 2-fold, from about 2-fold to about 150-fold, from 5-fold to 150-fold, from 5-fold to 100-fold, from 10-fold to 150-fold, from 10-fold to 100-fold, from 50-fold to 150-fold, from 50-fold to 100-fold, from 75-fold to 150-fold, or from 75-fold to 100-fold, as compared to a control or a normal reference sample). By "decreased expression" refers to an overall reduction in gene expression or protein expression, as compared to a control or a reference sample (e.g., 20% or greater, of 50% or greater, or of 75%, 80%, 85%, 90%, 95%, or greater. An increase or decrease in gene expression or protein expression can be determined using any useful methods known in the art or described herein (e.g., ELISA). For therapeutic applications, to "decrease" can refer to the reduction in the level of polypeptides or proteins associated with the disorder (e.g., a tauopathy, TBI, or stroke). For diagnostic or monitoring applications, to "decrease" can refer to a decrease in the level of protein or nucleic acid detected by the diagnostic or monitoring assays.

As used herein, the term "gene" means a segment of DNA that contains all the information for the regulated biosynthesis of an RNA product, including promoters, exons, introns, and other untranslated regions that control expression.

As used herein, the term "humanized" forms of non-human proteins (e.g., murine TCRs) are chimeric proteins which contain minimal sequence derived from non-human homologs of the protein. For the most part, humanized proteins are human TCRs in which variable region residues of the recipient are replaced by variable region residues from a non-human species (donor TCR) such as mouse, rat, rabbit or nonhuman primate having the desired specificity, affinity, and capacity.

As used herein, the terms "identical" or percent "identity", when used in the context of two or more nucleic acids or polypeptide sequences, refer to two or more sequences or subsequences that are the same or have a specified percentage of amino acid residues or nucleotides that are the same (i.e., about 60%, 65%, 70%, 75%, 80%, 85%, 90%, 91%, 92%, 93%, 94%, 95%, 96%, 97%, 98%, 99%, or higher identity over a specified region (e.g., nucleotide sequence encoding an antibody described herein or amino acid sequence of an antibody described herein), when compared and aligned for maximum correspondence over a comparison window or designated region) as measured using a BLAST or BLAST 2.0 sequence comparison algorithms with default parameters described below, or by manual alignment and visual inspection, e.g., NCBI web site). Such sequences are then said to be "substantially identical." This term also refers to, or can be applied to, the complement of a test sequence. The term also includes sequences that have deletions and/or additions, as well as those that have substitutions. In some embodiments, identity exists over a region that is at least about 25 amino acids or nucleotides in length, or 50-100 amino acids or nucleotides in length.

A "Kozak consensus sequence" or "Kozak sequence" is an mRNA sequence that is recognized by a ribosome as a translation start site. A Kozak sequence comprises a start codon (also known as an initiation codon) for initiation of translation and additional flanking nucleotides. The start codon specifies a methionine amino acid at the N-terminus of a translated polypeptide. The Kozak consensus sequence for vertebrates is known in the art (e.g. Kozak, M. 1987 Nucleic Acids Res. 15(20): 8125-48). In some embodiments, Kozak sequences can be modified to be "strong", meaning that the nucleotide sequence closely matches the consensus sequence, particularly at nucleotides +4 and −3 relative to the number one nucleotide. An "adequate" Kozak sequence has just one of these matching nucleotides while a "weak" Kozak sequence has neither matching nucleotide. The strength of a Kozak sequence directly correlates with the amount of polypeptides translated from an expressed mRNA. In general, strong Kozak sequences result in greater efficiency of translation of an expressed mRNA while fewer polypeptides are transcribed from mRNAs with weak Kozak sequences.

As used herein, "major histocompatibility complex" or "MHC" refers to a cell surface protein that presents antigens to T cells. Class I MHC molecules are recognized by CD8+ T cells. Class II MHC molecules are recognized by CD4+ T cells. An MHC molecule loaded with an antigen or epitope thereof is referred to as an antigen:MHC complex.

As used herein, the term "NK cell," also known as natural killer cell, refers to a type of lymphocyte that originates in the bone marrow and play a critical role in the innate immune system. NK cells provide rapid immune responses against viral-infected cells, tumor cells or other stressed cell, even in the absence of antibodies and major histocompatibility complex on the cell surfaces. NK cells may either be isolated or obtained from a commercially available source. Non-limiting examples of commercial NK cell lines include lines NK-92 (ATCC® CRL-2407™), NK-92MI (ATCC® CRL-2408™). Further examples include but are not limited to NK lines HANK1, KHYG-1, NKL, NK-YS, NOI-90, and YT. Non-limiting exemplary sources for such commercially available cell lines include the American Type Culture Collection, or ATCC, (http://www.atcc.org/) and the German Collection of Microorganisms and Cell Cultures (https://www.dsmz.de/).

As used herein, the term "operably linked" refers to two or more polynucleotides that are joined as part of the same nucleic acid molecule. In some embodiments, the joined polynucleotides are suitably positioned and oriented for transcription to be initiated from the same expression control element. In some embodiments, transcription of a polynucleotide operably linked to an expression control element (e.g., a promoter) is controlled, regulated, or influenced by the expression control element.

As used herein, the term "pharmaceutically-acceptable carrier" is intended to include any and all solvents, dispersion media, coatings, antibacterial and antifungal compounds, isotonic and absorption delaying compounds, and the like, compatible with pharmaceutical administration. Pharmaceutically-acceptable carriers and their formulations are known to one skilled in the art and are described, for example, in Remington's Pharmaceutical Sciences (20$^{th}$ edition, ed. A. Gennaro, 2000, Lippincott, Williams & Wilkins, Philadelphia, Pa.).

As used herein, the term "polynucleotide" or "nucleic acid" means any RNA or DNA, which may be unmodified or modified RNA or DNA. Polynucleotides include, without limitation, single- and double-stranded DNA, DNA that is a mixture of single- and double-stranded regions, single- and double-stranded RNA, RNA that is mixture of single- and double-stranded regions, and hybrid molecules comprising DNA and RNA that may be single-stranded or, more typically, double-stranded or a mixture of single- and double-stranded regions. In addition, polynucleotide refers to triple-stranded regions comprising RNA or DNA or both RNA and DNA. The term polynucleotide also includes DNAs or RNAs containing one or more modified bases and DNAs or RNAs with backbones modified for stability or for other reasons.

As used herein, the terms "polypeptide", "peptide" and "protein" are used interchangeably herein to mean a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art. Such modifications are well described in basic texts and in more detailed monographs, as well as in a voluminous research literature.

A polypeptide, peptide, polynucleotide, or cell may be said to be "isolated" or "substantially pure" when physical, mechanical, or chemical methods have been employed to remove the polypeptide, peptide, polynucleotide, or cell from other cells or cellular constituents. An isolated polypeptide, peptide, polynucleotide, or cell (e.g., an isolated cell), "substantially pure" or "substantially pure and isolated" polypeptide, peptide, polynucleotide, or cell is typically considered removed from cellular constituents and substantially pure when it is at least 60% by weight free from the proteins and naturally occurring organic molecules with which it is naturally associated. The polypeptide may be at least 75%, 80%, 85%, 90%, 95%, or 99% by weight pure. A substantially pure polypeptide, peptide, polynucleotide, or cell (e.g., a substantially pure antibody or fragment thereof) may be obtained by standard techniques, for example, by expression of a recombinant nucleic acid encoding the polypeptide, or by chemically synthesizing the polypeptide. Purity can be measured by any appropriate method, e.g., by column chromatography, polyacrylamide gel electrophoresis, or HPLC analysis.

As used herein, the term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the material is derived from a cell so modified. Thus, for example, recombinant cells express genes that are not found within the native (non-recombinant) form of the cell or express native genes that are otherwise abnormally expressed, under expressed or not expressed at all.

As used herein, the term "separate" therapeutic use refers to an administration of at least two active ingredients at the same time or at substantially the same time by different routes.

As used herein, the term "repeat" therapeutic use refers to administration of active ingredients at different times, the administration route being identical or different. More particularly, sequential use refers to the whole administration of an active ingredient before a second administration of the same or different active ingredient commences. It is thus possible to administer one of the active ingredients over several minutes, hours, days, months, or years before a second administration.

As used herein, the terms "subject", "individual" and "patient" are used interchangeably and refer to a human or non-human animal, e.g., domestic animals (e.g., dogs, cats and the like), farm animals (e.g., cows, sheep, pigs, horses and the like), wild animals, (bats, raccoons, foxes, skunks, squirrels, chipmunks, mice, rabbits, and the like), and laboratory animals (e.g., monkey, rats, mice, rabbits, guinea pigs and the like). In some embodiments, the subject is a mammal. In particular embodiments, the subject is a human.

As used herein, the term "switch" refers to a mechanism by which the expression, activation, or stability of a recombinant TCR or a component of a recombinant TCR is controlled (i.e. a mechanism to turn TCRs "on" or "off"). Switch mechanisms include but are not limited to TCR expression systems that require co-expression of more than one construct to be activated, suicide switches, safety switches, and TCRs that require multimerization for activation. In some embodiments, a switch is inducible.

As used herein, the term "T cell," refers to a type of lymphocyte that matures in the thymus. T cells play an important role in cell-mediated immunity and are distinguished from other lymphocytes, such as B cells, by the presence of a T-cell receptor on the cell surface. T-cells may either be isolated or obtained from a commercially available source. "T cell" includes all types of immune cells expressing CD3 including T-helper cells (CD4+ cells), cytotoxic T-cells (CD8+ cells), natural killer T-cells, T-regulatory cells (Treg) and gamma-delta T cells. A "cytotoxic cell" includes CD8+ T cells, natural-killer (NK) cells, and neutrophils, which cells are capable of mediating cytotoxicity responses. Non-limiting examples of commercially available T-cell lines include lines BCL2 (AAA) Jurkat (ATCC® CRL-2902™), BCL2 (S70A) Jurkat (ATCC® CRL-2900™), BCL2 (S87A) Jurkat (ATCC® CRL-2901™), BCL2 Jurkat (ATCC® CRL-2899™), Neo Jurkat (ATCC® CRL-2898™) TALL-104 cytotoxic human T cell line (ATCC #CRL-11386). Further examples include but are not limited to mature T-cell lines, e.g., such as Deglis, EBT-8, HPB-MLp-W, HUT 78, HUT 102, Karpas 384, Ki 225, My-La, Se-Ax, SKW-3, SMZ-1 and T34; and immature T-cell lines, e.g., ALL-SIL, Be13, CCRF-CEM, CML-T1, DND-41, DU.528, EU-9, HD-Mar, HPB-ALL, H-SB2, HT-1, JK-T1, Jurkat, Karpas 45, KE-37, KOPT-K1, K-T1, L-KAW, Loucy, MAT, MOLT-1, MOLT 3, MOLT-4, MOLT 13, MOLT-16, MT-1, MT-ALL, P12/Ichikawa, Peer, PER0117, PER-255, PF-382, PFI-285, RPMI-8402, ST-4, SUP-T1 to T14, TALL-1, TALL-101, TALL-103/2, TALL-104, TALL-105, TALL-106, TALL-107, TALL-197, TK-6, TLBR-1, -2, -3, and -4, CCRF-HSB-2 (CCL-120.1), J.RT3-T3.5 (ATCC TIB-153), J45.01 (ATCC CRL-1990), J.CaM1.6 (ATCC CRL-2063), RS4; 11 (ATCC CRL-1873), CCRF-CEM (ATCC CRM-CCL-119); and cutaneous T-cell lymphoma lines, e.g., HuT78 (ATCC CRM-TIB-161), MJ[G11] (ATCC CRL-8294), HuT102 (ATCC TIB-162). Null leukemia cell lines, including but not limited to REH, NALL-1, KM-3, L92-221, are a another commercially available source of immune cells, as are cell lines derived from other leukemias and lymphomas, such as K562 erythroleukemia, THP-1 monocytic leukemia, U937 lymphoma, HEL erythroleukemia, HL60 leukemia, HMC-1 leukemia, KG-1 leukemia, U266 myeloma. Non-limiting exemplary sources for such commercially available cell lines include the American Type Culture Collection, or ATCC, (http://www.atcc.org/) and the German Collection of Microorganisms and Cell Cultures (https://www.dsmz.de/).

As used herein, the term "T cell receptor" or "TCR" refers to a heterodimeric cell surface protein of the immunoglobulin super-family which is associated with invariant proteins of the CD3 complex involved in mediating signal transduction. The TCR is composed of two cognate protein chains: an alpha (α) chain and a beta (β) chain (encoded by TRA (Entrez gene: 6955) and the TRB gene (Entrez gene: 6957), respectively), or a gamma (γ) chain and a delta (δ) chain (encoded by TRG (Entrez gene: 6965) and TRD gene (Entrez gene: 6964), respectively). Each chain is composed of two extracellular domains: a variable (V) region and a constant (C) region. The constant region is proximal to the cell membrane, followed by a transmembrane region and a short cytoplasmic tail, while the variable region binds to the antigen:MHC complex. The variable domain of both the TCR α-chain and β-chain each have three hypervariable or complementarity determining regions (CDRs). There is also an additional area of hypervariability on the β-chain (HV4) that does not normally contact antigen and, therefore, is not considered a CDR. CDR3 is the main CDR responsible for recognizing processed antigen, although CDR1 of the alpha chain has also been shown to interact with the N-terminal part of the antigenic peptide, whereas CDR1 of the β-chain interacts with the C-terminal part of the peptide. CDR2 is thought to recognize the MHC. CDR4 of the β-chain is not thought to participate in antigen recognition, but has been shown to interact with superantigens. The constant domain of the TCR consists of short connecting sequences in which a cysteine residue forms disulfide bonds, which form a link between the two chains.

The diverse repertoire of TCRs in a subject is accomplished by V(D)J recombination, a somatic recombination mechanism that rearranges variable (V), joining (J), and diversity (D) gene segments. In humans, the TRA gene locus comprises 54 TRAV (V) segments, 61 TRAJ (J) segments, and a unique constant TRAC (C) segment. The TRB gene locus comprises 64-67 TRBV (V) segments, 2 TRBD (D) segments, 14 TRBJ (J) segments, and 2 TRBC (C) segments. The TRG gene locus comprises 12-15 TRGV (V) segments, 5 TRGJ (J) segments, and 2 TRGC (C) segments. The TRD gene locus is embedded in the TRA gene locus and contains 8 TRDV or TRAV/DV (V) segments, 3 TRDD (D) segments, 4 TRDJ (J) segments, and one TRDC (C) segment. Non-limiting examples of TCR amino acid sequences are known in the art and provided herein.

Human TCR (α) Chain TRAC Segment:

```
                                                (SEQ ID NO: 2)
PNIQNPDPAVYQLRDSKSSDKSVCLFTDFDSQTNVSQSKDSDVYITDKTV
LDMRSMDFKSNSAVAWSNKSDFACANAFNNSIIPEDTFFPSPESSCDVKL
VEKSFETDTNLNFQNLSVIGFRILLLKVAGFNLLMTLRLWSS
```

Human TCR (β) Chain TRBC1 Segment:

```
                                                (SEQ ID NO: 3)
EDLNKVFPPEVAVFEPSEAEISHTQKATLVCLATGFFPDHVELSWWVNGK

EVHSGVSTDPQPLKEQPALNDSRYCLSSRLRVSATFWQNPRNHFRCQVQF

YGLSENDEWTQDRAKPVTQIVSAEAWGRADCGFTSVSYQQGVLSATILYE

ILLGKATLYAVLVSALVLMAMVKRKDF
```

Human TCR (β) Chain TRBC2 Segment:

(SEQ ID NO: 4)
DLKNVFPPEVAVFEPSEAEISHTQKATLVCLATGFYPDHVELSWWVNGKE

VHSGVSTDPQPLKEQPALNDSRYCLSSRLRVSATFWQNPRNHFRCQVQFY

GLSENDEWTQDRAKPVTQIVSAEAWGRADCGFTSESYQQGVLSATILYEI

LLGKATLYAVLVSALVLMAMVKRKDSRG

Human TCR (γ) Chain TRGC1 Segment:

(SEQ ID NO: 5)
DKQLDADVSPKPTIFLPSIAETKLQKAGTYLCLLEKFFPDVIKIHWQEKK

SNTILGSQEGNTMKTNDTYMKFSWLTVPEKSLDKEHRCIVRHENNKNGVD

QEIIFPPIKTDVITMDPKDNCSKDANDTLLLQLTNTSAYYMYLLLLLKSV

VYFAIITCCLLRRTAFCCNGEKS

Human TCR (γ) Chain TRGC2 Segment:

(SEQ ID NO: 6)
DKQLDADVSPKPTIFLPSIAETKLQKAGTYLCLLEKFFPDIIKIHWQEKK

SNTILGSQEGNTMKTNDTYMKFSWLTYPEESLDKEHRCIVRHENNKNGID

QETIFPPIKTDVTTVDPKDSYSKDANDVITMDPKDNWSKDANDTLLLQLT

NTSAYYMYLLLLLKSVVYFAIITCCLLGRTAFCCNGEKS

Human TCR (δ) Chain TRDC Segment:

(SEQ ID NO: 7)
SQPHTKPSVFVMKNGTNVACLVKEFYPKDIRINLVSSKKITEFDPAIVI

SPSGKYNAVKLGKYEDSNSVTCSVQHDNKTVHSTDFEVKTDSTDHVKPK

ETENTKQPSKSCHKPKAIVHTEKVNMMSLTVLGLRMLFAKTVAVNFLLT

AKLFFL

As used herein, the term "therapeutic agent" is intended to mean a nucleic acid, recombinant TCR, vector, cell, or population of cells that, when present in an effective amount, produces a desired therapeutic effect on a subject in need thereof.

Amino acid sequence modification(s) of the TCRs described herein are contemplated. For example, it may be desirable to improve the binding affinity and/or other biological properties of the TCR. Amino acid sequence variants of an TCR are prepared by introducing appropriate nucleotide changes into the TCR nucleic acid, or by peptide synthesis. Such modifications include, for example, deletions from, and/or insertions into and/or substitutions of, residues within the amino acid sequences of the TCR. Any combination of deletion, insertion, and substitution is made to obtain the TCR of interest, as long as the obtained TCR possesses the desired properties. The modification also includes the change of the pattern of glycosylation of the protein. The sites of greatest interest for substitutional mutagenesis include the hypervariable regions, but FR alterations are also contemplated. "Conservative substitutions" are shown in the Table below.

TABLE 1

Amino Acid Substitutions

| Original Residue | Exemplary Substitutions | Conservative Substitutions |
| --- | --- | --- |
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

As used herein, "specifically binds" refers to a molecule (e.g., a TCR) which recognizes and binds another molecule (e.g., an antigen:MHC complex), but that does not substantially recognize and bind other molecules. The terms "specific binding," "specifically binds to," or is "specific for" a particular molecule (e.g., a particular cell, antigen, epitope, or antigen:MHC complex), as used herein, can be exhibited, for example, by a molecule having a $K_d$ for the molecule to which it binds to of at least about $10^{-4}$ M, $10^{-5}$ M, $10^{-6}$ M, $10^{-7}$ M, $10^{-8}$ M, $10^{-9}$ M, $10^{-10}$ M, $10^{-11}$ M, $10^{-12}$ M, or greater. The term "specifically binds" may also refer to binding where a molecule (e.g., a TCR) binds to a particular cell, antigen, epitope, or antigen:MHC complex without substantially binding to any other cell, antigen, epitope, or antigen:MHC complex. For example, the TCR may have, for example, at least 10- to 100-fold greater affinity (e.g., $10^1$-, $10^2$-, $10^3$-, $10^4$-, $10^5$-, $10^6$-, $10^7$-, $10^8$-, $10^9$-, or $10^{10}$-fold greater affinity) to one antigen:MHC complex than to another antigen:MHC complex.

As used herein, the term "vector" refers to a nucleic acid construct deigned for transfer between different hosts, including but not limited to a plasmid, a virus, a cosmid, a phage, a BAC, a YAC, etc. In some embodiments, plasmid vectors may be prepared from commercially available vectors. In other embodiments, viral vectors may be produced from baculoviruses, retroviruses, adenoviruses, AAVs, etc. according to techniques known in the art. In one embodiment, the viral vector is a lentiviral vector.

The term "promoter" as used herein refers to any sequence that regulates the expression of a coding sequence, such as a gene. Promoters may be constitutive, inducible, repressible, or tissue-specific, for example. A "promoter" is a control sequence that is a region of a polynucleotide sequence at which initiation and rate of transcription are controlled. It may contain genetic elements at which regulatory proteins and molecules may bind such as RNA polymerase and other transcription factors. Non-limiting examples of promoters include p2A, CMV, and E1α.

The term "transduce" or "transduction" as it is applied to the production of recombinant cells refers to the process whereby a foreign nucleotide sequence is introduced into a cell. In some embodiments, this transduction is done via a vector.

"Treating" or "treatment" as used herein covers the treatment of a disease or disorder described herein, in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder. By "treating cancer" it is meant that the cancer or cancer cells are, e.g., alleviated, reduced, cured, or placed in a state of remission. By "treating a viral infection" it is meant that the virus or viral load is, e.g., alleviated, reduced, cured, or placed in a state of remission It is also to be appreciated that the various modes of treatment of cancer and viral infections as described herein are intended to mean "substantial," which includes total but also less than total treatment, and wherein some biologically or medically relevant result is achieved such as extended lifespan of the subject. The treatment may be a continuous prolonged treatment to prevent recurrence, or few time administrations for acute treatment.

I. Compositions of the Present Technology

In one aspect, the present technology provides a recombinant T cell receptor (TCR) library vector comprising: (a) a vector backbone; and (b) a first polynucleotide encoding a TCRα polypeptide and a second polynucleotide encoding a TCRβ polypeptide; or (b) a first polynucleotide encoding a TCRγ polypeptide and a second polynucleotide encoding a TCRδ polypeptide; wherein the first and second polynucleotides are a cognate pair, and wherein the first polynucleotide and the second polynucleotide are derived from mRNA isolated from a single lysed T cell that is present in a compartment. In some embodiments, the mRNA of the single lysed T cell is isolated using an mRNA capture reagent or reverse transcription-PCR (RT-PCR). Additionally or alternatively, in some embodiments, the compartment containing the contents of the single lysed T cell is a microwell (e.g., a microwell within a 96-well plate) or a droplet. In some embodiments, the mRNA of a single lysed T cell is isolated inside a compartment, without the use of an mRNA capture reagent.

The term "vector" intends a recombinant vector that retains the ability to infect and transduce non-dividing and/or slowly-dividing cells and integrate into the target cell's genome. In some embodiments, the vector is derived from or based on a wild-type virus. In further embodiments, the vector is derived from or based on a wild-type lentivirus, retrovirus, adenovirus, or adeno-associated virus. Examples of such, include without limitation, human immunodeficiency virus (HIV), human T-lymphotropic virus type 1 (HTLV-1), human T-lymphotropic virus type 2 (HTLV-2), human adenovirus (HadV-1 to 57), adeno-associated virus (AAV), equine infectious anaemia virus (EIAV), simian immunodeficiency virus (SIV) and feline immunodeficiency virus (FIV), and murine leukemia virus (MLV). It will be evident that a viral vector according to the present disclosure need not be confined to the components of a particular virus. The viral vector may comprise components derived from two or more different viruses, and may also comprise synthetic components.

In certain embodiments of the vector, the vector backbone is selected from a group consisting of a retroviral, a lentiviral, an adenoviral, and an adeno-associated viral vector backbone. The genome of the vector backbone comprises components from the virus from which it was originally derived. For example, in some embodiments, a vector backbone contains essential vector components compatible with the RNA genome, including reverse transcription and integration systems. In some embodiments, these include gag and pol proteins derived from a particular retrovirus. In some embodiments, the structural components of the vector backbone have been altered genetically or otherwise so as to provide desired useful properties. For example, the vector host range and target cell types can be altered by using different env genes in the vector production system to give the vector a different target specificity.

In a particular embodiment, the vector backbone is a lentiviral vector backbone, e.g., pLVX. Lentiviral vectors are based on or derived from oncoretroviruses (the sub-group of retroviruses containing MLV) and lentiviruses (the sub-group of retroviruses containing HIV). Nonlimiting examples include ASLV, SNV and RSV, all of which have been split into packaging and vector components for lentiviral vector particle production systems. The lentiviral vector particle according to the present disclosure may be based on a genetically or otherwise (e.g., by specific choice of packaging cell system) altered version of a particular retrovirus.

Non-limiting, exemplary vector backbones are known in the art, e.g., see U.S. Pat. Nos. 6,924,123; 7,056,699; 7,07,993; 7,419,829 and 7,442,551, incorporated herein by reference, and Invitrogen's pLenti series versions 4, 6, and 6.2 "ViraPower" system, pHIV-7-GFP, lab generated and used by the City of Hope Research Institute; "Lenti-X" lentiviral vector, pLVX, manufactured by Clontech; pLKO.1-puro, manufactured by Sigma-Aldrich; pLemiR, manufactured by Open Biosystems; and pLV, lab generated and used by Charite Medical School, Institute of Virology (CBF), Berlin, Germany.

Certain retroviral sequences facilitate integration into the target cell genome (see, e.g. U.S. Pat. No. 6,924,123). Each retroviral genome comprises genes called gag, pol and env which code for virion proteins and enzymes. These genes are flanked at both ends by regions called long terminal repeats (LTRs). The LTRs are responsible for proviral integration, and transcription. They also serve as enhancer-promoter sequences capable of controlling the expression of the viral genes. Encapsidation of the retroviral genome occurs by virtue of a psi sequence located at the 5' end of the viral genome. The LTRs themselves are identical sequences that can be divided into three elements, which are called U3, R and U5. U3 is derived from the sequence unique to the 3' end of the RNA. R is derived from a sequence repeated at both ends of the RNA, and U5 is derived from the sequence unique to the 5'end of the RNA. The sizes of the three elements can vary considerably among different retroviruses. U3 contains most of the expression control elements of the provirus, which include the promoter and multiple enhancer sequences responsive to cellular and in some cases, viral transcriptional activator proteins.

With regard to the structural genes gag, pol and env themselves, gag encodes the internal structural protein of the virus. Gag protein is proteolytically processed into the mature proteins MA (matrix), CA (capsid) and NC (nucleocapsid). The pol gene encodes the reverse transcriptase (RT), which contains DNA polymerase, associated RNase H and integrase (IN), which mediate replication of the genome.

Viral particles are produced by expressing the vector RNA genome from a DNA construct encoding it in a host cell. In some embodiments, the components of the viral particles that are not encoded by the vector backbone are provided in trans by additional nucleic acid sequences (the "packaging system", which usually includes either or both of the gag/pol and env genes) expressed in the host cell. In some embodiments, the set of sequences required for the production of the viral vector particles are introduced into the host cell by transient transfection, or integrated into the host cell genome, or provided through use of a packaging cell line. The techniques involved are known to those skilled in the art.

In some embodiments, the method or process of derivation of the first polynucleotide and second polynucleotide results in structural features in the first polynucleotide and/or the second polynucleotide that are distinct from other vectors and methods known in the art. For example, use of an mRNA capture reagent with the individual compartment for the lysed T cell allows for capture of a cognate pair of TCR polynucleotides. Other non-limiting examples of structural features include restriction enzyme recognition sites, integrated primer sites, and sequences derived from the mRNA capture reagent.

In some embodiments of the vector, the mRNA capture reagent is selected from the group consisting of a poly(dT) coated bead, an oligonucleotide-coated bead, a hydrogel bead, and a printed oligo on the surface of a microarray well. For example, the mRNA capture agent can be a solid support, such as a bead, comprising immobilized oligonucleotides or polymer networks such as dextran and agarose. In some embodiments, the bead is a silica bead or a magnetic bead. In some embodiments, the mRNA capture agent comprises oligonucleotides which hybridize mRNA. For example, the oligonucleotides may comprise at least one poly(T) and/or primers specific to a transcript of interest. In certain embodiments, a bead of the mRNA capture reagent is smaller than the individual cells that being isolated (e.g., T cells). In some embodiments, sequestering single T cells with an mRNA capture agent is performed prior to lysis of the T cell. In other embodiments, sequestering single T cells with the mRNA capture agent is performed concurrently with T cell lysis. Thus, in some embodiments, single T cells and an mRNA capture agents are isolated into individual microvesicles in an emulsion in the presence of a cell lysis solution.

In some embodiments, the individual compartment has a volume of 100 nL or less, 50 nL or less, 40 nL or less, 30 nL or less, 20 nL or less, 10 nL or less, 5 nL or less. In particular embodiments, the individual compartment has a volume of 5 nL or less. In some embodiments, the individual compartment is a droplet or microvesicle, optionally in an emulsion. In some embodiments, the compartment is a well. In certain embodiments, the well is located in a printed polymer slide, a plastic plate, a microtiter plate, or a gel. In some embodiments, the well is sealed with a permeable membrane prior to lysis of the T cell or prior to performing RT-PCR. Compartmentalized preparation as described herein enables characterization of the library and minimizes the likelihood of PCR error variants which may be included in the final drug product. This reduces the risk that the final therapeutic cell composition contains uncharacterizable and potentially very dangerous variants, which may induce side effects and/or off-target TCR binding specificity.

In some embodiments, the mRNA of the single lysed T cell is reverse transcribed into cDNA using any method known in the art. For example, in some embodiments, reverse transcription is performed using overlap extension (OE) reverse transcription PCR (RT-PCR). The reaction mix for OE-RT-PCR includes primers designed to create a single PCR product comprising the cDNA of two or more transcripts of interest covalently linked together. Primer design for OE-RT-PCR determines which transcripts of interest (e.g. TCR gene transcripts) expressed by a given cell are linked together. For example, in certain embodiments, primers are designed that cause the respective cDNAs from cognate pair TCR chain transcripts to be covalently linked together. Non-limiting examples of OE-RT-PCR reaction conditions are provided in Table 3 herein. Non-limiting examples of PCR primers suitable for performing the reaction to obtain linked TCR cDNAs are provided in Table 4 herein. The linked cDNA products of OE RT-PCR are recovered and used as a template for nested PCR, which amplifies the linked transcripts of interest. Exemplary reaction conditions for nested PCR are provided in Table 5 herein. In some embodiments, the purified products of nested PCR are then sequenced and pairing information is analyzed. In some embodiments, restriction and ligation may be used to link cDNA of multiple transcripts of interest. In other embodiments, recombination may be used to link cDNA of multiple transcripts of interest.

In some embodiments, the TCRα polypeptide comprises at least one TRAV segment and a TRAC segment or an equivalent of each thereof. In some embodiments, the TCRα polypeptide comprises at least one TRAV segment, a TRAC segment, and at least one TRAD segment. In some embodiments, the TCRα polypeptide comprises at least one TRAV segment, a TRAC segment, at least one TRAD segment, and at least one TRAJ segment. In some embodiments, the TCRα polypeptide comprises at least one TRAV segment, a TRAC segment, and at least one TRAJ segment.

In some embodiments, the TCRβ polypeptide comprises at least one TRBV segment and a TRBC segment or an equivalent of each thereof. In some embodiments, the TCRβ polypeptide comprises at least one TRBV segment, at least one TRBC segment, and at least one TRBD segment. In some embodiments, the TCRβ polypeptide comprises at least one TRBV segment, at least one TRBC segment, at least one TRBD segment, and at least one TRBJ segment. In some embodiments, the TCRβ polypeptide comprises at least one TRBV segment, at least one TRBC segment, and at least one TRBJ segment.

In some embodiments, the TCRγ polypeptide comprises at least one TRGV segment and a TRGC segment or an equivalent of each thereof. In some embodiments, the TCRγ polypeptide comprises at least one TRGV segment, at least one TRGC segment, and at least one TRGD segment. In some embodiments, the TCRγ polypeptide comprises at least one TRGV segment, at least one TRGC segment, at least one TRGD segment, and at least one TRGJ segment. In some embodiments, the TCRγ polypeptide comprises at least one TRGV segment, at least one TRGC segment, and at least one TRGJ segment.

In some embodiments, the TCRδ polypeptide comprises at least one TRDV segment and a TRDC segment or an equivalent of each thereof. In some embodiments, the TCRδ polypeptide comprises at least one TRDV segment, at least one TRDC segment, and at least one TRDD segment. In some embodiments, the TCRδ polypeptide comprises at least one TRDV segment, at least one TRDC segment, at least one TRDD segment, and at least one TRDJ segment. In some embodiments, the TCRδ polypeptide comprises at least one TRDV segment, at least one TRDC segment, and at least one TRDJ segment.

In some embodiments of the vector, the first polynucleotide and the second polynucleotide are operably linked, optionally via a linker polynucleotide. In some embodiments, the linker polynucleotide encodes a linker polypeptide. As used herein, the term "linker polypeptide" relates to any amino acid sequence comprising from 1 to 10, or alternatively, 8 amino acids, or alternatively 6 amino acids, or alternatively 5 amino acids that may be repeated from 1 to 10, or alternatively to about 8, or alternatively to about 6, or alternatively about 5, or 4 or alternatively 3, or alternatively 2 times. For example, the linker may comprise up to 15 amino acid residues consisting of a pentapeptide repeated three times. In one aspect, the linker sequence is a (Glycine4Serine)3 (SEQ ID NO: 8) flexible polypeptide linker comprising three copies of gly-gly-gly-gly-ser (SEQ ID NO: 9), or equivalents thereof. Non-limiting examples of linker sequences are known in the art, e.g., GGGGSGGGGSGGGG (SEQ ID NO: 10) (and equivalents thereof); the tripeptide EFM; or Glu-Phe-Gly-Ala-Gly-Leu-Val-Leu-Gly-Gly-Gln-Phe-Met (SEQ ID NO: 11), and equivalents of each thereof. In some embodiments of the vector, the first polynucleotide and the second polynucleotide have been operably linked by reverse transcription and PCR amplification of the captured T cell mRNA.

In some embodiments of the vector, the first polynucleotide and the second polynucleotide have been linked and/or cloned into the vector backbone using a restriction enzyme that cleaves at a target restriction endonuclease site that is natively found in TCR genes. In certain embodiments, the target restriction endonuclease site occurs in TCR genes with low frequency. "Low frequency" refers to a site that occurs fewer than 20, fewer than 15, fewer than 10, fewer than 5, or fewer than 2 times in a TCR gene. In certain embodiments, the target restriction endonuclease site comprises a silent mutation that does not alter the expressed TCR polypeptide sequence. Non-limiting examples of restriction endonuclease recognition sites are provided in Tables 6 and 7 herein. In some embodiments, the first polynucleotide and/or the second polynucleotide have been altered to incorporate at least one, at least two, at least 3, at least four, at least 5, at least 5, at least 7, at least 8, at least 9, or at least 10 target restriction endonuclease sites disclosed in Table 6 or Table 7.

In certain embodiments of the vector, the vector further comprises at least one, at least 2, at least 3, or at least 4 polynucleotides encoding an expression control element. As used herein, an "expression control element" intends a polynucleotide that directly or indirectly facilitates, promotes, regulates, or influences the expression of a polynucleotide. In some embodiments, the expression control element activates expression of a polynucleotide. In some embodiments, the expression control element maintains expression of a polynucleotide. In some embodiments, the expression control element enhances expression of a polynucleotide. In some embodiments, the expression control element stabilizes a transcript of a polynucleotide. In some embodiments, the expression control element suppresses expression of a polynucleotide. In some embodiments, the activity of the expression control element is inducible. In some embodiments, the expression control element is operably linked to the first polynucleotide and/or the second polynucleotide. In some embodiments, the expression control element is upstream (5') to the first polynucleotide and/or the second polynucleotide. In some embodiments, the expression control element is downstream (3') to the first polynucleotide and/or the second polynucleotide. In certain embodiments, the polynucleotide encoding the expression control element is located between the first polynucleotide and the second polynucleotide. In some embodiments, the expression control element is selected from the group consisting of: a promoter, a p2A sequence, an enhancer, and an internal ribosome entry site (IRES) sequence.

A p2A sequence is a short peptide (about 20 amino acids) that produces equimolar levels of multiple genes from the same mRNA. The peptides are thought to function by causing the ribosome skip the synthesis of a peptide bond at the C-terminus of a 2A element, leading to separation between the end of the 2A sequence and the next peptide downstream. The resulting "cleavage" occurs between the Glycine and Proline residues found on the C-terminus, meaning the upstream cistron will have a few additional residues added to the end, while the downstream cistron will start with the Proline. In particular embodiments, the p2A sequence is selected from the group consisting of:

```
T2A:
                                   (SEQ ID NO: 12)
(GSG) EGRGSLLTCGDVEENPGP

P2A:
                                   (SEQ ID NO: 13)
(GSG) ATNFSLLKQAGDVEENPGP

E2A:
                                   (SEQ ID NO: 14)
(GSG) QCTNYALLKLAGDVESNPGP

F2A:
                                   (SEQ ID NO: 15)
(GSG) VKQTLNFDLLKLAGDVESNPG
```

A promoter is a regulatory polynucleotide that provides a control point for regulated transcription of a polynucleotide. In some embodiments, the promoter is selected from the group consisting of: CMV, EF1a, SV40, PGK1, UBC, MNDU3, human beta actin, CAG, TRE, UAS, Ac5, Polyhedrin, CaMKIIa, GAL1, GAL10, GDS, ADH1, CaMV35S, Ubi, H1, and U6. In particular embodiments, the promoter is an EF1α promoter or a CMV promoter.

An internal ribosome entry site is an RNA element that allows for translation initiation in a cap-independent manner, as part of the greater process of protein synthesis. In eukaryotic translation, initiation typically occurs at the 5' end of mRNA molecules, since 5' cap recognition is required for the assembly of the initiation complex. The location for IRES elements is often in the 5'UTR, but can also occur elsewhere in mRNAs. In certain embodiments, the IRES is an FMDV or an EMCV IRES sequence. A non-limiting example of a polynucleotide encoding an IRES sequence (EMCV) is provided herein:

```
                                   (SEQ ID NO: 16)
TATGCTAGTACGTCTCTCAAGGATAAGTAAGTAATATTAAGGTACGGGAG

GTATTGGACAGGCCGCAATAAAATATCTTTATTTTCATTACATCTGTGTG

TTGGTTTTTTGTGTGAATCGATAGTACTAACATACGCTCTCCATCAAAAC

AAAACGAAACAAAACAAACTAGCAAAATAGGCTGTCCCCAGTGCAAGTGC

AGGTGCCAGAACATTTCTCTGGCCTAACTGGCCGGTACCTGAGCTCTAGT

TTCACTTTCCCTAGTTTCACTTTCCCTAGTTTCACTTTCCCTAGTTTCAC

TTTCCCTAGTTTCACTTTCCCCTCGAGGATATCAAGATCTGGCCTCGGCG

GCCAG
```

An enhancer is a region of DNA that can be bound by proteins (e.g. transcription factors) to increase the likelihood that transcription of a particular target polynucleotide will occur. Enhancers are cis-acting. In some embodiments, they are between 50-1500 base pairs in length. In some embodiments, they are located upstream, downstream, within a target polynucleotide. In some embodiments, the enhancer is selected from the group consisting of CENTG2, GADD45G, and WPRE enhancers. In particular embodiments, the enhancer is Woodchuck Hepatitis Virus (WHP) Posttranscriptional Regulatory Element (WPRE), a DNA sequence that, when transcribed, creates a tertiary structure enhancing expression. WPRE is a tripartite regulatory element with gamma, alpha, and beta components. In some embodiments, the enhancer comprises just the alpha component of WPRE. In other embodiments, the enhancer comprises the full tripartite WPRE sequence. When used alone without the gamma and beta WPRE components, the alpha component is only 9% as active as the full tripartite WPRE.

WPRE Alpha Sequence:

```
                                          (SEQ ID NO: 17)
GCCACGGCGGAACTCATCGCCGCCTGCCTTGCCCGCTGCTGGACAGGGGC
TCGGCTGTTGGGCACTGACAATTCCGTGGT
```

Full Tripartite WPRE Sequence:

```
                                          (SEQ ID NO: 18)
AATCAACCTCTGGATTACAAAATTTGTGAAAGATTGACTGGTATTCTTA

ACTATGTTGCTCCTTTTACGCTATGTGGATACGCTGCTTTAATGCCTTT

GTATCATGCTATTGCTTCCCGTATGGCTTTCATTTTCTCCTCCTTGTAT

AAATCCTGGTTGCTGTCTCTTTATGAGGAGTTGTGGCCCGTTGTCAGGC

AACGTGGCGTGGTGTGCACTGTGTTTGCTGACGCAACCCCCACTGGTTG

GGGCATTGCCACCACCTGTCAGCTCCTTTCCGGGACTTTCGCTTTCCCC

CTCCCTATTGCCACGGCGGAACTCATCGCCGCCTGCCTTGCCCGCTGCT

GGACAGGGGCTCGGCTGTTGGGCACTGACAATTCCGTGGTGTTGTCGGG

GAAGCTGACGTCCTTTCCATGGCTGCTCGCCTGTGTTGCCACCTGGATT

CTGCGCGGGACGTCCTTCTGCTACGTCCCTTCGGCCCTCAATCCAGCGG

ACCTTCCTTCCCGCGGCCTGCTGCCGGCTCTGCGGCCTCTTCCGCGTCT

TCGCCTTCGCCCTCAGACGAGTCGGATCTCCCTTTGGGCCGCCTCCCCG

CCTG
```

In some embodiments of the vector, the vector is circularized. In some embodiments, the vector has been circularized prior to incorporation of the expression control element into the vector. In other embodiments, the vector has been circularized after incorporation of the expression control element into the vector.

In certain embodiments of the vector, the expression control element has been incorporated near a protospacer adjacent motif (PAM). In these embodiments, the expression control element is inserted into the vector via a CRISPR/Cas mediated mechanism. In other embodiments, the expression control element has been incorporated into the vector using a DNA-modifying enzyme selected from a restriction enzyme or a TALEN.

In certain embodiments, the vector further comprises one or more polynucleotides encoding a transposon to facilitate integration of the at least one of the first polynucleotide and the second polynucleotide into a target cell or a host cell. Sleeping Beauty transposase inserts a transposon into a TA dinucleotide base pair in a recipient DNA sequence. For example, in some embodiments, transposons flanking the first polynucleotide and the second polynucleotide facilitate integration into the recombinant cell genome or the immune cell genome at a TA dinucleotide. In some embodiments, the vector backbone is derived from or comprises a non-viral vector. Advantages of non-viral vectors include the ease and relatively low cost of producing sufficient amounts required to meet the entire patient population, stability during storage and lack of immunogenicity. A non-limiting example of a transposon system suitable for use in the vectors of the present technology is a Sleeping Beauty transposon system (see, e.g., Kebriaei, P. et al. (2017) *Trends in Genetics* 33: 852-70, incorporated herein by reference). A Sleeping Beauty transposon system consists of two components: (i) a transposon containing a gene-expression cassette and (ii) a source of transposase enzyme. By transposing the expression cassette from a plasmid into the genome, sustained transcription of a transgene can be achieved. Exemplary Sleeping beauty transposase vectors include but are not limited to: pSBbi (Kowarz, E. et al. *Biotechnol J*. 10(4): 647-53, available from Addgene), pCMV(CAT)T7-SB100 (Mátés, L. et al. *Nat Genet*. 2009 June; 41(6):753-61, available from Addgene), and pT2/LTR7 (Wang, J. et al. *Nature*. 2014 Dec. 18; 516(7531):405-9, available from Addgene).

In some embodiments of the vector, the vector further comprises one or more polynucleotides encoding a detectable marker or a purification marker. In particular embodiments, the detectable marker is a fluorescent protein selected from the group consisting of GFP, YFP, RFP, dTomato, cherry, Cy3, Cy 5, Cy 5.5, Cy 7, DNP, AMCA, Biotin, Digoxigenin, Tamra, Texas Red, rhodamine, Alexafluors, FITC, and TRITC.

In some embodiments of the vector, the vector further comprises one or more polynucleotides encoding a selectable marker. In particular embodiments, the selectable marker confers a positive selection trait in a eukaryotic cell, e.g., blasticidin (bsd gene), G418/Geneticin (neo gene), hygromycin B (hygB gene), puromycin (pac gene), or zeocin (Sh bla gene). In some embodiments, the selectable marker confers a positive selection trait in a bacterial cell, e.g., beta-lactamase gene.

In some embodiments of the vector, the vector further comprises one or more polynucleotides encoding a switch mechanism for controlling expression and/or activation of the first polynucleotide and the second polynucleotide. In other embodiments of the vector, the recombinant TCR encoded by the first polynucleotide and the second polynucleotide comprises a switch mechanism. In particular embodiments, the switch mechanism is a suicide switch, e.g. iCaspase 9, a safety mechanism which can be activated to cause the apoptosis or death of cells comprising a TCR library.

For example, in some embodiments a TCR may comprise an extracellular domain with a target-specific binding element that comprises a label, binding domain, or tag that is specific for a molecule other than the target antigen that is expressed on or by a target cell. In such embodiments, the specificity of the TCR is provided by a second construct that comprises, consists, or consists essentially of a target antigen binding domain and a domain that is recognized by or binds to the label, binding domain, or tag on the TCR. See, e.g., WO 2013/044225, WO 2016/000304, WO 2015/057834, WO 2015/057852, WO 2016/070061, U.S. Pat. No. 9,233,125, US 2016/0129109. In this way, a T-cell that expresses the TCR can be administered to a subject, but it cannot bind its target antigen until the second composition comprising the antigen-specific binding domain is administered.

In other embodiments, a TCR is modified to require multimerization in order to be activated (see, e.g., US 2015/0368342, US 2016/0175359, US 2015/0368360) and/or an exogenous signal, such as a small molecule drug (US 2016/0166613, Yung et al., Science, 2015).

In some embodiments, the vector comprises a polynucleotide encoding a "suicide switch" or "safety switch" to induce cell death of the vector-expressing cells following treatment (Buddee et al., PLoS One, 2013) or to downregulate expression of the TCR following binding to the target antigen (WO 2016/011210). For example, vectors can comprise a suicide gene that confers sensitivity to an antibody or prodrug that can be administered to cease TCR activity. In some embodiments, the antibody or prodrug is administered to a subject that has received TCR library therapy upon the occurrence of an adverse event. Exemplary suicide genes include but are not limited to herpes simplex virus-thymidine kinase (HSV-TK) which renders cells susceptible to ganciclovir (Bonini et al. Science 276: 1719-1724 (1997)), inducible Caspase 9 (iCaspase9) which allows for dimerization and activation of apoptosis when activated by a dimerizer drug (Gargett et al., Front Pharmacol, 2014 5:235), and truncated EGFR which renders cells susceptible to cetuximab (Wang et al. Blood 118: 1255-63 (2011)).

In some embodiments of the vector, the vector further comprises one or more polynucleotides encoding a Kozak consensus sequence. In some embodiments, the Kozak consensus sequence is strong, adequate, or weak.

In some embodiments of the vector, the T cell was screened for reactivity with a target cell or disease antigen prior to lysis. In certain embodiments of the vector, the TCR encoded by the vector has binding specificity for or is activated by a target cell or disease antigen. In certain embodiments, the target cell is a cancer cell, a cell infected with a virus, a cell derived from a subject infected with a virus, a tumor cell, or a tissue biopsy cell isolated from a subject suspected of having a viral infection or cancer. In some embodiments, the cell was isolated from a subject. In some embodiments of the vector, the TCR is screened for specific binding to an disease antigen:MHC complex.

In certain embodiments, the disease antigen is a viral antigen derived from a virus selected from the group consisting of adenovirus, CMV, coronavirus, coxsackievirus, Dengue virus, Epstein-Barr virus (EBV), enterovirus 71 (EV71), Ebola virus, hepatitis A (HAV), hepatitis B (HBV), cytomegalovirus (CMV), hepatitis C (HCV), hepatitis D (HDV), hepatitis E (HEV), human immunodeficiency virus (HIV), human papillomavirus (HPV), herpes simplex virus (HSV), human T-lymphotropic virus (HTLV), influenza A virus, influenza B virus, Japanese encephalitis, leukemia virus, measles virus, molluscum contagiosum, orf virus, parvovirus, rabies virus, respiratory syncytial virus, rift valley fever virus, rubella virus, rotavirus, tick-borne encephalitis (TBEV), simian immunodeficiency virus, tobacco etch virus (TEV), varicella zoster virus, variola, West Nile virus, Zika virus, and Chikungunya virus.

In other embodiments, the disease antigen is a tumor antigen selected from the group consisting of CD45, glypican-3, IGF2B3, Kallikrein 4, KIF20A, Lengsin, Meloe, mucin 5AC (MUC5AC), survivin, cyclin-A1, MAGE-A1, MAGE-C1, MAGE-C2, SSX2, XAGE1b/GAGED2A, CD19, CD20, CD22, CD52, epidermal growth factor receptor (EGFR), human epidermal growth factor receptor 2 (HER2), tumor necrosis factor receptor superfamily, member 10a (TRAILR1), receptor activator of nuclear factor kappa-B ligand (RANKL), insulin-like growth factor 1 receptor (IGF1R), epithelial cell adhesion molecule (EpCAM), and carcinoembryonic antigen (CEA).

Figure 13:
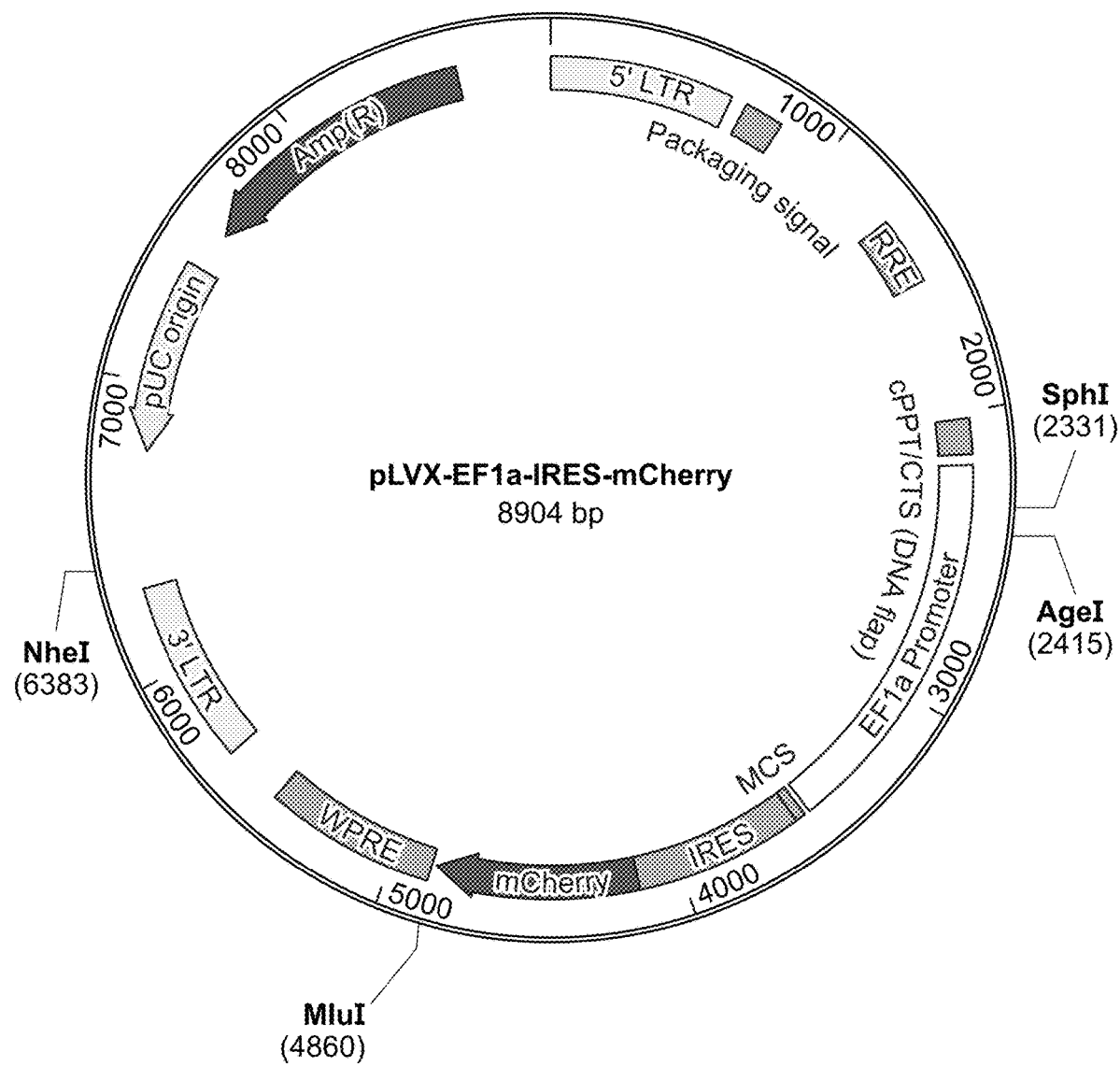
FIG. 13 shows a vector map for the original pLVX-EF1α-IRES-mCherry vector.
Figure 14:
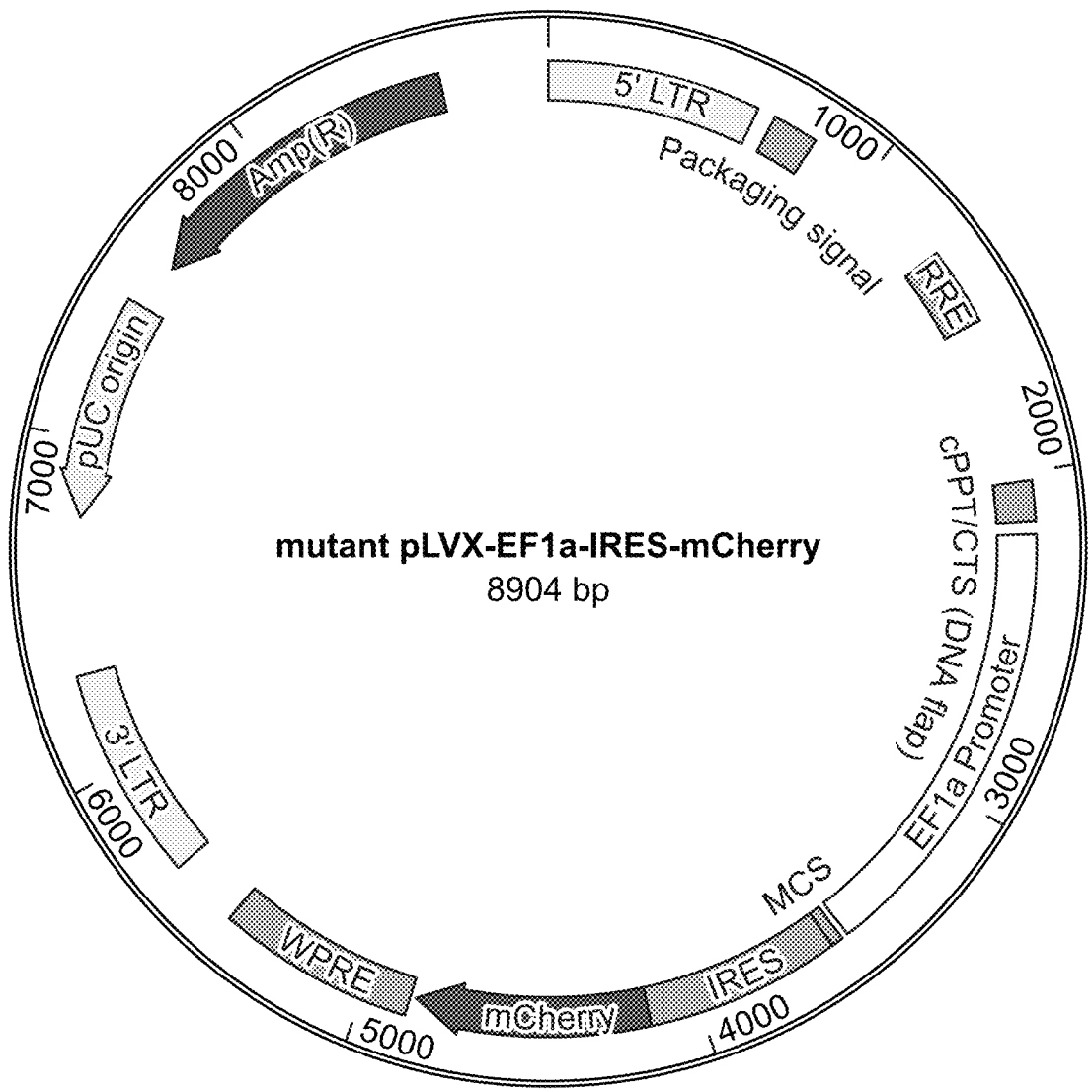
FIG. 14 shows a vector map for the modified pLVX-EF1α-IRES-mCherry vector, in which the excess AgeI, SphI, NheI and MluI restriction sites were eliminated by performing site-directed mutagenesis.

By way of example only, in some embodiments, the original destination cloning vector (for example, pLVX-EF1α-IRES-mCherry) may contain multiple recognition sites for restriction enzymes, such as AgeI (2415), SphI (2331), NheI (8192) and MluI (6669) cutting sites (numbers indicate the location of these cutting sites). See FIG. 13. In some embodiments, the excess restriction enzyme sites for AgeI, SphI, NheI and MluI may be eliminated by performing site-directed mutagenesis (see FIG. 14). In some embodiments, the excess restriction enzyme sites to be removed from the destination cloning vector may be any of those listed in Table 7 or Table 8. In other embodiments, the excess restriction enzyme sites may be substituted with other known restriction enzyme sites that permit T cell receptor paired alpha:beta cloning into linear or circularized vector formats.

Original pLVX-EF1α-IRES Mcherry Vector Sequence

```
                                              (SEQ ID NO: 19)
tggaagggctaattcactcccaaagaagacaagatatccttgatctgtgg atctaccacacacaaggctacttccctgattagcagaactacacaccagg gccaggggtcagatatccactgacctttggatggtgctacaagctagtac cagttgagccagataaggtagaagaggccaataaaggagagaacaccagc ttgttacaccctgtgagcctgcatgggatggatgacccggagagagaagt gttagagtggaggtttgacagccgcctagcatttcatcacgtggcccgag agctgcatccggagtacttcaagaactgctgatatcgagcttgctacaag ggactttccgctggggactttccagggaggcgtggcctgggcgggactgg gggagtggcgagccctcagatcctgcatataagcagctgcttttttgcctgt actgggtctctctggttagaccagatctgagcctgggagctctctggcta actagggaacccactgcttaagcctcaataaagcttgccttgagtgcttc aagtagtgtgtgcccgtctgttgtgtgactctggtaactagagatccctc agaccctttagtcagtgtggaaaatctctagcagtggcgcccgaacagg gacttgaaagcgaaagggaaaccagaggagctctctcgacgcaggactcg gcttgctgaagcgcgcacggcaagaggcgaggggcggcgactggtgagta cgccaaaaattttgactagcggaggctagaaggagagagatgggtgcgag agcgtcagtattaagcgggggagaattagatcgcgatgggaaaaaattcg gttaaggccaggggaaagaaaaaatataaattaaaacatatagtatggg caagcagggagctagaacgattcgcagttaatcctggcctgttagaaaca tcagaaggctgtagacaaatactgggacagctacaaccatcccttcagac aggatcagaagaacttagatcattatataatacagtagcaaccctctatt gtgtgcatcaaaggatagagataaaagacaccaaggaagctttagacaag atagaggaagagcaaaacaaaagtaagaccaccgcacagcaagcggccgg ccgctgatcttcagacctggaggaggagatatgagggacaattggagaag tgaattatataaatataaagtagtaaaaattgaaccattaggagtagcac ccaccaaggcaaagagaagagtggtgcagagagaaaaaagagcagtggga
```

-continued

```
ataggagctttgttccttgggttcttgggagcagcaggaagcactatggg
cgcagcgtcaatgacgctgacggtacaggccagacaattattgtctggta
tagtgcagcagcagaacaatttgctgagggctattgaggcgcaacagcat
ctgttgcaactcacagtctggggcatcaagcagctccaggcaagaatcct
ggctgtggaaagatacctaaaggatcaacagctcctggggatttggggtt
gctctggaaaactcatttgcaccactgctgtgccttggaatgctagttgg
agtaataaatctctggaacagatttggaatcacacgacctggatggagtg
ggacagagaaattaacaattacacaagcttaatacactccttaattgaag
aatcgcaaaaccagcaagaaaagaatgaacaagaattattggaattagat
aaatgggcaagtttgtggaattggtttaacataacaaattggctgtggta
tataaaattattcataatgatagtaggaggcttggtaggtttaagaatag
ttttgctgtacttctatagtgaatagagttaggcagggatattcacca
ttatcgtttcagacccacctcccaaccccgaggggacccgacaggcccga
aggaatagaagaagaaggtggagagagagacagagacagatccattcgat
tagtgaacggatctcgacggtatcgcctttaaaagaaaagggggattgg
ggggtacagtgcaggggaaagaatagtagacataatagcaacagacatac
aaactaaagaattacaaaaacaaattacaaaaattcaaaattttcgggtt
tattacagggacagcagagatccagtttatcgatgagtaattcatacaaa
aggactcgcccctgccttggggaatcccagggaccgtcgttaaactccca
ctaacgtagaacccagagatcgctgcgttccgcccccctcaccgcccgc
tctcgtcatcactgaggtggagaagagcatgcgtgaggctccggtgcccg
tcagtgggcagagcgcacatcgcccacagtccccgagaagttggggggag
gggtcggcaattgaaccggtgcctagagaaggtggcgcggggtaaactgg
gaaagtgatgtcgtgtactggctccgccttttccgagggtgggggaga
accgtatataagtgcagtagtcgccgtgaacgttcttttttcgcaacgggt
ttgccgccagaacacaggtaagtgccgtgtgtggttccgcgggcctggc
ctctttacgggttatggcccttgcgtgccttgaattacttccacgcccct
ggctgcagtacgtgattcttgatcccgagcttcgggttggaagtgggtgg
gagagttcgaggccttgcgcttaaggagccccttcgcctcgtgcttgagt
tgaggcctggcttgggcgctggggccgccgcgtgcgaatctggtggcacc
ttcgcgcctgtctcgctgctttcgataagtctctagccatttaaaatttt
tgatgacctgctgcgacgcttttttctggcaagatagtcttgtaaatgc
gggcaagatctgcacactggtatttcggttttttggggccgcgggcggcg
acggggcccgtgcgtcccagcgcacatgttcggcgaggcggggcctgcga
gcgcggccaccgagaatcggacgggggtagtctcaagctggccggcctgc
tctggtgcctggcctcgcgccgccgtgtatcgccccgccctgggcggcaa
ggctggcccggtcggcaccagttgcgtgagcggaaagatggccgcttccc
ggccctgctgcaggagctcaaaatggaggacgcggcgctcgggagagcg
ggcgggtgagtcacccacacaaaggaaaagggcctttccgtcctcagccg
tcgcttcatgtgactccacggagtaccgggcgccgtccaggcacctcgat
tagttctcgagcttttggagtacgtcgtctttaggttggggggaggggtt
```

-continued

```
ttatgcgatggagtttccccacactgagtgggtggagactgaagttaggc
cagcttggcacttgatgtaattctccttggaatttgcccttttgagttt
ggatcttggttcattctcaagcctcagacagtggttcaaagttttttttct
tccatttcaggtgtcgtgaggatctatttccggtgaattcctcgagacta
gttctagagcggccgcggatcccgcccctctccctcccccccccctaacg
ttactggccgaagccgcttggaataaggccggtgtgcgtttgtctatatg
ttattttccaccatattgccgtcttttggcaatgtgagggcccggaaacc
tggccctgtcttcttgacgagcattcctaggggtcttccctctcgcca
aggaatgcaaggtctgttgaatgtcgtgaaggaagcagttcctctggaa
gcttcttgaagacaaacaacgtctgtagcgaccctttgcaggcagcggaa
ccccccacctggcgacaggtgcctctgcggccaaaagccacgtgtataag
atacacctgcaaaggcggcacaaccccagtgccacgttgtgagttggata
gttgtggaaagagtcaaatggctcacctcaagcgtattcaacaaggggct
gaaggatgcccagaaggtaccccattgtatgggatctgatctggggcctc
ggtgcacatgctttacatgtgtttagtcgaggttaaaaaacgtctaggcc
ccccgaaccacggggacgtggttttcctttgaaaaacacgatgataatat
ggtgagcaagggcgaggaggataacatggccatcatcaaggagttcatgc
gcttcaaggtgcacatggagggctccgtgaacggccacgagttcgagatc
gagggcgagggcgagggccgcccctacgagggcacccagaccgccaagct
gaaggtgaccaagggtggccccctgcccttcgcctgggacatcctgtccc
ctcagttcatgtacggctccaaggcctacgtgaagcaccccgccgacatc
cccgactacttgaagctgtccttccccgagggcttcaagtgggagcgcgt
gatgaacttcgaggacggcggcgtggtgaccgtgacccaggactcctccc
tgcaggacggcgagttcatctacaaggtgaagctgcgcggcaccaacttc
ccctccgacggccccgtaatgcagaagaagaccatgggctgggaggcctc
ctccgagcggatgtaccccgaggacggcgccctgaagggcgagatcaagc
agaggctgaagctgaaggacggcggccactacgacgctgaggtcaagacc
acctacaaggccaagaagcccgtgcagctgcccggcgcctacaacgtcaa
catcaagttggacatcaccctcccacaacgaggactacaccatcgtggaac
agtacgaacgcgccgagggccgccactccaccggcggcatggacgagctg
tacaagtgaacgcgtctggaacaatcaacctctggattacaaaatttgtg
aaagattgactggtattcttaactatgttgctccttttacgctatgtgga
tacgctgctttaatgcctttgtatcatgctattgcttcccgtatggcttt
cattttctcctccttgtataaatcctggttgctgtctctttatgaggagt
tgtggcccgttgtcaggcaacgtggcgtggtgtgcactgtgtttgctgac
gcaaccccactggttggggcattgccaccacctgtcagctcctttccgg
gactttcgctttccccctccctattgccacggcggaactcatcgccgcct
gccttgcccgctgctggacaggggctcggctgttgggcactgacaattcc
gtggtgttgtcggggaagctgacgtcctttccatggctgctcgcctgtgt
tgccacctggattctgcgcgggacgtccttctgctacgtcccttcggccc
```

```
tcaatccagcggaccttccttcccgcggcctgctgccggctctgcggcct
cttccgcgtcttcgccttcgccctcagacgagtcggatctccctttgggc
cgcctccccgcctggaattaattctgcagtcgagacctagaaaaacatgg
agcaatcacaagtagcaatacagcagctaccaatgctgattgtgcctggc
tagaagcacaagaggaggaggtgggttttccagtcacacctcaggta
cctttaagaccaatgacttacaaggcagctgtagatcttagccacttttt
aaaagaaaagagggactggaagggctaattcactcccaacgaagacaag
atatccttgatctgtggatctaccacacacaaggctacttccctgattag
cagaactacacaccagggccaggggtcagatatccactgacctttggatg
gtgctacaagctagtaccagttgagccagataaggtagaagaggccaata
aaggagagaacaccagcttgttacaccctgtgagcctgcatgggatggat
gacccggagagagaagtgttagagtggaggtttgacagccgcctagcatt
tcatcacgtggcccgagagctgcatccggagtacttcaagaactgctgat
atcgagcttgctacaagggactttccgctggggactttccagggaggcgt
ggcctgggcgggactggggagtggcgagccctcagatcctgcatataagc
agctgctttttgcctgtactgggtctctctggttagaccagatctgagcc
tgggagctctctggctaactagggaacccactgcttaagcctcaataaag
cttgccttgagtgcttcaagtagtgtgtgcccgtctgttgtgtgactctg
gtaactagagatccctcagacccttttagtcagtgtggaaaatctctagc
agtagtagttcatgtcatcttattattcagtatttataacttgcaaagaa
atgaatatcagagagtgagaggccttgacattgctagcgtttaccgtcga
cctctagctagagcttggcgtaatcatggtcatagctgtttcctgtgtga
aattgttatccgctcacaattccacacaacatacgagccggaagcataaa
gtgtaaagcctggggtgcctaatgagtgagctaactcacattaattgcgt
tgcgctcactgcccgctttccagtcgggaaacctgtcgtgccagctgcat
taatgaatcggccaacgcgcggggagaggcggtttgcgtattgggcgctc
ttccgcttcctcgctcactgactcgctgcgctcggtcgttcggctgcggc
gagcggtatcagctcactcaaaggcggtaatacggttatccacagaatca
ggggataacgcaggaaagaacatgtgagcaaaaggccagcaaaaggccag
gaaccgtaaaaaggccgcgttgctggcgtttttccataggctccgccccc
ctgacgagcatcacaaaaatcgacgctcaagtcagaggtggcgaaacccg
acaggactataaagataccaggcgtttccccctggaagctccctcgtgcg
ctctcctgttccgaccctgccgcttaccggatacctgtccgcctttctcc
cttcgggaagcgtggcgctttctcatagctcacgctgtaggtatctcagt
tcggtgtaggtcgttcgctccaagctgggctgtgtgcacgaaccccccgt
tcagcccgaccgctgcgccttatccggtaactatcgtcttgagtccaacc
cggtaagacacgacttatcgccactggcagcagccactggtaacaggatt
agcagagcgaggtatgtaggcggtgctacagagttcttgaagtggtggcc
taactacggctacactagaagaacagtatttggtatctgcgctctgctga
agccagttaccttcggaaaaagagttggtagctcttgatccggcaaacaa
accaccgctggtagcggtggtttttttgtttgcaagcagcagattacgcg
```

```
cagaaaaaaggatctcaagaagatcctttgatcttttctacggggtctg
acgctcagtggaacgaaaactcacgttaagggattttggtcatgagatta
tcaaaaaggatcttcacctagatccttttaaattaaaaatgaagttttaa
atcaatctaaagtatatatgagtaaacttggtctgacagttaccaatgct
taatcagtgaggcacctatctcagcgatctgtctatttcgttcatccata
gttgcctgactccccgtcgtgtagataactacgatacgggagggcttacc
atctggccccagtgctgcaatgataccgcgagacccacgctcaccggctc
cagatttatcagcaataaaccagccagccggaagggccgagcgcagaagt
ggtcctgcaactttatccgcctccatccagtctattaattgttgccggga
agctagagtaagtagttcgccagttaatagtttgcgcaacgttgttgcca
ttgctacaggcatcgtggtgtcacgctcgtcgtttggtatggcttcattc
agctccggttcccaacgatcaaggcgagttacatgatcccccatgttgtg
caaaaaagcggttagctccttcggtcctccgatcgttgtcagaagtaagt
tggccgcagtgttatcactcatggttatggcagcactgcataattctctt
actgtcatgccatccgtaagatgcttttctgtgactggtgagtactcaac
caagtcattctgagaatagtgtatgcggcgaccgagttgctcttgcccgg
cgtcaatacgggataataccgcgccacatagcagaactttaaaagtgctc
atcattggaaaacgttcttcggggcgaaaactctcaaggatcttaccgct
gttgagatccagttcgatgtaacccactcgtgcacccaactgatcttcag
catcttttactttcaccagcgtttctgggtgagcaaaaacaggaaggcaa
aatgccgcaaaaaagggaataagggcgacacggaaatgttgaatactcat
actcttcctttttcaatattattgaagcatttatcagggttattgtctca
tgagcggatacatatttgaatgtatttagaaaaataaacaaataggggtt
ccgcgcacatttccccgaaaagtgccacctgacgtcgacggatcgggaga
tcaacttgtttattgcagcttataatggttacaaataaagcaatagcatc
acaaatttcacaaataaagcatttttttcactgcattctagttgtggttt
gtccaaactcatcaatgtatcttatcatgtctggatcaactggataactc
aagctaaccaaaatcatcccaaacttcccaccccataccctattaccact
gccaattacctgtggtttcatttactctaaacctgtgattcctctgaatt
attttcattttaaagaaattgtatttgttaaatatgtactacaaacttag
tagt
```

Modified pLVX-EF1α-IRES Mcherry Vector Sequence (SEQ ID NO: 20)
```
tggaagggctaattcactcccaaagaagacaagatatccttgatctgtgg
atctaccacacacaaggctacttccctgattagcagaactacacaccagg
gccaggggtcagatatccactgacctttggatggtgctacaagctagtac
cagttgagccagataaggtagaagaggccaataaaggagagaacaccagc
ttgttacaccctgtgagcctgcatgggatggatgacccggagagagaagt
gttagagtggaggtttgacagccgcctagcatttcatcacgtggcccgag
agctgcatccggagtacttcaagaactgctgatatcgagcttgctacaag
```

-continued ggactttccgctggggactttccagggaggcgtggcctgggcgggactgg ggagtggcgagccctcagatcctgcatataagcagctgcttttttgcctgt actgggtctctctggttagaccagatctgagcctgggagctctctggcta actagggaacccactgcttaagcctcaataaagcttgccttgagtgcttc aagtagtgtgtgcccgtctgttgtgtgactctggtaactagagatccctc agacccttttagtcagtgtggaaaatctctagcagtggcgcccgaacagg gacttgaaagcgaaagggaaaccagaggagctctctcgacgcaggactcg gcttgctgaagcgcgcacggcaagaggcgaggggcggcgactggtgagta cgccaaaattttgactagcggaggctagaaggagagagatgggtgcgag agcgtcagtattaagcgggggagaattagatcgcgatgggaaaaaattcg gttaaggccagggggaagaaaaaatataaattaaaacatatagtatggg caagcagggagctagaacgattcgcagttaatcctggcctgttagaaaca tcagaaggctgtagacaaatactgggacagctacaaccatcccttcagac aggatcagaagaacttagatcattatataatacagtagcaaccctctatt gtgtgcatcaaaggatagagataaaagacaccaaggaagctttagacaag atagaggaagagcaaaacaaaagtaagaccaccgcacagcaagcggccgg ccgctgatcttcagacctggaggaggagatatgagggacaattggagaag tgaattatataaatataaagtagtaaaaattgaaccattaggagtagcac ccaccaaggcaaagagaagagtggtgcagagagaaaaaagagcagtggga ataggagctttgttccttgggttcttgggagcagcaggaagcactatggg cgcagcgtcaatgacgctgacggtacaggccagacaattattgtctggta tagtgcagcagcagaacaatttgctgagggctattgaggcgcaacagcat ctgttgcaactcacagtctgggcatcaagcagctccaggcaagaatcct ggctgtggaaagatacctaaaggatcaacagctcctggggatttggggtt gctctggaaaactcatttgcaccactgctgtgccttggaatgctagttgg agtaataaatctctggaacagatttggaatcacacgacctggatggagtg ggacagagaaattaacaattacacaagcttaatacactccttaattgaag aatcgcaaaaccagcaagaaaagaatgaacaagaattattggaattagat aaatgggcaagtttgtggaattggtttaacataacaaattggctgtggta tataaaattattcataatgatagtaggaggcttggtaggtttaagaatag tttttgctgtactttctatagtgaatagagttaggcagggatattcacca ttatcgtttcagacccacctcccaaccccgaggggacccgacaggcccga aggaatagaagaagaaggtggagagagagacagagacagatccattcgat tagtgaacggatctcgacggtatcgcctttaaaagaaaggggggattgg ggggtacagtgcaggggaaagaatagtagacataatagcaacagacatac aaactaaagaattacaaaaacaaattacaaaaattcaaaattttcgggtt tattacagggacagcagagatccagtttatcgatgagtaattcatacaaa aggactcgcccctgccttggggaatcccagggaccgtcgttaaactccca ctaacgtagaacccagagatcgctgcgttccgcccctcacccgcccgc tctcgtcatcactgaggtggagaagagcaagcgtgaggctccggtgcccg tcagtgggcagagcgcacatcgcccacagtccccgagaagttgggggag gggtcggcaattgatccggagcctagagaaggtggcgcggggtaaactgg gaaagtgatgtcgtgtactggctccgcctttttcccgagggtgggggaga accgtatataagtgcagtagtcgccgtgaacgttcttttttcgcaacggt ttgccgccagaacacaggtaagtgccgtgtgtggttcccgcgggcctggc ctctttacgggttatggccctgcgtgccttgaattacttccacgcccct ggctgcagtacgtgattcttgatcccgagcttcgggttggaagtgggtgg gagagttcgaggccttgcgcttaaggagcccctccgcctcgtgcttgagt tgaggcctggcttgggcgctggggccgccgcgtgcgaatctggtggcacc ttcgcgcctgtctcgctgctttcgataagtctctagccatttaaaatttt tgatgacctgctgcgacgctttttttctggcaagatagtcttgtaaatgc gggccaagatctgcacactggtatttcggttttttggggccgcgggcggcg acggggcccgtgcgtcccagcgcacatgttcggcgaggcggggcctgcga gcgcggccaccgagaatcggacggggggtagtctcaagctggccggcctgc tctggtgcctggcctcgccgccgtgtatcgccccgccctgggcggcaa ggctggcccggtcggcaccagttgcgtgagcggaaagatggccgcttccc ggccctgctgcagggagctcaaaatggaggacgcggcgctcgggagagcg ggcgggtgagtcacccacacaaaggaaaagggcctttccgtcctcagccg tcgcttcatgtgactccacggagtaccgggcgccgtccaggcacctcgat tagttctcgagcttttggagtacgtcgtctttaggttggggggaggggtt ttatgcgatggagtttccccacactgagtgggtggagactgaagttaggc cagcttggcacttgatgtaattctccttggaatttgcccttttgagttt ggatcttggttcattctcaagcctcagacagtggttcaaagttttttcct tccatttcaggtgtcgtgaggatctatttccggtgaattcctcgagacta gttctagagcggccgcggatcccgcccctctccctccccccccctaacg ttactggccgaagccgcttggaataaggccggtgtgcgtttgtctatatg ttattttccaccatattgccgtcttttggcaatgtgagggcccggaaacc tggccctgtcttcttgacgagcattcctaggggtctttcccctctcgcca aaggaatgcaaggtctgttgaatgtcgtgaaggaagcagttcctctggaa gcttcttgaagacaaacaacgtctgtagcgacccctttgcaggcagcggaa ccccccacctggcgacaggtgcctctgcggccaaaagccacgtgtataag atacacctgcaaaggcggcacaaccccagtgccacgttgtgagttggata gttgtggaaagagtcaaatggctcacctcaagcgtattcaacaaggggct gaaggatgcccagaaggtaccccattgtatgggatctgatctggggcctc ggtgcacatgctttacatgtgtttagtcgaggttaaaaaacgtctaggcc ccccgaaccacggggacgtggttttccttttgaaaaacacgatgataatat ggtgagcaagggcgaggaggataacatggccatcatcaaggagttcatgc gcttcaaggtgcacatggagggctccgtgaacggccacgagttcgagatc gagggcgagggcgagggccgcccctacgagggcacccagaccgccaagct gaaggtgaccaagggtggccccctgcccttcgcctgggacatcctgtccc ctcagttcatgtacggctccaaggcctacgtgaagcaccccgccgacatc

```
cccgactacttgaagctgtccttccccgagggcttcaagtgggagcgcgt gatgaacttcgaggacggcggcgtggtgaccgtgacccaggactcctccc tgcaggacggcgagttcatctacaaggtgaagctgcgcggcaccaacttc ccctccgacggccccgtaatgcagaagaagaccatgggctgggaggcctc ctccgagcggatgtaccccgaggacggcgccctgaagggcgagatcaagc agaggctgaagctgaaggacggcggccactacgacgctgaggtcaagacc acctacaaggccaagaagcccgtgcagctgcccggcgcctacaacgtcaa catcaagttggacatcacctcccacaacgaggactacaccatcgtggaac agtacgaacgcgccgagggccgccactccaccggcggcatggacgagctg tacaagtgaacccgtctggaacaatcaacctctggattacaaaatttgtg aaagattgactggtattcttaactatgttgctccttttacgctatgtgga tacgctgctttaatgcctttgtatcatgctattgcttcccgtatggcttt cattttctcctccttgtataaatcctggttgctgtctctttatgaggagt tgtggcccgttgtcaggcaacgtggcgtggtgtgcactgtgtttgctgac gcaaccccactggttggggcattgccaccacctgtcagctcctttccgg gactttcgctttccccctccctattgccacggcggaactcatcgccgcct gccttgcccgctgctggacaggggctcggctgttgggcactgacaattcc gtggtgttgtcggggaagctgacgtccttccatggctgctcgcctgtgt tgccacctggattctgcgcgggacgtccttctgctacgtcccttcggccc tcaatccagcggaccttccttcccgcggcctgctgccggctctgcggcct cttccgcgtcttcgccttcgccctcagacgagtcggatctcccttttgggc cgcctccccgcctggaattaattctgcagtcgagacctagaaaaacatgg agcaatcacaagtagcaatacagcagctaccaatgctgattgtgcctggc tagaagcacaagaggaggaggaggtgggttttccagtcacacctcaggta cctttaagaccaatgacttacaaggcagctgtagatcttagccacttttt aaaagaaaagagggggactggaagggctaattcactcccaacgaagacaag atatccttgatctgtggatctaccacacacaaggctacttccctgattag cagaactacacaccagggccaggggtcagatatccactgacctttggatg gtgctacaagctagtaccagttgagccagataaggtagaagaggccaata aaggagagaacaccagcttgttacaccctgtgagcctgcatgggatggat gacccggagagagaagtgttagagtggaggtttgacagccgcctagcatt tcatcacgtggcccgagagctgcatccggagtacttcaagaactgctgat atcgagcttgctacaagggactttccgctggggactttccagggaggcgt ggcctgggcgggactggggagtggcgagccctcagatcctgcatataagc agctgctttttgcctgtactgggtctctctggttagaccagatctgagcc tgggagctctctggctaactagggaacccactgcttaagcctcaataaag cttgccttgagtgcttcaagtagtgtgtgcccgtctgttgtgtgactctg gtaactagagatccctcagacccttttagtcagtgtggaaaatctctagc agtagtagttcatgtcatcttattattcagtatttataacttgcaaagaa atgaatatcagagagtgagaggccttgacattgcttgcgtttaccgtcga
```

```
cctctagctagagcttggcgtaatcatggtcatagctgtttcctgtgtga aattgttatccgctcacaattccacacaacatacgagccggaagcataaa gtgtaaagcctggggtgcctaatgagtgagctaactcacattaattgcgt tgcgctcactgcccgctttccagtcgggaaacctgtcgtgccagctgcat taatgaatcggccaacgcgcggggagaggcggtttgcgtattgggcgctc ttccgcttcctcgctcactgactcgctgcgctcggtcgttcggctgcggc gagcggtatcagctcactcaaaggcggtaatacggttatccacagaatca ggggataacgcaggaaagaacatgtgagcaaaaggccagcaaaaggccag gaaccgtaaaaaggccgcgttgctggcgtttttccataggctccgccccc ctgacgagcatcacaaaaatcgacgctcaagtcagaggtggcgaaacccg acaggactataaagataccaggcgtttccccctggaagctccctcgtgcg ctctcctgttccgaccctgccgcttaccggatacctgtccgcctttctcc cttcgggaagcgtggcgctttctcatagctcacgctgtaggtatctcagt tcggtgtaggtcgttcgctccaagctgggctgtgtgcacgaaccccccgt tcagcccgaccgctgcgccttatccggtaactatcgtcttgagtccaacc cggtaagacacgacttatcgccactggcagcagccactggtaacaggatt agcagagcgaggtatgtaggcggtgctacagagttcttgaagtggtggcc taactacggctacactagaagaacagtatttggtatctgcgctctgctga agccagttaccttcggaaaaagagttggtagctcttgatccggcaaacaa accaccgctggtagcggtggtttttttgtttgcaagcagcagattacgcg cagaaaaaaaggatctcaagaagatcctttgatcttttctacggggtctg acgctcagtggaacgaaaactcacgttaagggattttggtcatgagatta tcaaaaaggatcttcacctagatccttttaaattaaaaatgaagttttaa atcaatctaaagtatatatgagtaaacttggtctgacagttaccaatgct taatcagtgaggcacctatctcagcgatctgtctatttcgttcatccata gttgcctgactccccgtcgtgtagataactacgatacgggagggcttacc atctggccccagtgctgcaatgataccgcgagacccacgctcaccggctc cagatttatcagcaataaaccagccagccggaagggccgagcgcagaagt ggtcctgcaactttatccgcctccatccagtctattaattgttgccggga agctagagtaagtagttcgccagttaatagtttgcgcaacgttgttgcca ttgctacaggcatcgtggtgtcacgctcgtcgtttggtatggcattca gctccggttcccaacgatcaaggcgagttacatgatcccccatgttgtgc aaaaaagcggttagctccttcggtcctccgatcgttgtcagaagtaagtt ggccgcagtgttatcactcatggttatggcagcactgcataattctctta ctgtcatgccatccgtaagatgcttttctgtgactggtgagtactcaacc aagtcattctgagaatagtgtatgcggcgaccgagttgctcttgcccgc gtcaatacgggataataccgcgccacatagcagaactttaaaagtgctca tcattggaaaacgttcttcggggcgaaaactctcaaggatcttaccgctg ttgagatccagttcgatgtaacccactcgtgcacccaactgatcttcagc atcttttactttcaccagcgtttctgggtgagcaaaaacaggaaggcaaa atgccgcaaaaaagggaataagggcgacacggaaatgttgaatactcata
```

-continued ctatcattttcaatattattgaagcatttatcagggttattgtctcatga gcggatacatatttgaatgtatttagaaaaataaacaaatagggggttccg cgcacatttccccgaaaagtgccacctgacgtcgacggatcgggagatca acttgtttattgcagcttataatggttacaaataaagcaatagcatcaca aatttcacaaataaagcattttttcactgcattctagttgtggtttgtc caaactcatcaatgtatcttatcatgtctggatcaactggataactcaag -continued ctaaccaaaatcatcccaaacttcccacccataccctattaccactgcc aattacctgtggtttcatttactctaaacctgtgattcctctgaattatt ttcattttaaagaaattgtatttgttaaatatgtactacaaacttagtag
t Non-limiting examples of nucleic acid sequences of vectors of the present disclosure are provided herein in Table 2 and illustrated in FIG. 3-12.

TABLE 2

Exemplary Vector Sequences pLVX-CMV-TCR1-pTert-iCas9 (FIG. 3):

```
tggaagggctaattcactcccaaagaagacaagatatccttgatctgtggatctaccacacacaaggctacttccctgattagcagaact
acacaccagggccagggggtcagatatccactgacctttggatggtgctacaagctagtaccagttgagccagataaggtagaagagg
ccaataaaggagagaaacaccagcttgttcaccctgtgagcctgcatgggatggatgaccggagagagaagtgttagagtggaggt
ttgacagccgcctagcattcatcacgtgggcccgagagctgcatccggagtacttcaagaactgctgatatcgagcttgctacaaggga
ctttccgctggggacttccagggaggcgtggcctgggcgggactggggagtggcgagccctcagatcctgcatataagcagctgct
ttttgcctgtactgggtctctctggttagaccagatctgagcctgggagctctctggctaactagggaacccactgcttaagcctcaataa
agcttgccttgagtgcttcaagtagtgtgtgcccgtctgttgtgtgactgtaactagagatccctcagaccctttagtcagtgtggaa
aatctctagcagtggcgcccgaacagggacttgaaagcgaaagggaaaccagaggagctctctcgacgcaggactcggcttgctga
agcgcgcacggcaagaggcgaggggcggcgactggtgagtacgccaaaaattttgactagcggaggctagaaggagagagatgg
gtgcgagagcgtcagtattaagcggggggagaattagatcgcgatgggaaaaaattcggttaaggccagggggaaagaaaaaatata
aattaaaacatatagtatgggcaagcagggagctagaacgattcgcagttaactcctggcctgttagaaacatcagaaggctgtagacaa
atactgggacagctacaaccatccccttcagacaggatcagaagaacttagatcattatataatacagtagcaaccctctattgtgtgcatc
aaaggatagagataaaagacaccaaggaagctttagcaagatagaggaagagcaaaacaaaagtaagaccaccgcacagcaag
cggccggccgctgatcttcagacctggaggaggagatatgagggacaattggagaagtgaattatataaatataagtagtaaaaattg
aaccattaggagtagcaccctaccaaggcaaaagagaagagtggtgcagagagaaaaagagcagtgggaataggagctttgttcctt
gggttcttgggagcagcaggaagcactatgggcgcagcgtcaatgacgctgacggtacaggccagacaattattgtctggtatagtgc
agcagcagaacaatttgctgagggctattgaggcgcaacagcatctgttgcaactcacagtctggggcatcaagcagctccaggcaa
gaatcctggctgtggaaagatacctaaaggatcaacagctcctggggatttggggttgctctggaaaactcatttgcaccactgctgtgc
cttggaatgctagttggagtaataaatctctggaacagatttggaatcacacgacctggatggagtgggacagagaaattaacaattaca
caagataatacactccttaattgaagaatcgcaaaaccagcaagaaaagaatgaacaagaattattggaattagataaatgggcaagtt
tgtggaattggtttaacataacaaattggctgtggtatataaaattattcataatgatagtaggaggcttggtaggtttaagaatagttttgct
gtactttctatagtgaatagagttaggcagggatattcaccattatcgtttcagacccacctcccaacccgaggggacccgacaggcc
cgaaggaatagaagaagaaggtggagagagagacagagacagatccattcgattagtgaacggatctcgacggtatcgcctttaaaa
gaaaaggggggactggggggtacagtgcagggggaaaagaatagcaataagcatacaaactaaagaattacaaaaa
caaattacaaaaattcaaaattttcgggtttattacagggacagcagagatccagtttatcgataagcttgggagttccgcgttacataactt
acggtaaatggcccgcctggctgaccgcccaacgacccccgcccattgacgtcaataatgacgtatgttcccatagtaacgccaatag
ggactttccattgacgtcaatgggtggagtatttacggtaaactgcccacttggcagtacatcaagtgtatcatatgccaagtacgcccc
tattgacgtcaatgacggtaaatggcccgcctggcattatgcccagtacatgaccttatgggactttcctacttggcagtacatctacgtat
tagtcatcgctattaccatggtgatgcggttttggcagtacatcaatgggcgtggatagcggtttgactcacggggatttccaagtctcca
ccccattgacgtcaatgggagtttgttttggcaccaaaatcaacgggactttccaaaatgtcgtaacaactccgccccattgacgcaaat
gggcggtaggcgtgtacggtgggaggtctatataagcagagctcgtttagtgaaccgtcagatcgcctggagacgccatccacgctgt
tttgacctccatagaagacaccgactctactagaggatctatttccggtgAATTCGCCACCatgagcctcgggctcctgtgctg
tggggcctttttctctcctgtgggcaggaccggtgGAAGCTGACATCTACCAGACCCCAAGATACCTTG
TTATAGGGACAGGAAAGAAGATCACTCTGGAATGTTCTCAAACCATGGGCCATG
ACAAAATGTACTGGTATCAACAAGATCCAGGAATGGAACTACACCTCATCCACT
ATTCCTATGGAGTTAATTCCACAGAGAAGGGAGATCTTTCCTCTGAGTCAACAGT
CTCCAGAATAAGGACGGAGCATTTTCCCCTGACCCTGGAGTCTGCCAGGCCCTCA
CATACCTCTCAGTACCTCTGTGCCAGCAGTCGGACGCCCAACATTCAGTACTTCG
GCGCCGGGACCCGGCTCTCAGTGCTGGAGGACCTGAAAAACGTGTTCCCACCCG
AACTAGTCgtgtttgagccatcagaagcagagatctcccacaccaaaaggccacactggtgtgcctggccacaggcttctac
cccgaccacgtggagctgagctggtgggtgaatgggaaggaggtgcacagtggggtcagcacagaccccgcagcccctcaaggag
cagcccgccctcaatgactccagatactgcctgagcagccgcctgagggtctcggccacctctggcagaaccccgcaaccacttc
cgctgtcaagtccagttctacgggctctcggagaatgacgagtggaccaggataggggcaaacctgtcacccagatcgtcagcgcc
gaggcctggggtagagcagactgtggatcacctccgagtataccagcaagggggtcctgtctgccaccatcctctatgagatcttgct
agggaaggccaccttgtatgccgtgctggtcagtgcctcgtgctgatggccatggtcaagagaaaggattccagaggcGGGAG
CGGAGCCACGAACTTCTCTCTGTTAAAGCAAGCAGGAGACGTGGAAGAAAACCC
CGGTCCTAtgacacgagttagcttgctgtgggcagtcgtggtctccacctgtctcgagtccggcatgGGTCAACAGCT
GAATCAGAGTCCTCAATCTATGTTTATCCAGGAAGGAGAAGATGTCTCCATGAAC
TGCACTTCTTCAAGCATATTTAACACCTGGCTATGGTACAAGCAGGAACCTGGG
AAGGTCCTGTCCTCTTGATAGCCTTATATAAGGCTGGTGAATTGACCTCAAATGG
AAGACTGACTGCTCAGTTTGGTATAACCAGAAAGGACAGCTTCCTGAATATCTCA
GCATCCATACCTAGTGATGTAGGCATCTACTTCTGTGCTGGCACATACCAGAAAG
TTACCTTTGGAACTGGAACAAAGCTCCAAGTCATCCCAAATATCCAGAACCCTGA
CCCTGCCGTGTACCAGCTGAGAGACTCTAAATCCAGTGACAAGTCTGTCTGCctattc
accgatttgatttctcaaacaaatgtgtcacaaagtaaggattctgatgtgtatatcacagacaaaactgtgctagacatgaggtctatgga
cttcaagagcaacagtgctgtggcctggacaacaaatctgactttgcatgcgcaaacgccttcaacaacagcattattccagaagaca
ccttcttcccagcccagaaagttcctgtgatgtcaagctggtcgagaaaagctttgaaacagatacgaacctaaactttcaaaacctgtc
agtgattgggttccgaatcctcctcctgaaagtggccgggtttaatctgctcatgacgctgcggctgtggtccagcTGActcgaggga
tcccgcccctctccctccccccccccctaacgttactggccgaagccgcttggaataaggccggtgtgcgtttgtctatatgttatttccac
catattgccgtcttttggcaatgtgagggcccggaaacctggccctgtcttcttgacgagcattcctaggggtctttcccctctcgccaaa
```

TABLE 2-continued

Exemplary Vector Sequences

```
ggaatgcaaggtctgttgaatgtcgtgaaggaagcagttcctctggaagatcttgaagacaaacaacgtctgtagcgaccctttgcag
gcagcggaaccccccacctggcgacaggtgcctctgcggccaaaagccacgtgtataagatacacctgcaaaggcggcacaaccc
cagtgccacgttgtgagttggatagttgtggaaagagtcaaatggctcacctcaagcgtattcaacaaggggctgaaggatgcccaga
aggtacccattgtatgggatctgatctggggcctcggtgcacatgattacatgtgtttagtcgaggttaaaaaacgtctaggccccccg
aaccacggggacgtggttttcctttgaaaaacacgatgataatatggtgagcaagggcgaggaggataacatggccatcatcaagga
gttcatgcgcttcaaggtgcacatggagggctccgtgaacggccacgagttcgagatcgagggcgagggcgagggccgcccctac
gagggcacccagaccgccaagctgaaggtgaccaagggtggccccctgcccttcgcctgggacatcctgtcccctcagttcatgtac
ggctccaaggcctacgtgaagcaccccgccgacatccccgactacttgaagcgtgtccttccccgagggcttcaagtgggagcgcgtg
atgaacttcgaggacggcggcgtggtgaccgtgacccaggactcctccctgcaggacggcgagttcatctacaaggtgaagcgcg
cggcaccaacttcccctcgacggcccgtaatgcagaagaagaccatgggctgggaggcctcctccgagcggatgtaccccgag
gacgggcgccctgaagggcgagatcaagcagaggctgaagctgaaggacggcggctactacgacgctgaggtcaagaccaacctac
aaggccaagaagcccgtgcagctgcccggcgcctacaacgtcaacatcaagttggacatcacctcccacaacgaggactacaccat
cgtgaacagtacgaacgcgccgagggccgccactccaccggcggcatgacgagctgtacaagtgaacgcgtctgaacaagct
ttttcccgtatcccccaggtgtctgcaggctcaaagagcagcgagaagcgttcagaggaaagcgatcccgtgccaccttcccgtg
cccgggctgtccccgcacgctgcccgctcggggatgcggggagccgccggaccggagcgagccccgggggctcgctgctg
ccccctagcgggggagggacgtaattacatccctgggggctttgggggggctgtcccgtgagctcttactccctatcagtgatag
agaacgtatgaagagtttactccctatcagtgatagagaacgtatgcagactttactccctatcagtgatagagaacgtataaggagttta
ctccctatcagtgatagagaacgtatgaccagtttactccctatcagtgatagagaacgtatctacagtttactccctatcagtgatagaga
acgtatatccagtttactccctatcagtgatagagaacgtatgtgcgaggtaggcgtgtacggtgggcgcctataaaagcagagctcgttt
agtgaaccgtcagatcgcctggagcaattccacaacacttttgtatatacttATGCTCGAGGGAGTGCAGGTGGA
GACTATCTCCCCAGGAGACGGGCGCACCTTCCCCAAGCGCGGCCAGACCTGCGT
GGTGCACTACACCGGGATGCTTGAAGATGGAAAGAAAGTTGATTCCTCCCGGGA
CAGAAACAAGCCCTTTAAGTTTATGCTAGGCAAGCAGGAGGTGATCCGAGGCTG
GGAAGAAGGGGTTGCCCAGATGAGTGTGGGTCAGAGAGCCAAACTGACTATATC
TCCAGATTATGCCTATGGTGCCACTGGGCACCCAGGCATCATCCCACCACATGCC
ACTCTCGTCTTCGATGTGGAGCTTCTAAAACTGGAATCTGGCGGTGGATCCGGAG
TCGACGGATTTGGTGATGTCGGTGCTCTTGAGAGTTTGAGGGGAAATGCAGATTT
GGCTTACATCCTGAGCATGGAGCCCTGTGGCCACTGCCTCATTATCAACAATGTG
AACTTCTGCCGTGAGTCCGGGCTCCGCACCCGCACTGGCTCCAACATCGACTGTG
AGAAGTTGCGGCGTCGCTTCTCCTCGCTGCATTTCATGGTGGAGGTGAAGGGCGA
CCTGACTGCCAAGAAAATGGTGCTGGCTTTGCTGGAGCTGGCGCGGCAGGACCA
CGGTGCTCTGGACTGCTGCGTGGTGGTCATTCTCTCTCACGGCTGTCAGGCCAGC
CACCTGCAGTTCCCAGGGGCTGTCTACGGCACAGATGGATGCCCTGTGTCGGTCG
AGAAGATTGTGAACATCTTCAATGGGACCAGCTGCCCCAGCCTGGGAGGGAAGC
CCAAGCTCTTTTTCATCCAGGCCTGTGGTGGGGAGCAGAAAGACCATGGGTTTGA
GGTGGCCTCCACTTCCCCTGAAGACGAGTCCCCTGGCAGTAACCCCGAGCCAGAT
GCCACCCCGTTCCAGGAAGGTTTGAGGACCTTCGACCAGCTGGACGCCATATCTA
GTTTGCCCACACCCAGTGACATCTTTGTGTCCTACTCTACTTTCCCAGGTTTTGTT
TCCTGGAGGGACCCCAAGAGTGGCTCCTGGTACGTTGAGACCCTGGACGACATCT
TTGAGCAGTGGGCTCACTCTGAAGACCTGCAGTCCCTCCTGCTTAGGGTCGCTAA
TGCTGTTTCGGTGAAAGGGATTTATAAACAGATGCCTGGTTGCTTTAATTTCCTCC
GGAAAAAACTTTTCTTTAAAACATCAGTCGACTATCCGTACGACGTACCAGACTA
CGCACTCGACTAAaagcttttttccccgtatcccccccaggtgtctgcaggctcaaagagcagcgagaagcgttcagaggaa
agcgatcccgtgccaccttcccgtgcccgggctgtccccgcacgctgcccggctcggggatgcgggggagcgccggaccggag
cggagcccgggcggctcgctgctgccccctagcgggggagggacgtaattacatccctgggggctttgggaggggctgtcccc
gtgagctcaatcaacctctggattacaaaatttgtgaaagattgactggtattcttaactatgttgctccttttacgctatgtggatacgctgct
ttaatgcctttgtatcatgctattgcttcccgtatggctttcattttctcctccttgtataaatcctggttgctgtctctttatgaggagttgtggcc
cgttgtcaggcaacgtggcgtggtgtgcactgtgtttgctgacgcaaccccccactggttggggcattgccaccacctgtcagctcctttc
cgggactttcgctttccccctccctattgccacggcggaactcatcgcgcctgccttgcccgctgctgacagggcctcggctgttgg
gcactgacaattccgtggtgtgtgtcggggaagctgacgtcctttccatggctgctgcctgtgttgccacctggattctgcgcgggacgt
ccttctgctacgtccatcggccctcaatccagcggaccttccttcccgcggcctgctgccggctctgcggcctcttccgcgtcttcgcct
tcgccctcagacgagtcggatctcccttttgggcgcctccccgcctggaattaattctgcagtcgagaccctagaaaaacatggagcaat
cacaagtagcaatacagcagctaccaatgctgattgtgcctggctagaagcacaagaggagaggtgggttttccagtcacacct
caggtaccttttaagaccaatgacttacaaggcagctgtagatcttagccacttttttaaaagaaaagaggggactggaagggctaattcac
tcccaacgaagacaagatatccttgatctgtggatctaccacacacaaggctacttccctgattagcagaactacacaccagggccagg
ggtcagatatccactgacctttggatggtgctacaagctagtaccagttgagccagataaggtagaagaggccaataaaggagagaac
accagcttgttacaccctgtgagcctgcatgggatggatgaccgggagagagtgttagagtggaggtttgacagccgcctagcat
ttcatcacgtggcccgagagctgcatccggagtacttcaagaactgctgatatcgagcttgctacaagggactttccgctgggactttc
cagggaggcgtggcctgggcgggactgggagtgcgagcccccagatcctgcatataagcagctgcttttttgcctgtactgggtctc
tctggttagaccagatctgagcctgggagctctctggctaactagggaaccactgcttaagcctcaataaagcttgccttgagtgcttca
agtagtgtgtgcccgtctgttgtgactctggtaactagagatccctcagacccctttagtcagtgtggaaaatctctagcagtagtagttc
atgtcatcttattattcagtatttataacttgcaaagaaatgaatatcagagagtgagaggccttgacattgctagcgtttaccgtcgacctct
agctagagctggcgtaatcatggtcatagctgtttcctgtgtgaaattgttatccgctcacaattccacacaacatacgagccggaagca
taaagtgtaaagcctggggtgcctaatgagtgagctaactcacattaattgcgttgcgctcactgcccgctttccagtcgggaaacctgt
cgtgccagctgcattaatgaatcggccaacgcgcggggagaggcggtttgcgtattgggcgctcttccgcttcctcgctcactgactcg
ctgcgctcggtcgttcggctgcggcgagcggtatcagctcactcaaaggcggtaatacggttatccacagaatcaggggataacgca
ggaaagaacatgtgagcaaaaggccagcaaaaggccaggaaccgtaaaaaggccgcgttgctggcgtttttccataggctccgcc
ccctgacgagcatcacaaaaatcgacgctcaagtcagaggtggcgaaacccgacaggactataaagataccaggcgtttccccctgg
aagctccctcgtgcgctctcctgttccgaccctgccgcttaccggatacctgtccgcctttctccttcgggaagcgtggcgctttctcata
gctcacgctgtaggtatctcagttcggtgtaggtcgttcgctccaagctgggctgtgcacgaaccccccgttcagcccgaccgctgc
gccttatccggtaactatcgtcttgagtccaacccggtaagacacgacttatcgccactggcagcagccactggtaacaggattagcag
agcgaggtatgtaggcggtgctacagagttcttgaagtggtggcctaactacggctacactagaagaacagtatttggtatctgcgctct
gctgaagccagttaccttcggaaaaagagttggtagctcttgatccggcaaacaaaccaccgctggtagcggtggtttttttgtttgcaag
cagcagattacgcgcagaaaaaaaggatctcaagaagatcctttgatcttttctacggggtctgacgctcagtggaacgaaaactcacg
ttaagggattttggtcatgagattatcaaaaaggatcttcacctagatccttttaaattaaaaatgaagttttaaatcaatctaaagtatatatg
agtaaacttggtctgacagttaccaatgcttaatcagtgaggcacctatctcagcgatctgtctatttcgttcatccatagttgcctgactcc
ccgtcgtgtagataactacgatacgggagggcttaccatctggccccagtgctgcaatgataccgcgagacccacgctcaccggctc
cagatttatcagcaataaaccagccagccggaagggccgagcgcagaagtggtcctgcaactttatccgcctccatccagtctattaat
```

TABLE 2-continued

Exemplary Vector Sequences

```
tgttgccgggaagctagagtaagtagttcgccagttaatagtttgcgcaacgttgttgccattgctacaggcatcgtggtgtcacgctcgt
cgtttggtatggcttcattcagctccggttcccaacgatcaaggcgagttacatgatcccccatgttgtgcaaaaaagcggttagctcctt
cggtcctccgatcgttgtcagaagtaagttggccgcagtgttatcactcatggttatggcagcactgcataattctcttactgtcatgccatc
cgtaagatgcttttctgtgactggtgagtactcaaccaagtcattctgagaatagtgtatgcggcgaccgagttgctcttgcccggcgtca
atacgggataataccgcgccacatagcagaactttaaaagtgctcatcattggaaaacgttcttcggggcgaaaactctcaaggatctta
ccgctgttgagatccagttcgatgtaacccactcgtgcacccaactgatcttcagcatcttttactttcaccagcgtttctgggtgagcaaa
aacaggaaggcaaaatgccgcaaaaaagggaataagggcgacacggaaatgttgaatactcatactcttcctttttcaatattattgaag
catttatcagggttattgtctcatgagcggatacatatttgaatgtatttagaaaaataaacaaatagggggttccgcgcacatttccccgaaa
agtgccacctgacgtcgacggatcgggagatcaacttgtttattgcagcttataatggttacaaataaagcaatagcatcacaaatttcac
aaataaagcatttttttcactgcattctagttgtggtttgtccaaactcatcaatgtatcttatcatgtctggatcaactggataactcaagctaa
ccaaaatcatcccaaacttcccaccccatacctattaccactgccaattacctgtggtttcatttactctaaacctgtgattcctctgaattat
tttcattttaaagaaattgtatttgttaaatatgtactacaaaacttagtagt (SEQ ID NO: 21)

pLVX-CMV-TCR2-pTert-iCas9 (FIG. 4):
tggaagggctaattcactcccaaagaagacaagatatccttgatctgtggatctaccacacacaaggctacttccctgattagcagaact
acacaccagggccaggggtcagatatccactgacctttggatggtgctacaagctagtaccagttgagccagataaggtagaagagg
ccaataaaggagagaacaccagcttgttacaccctgtgagcctgcatgggatggatgacccggagagagaagtgttagagtggaggt
ttgacagccgcctagcattttcatcacgtggcccgagagctgcatccggagtacttcaagaactgctgatatcgagctgctacaaggga
ctttccgctggggacttttccaggggaggcgtggcctgggcgggactggggagtggcgagccctcagatcctgcatataagcagctgct
ttttgcctgtactgggtctctctggttagaccagatctgagcctgggagctctctgctaactagggaacccactgcttaagcctcaataa
agcttgccttgagtgcttcaagtagtgtgtgcccgtctgttgtgtgactctggtaactagagatccctcagacccttttagtcagtgtggaa
aatctctagcagtggcgcccgaacagggacttgaaagcgaaagggaaaccagaggagctctctcgacgcaggactcggcttgctga
agcgcgcacggcaagaggcgaggggcggcgactggtgagtacgccaaaattttgactagcggaggctagaaggagagagatgg
gtgcgagagcgtcagtattaagcgggggagaattagatcgcgatgggaaaaaattcggttaaggccagggggaaagaaaaaatata
aattaaaacatatagtatgggcaagcagggagctagaacgattcgcagttaatcctggcctgttagaaacatcagaaggctgtagacaa
atactgggacagctacaaccatcccttcagacaggatcagaagaacttagatcattatataatacagtagcaaccctctattgtgtgcatc
aaaggatagagatataaaagacaccaaggaagctttagacaagatagaggaagagcaaaacaaaagtaagaccaccgcacagcaag
cggccggccgctgatcttcagacctggaggaggagatatgagggacaattggagaagtgaattatataaatataaagtagtaaaattg
aaccattaggagtagcacccaccaaggcaaagagaagagtggtgcagagagaaaaaagagcagtgggaataggagctttgttccttt
gggttcttgggagcagcaggaagcactatgggcgcagcgtcaatgacgctgacggtacaggccagacaattattgtctggtatagtgc
agcagcagaacaatttgctgagggctattgaggcgcaacagcatctgttgcaactcacagtctggggcatcaagcagctccaggcaa
gaatcctggctgtggaaagatacctaaaggatcaacagctcctggggatttggggttgctctggaaaactcatttgcaccactgctgtgc
cttggaatgctagttggagtaataaatctctggaacagatttggaatcacacgacctggatggagtgggacagagaaattaacaattaca
caagcttaatacactccttaattgaagaatcgcaaaaccagcaagaaaagaatgaacaagaattattggaattagataaatgggcaagtt
tgtggaattggtttaacataacaaattggctgtggtatataaaattattcataatgatagtaggaggcttggtaggtttaagaatagtttttgct
gtactttctatagtgaatagagttaggcagggatattcaccattatcgtttcagacccacctcccaaccccgaggggacccgacaggcc
cgaaggaatagaagaagaaggtggagagagagacagagacagatccattcgattagtgaacggatctcgacggtatcgccttaaaa
gaaaaggggggattggggggtacagtgcaggggaaagaatagtagacataatagcaacagacatacaaactaaagaattacaaaaa
caaattacaaaaattcaaaattttcgggtttattacagggacagcagagatccagtttatcgataagcttgggagttccgcgttacataactt
acggtaaatgcccgcctggctgaccgcccaacgaccccgccatgcccattgacgtcaataatgacgtatgttcccatagtaacgccaatag
ggactttccattgacgtcaatgggtggagtatttacggtaaactgcccacttggcagtacatcaagtgtatcatatgccaagtacgcccc
tattgacgtcaatgacggtaaatggcccgcctggcattatgcccagtacatgaccttatgggactttcctacttggcagtacatctacgtat
tagtcatcgctattaccatggtgatgcggttttggcagtacatcaatgggcgtggatagcggtttgactcacggggatttccaagtctcca
ccccattgacgtcaatgggagtttgttttggcaccaaaatcaacgggactttccaaaatgtcgtaacaactccgccccattgacgcaaat
gggcggtaggcgtgtacggtgggaggtctatataagcagagctcgtttagtgaaccgtcagatcgcctggagacgccatccacgctgt
tttgacctccatagaagacaccgactctactagaggatctatttccggtgAATTCGCCACCatgggaccaggctcctatctg
ggcactgattgtctcctcggaaCCGGTCCGGTTGAAGCTGACATCTACCAGACCCCAAGATAC
CTTGTTATAGGGACAGGAAAGAAGATCACTCTGGAATGTTCTCAAACCATGGGC
CATGACAAAATGTACTGGTATCAACAAGATCCAGGAATGGAACTACACCTCATC
CACTATTCCTATGGAGTTAATTCCACAGAGAAGGGAGATCTTTCCTCTGAGTCAA
CAGTCTCCAGAATAAGGACGGAGCATTTTCCCCTGACCCTGGAGTCTGCCAGGCC
CTCACATACCTCTCAGTACCTCTGTGCCAGCAGTCGGACGCCCAACATTCAGTAC
TTCGGCGCCGGGACCCGGCTCTCAGTGCTGGAGGACCTGAAAAACGTGTTCCCAC
CCGAgGCGGCCGCgtttgagccatcagaagcagagatctcccacacccaaaaggccacactggtgtgcctggccacagg
cttctaccccgaccacgtggagctgagctggtgggtgaatgggaaggaggtgcacagtggggtcagcacagacccgcagcccctc
aaggagcagcccgcccctcaatgactccagatactgcctgagcagccgcctgagggtctcggccacctctggcagaaccccgcaa
ccacttccgctgtcaagtccagttctacgggctctcggagaatgaccagtagcacccagatagggccaaacctgtctgccaccatcgtc
agcgccgaggcctggggtagagcagactgtggcttcacctccgagtcttaccagcaagggctcctgtctgccaccatcctctatgaga
tcttgctaggtgaaggccaccttgtatgccgtgctggtcagtgccctcgtgctgatggccatggtcaagagaaaggattccagaggcG
GGAGCGGAGCCACGAACTTCTCTCTGTTAAAGCAAGCAGGAGACGTGGAAGAAA
ACCCCGGTCCTatgaactcctctctgacttttctaattctgatcttaatgtttggaggaACTAGTGGTCAACAGC
TGAATCAGAGTCCTCAATCTATGTTTATCCAGGAAGGAGAAGATGTCTCCATGAA
CTGCACTTCTTCAAGCATATTTAACACCTGGCTATGGTACAAGCAGGAACCTGGG
GAAGGTCCTGTCCTCTTGATAGCCTTATATAAGGCTGGTGAATTGACCTCAAATG
GAAGACTGACTGCTCAGTTTGGTATAACCAGAAAGGACAGCTTCCTGAATATCTC
AGCATCCATACCTAGTGATGTAGGCATCTACTTCTGTGCTGGCACATACCAGAAA
GTTACCTTTGGAACTGGAACAAAGCTCCAAGTCATCCCAAATATCCAGAACCCTG
ACCCTGCCGTGTACCAGCTGAGAGACTCTAAATCCAGTGACAAGTCTGCATGCctat
tcaccgattttgattctcaaacaaatgtgtcacaaagtaaggattctgatgtgtatatcacagacaaaactgtgctagacatgaggtctatg
gacttcaagagcaacagtgctgtggcctggagcaacaaatctgactttgcatgtgcaaacgccttcaacaacagcattattccagaaga
caccttcttcccagcccagaaagttcctgtgatgtcaagctggtcgagaaaagctttgaaacagatacgaacctaaactttcaaaacct
gtcagtgattgggttccgaatcctcctcctgaaagtggccgggtttaatctgctcatgacgctgcggctgtggtccagcTGActcgag
ggatccgcccctctccctcccccccccctaacgttactggccgaagccgcttggaataaggccggtgtgcgtttgtctatatgttatttc
cacatattgccgtcttttggcaatgtgagggcccggaaacctggccctgtcttcttgacgagcattcctagggggtctttcccctctcgcc
aaaggaatgcaaggtctgttgaatgtcgtgaaggaagcagttcctctggaagcttcttgaagacaaacaactgtctgagcgaccctttgc
aggcagcggaacccccacctggcgacaggtgcctctgcggccaaaagccacgtgtataagatacacctgcaaaggcggcacaac
cccagtgccacgttgtgagttggatagttgtggaaagagtcaaatggctcacctcaagcgtattcaacaaggggctgaaggatgccca
gaaggtaccccattgtatgggatctgatctggggcctcggtgcacatgctttacatgtgtttagtcgaggttaaaaaacgtctaggccccc
```

TABLE 2-continued

Exemplary Vector Sequences

```
cgaaccacggggacgtggttttcctttgaaaaacacgatgataatatggtgagcaagggcgaggaggataacatggccatcatcaag
gagttcatgcgcttcaaggtgcacatggagggctccgtgaacggccacgagttcgagatcgagggcgagggcgagggccgcccct
acgagggcacccagaccgccaagctgaaggtgaccaagggtggccccctgcccttcgcctgggacatcctgtcccctcagttcatgt
acggctccaaggcctacgtgaagcaccccgccgacatccccgactacttgaagctgtccttccccgagggcttcaagtgggagcgcg
tgatgaacttcgaggacggcggcgtggtgaccgtgacccaggactcctccctgcaggacggcgagttcatctacaaggtgaagctgc
gcggcaccaacttccctcgacggccccgtaatgcagaagaagaccatgggctgggaggcctcctccgagcggatgtaccccga
ggacggcgccctgaagggcgagatcaagcagaggctgaagctgaaggacggcggccactacgacgctgaggtcaagaccaccta
caaggccaagaagcccgtgcagctgcccggcgcctacaacgtcaacatcaagttggacatcacctcccacaacgaggactacacca
tcgtggaacagtacgaacgcgccgagggccgccactccaccggcggcatggacgagctgtacaagtgaacgcgtctggaacaagc
ttttcccgtatcccccaggtgtctgcaggctcaaagagcagcgagaagcgttcagaggaaagcgatcccgtgccaccttcccgt
gcccgggctgtccccgcacgctgccggctcggggatgcgggggagcggccggaccggagcggagcccgggcggctcgctgct
gcccctagcggggagggacgtaattacatccctgggggctttgggggggggctgtccccgtgagctcttactccctatcagtgata
gagaacgtatgaagagtttactccctatcagtgatagagaacgtatgcagactttactccctatcagtgatagagaacgtataaggagttt
actccctatcagtgatagagaacgtatgaccagtttactccctatcagtgatagagaacgtatctacagtttactccctatcagtgatagag
aacgtatatccagtttactccctatcagtgatagagaacgtatggcgagtgtggcgtacgggtgggcgcctataaaagcagagctcgtt
tagtgaaccgtcagatcgcctggagcaattccacaacacttttgtcttatacttATGCTCGAGGGAGTGCAGGTGGA
GACTATCTCCCCAGGAGACGGGCGCACCTTCCCCAAGCGCGGCCAGACCTGCGT
GGTGCACTACACCGGGATGCTTGAAGATGGAAAGAAAGTTGATTCCTCCCGGGA
CAGAAACAAGCCCTTTAAGTTTATGCTAGGCAAGCAGGAGGTGATCCGAGGCTG
GGAAGAAGGGGTTGCCCAGATGAGTGTGGGTCAGAGAGCCAAACTGACTATATC
TCCAGATTATGCCTATGGTGCCACTGGGCACCCAGGCATCATCCCACCACATGCC
ACTCTCGTCTTCGATGTGGAGCTTCTAAAACTGGAATCTGGCGGTGGATCCGGAG
TCGACGGATTTGGTGATGTCGGTGCTCTTGAGAGTTTGAGGGGAAATGCAGATTT
GGCTTACATCCTGAGCATGGAGCCCTGTGGCCACTGCCTCATTATCAACAATGTG
AACTTCTGCCGTGAGTCCGGGCTCCGCACCCGCACTGGCTCCAACATCGACTGTG
AGAAGTTGCGGCGTCGCTTCTCCTCGCTGCATTTCATGGTGGAGGTGAAGGGCGA
CCTGACTGCCAAGAAAATGGTGCTGGCTTTGCTGGAGCTGGCGCGGCAGGACCA
CGGTGCTCTGGACTGCTGCGTGGTGGTCATTCTCTCTCACGGCTGTCAGGCCAGC
CACCTGCAGTTCCCAGGGGCTGTCTACGGCACAGATGGATGCCCTGTGTCGGTCG
AGAAGATTGTGAACATCTTCAATGGGACCAGCTGCCCCAGCCTGGGAGGGAAGC
CCAAGCTCTTTTTCATCCAGGCCTGTGGTGGGGAGCAGAAAGACCATGGTTTGA
GGTGGCCTCCACTTCCCCTGAAGACGAGTCCCCTGGCAGTAACCCCGAGCCAGAT
GCCACCCCGTTCCAGGAAGGTTTGAGGACCTTCGACCAGCTGGACGCCATATCTA
GTTTGCCCACACCCAGTGACATCTTTGTGTCCTACTCTACTTTCCCAGGTTTTGTT
TCCTGGAGGGACCCCAAGAGTGGCTCCTGGTACGTTGAGACCCTGGACGACATCT
TTGAGCAGTGGGCTCACTCTGAAGACCTGCAGTCCCTCCTGCTTAGGGTCGCTAA
TGCTGTTTCGGTGAAAGGGATTTATAAACAGATGCCTGGTTGCTTTAATTTCCTCC
GGAAAAAACTTTTCTTTAAAACATCAGTCGACTATCCGTACGACGTACCAGACTA
CGCACTCGACTAAaagcttttttccccgtatcccccaggtgtctgcaggctcaaagagcagcgagaagcgttcagaggaa
agcgatcccgtgccaccttcccgtgcccgggctgtccccgcacgctgccggctcggggatgcgggggagcggccggag
cggagcccgggcggctcgctgctgccccctagcggggagggacgtaattacatccctgggggctttgggaggggctgtcccc
gtgagctcaatcaacctctggattacaaaatttgtgaaagattgactggtattcttaactatgttgctccttttacgctatgtggatacgctgct
ttaatgcattgtatcatgctattgatcccgtatggctttcattttctcctccttgtataaatcctggttgctgtctctttatgaggagttgtggcc
cgttgtcaggcaacgtggcgtggtgtgcactgtgtttgctgacgcaaccccactggttgggcattgccaccacctgtcagctcctttc
cgggactttcgctttccccctcccctattgccacggcggaactcatcgccgcctgccttgcccgctgctggacagggggctcggctgttgg
gcactgacaattccgtggtgttgtcggggaagctgacgtcctttccatggctgctcgcctgtgttgccacctggattctgcgcgggacgt
ccttctgctacgtccatcggccctcaatccagcggaccttccttcccgcggcctgctgccggctctgcggcctcttccgcgtcttcgcct
tcgccctcagacggctcggatctccctttgggccgcctccccgcctggaattaattctgcagtcgagacctagaaaaacatggagcaat
cacaagtagcaatacagcagctaccaatgctgattgtgcctggctagaagcacaagaggaggaggtgggttttccagtcacacct
caggtacctttaagaccaatgacttacaaggcagctgtagatcttagccacttttttaaaagaaaagaggggactggaagggctaattcac
tcccaacgaagacaagatatccttgatctgtggatctaccacacacaaggctacttccctgattagcagaactacacaccagggccagg
ggtcagatatccactgacctttggatggtgctacaagctagtaccagttgagccagataaggtagaagaggccaataaaggagagaac
accagcttgttacaccctgtgagcctgcatgggatggatgacccggagagagaagtgttagagtggaggtttgacagccgcctagcat
ttcatcacgtggcccgagagctgcatccggagtacttcaagaactgctgatatcgagcttgctacaagggactttccgctggggactttc
cagggaggcgtggcctgggcgggactggggagtggcgagcccccagatcctgcatataagcagctgcttttttgcctgtactgggtctc
tctggttagaccagatctgagcctgggagctctctggctaactagggaacccactgcttaagcctcaataaagcttgccttgagtgcttca
agtagtgtgtgcccgtctgttgtgtgactctggtaactagagatccctcagaccctttagtcagtgtggaaaatctctagcagtagtagttc
atgtcatcttattattcagtatttataacttgcaaagaaatgaatatcagagagtgagaggccttgacattgctagcgtttaccgtcgacctct
agctagagcttggcgtaatcatggtcatagctgtttcctgtgtgaaattgttatccgctcacaattccacacaacatacgagccggaagca
taaagtgtaaagcctggggtgcctaatgagtgagctaactcacattaattgcgttgcgctcactgcccgctttccagtcgggaaacctgt
cgtgccagctgcattaatgaatcggccaacgcggggagaggcggtttgcgtattgggcgctcttccgcttcctcgctcactgactcg
ctgcgctcggtcgttcggctgcggcgagcggtatcagctcactcaaaggcggtaatacggttatccacagaatcaggggataacgc
aggaaagaacatgtgagcaaaaggccagcaaaaggccaggaaccgtaaaaaggccgcgttgctggcgtttttccataggctccgcc
ccctgacgagcatcacaaaaatcgacgctcaagtcagaggtggcgaaacccgacaggactataaagataccaggcgtttccctgg
aagctccctcgtgcgctctcctgttccgaccctgccgcttaccggatacctgtccgcctttctcccttcgggaagcgtggcgctttctcata
gctcacgctgtaggtatctcagttcggtgtaggtcgttcgctccaagctgggctgtgtgcacgaaccccccgttcagcccgaccgctgc
gccttatccggtaactatcgtcttgagtccaacccggtaagacacgacttatcgccactggcagcagccactggtaacaggattagcag
agcgaggtatgtaggcggtgctacagagttcttgaagtggtggcctaactacggctacactagaagaacagtatttggtatctgcgctct
gctgaagccagttaccttcggaaaaagagttggtagctcttgatccggcaaacaaaccaccgctggtagcggtggtttttttgtttgcaag
cagcagattacgcgcagaaaaaaaggatctcaagaagatcctttgatcttttctacggggtctgacgctcagtggaacgaaaactcacg
ttaagggattttggtcatgagattatcaaaaaggatcttcacctagatccttttaaattaaaaatgaagttttaaatcaatctaaagtatatatg
agtaaacttggtctgacagttaccaatgcttaatcagtgaggcacctatctcagcgatctgtctatttcgttcatccatagttgcctgactcc
ccgtcgtgtagataactacgatacgggagggcttaccatctggccccagtgctgcaatgataccgcgagacccacgctcaccggctc
cagatttatcagcaataaaccagccagccggaagggccgagcgcagaagtggtcctgcaactttatccgcctccatccagtctattaat
tgttgccgggaagctagagtaagtagttcgccagttaatagtttgcgcaacgttgttgccattgctacaggcatcgtggtgtcacgctcgt
cgtttggtatggcttcattcagctccggttcccaacgatcaaggcgagttacatgatccccatgttgtgcaaaaaagcggttagctcctt
cggtcctccgatcgttgtcagaagtaagttggccgcagtgttatcactcatggttatggcagcactgcataattctcttactgtcatgccatc
cgtaagatgcttttctgtgactggtgagtactcaaccaagtcattctgagaatagtgtatgcggcgaccgagttgctcttgcccggcgtca
```

TABLE 2-continued

Exemplary Vector Sequences atacgggataataccgcgccacatagcagaactttaaaagtgctcatcattggaaaacgttcttcggggcgaaaactctcaaggatctta
ccgctgttgagatccagttcgatgtaacccactcgtgcacccaactgatcttcagcatcttttactttcaccagcgtttctgggtgagcaaa
aacaggaaggcaaaatgccgcaaaaaagggaataagggcgacacggaaatgttgaatactcatactatcattttcaatattattgaag
catttatcagggttattgtctcatgagcggatacatatttgaatgtatttagaaaaataaacaaatagggggttccgcgcacatttccccgaaa
agtgccacctgacgtcgacggatcgggagatcaacttgtttattgcagcttataatggttacaaataaagcaatagcatcacaaatttcac
aaatttaaagcatttttttttcactgcattctagttgtggtttgtccaaactcatcaatgtatcttatcatgtctggatcaactggataactcaagctaa
ccaaaatcatcccaaacttcccaccccatacccctattaccactgccaattacctgtggttttcatttactctaaacctgtgattcctctgaattat
ttttcattttaaagaaattgtatttgttaaatatgtactacaaacttagtagt (SEQ ID NO: 22)

pLVX-CMV-TCR3-pTert-iCas9 (FIG. 5):
tggaagggctaattcactcccaaagaagacaagatatccttgatctgtggatctaccacacacaaggctacttcctgattagcagaact
acacaccagggccaggggtcagatatccactgacctttggatggtgctacaagctagtaccagttgagccagataaggtagaagagg
ccaataaaggagagaacaccagcttgttacaccctgtgagcctgcatgggatggatgacccggagagagaagtgttagagtggaggt
ttgacagccgcctagcatttcatcacgtggcccgagagctgcatccggagtacttcaagaactgctgatatcgagcttgctacaaggga
ctttccgctggggacttttccagggaggcgtggcctgggcgggactggggagtggcgagccctcagatcctgcatataagcagctgct
ttttgcctgtactgggtctctctggttagaccagatctgagcctgggagctctctggctaactagggaacccactgcttaagcctcaataa
agcttgccttgagtgatcaagtagtgtgtgcccgtctgttgtgtgactctggtaactagagatccctcagaccctttttagtcagtgtggaa
aatctctagcagtggcgcccgaacagggacttgaaagcgaaagggaaaccagaggagctctctcgacgcaggactcggcttgctga
agcgcgcacggcaagaggcgaggggcggcgactggtgagtacgccaaaaatttttgactagcggaggctagaaggagagatgg
gtgcgagagcgtcagtattaagcggggagaattagatcgcgatgggaaaaaattcggttaaggccagggggaaagaaaaaatata
aattaaaacatatagtatgggcaagcagggagctagaacgattcgcagttaatcctggcctgttagaaacatcagaaggctgtagacaa
atactgggacagctacaaccatcccttcagacaggatcagaagaacttagatcattatataatacagtagcaaccctctattgtgtgcatc
aaaggatagagataaaagacaccaaggaagcttttagacaagatagaggaagagcaaaacaaaagtaagaccaccgcacagcaag
cggccggccgctgatcttcagacctggaggaggatatgagggacaattggagaagtgaattatataaatataagtagtaaaaattg
aaccattaggagtagcaccaccaaggcaaagagaagagtggtgcagagagaaaaaagagcagtgggaataggagctttgttccttt
gggttcttgggagcagcaggaagcactatgggcgcagcgtcaatgacgctgacggtacaggccagacaattattgtctggtatagtgc
agcagcagaacaatttgctgagggctattgaggcgcaacagcatctgttgcaactcacagtctggggcatcaagcagctccaggcaa
gaatcctggctgtggaaagatacctaaaggatcaacagctcctggggatttggggttgctctggaaaactcatttgcaccactgctgtgc
cttggaatgctagttggagtaataaatctctggaacagatttggaatcacacgacctggatggagtgggacagagaaattaacaattaca
caagataatacactccttaattgaagaatcgcaaaaccagcaagaaaagaatgaacaagaattattggaattagataaatgggcaagtt
tgtggaattggtttaacataacaaattggctgtggtatataaaattattcataatgatagtaggaggcttggtaggtttaagaatagttttgct
gtactttctatagtgaatagagttaggcagggatattcaccattatcgtttcagacccacctcccaacccgaggggacccgacaggcc
cgaaggaatagaagaagaaggtggagagagagacagagacagatccattcgattagtgaacggatctcgacggtatcgccttaaa
gaaaagggggggattggggggtacagtgcaggggaaagaatagtagacataatagcaacagacatacaaactaaagaattacaaaa
caaattacaaaaattcaaaattttcgggtttattacagggacagcagagatccagtttatcgataagcttgggagttccgcgttacataactt
acggtaaatggcccgcctggctgaccgcccaacgacccccgcccattgacgtcaataatgacgtatgttcccatagtaacgccaatag
ggactttccattgacgtcaatgggtggagtatttacggtaaactgcccacttggcagtacatcaagtgtatcatatgccaagtacgcccc
tattgacgtcaatgacggtaaatggcccgcctggcattatgcccagtacatgaccttatgggactttcctacttggcagtacatctacgtat
tagtcatcgctattaccatggtgatgcggttttggcagtacatcaatgggcgtggatagcggtttgactcacggggatttccaagtctcca
ccccattgacgtcaatgggagtttgttttggcaccaaaatcaacgggactttccaaaatgtcgtaacaactccgccccattgacgcaaat
gggcggtaggcgtgtacggtgggaggtctatataagcagagctcgtttagtgaaccgtcagatcgcctggagacgccatccacgctgt
tttgacctccatagaagacaccgactctactagaggatctatttccggtgAATTCGCCACCatgggcacaaggttgttcttctctat
gtggcccttttgtctcctgtggaccggtcacatgGAAGCTGACATCTACCAGACCCCAAGATACCTTGT
TATAGGGACAGGAAAGAAGATCACTCTCTGGAATGTTCTCAAACCATGGGCCATGA
CAAAATGTACTGGTATCAACAAGATCCAGGAATGGAACTACACCTCATCCACTAT
TCCTATGGAGTTAATTCCACAGAGAAGGGAGATCTTTCCTCTGAGTCAACAGTCT
CCAGAATAAGGACGGAGCATTTTCCCCTGACCCTGGAGTCTGCCAGGCCCTCACA
TACCTCTCAGTACCTCTGTGCCAGCAGTCGGACGCCCAACATTCAGTACTTCGGC
GCCGGGACCCGGCTCTCAGTGCTGgaggacctgaaaaacgtgttcccacccgaggtcgctgtgtttgagccatc
agaagcagagatctcccacacccaaaaggccacACTAGTgtgcctggccacaggcttctaccccgaccacgtggagctgagct
ggtgggtgaatgggaaggaggtgcacagtgggtcagcacagacccgcagccccccaaggagcagcccgccctcaatgactcca
gatactgcctgagcagccgcctgagggtctcggccaccttctggcagaaccccgcaacccacttccgtgtcaagtccagttctacgg
gctctcggagaatgacgagtggacccaggatagggccaaacctgtcacccagatcgtcagcgccgaggcctggggtagagcagac
tgtggcttcacctccgagtcttaccagcaagggtcctgtctgtctgccaccatcctctatgagatcttgctagggaaggccaccttgtatgcc
gtgctggtcagtgccctcgtgctgatggccatggtcaagagaaaggattccagaggcGGGAGCGGAGCCACGAAC
TTCTCTCTGTTAAAGCAAGCAGGAGACGTGGAAGAAAACCCCGGTCCTATggcaggca
ttcgagctttatttatgtacttgtggctgcagctggactgggtctcgagaGGTCAACAGCTGAATCAGAGTCCTC
AATCTATGTTTATCCAGGAAGGAGAAGATGTCTCCATGAACTGCACTTCTTCAAG
CATATTTAACACCTGGCTATGGTACAAGCAGGAACCTGGGGAAGGTCCTGTCCTC
TTGATAGCCTTATATAAGGCTGGTGAATTGACCTCAAATGGAAGACTGACTGCTC
AGTTTGGTATAACCAGAAGGACAGCTTCCTGAATATCTCAGCATCCATACCTAG
TGATGTAGGCATCTACTTCTGTGCTGGCACATACCAGAAAGTTACCTTTGGAACT
GGAACAAAGCTCCAAGTCATCCCAaatatccagaaccctgaccctgccgtgtaccagctgagagactctaaatc
cagtgacaagtctgtctgcctattcaccgattttgattctcaaacaaatgtgtcacaaagtaaggattctgatgtgtatatcacagacaaaa
ctgtgctagacatgaggtctatggactcaagaagcaacgtGCGGCCGCctggagcaacatctgactttgcatgtgcaaacgc
cttcaacaacagcattattccagaagacaccttcttccccagcccagaaagttcctgtgatgtcaagctggtcgagaaaagctttgaaac
agatacgaacctaaactttcaaaacctgtcagtgattgggttccgaatcctcctcctgaaagtggcgggtttaatctgctcatgacgctg
cggctgtggtccagcTGActcgagggatcccgcccctctccctccccccccctaacgttactggccgaagccgcttggaataagg
ccggtgtgcgtttgtctatatgttattttccaccatattgccgtcttttggcaatgtgagggcccggaaacctggccctgtcttcttgacgag
cattcctaggggtattccctctcgccaaaggaatgcaaggtctgttgaatgtcgtgaaggaagcagttcctctggaagcttcttgaaga
caaacaacgtctgtagcgaccctttgcaggcagcggaaccccccacctggcgacaggtgcctctgcggccaaaagccacgtgtata
agatacacctgcaaaggcggcacaaccccagtgccacgttgtgagttggatagttgtggaaagagtcaaatggctcacctcaagcgta
ttcaacaaggggctgaaggatgcccagaaggtaccccattgtatgggatctgatctggggcctcggtgcacatgctttacatgtgtttag
tcgaggttaaaaaacgtctaggccccccgaaccacgggacgtggttttcctttgaaaaacacgatgataatatggccacaaggcgg
aggaggataacatggccatcatcaaggagttcatgcgcttcaaggtgcacatggagggctccgtgaacggccacgagttcgagatcg
agggcgagggcgagggccgcccctacgagggcacccagaccgccaagctgaaggtgaccaaggggtggcccctgcccttcgcct
gggacatcctgtcccctcagttcatgtacggctccaaggcctacgtgaagcaccccgccgacatccccgactacttgaagctgtccttc
cccgagggcttcaagtgggagcgcgtgatgaacttcgaggacggcggcgtggtgaccgtgacccaggactcctccctgcaggacg TABLE 2-continued Exemplary Vector Sequences

```
gcgagttcatctacaaggtgaagctgcgcggcaccaacttccctccgacggccccgtaatgcagaagaagaccatgggctgggag
gcctcctccgagcggatgtaccccgaggacggcgccctgaagggcgagatcaagcagaggctgaagctgaaggacggcggcca
ctacgacgctgaggtcaagaccacctacaaggccaagaagcccgtgcagctgcccggcgcctacaacgtcaacatcaagttggaca
tcacctcccacaacgaggactacaccatcgtggaacagtacgaacgcgccgagggccgccactccaccggcggcatggacgagct
gtacaagtgaacgcgtctggaacaagattttccccgtatcccccaggtgtctgcaggctcaaagagcagcgagaagcgttcagagg
aaagcgatcccgtgccaccttccccgtgcccgggctgtccccgcacgctgccggctcggggatgcggggggagcgccggaccgg
agcggagcccggggcggctcgctgctgcccccctagcggggagggacgtaattacatccctgggggcttgggggggctgtcc
ccgtgagctcttactccctatcagtgatagagaacgtatgaagagtttactccctatcagtgatagagaacgtatgcagactttactcccta
tcagtgatagagaacgtataaggagtttactccctatcagtgatagagaacgtatgaccagtttactccctatcagtgatagagaacgtat
ctacagtttactccctatcagtgatagagaacgtatatccagtttactccctatcagtgatagagaacgtatgtcgaggtaggcgtgtacg
gtgggcgcctataaaagcagagctcgtttagtgaaccgtcagatcgcctggagcaattccacaacacttttgtcttatacttATGCTC
GAGGGAGTGCAGGTGGAGACTATCTCCCCAGGAGACGGGCGCACCTTCCCCAAG
CGCGGCCAGACCTGCGTGGTGCACTACACCGGGATGCTTGAAGATGGAAAGAAA
GTTGATTCCTCCCGGGACAGAAACAAGCCCTTTAAGTTTATGCTAGGCAAGCAGG
AGGTGATCCGAGGCTGGGAAGAAGGGGTTGCCCAGATGAGTGTGGGTCAGAGAG
CCAAACTGACTATATCTCCAGATTATGCCTATGGTGCCACTGGGCACCCAGGCAT
CATCCCACCACATGCCACTCTCGTCTTCGATGTGGAGCTTCTAAAACTGGAATCT
GGCGGTGGATCCGGAGTCGACGGATTTGGTGATGTCGGTGCTCTTGAGAGTTTGA
GGGGAAATGCAGATTTGGCTTACATCCTGAGCATGGAGCCCTGTGGCCACTGCCT
CATTATCAACAATGTGAACTTCTGCCGTGAGTCCGGGCTCCGACCCCGCACTGGC
TCCAACATCGACTGTGAGAAGTTGCGGCGTCGCTTCTCCTGCTGCATTTCATGG
TGGAGGTGAAGGGCGACCTGACTGCCAAGAAAATGGTGCTGGCTTTGCTGGAGC
TGGCGCGGCAGGACCACGGTGCTCTGGACTGCTGCGTGGTGGTCATTCTCTCTCA
CGGCTGTCAGGCCAGCCACCTGCAGTTCCCAGGGGCTGTCTACGGCACAGATGG
ATGCCCTGTGTCGGTCGAGAAGATTGTGAACATCTTCAATGGGACCAGCTGCCCC
AGCCTGGGAGGGAAGCCCAAGCTCTTTTTCATCCAGGCCTGTGGTGGGGAGCAG
AAAGACCATGGGTTTGAGGTGGCCTCCACTTCCCCTGAAGACGAGTCCCCTGGCA
GTAACCCCGAGCCAGATGCCACCCCGTTCCAGGAAGGTTTGAGGGACCTTCGACC
AGCTGGACGCCATATCTAGTTTGCCCACACACCCAGTGACATCTTTGTGTCCTACTCT
ACTTTCCCAGGTTTTGTTTCCTGGAGGGACCCCAAGAGTGGCTCCTGGTACGTTG
AGACCCTGGACGACATCTTTGAGCAGTGGGCTCACTCTGAAGACCTGCAGTCCCT
CCTGCTTAGGGTCGCTAATGCTGTTTCGGTGAAAGGGATTTATAAACAGATGCCT
GGTTGCTTTAATTTCCTCCGGAAAAAACTTTTCTTTAAAACATCAGTCGACTATCC
GTACGACGTACCAGACTACGCACTCGACTAAaagatttccccgtatcccccaggtgtctgcaggctc
aaagagcagcgagaagcgttcagaggaaagcgatcccgtgccaccttccccgtgcccgggctgtccccgcacgctgccggctcgg
ggatgcggggggagcgccggaccggagcggagcccggggcggctcgctgctgcccccctagcggggaggagcgtaattacatc
cctgggggattgggaggggctgtcccccgtgagctcaatcaacctctggattacaaaatttgtgaaagattgactggtattcttaactat
gttgctccttttacgctatgtggatacgctgcttaatgcctttgtatcatgctattgcttcccgtatggctttcatttctcctccttgtataaatc
ctggttgctgtctctttatgaggagttgtggcccgttgtcaggcaacgtggcgtggtgtgcactgtgtttgctgacgcaaccccactggt
tggggcattgccaccacctgtcagctccttccgggacttctgtctccccctccctattgccacggcgaactcatcgccgcctgcctttg
cccgctgctggacaggggctcggctgttgggcactgacaattccgtggtgttgtcggggaagctgacgtccttccatggctgctcgcc
tgtgttgccacctggattctgcgcgggacgtcttctgctacgtcccttcggccctcaatccagcggaccttccttcccgcggcctgctg
ccggctctgcggcctcttccgcgtcttcgcttcgccctcagacgagtcggatctcccctttgggccgcctcccgcctggaattaattctg
cagtcgagacctagaaaaacatgagcaatcacaagtagcaatacagcagctaccaatgctgattgtgcctggctagaagcacaaga
ggaggaggaggtgggttttccagtcacacctcaggtacctttaagaccaatgacttacaaggcagctgtagatcttagccacttttaaa
gaaaagaggggactggaagggctaattcactcccaacgaagacaagatatccttgatctgtggatctaccacacacaaggctacttcc
ctgattagcagaactacacaccagggccagggcagatatccactgacctttggatggtgctacaagctagtaccagttgagccagat
aaggtagaagaggccaataaaggagagaacaccagcttgttacaccctgtgagcctgcatgggatggatgacccggagagagaagt
gttagagtggaggtttgacagccgcctagcatttcatcacgtggcccgagagctgcatccggagtacttcaagaactgctgatatcgag
cttgctacaagggactttccgctggggactttccagggaggcgtggcctgggcgggactggggagtggcgagccctcagatcctgc
atataagcagctgctttttgcctgtactgggtctctctggttagaccagatctgagcctgggagctctctggctaactagggaacccactg
cttaagcctcaataaagcttgccttgagtgcttcaagtagtgtgtgcccgtctgttgtgtgactctggtaactagagatccctcagaccctt
tagtcagtgtggaaaatctctagcagtagtagttcatgtcatcttattattcagtatttataacttgcaaagaaatgaatatcaagagagtgaga
ggccttgacattgctagcgtttaccgtcgacctctagctagagcttggcgtaatcatggtcatagctgtttcctgtgtgaaattgttatccgc
tcacaattccacacaacatacgagccggaagcataaagtgtaaagcctggggtgcctaatgagtgagctaactcacattaattgcgttg
cgctcactgcccgctttccagtcgggaaacctgtcgtgccagctgcattaatgaatcggccaacgcgcggggagaggcggtttgcgta
ttgggcgctcttccgcttcctcgctcactgactcgctgcgctcggtcgttcggctgcggcgagcggtatcagctcactcaaaggcggta
atacggttatccacagaatcaggggataacgcaggaaagaacatgtgagcaaaaggccagcaaaaggccaggaaccgtaaaaagg
ccgcgttgctggcgtttttccataggctccgcccccctgacgagcatcacaaaaatcgacgctcaagtcagaggtggcgaaacccgac
aggactataaagataccaggcgtttccccctggaagctccctcgtgcgctctcctgttccgaccctgccgcttaccggatacctgtccgc
ctttctcccttcgggaagcgtggcgctttctcatagctcacgctgtaggtatctcagttcggtgtaggtcgttcgctccaagctgggctgtg
tgcacgaaccccccgttcagcccgaccgctgcgccttatccggtaactatcgtcttgagtccaacccggtaagacacgacttatcgcca
ctggcagcagccactggtaacaggattagcagagcgaggtatgtaggcggtgctacagagttcttgaagtggtggcctaactacggct
acactagaagaacagtatttggtatctgcgctctgctgaagccagttaccttcggaaaaagagttggtagctcttgatccggcaaacaaa
ccaccgctggtagcggtggtttttttgtttgcaagcagcagattacgcgcagaaaaaaaggatctcaagaagatcctttgatcttttctacg
gggtctgacgctcagtggaacgaaaactcacgttaagggattttggtcatgagattatcaaaaaggatcttcacctagatccttttaaatta
aaaatgaagttttaaatcaatctaaagtatatatgagtaaacttggtctgacagttaccaatgcttaatcagtgaggcacctatctcagcgat
ctgtctatttcgttcatccatagttgcctgactccccgtcgtgtagataactacgatacgggagggcttaccatctggccccagtgctgca
atgataccgcgagacccacgctcaccggctccagatttatcagcaataaaccagccagccggaagggccgagcgcagaagtggtcc
tgcaactttatccgcctccatccagtctattaattgttgccgggaagctagagtaagtagttcgccagttaatagtttgcgcaacgttgttgc
cattgctacaggcatcgtggtgtcacgctcgtcgtttggtatggcttcattcagctccggttcccaacgatcaaggcgagttacatgatcc
cccatgttgtgcaaaaaagcggttagctccttcggtcctccgatcgttgtcagaagtaagttggccgcagtgttatcactcatggttatgg
cagcactgcataattctcttactgtcatgccatccgtaagatgcttttctgtgactggtgagtactcaaccaagtcattctgagaatagtgtat
gcggcgaccgagttgctcttgcccggcgtcaatacgggataataccgcgccacatagcagaactttaaaagtgctcatcattggaaaa
cgttcttcggggcgaaaactctcaaggatcttaccgctgttgagatccagttcgatgtaacccactcgtgcacccaactgatcttcagcat
cttttactttcaccagcgtttctgggtgagcaaaaacaggaaggcaaaatgccgcaaaaaagggaataagggcgacacggaaatgttg
aatactcatactcttcctttttcaatattattgaagcatttatcagggttattgtctcatgagcggatacatatttgaatgtatttagaaaaataaa
caaataggggttccgcgcacatttccccgaaaagtgccacctgacgtcgacggatcgggagatcaacttgtttattgcagcttataatgg
```

TABLE 2-continued

Exemplary Vector Sequences ttacaaataaagcaatagcatcacaaatttcacaaataaagcatttttttcactgcattctagttgtggtttgtccaaactcatcaatgtatctta
tcatgtctggatcaactggataactcaagctaaccaaaatcatcccaaacttccacccatacctattaccactgccaattacctgtggt
ttcatttactctaaacctgtgattcctctgaattattttcattttaaagaaattgtatttgttaaatatgtactacaaacttagtagt (SEQ ID
NO: 23)

pLVX-CMV-TCR4-pTert-iCas9 (FIG. 6):
tggaagggctaattcactcccaaagaagacaagatatccttgatctgtggatctaccacacacaaggctacttccctgattagcagaact
acacaccagggccaggggtcagatatccactgacctttggatggtgctacaagctagtaccagttgagccagataaggtagaagagg
ccaataaaggagagaacaccagcttgttacaccctgtgagcctgcatgggatggatgacccggagagagaagtgttagagtggaggt
ttgacagccgcctagcatttcatcacgtggcccgagagctgcatccggagtacttcaagaactgctgatatcgagcttgctacaaggga
ctttccgctggggacttttccagggaggcgtggcctgggcgggactggggagtggcgagccctcagatcctgcatataagcagctgct
ttttgcctgtactgggtctctctggttagaccagatctgagcctgggagctctctggctaactagggaacccactgcttaagcctcaataa
agcttgccttgagtgatcaagtagtgtgtgcccgtctgttgtgtgactctggtaactagagatccctcagaccccttttagtcagtgtggaa
aatctctagcagtggcgcccgaacagggacttgaaagcgaaagggaaaccagaggagctctctcgacgcaggactcggcttgctga
agcgcgcacggcaagaggcgaggggcggcgactggtgagtacgccaaaaattttgactagcggaggctagaaggagagagatgg
gtgcgagagcgtcagtattaagcggggagaattagatcgcgatgggaaaaaattcggttaaggccaggggaaagaaaaaatata
aattaaaacatatagtatgggcaagcagggagctagaacgattcgcagttaatcctggcctgttagaaacatcagaaggctgtagacaa
atactgggacagctacaaccatcccttcagacaggatcagaagaacttagatcattatataatacagtagcaaccctctattgtgtgcatc
aaaggatagagataaaagacaccaaggaagctttagacaagataagaggaagagcaaaacaaaagtaagacaccgcacagcaag
cggccggccgctgatcttcagacctcggaggaggacagatatgagggacaattggagaagtgaattatataaatatatatagtagtaaaaattg
aaccattaggagtagcacccaccaaggcaaagagaagagtggtgcagagagaaaaaagagcagtgggaataggagctttgttcctt
gggttcttgggagcagcaggaagcactatgggcgcagcgtcaatgacgctgacggtacaggccagacaattattgtctggtatagtgc
agcagcagaacaatttgctgagggctattgaggcgcaacagcatctgttgcaactcacagtctggggcatcaagcagctccaggcaa
gaatcctggctgtggaaagatacctaaaggatcaacagctcctggggatttggggttgctctggaaaactcatttgcaccactgctgtgc
cttggaatgctagttggagtaataaatctctggaacagatttggaatcacacgacctggatggagtgggacagagaaattaacaattaca
caagataatacactccttaattgaagaatcgcaaaaccagcaagaaaagaatgaacaagaattattggaattagataaatgggcaagtt
tgtggaattggtttaacataacaaatttggctgtggtatataaaattattcataatgatagtaggaggcttggtaggtttaagaatagtttttgct
gtactttctatagtgaatagagttaggcagggatattccaccattatcgtttcagacccaccctcccaaccccgagggaccccgacaggcc
cgaaggaatagaagaagaaggtggagagagagacagagacagatccattcgattagtgaacggatctcgacggtatcgccttaaaa
gaaaagggggggattgggggtacagtgcagggaaagaatagtagacataatagcaacagacatacaaactaaagaattacaaaaa
caaattacaaaaattcaaaattttcgggtttattacagggacagcagagatccagtttatcgataagcttgggagttccgcgttacataactt
acggtaaatggcccgcctggctgaccgcccaacgacccccgcccattgacgtcaataatgacgtatgttcccatagtaacgccaatag
ggactttccattgacgtcaatgggtggagtatttacggtaaactgcccacttggcagtacatcaagtgtatcatatgccaagtacgcccc
tattgacgtcaatgacggtaaatggcccgcctggcattatgcccagtacatgaccttatgggactttcctacttggcagtacatctacgtat
tagtcatcgctattaccatggtgatgcggttttggcagtacatcaatgggcgtggatagcggtttgactcacggggatttccaagtctcca
ccccattgacgtcaatgggagtttgttttggcaccaaaatcaacgggactttccaaaatgtcgtaacaactccgccccattgacgcaaat
gggcggtaggcgtgtacggtgggaggtctatataagcagagctcgtttagtgaaccgtcagatcgcctggagacgccatccacgctgt
tttgacctccatagaagacaccgactctactagaggatctatttccggtgAATTCGCCACCatgggaatcaggctcctgtgtcg
tgtggcctttgtgttcctggctgtaggactagtaGAAGCTGACATCTACCAGACCCCAAGATACCTTGT
TATAGGGACAGGAAAGAAGATCACTCTGGAATGTTCTCAAACCATGGGCCATGA
CAAAATGTACTGGTATCAACAAGATCCAGGAATGGAACTACACCTCATCCACTAT
TCCTATGGAGTTAATTCCACAGAGAAGGGAGATCTTTCCTCTGAGTCAACAGTCT
CCAGAATAAGGACGGAGCATTTTCCCCTGACCCTGGAGTCTGCCAGGCCCTCACA
TACCTCTCAGTACCTCTGTGCCAGCAGTCGGACGCCCAACATTCAGTACTTCGGC
GCCGGGACCCGGCTCTCAGTGCTGgaggacctgaaaaacgtgttcccacccgaggtcgctgtgtttgagccatc
agaagcagagatctcccacacccaaaaggccacACTgGCAtgcctggccacaggcttctaccccgaccacgtggagctgagc
tggtgggtgaatgggaaggaggtgcacagtggggtcagcacagacccgcagcccctcaaggagcagcccgccctcaatgactcca
gatactgcctgagcagccgcctgagggtctcggccacctctgcagaacccaacctcccgctgcaagtcatccgttctacgg
gctctcggagaatgacgagtggaccccaggataggggccaaacctgtcacccagatcgtcagcgccgaggcctgggtagagcagac
tgtggcttcacctccgagtcttaccagcaagggcctgtctgctgccaccatcctctatgagatcttgctagggaaggccaccttgtatgcc
gtgctggtcagtgccctcgtgctgatggccatggtcaagagaaaggattccagaggcGGGAGCGGAGCCACGAAC
TTCTCTCTGTTAAAGCAAGCAGGAGACGTGGAAGAAAACCCTGGACCTatgacacgagt
tagcttgctgtgggcagtcgtggtctccacctgtctcgagtccggcatgGGTCAACAGCTGAATCAGAGTCCTC
AATCTATGTTTATCCAGGAAGGAGAAGATGTCTCCATGAACTGCACTTCTTCAAG
CATATTTAACACCTGGCTATGGTACAAGCAGGAACCTGGGGAAGGTCCTGTCCTC
TTGATAGCCTTATATAAGGCTGGTGAATTGACCTCAAATGGAAGACTGACTGCTC
AGTTTGGTATAACCAGAAAGGACAGCTTCCTGAATATCTCAGCATCCATACCTAG
TGATGTAGGCATCTACTTCTGTGCTGGCACATACCAGAAAGTTACCTTTGGAACT
GGAACAAAGCTCCAAGTCATCCCAaatatccagaaccctgaccctgccgtgtaccagctgagagactctaaatc
cagtgacaagtctgtctgcctattcaccgattttgattctcaaacaaatgtgtcacaaagtaaggattctgatgtgtatatcacagacaaaa
ctgtgctagacatgaggtctatgactttcaagacgcaggGCGGCCgcctggagcaaaatctgacttttgccatgcatgatcatacgg
cttcaacaacagcattattccagaagacacctccttccccagcccagaaagttcctgtgatgtcaagctggtcgagaaaagctttgaaac
agatacgaacctaaactttcaaaacctgtcagtgattgggttccgaatcctcctcctgaaagtggccgggtttaatctgctcatgacgctg
cggctgtggtccagcTGActcgagggatcccgcccctctccctccccccccctaacgttactggccgaagccgcttggaataagg
ccggtgtgcgtttgtctatatgttattttccaccatattgccgtcttttggcaatgtgagggcccggaaacctggccctgtcttcttgacgag
cattcctaggggtattcccctctcgccaaaggaatgcaaggtctgttgaatgtcgtgaaggaagcagttcctctggaagcttcttgaaga
caaacaacgtctgtagcgaccctttgcaggcagcggaaccccccacctggcgacaggtgcctctgcggccaaaagccacgtgtata
agatacacctgcaaaggcggcacaaccccagtgccacgttgtgagttggatagttgtggaaagagtcaaatggctcacctcaagcgta
ttcaacaaggggctgaaggatgcccagaaggtaccccattgtatgggatctgatctggggcctcggtgcacatgctttacatgtgtttag
tcgaggttaaaaaacgtctaggccccccgaaccacgggacgtggttttcctttgaaaaacacgatgataatatggccacaaggtgggccg
aggaggataacatggccatcatcaaggagttcatgcgcttcaaggtgcacatggagggctccgtgaacggccacgagttcgagatcg
agggcgagggcgagggccgcccctacgagggcacccagaccgccaagctgaaggtgaccaagggtggccccctgcccttcgcct
gggacatcctgtcccctcagttcatgtacggctccaaggcctacgtgaagcaccccgccgacatccccgactacttgaagctgtccttc
cccgagggcttcaagtgggagcgcgtgatgaacttcgaggacggcggcgtggtgaccgtgacccaggactcctccctgcaggacgg
cgagttcatctacaaggtgaagctgcgcggcaccaacttccctcctcgacggccccgtaatgcagaagaagaccatgggctgggag
gcctcctccgagcggatgtaccccgaggacgcgccgaagggcgagatcaagcagaggctgaagctgaaggacggcggccca
ctacgacgctgaggtcaagaccacctacaaggccaagaagcccgtgcagctgcccggcgcctacaacgtcaacatcaagttggaca
tcacctcccacaacgaggactacaccatcgtggaacagtacgaacgcgccgagggccgccactccaccggcggcatggacgagct TABLE 2-continued Exemplary Vector Sequences

```
gtacaagtgaacgcgtctggaacaagcttttcccgtatcccccaggtgtctgcaggctcaaagagcagcgagaagcgttcagagg
aaagcgatcccgtgccaccttccccgtgcccgggctgtccccgcacgctgccggctcggggatgcgggggagcgccggaccgg
agcggagccccgggcggctcgctgctgcccccctagcgggggagggacgtaattacatccctggggggcttgggggggggctgtcc
ccgtgagctcttactccctatcagtgatagagaacgtatgaagagtttactccctatcagtgatagagaacgtatgcagactttactcccta
tcagtgatagagaacgtataaggagtttactccctatcagtgatagagaacgtatgaccagtttactccctatcagtgatagagaacgtat
ctacagtttactccctatcagtgatagagaacgtatatccagtttactccctatcagtgatagagaacgtatgtcgaggtaggcgtgtacg
gtgggcgcctataaaagcagagctcgtttagtgaaccgtcagatcgcctggagcaattccacaacacttttgtcttatacttATGCTC
GAGGGAGTGCAGGTGGAGACTATCTCCCCAGGAGACGGGCGCACCTTCCCCAAG
CGCGGCCAGACCTGCGTGGTGCACTACACCGGGATGCTTGAAGATGGAAAGAAA
GTTGATTCCTCCCGGGACAGAAACAAGCCCTTTAAGTTTATGCTAGGCAAGCAGG
AGGTGATCCGAGGCTGGGAAGAAGGGGTTGCCCAGATGAGTGTGGGTCAGAGAG
CCAAACTGACTATATCTCCAGATTATGCCTATGGTGCCACTGGGCACCCAGGCAT
CATCCCACCACATGCCACTCTCGTCTTCGATGTGGAGCTTCTAAAACTGGAATCT
GGCGGTGGATCCGGAGTCGACGGATTTGGTGATGTCGGTGCTCTTGAGAGTTTGA
GGGGAAATGCAGATTTGGCTTACATCCTGAGCATGGAGCCCTGTGGCCACTGCCT
CATTATCAACAATGTGAACTTCTGCCGTGAGTCCGGGCTCCGCACCCGCACTGGC
TCCAACATCGACTGTGAGAAGTTGCGGCGTCGCTTCTCCTGCTGCATTTCATGG
TGGAGGTGAAGGGCGACCTGACTGCCAAGAAAATGGTGCTGGCTTTGCTGGAGC
TGGCGCGGCAGGACCACGGTGCTCTGGACTGCTGCGTGGTGGTCATTCTCTCTCA
CGGCTGTCAGGCCAGCCACCTGCAGTTCCCAGGGGCTGTCTACGGCACAGATGG
ATGCCCTGTGTCGGTCGAGAAGATTGTGAACATCTTCAATGGGACCAGCTGCCCC
AGCCTGGGAGGGAAGCCCAAGCTCTTTTTCATCCAGGCCTGTGGTGGGGAGCAG
AAAGACCATGGGTTTGAGGTGGCCTCCACTTCCCCTGAAGACGAGTCCCCTGGCA
GTAACCCCGAGCCAGATGCCACCCCGTTCCAGGAAGGTTTGAGGGACCTTCGACC
AGCTGGACGCCATATCTAGTTTGCCCACACCCAGTGACATCTTTGTGTCCTACTCT
ACTTTCCCAGGTTTTGTTTCCTGGAGGGACCCCAAGAGTGGCTCCTGGTACGTTG
AGACCCTGGACGACATCTTTGAGCAGTGGGCTCACTCTGAAGACCTGCAGTCCCT
CCTGCTTAGGGTCGCTAATGCTGTTTCGGTGAAAGGGATTTATAAACAGATGCCT
GGTTGCTTTAATTTCCTCCGGAAAAAACTTTTCTTTAAAACATCAGTCGACTATCC
GTACGACGTACCAGACTACGCACTCGACTAAaagattttcccgtatcccccaggtgtctgcaggctc
aaagagcagcgagaagcgttcagaggaaagcgatcccgtgccaccttccccgtgcccgggctgtccccgcacgctgccggctcgg
ggatgcgggggagcgccggaccggagcggagccccgggcggctcgctgctgcccccctagcgggggagggacgtaattacatc
cctgggggctttgggagggggctgtccccgtgagctcaatcaacctctggattacaaaatttgtgaaagattgactggtattcttaactat
gttgctccttttacgctatgtggatacgctgcttttaatgcctttgtatcatgctattgcttcccgtatggctttcatttctcctccttgtataaatc
ctggttgctgtctctttatgaggagttgtgcccgttgtcaggcaacgtggcgtggtgtgcactgtgtttgctgacgcaaccccactggt
tgggcattgccaccacctgtcagctccttccggggacttttgcttttcccctccctattgccacggcggaactcatcgccgcctgccttg
cccgctgctggacaggggctcggctgttgggcactgacaattccgtggtgttgtcggggaagctgacgtccttccatggctgctcgcc
tgtgttgccacctggattctgcgcgggacgtccttctgctacgtccccttcggccctcaatccagcggaccttccttcccgcggcctgctg
ccggctctgcgcctatccgcgtatcgccttcgccctcagacgagtcggatctccattgggccgcctccccgcctggaattaattctg
cagtcgagacctagaaaaacatggagcaatcacaagtagcaatacagcagctaccaatgctgattgtgcctggctagaagcacaaga
ggaggaggaggtgggttttccagtcacacctcaggtacctttaagaccaatgacttacaaggcagctgtagatcttagccactttttaaaa
gaaaagaggggactggaagggctaattcactcccaacgaagacaagatatccttgatctgtggatctaccacacacaaggctacttcc
ctgattagcagaactacacaccagggccaggggtcagatatccactgacctttggatggtgctacaagctagtaccagttgagccagat
aaggtagaagaggccaataaaggagagaacaccagcttgttacaccctgtgagcctgcatgggatgacccgagagaagaagaagt
gttagagtggaggtttgacagccgcctagcatttcatcacgtggcccgagagctgcatccggagtacttcaagaactgctgatatcgag
cttgctacaagggactttccgctggggactttccagggaggcgtggcctgggcgggactggggagtggcgagccctcagatcctgc
atataagcagctgctttttgcctgtactgggtctctctggttagaccagatctgagcctgggagctctctggctaactagggaacccactg
cttaagcctcaataaagcttgccttgagtgatcaagtagtgtgtgcccgtctgttgtgtgactctggtaactagagatccctcagacccttt
tagtcagtgtggaaaatctctagcagtagtagttcatgtcatcttattattcagtatttataacttgcaaagaaatgaatatcagagagtgaga
ggccttgacattgctagcgtttaccgtcgacctctagctagagcttggcgtaatcatggtcatagctgtttcctgtgtgaaattgttatccgc
tcacaattccacacaacatacgagccggaagcataaagtgtaaagcctggggtgcctaatgagtgagctaactcacattaattgcgttg
cgctcactgcccgctttccagtcgggaaacctgtcgtgccagctgcattaatgaatcggccaacgcgcggggagaggcggtttgcgta
ttgggcgctcttccgcttcctcgctcactgactcgctgcgctcggtcgttcggctgcggcgagcggtatcagctcactcaaaggcggta
atacggttatccacagaatcaggggataacgcaggaaagaacatgtgagcaaaaggccagcaaaaggccaggaaccgtaaaaagg
ccgcgttgctggcgtttttccataggctccgcccccctgacgagcatcacaaaaatcgacgctcaagtcagaggtggcgaaacccgac
aggactataaagataccaggcgtttccccctggaagctccctcgtgcgctctcctgttccgaccctgccgcttaccggatacctgtccgc
ctttctcccttcgggaagcgtggcgctttctcatagctcacgctgtaggtatctcagttcggtgtaggtcgttcgctccaagctgggctgtg
tgcacgaaccccccgttcagcccgaccgctgcgccttatccggtaactatcgtcttgagtccaacccggtaagacacgacttatcgcca
ctggcagcagccactggtaacaggattagcagagcgaggtatgtaggcggtgctacagagttcttgaagtggtggcctaactacggct
acactagaagaacagtatttggtatctgcgctctgctgaagccagttaccttcggaaaaagagttggtagctcttgatccggcaaacaaa
ccaccgctggtagcggtggtttttttgtttgcaagcagcagattacgcgcagaaaaaaaggatctcaagaagatcctttgatcttttctacg
gggtctgacgctcagtggaacgaaaactcacgttaagggattttggtcatgagattatcaaaaaggatcttcacctagatccttttaaatta
aaaatgaagttttaaatcaatctaaagtatatatgagtaaacttggtctgacagttaccaatgcttaatcagtgaggcacctatctcagcgat
ctgtctatttcgttcatccatagttgcctgactccccgtcgtgtagataactacgatacgggagggcttaccatctggccccagtgctgca
atgataccgcgagacccacgctcaccggctccagatttatcagcaataaaccagccagccggaagggccgagcgcagaagtggtcc
tgcaactttatccgcctccatccagtctattaattgttgccgggaagctagagtaagtagttcgccagttaatagtttgcgcaacgttgttgc
cattgctacaggcatcgtggtgtcacgctcgtcgtttggtatggcttcattcagctccggttcccaacgatcaaggcgagttacatgatcc
cccatgttgtgcaaaaaagcggttagctccttcggtcctccgatcgttgtcagaagtaagttggccgcagtgttatcactcatggttatgg
cagcactgcataattctcttactgtcatgccatccgtaagatgcttttctgtgactggtgagtactcaaccaagtcattctgagaatagtgtat
gcggcgaccgagttgctcttgcccggcgtcaatacgggataataccgcgccacatagcagaactttaaaagtgctcatcattggaaaa
cgttcttcggggcgaaaactctcaaggatcttaccgctgttgagatccagttcgatgtaacccactcgtgcacccaactgatcttcagcat
cttttactttcaccagcgtttctgggtgagcaaaaacaggaaggcaaaatgccgcaaaaaagggaataagggcgacacggaaatgttg
aatactcatactcattttcattttgaagcatttatcagggttattgtctcatgagcggatacatatttgaatgtatttagaaaaataaa
caaataggggttccgcgcacatttccccgaaaagtgccacctgacgtcgacggatcgggagatcaactgtttattgcagcttataatgg
ttacaaataaagcaatagcatcacaaatttcacaaataaagcatttttttcactgcattctagttgtggtttgtccaaactcatcaatgtatctta
tcatgtctggatcaactggataactcaagctaaccaaaatcatcccaaacttcccaccccataccctattaccactgccaattacctgtggt
ttcatttactctaaacctgtgattcctctgaattattttcatttttaaagaaattgtatttgttaaatatgtactacaaacttagtagt (SEQ ID
NO: 24)
```

TABLE 2-continued

Exemplary Vector Sequences pLVX-CMV-TCR5-pTert-iCas9 (FIG. 7):
tggaagggctaattcactcccaaagaagacaagatatccttgatctgtggatctaccacacacaaggctacttccctgattagcagaact
acacaccagggccaggggtcagatatccactgacctttggatggtgctacaagctagtaccagttgagccagataaggtagaagagg
ccaataaaggagagaacaccagcttgttacaccctgtgagcctgcatgggatggatgacccggagagagaagtgttagagtggaggt
ttgacagccgcctagcatttcatcacgtggcccgagagctgcatccggagtacttcaagaactgctgatatcgagcttgctacaaggga
ctttccgctggggactttccaggggaggcgtggcctgggcgggactggggagtggcgagccctcagatcctgcatataagcagctgct
ttttgcctgtactgggtctctctggttagaccagatctgagcctgggagctctctggctaactagggaacccactgcttaagcctcaataa
agcttgccttgagtgcttcaagtagtgtgtgcccgtctgttgtgtgactctggtaactagagatccctcagaccccttttagtcagtgtggaa
aatctctagcagtggcgcccgaacagggacttgaaagcgaaagggaaaccagaggagctctctcgacgcaggactcggcttgctga
agcgcgcacggcaagaggcgaggggcggcgactggtgagtacgccaaaaattttgactagcggaggctagaaggagagagatgg
gtgcgagagcgtcagtattaagcggggagaattagatcgcgatgggaaaaaattcggttaaggccaggggggaaagaaaaaatata
aattaaaacatatagtatgggcaagcagggagctagaacgattcgcagttaatcctggcctgttagaaacatcagaaggctgtagacaa
atactgggacagctacaaccatcccttcagacaggatcagaagaacttagatcattatataatacagtagcaaccctctattgtgtgcatc
aaaggatagagatataaagacaccaaggaagctttagacaagatagaggaagagcaaaacaaaagtaagcaccgcacagcaag
cggccggccgctgatcttcagacctcgaggagaggatatgagggacaattggagaagtgaattatataaatataaagtagtaaaattg
aaccattaggagtagcacccaccaaggcaaagagaagagtggtgcagagagaaaaaagagcagtgggaataggagctttgttcctt
gggttcttgggagcagcaggaagcactatgggcgcagcgtcaatgacgctgacggtacaggccagacaattattgtctggtatagtgc
agcagcagaacaatttgctgagggctattgaggcgcaacagcatctgttgcaactcacagtctggggcatcaagcagctccaggcaa
gaatcctggctgtggaaagataccctaaaggatcaacagctcctgggggatttggggttgctctggaaaactcatttgccaccactgctgtgc
cttggaatgctagttggagtaataaatctctggaacagatttggaatcacacgacctggatggagtgggacagagaaattaacaattaca
caagataatacactccttaattgaagaatcgcaaaaccagcaagaaaagaatgaacaagaattattggaattagataaatgggcaagtt
tgtggaattggtttaacataacaaatttggctggtatataaaattattcataatgatagtaggaggcttggtaggtttaagaataagtttttgct
gtactttctatagtgaatagagttaggcagggatattcaccattatcgtttcagacccacctcccaaccccgaggggacccgacaggcc
cgaaggaatagaagaagaaggtggagagagagacagagacagatccattcgattagtgaacggatctcgacggtatcgcctttaaaa
gaaaggggggattgggggtacagtgcagggggaaagaatagtagacataatagcaacagacatacaaactaaagaattacaaaaaa
caaattacaaaaattcaaaattttcgggtttattacagggacagcagagatccagtttatcgataagcttgggagttccgcgttacataactt
acggtaaatggcccgcctggctgaccgcccaacgacccccgcccattgacgtcaataatgacgtatgttcccatagtaacgccaatag
ggactttccattgacgtcaatgggtggagtatttacggtaaactgcccacttggcagtacatcaagtgtatcatatgccaagtacgcccc
tattgacgtcaatgacggtaaatggcccgcctggcattatgcccagtacatgaccttatgggactttcctacttggcagtacatctacgtat
tagtcatcgctattaccatggtgatgcggttttggcagtacatcaatgggcgtggatagcggtttgactcacggggatttccaagtctcca
ccccattgacgtcaatgggagtttgttttggcaccaaaatcaacgggactttccaaaatgtcgtaacaactccgccccattgacgcaaat
gggcggtaggcgtgtacggtgggaggtctatataagcagagctcgtttagtgaaccgtcagatcgcctggagacgccatccacgctgt
tttgacctccatagaagacaccgactctactagaggatctatttccggtgAATTCGCCACCatggcctccctgctgcttcttctgtg
gggccttttatctcctgggaaccggttccatgGAAGCTGACATCTACCAGACCCCAAGATACCTTGTT
ATAGGGACAGGAAAGAAGATCACTCTGGAATGTTCTCAAACCATGGGCCATGAC
AAAATGTACTGGTATCAACAAGATCCAGGAATGGAACTACACCTCATCCACTATT
CCTATGGAGTTAATTCCACAGAGAAGGGAGATCTTTCCTCTGAGTCAACAGTCTC
CAGAATAAGGACGGAGCATTTTCCCCTGACCCTGGAGTCTGCCAGGCCCTCACAT
ACCTCTCAGTACCTCTGTGCCAGCAGTCGGACGCCCAACATTCAGTACTTCGGCG
CCGGGACCCGGCTCTCAGTGCTGgaggacctgaaaaacgtgttcccacccgaggtcgctgtgtttgagccatca
gaagcagagatctcccacacccaaaaggccacACTAGTgtgcctggccacaggcttctaccccgaccacgtggagctgagct
ggtgggtgaatgggaaggaggtgcacagtggggtcagcacagacccgcagccctcaaggagcagcccgccctcaatgactcca
gatactgcctgagcagccgcctgagggtctcggccaccttctggcagaacccccaaccactcgcgtctcaagtccagttctacgg
gctctcggagaatgacgagtggaccaggataggcaaacctgtcacccagatcgtcagcgccgaggcctgggtagagcagac
tgtggcttcacctccgagtcttaccagcaaggggtcctgtctgccaccatcctctatgagatcttgctagggaaggccaccttgtatgcc
gtgctggtcagtgccctcgtgctgatggccatggtcaagagaaaggattccagaggcGGGAGCGGAGCCACGAAC
TTCTCTCTGTTAAAGCAAGCAGGAGACGTGGAAGAAAACCCTGGACCTatgaactcctct
ctggactttctaattctgatcttaatgtttggaggaACTAGTGGTCAACAGCTGAATCAGAGTCCTCAAT
CTATGTTTATCCAGGAAGGAGAAGATGTCTCCATGAACTGCACTTCTTCAAGCAT
ATTTAACACCTGGCTATGGTACAAGCAGGAACCTGGGGAAGGTCCTGTCCTCTTG
ATAGCCTTATATAAGGCTGGTGAATTGACCTCAAATGGAAGACTGACTGCTCAGT
TTGGTATAACCAGAAAGGACAGCTTCCTGAATATCTCAGCATCCATACCTAGTGA
TGTAGGCATCTACTTCTGTGCTGGCACATACCAGAAAGTTACCTTTGGAACTGGA
ACAAAGCTCCAAGTCATCCCAAATATCCAGAACCCTGACCCTGCCGTGTACCAGC
TGAGAGACTCTAAATCCAGTGACAAGTCTGCATGCctattcaccgattttgattctcaaacaaatgtgtc
acaaagtaaggattctgatgtgtatatcacagacaaaactgtgctagacatgaggtctatggacttcaagagcaacagtgctgtggcctg
gagcaacaaatctgactttgcatgtgcaaacgcctttcaacaacagcattattccagaagacaccttcttcccagcccagaaagttcctg
tgatgtcaagctggtcgagaaaagctttgaaacagatacgaacctaaactttcaaaacctgtcagtgattgggttccgaatcctcctcctg
aaagtggccgggtttaatctgctcatgacgctgcggctgtggtccagcTGActcgagggatcccgcccctctccctccccccccct
aacgttactggccgaagccgcttggaataaggccggtgtgcgtttgtctatatgttattttccaccatattgccgtcttttggcaatgtgagg
gcccggaaacctggccctgtatcttgacgagcattcctaggggtcttccccctctcgccaaaggaatgcaaggtctgttgaatgtcgtg
aaggaagcagttcctctggaagatcttgagacaaaacaacgtctgtagcgacccctttgcaggcagcggaaccccccacctggcgac
aggtgcctctgcggccaaaagccacgtgtataagatacacctgcaaaggcggcacaaccccagtgccacgttgtgagttggatagttg
tggaaagagtcaaatggctcacctcaagcgtattcaacaaggggctgaaggatgcccaccattgtatgggatctgatct
ggggcctcggtgcacatgctttacatgtgtttagtcgaggttaaaaaacgtctaggccccccgaaccacgggacgtggttttcctttga
aaaacacgatgataatatggttgagcaagggcgaggaggataacatggccatcatcaaggagttcatgcgcttcaaggtgcacatgga
gggctccgtgaacggccacgagttcgagatcgagggcgagggcgagggccgcccctacgagggcacccagaccgccaagctga
aggtgaccaagggtggccccctgcccttcgcctgggacatcctgtcccctcagttcatgtacggctccaaggcctacgtgaagcaccc
cgccgacatccccgactacttgaagctgtccttccccgagggcttcaagtgggagcgcgtgatgaacttcgaggacggcggcgtggt
gaccgtgacccaggactcctccctgcaggacggcgagttcatctacaaggtgaagctgcgcggcaccaacttcccctccgacggccc
cgtaatgcagaagaagaccatgggctgggaggcctcctccgagcggatgtaccccgaggacggcgccctgaagggcgagatca
agcagaggctgaagctgaaggacggcggccactacgacgctgaggtcaagaccacctacaaggccaagaagcccgtgcagctgc
ccggcgcctacaacgtcaacatcaagttggacatcacctcccacaacgaggactacaccatcgtggaacagtacgaacgcgccgag
ggccgccactccaccggcggcatggacgagctgtacaagtgaacgcgtctggaacaagcttttttcccgtatccccaggtgtctgc
aggctcaaagagcagcgagaagcgttcagaggaaagcgatcccgtgccaccttccccgtgcccgggctgtccccgcacgctgccg
gctcggggatgcggggggagcgccggaccggagcggagccccgggcggctcgctgctgccccctagcgggggagggacgtaa
ttacatccctgggggctttggggggggggctgtcccgtgagctcttactccctatcagtgatagagaacgtatgaagagtttactccctat TABLE 2-continued Exemplary Vector Sequences

```
cagtgatagagaacgtatgcagactttactccctatcagtgatagagaacgtataaggagttttactccctatcagtgatagagaacgtatg
accagtttactccctatcagtgatagagaacgtatctacagtttactccctatcagtgatagagaacgtatatccagtttactccctatcagt
gatagagaacgtatgtcgaggtaggcgtgtacggtgggcgcctataaaagcagagctcgtttagtgaaccgtcagatcgcctggagc
aattccacaacacttttgtcttatactTATGCTCGAGGGAGTGCAGGTGGAGACTATCTCCCCAGGA
GACGGGCGCACCTTCCCCAAGCGCGGCCAGACCTGCGTGGTGCACTACACCGGG
ATGCTTGAAGATGGAAAGAAAGTTGATTCCTCCCGGGACAGAAACAAGCCCTTT
AAGTTTTATGCTAGGCAAGCAGGAGGTGATCCGAGGCTGGGAAGAAGGGGTTGCC
CAGATGAGTGTGGGTCAGAGAGCCAAACTGACTATATCTCCAGATTATGCCTATG
GTGCCACTGGGCACCCAGGCATCATCCCACCCACATGCCACTCTCGTCTTCGATGT
GGAGCTTCTAAAACTGGAATCTGGCGGTGGATCCGGAGTCGACGGATTTGGTGA
TGTCGGTGCTCTTGAGAGTTTGAGGGGAAATGCAGATTTGGCTTACATCCTGAGC
ATGGAGCCCTGTGGCCACTGCCTCATTATCAACAATGTGAACTTCTGCCGTGAGT
CCGGGCTCCGCACCCGCACTGGCTCCAACATCGACTGTGAGAAGTTGCGGCGTCG
CTTCTCCTCGCTGCATTTCATGGTGGAGGTGAAGGGCGACCTGACTGCCAAGAA
ATGGTGCTGGCTTTGCTGGAGCTGGCGCGGCAGGACCACGGTGCTCTGGACTGT
GCGTGGTGGTCATTCTCTCTCACGGCTGTCAGGCCAGCCACCTGCAGTTCCCAGG
GGCTGTCTACGGCACAGATGGATGCCCTGTGTCGGTCGAGAAGATTGTGAACATC
TTCAATGGGACCAGCTGCCCCAGCCTGGGAGGGAAGCCCAAGCTCTTTTTCATCC
AGGCCTGTGGTGGGGAGCAGAAAGACCATGGGTTTGAGGTGGCCTCCACTTCCC
CTGAAGACGAGTCCCCTGGCAGTAACCCCGAGCCAGATGCCACCCCGTTCCAGG
AAGGTTTGAGGACCTTCGACCAGCTGGACGCCATATCTAGTTTGCCCACACCCAG
TGACATCTTTGTGTCCTACTCTACTTTCCCAGGTTTTGTTTCCTGGAGGGACCCCA
AGAGTGGCTCCTGGTACGTTGAGACCCTGGACGACATCTTTGAGCAGTGGGCTCA
CTCTGAAGACCTGCAGTCCCTCCTGCTTAGGGTCGCTAATGCTGTTTCGGTGAAA
GGGATTTATAAACAGATGCCTGGTTGCTTTAATTTCCTCCGGAAAAAACTTTTCTT
TAAAACATCAGTCGACTATCCGTACGACGTACCAGACTACGCACTCGACTAAaagc
ttttttcccgtatcccccaggtgtctgcaggctcaaagagcagcgagaagcgttcagaggaaagcgatcccgtgccaccttccccgt
gcccgggctgtccccgcacgctgccggctcgggatgcgggggagcgccggaccggagcggagccccgggcggctcgctgct
gcccctagcggggagggacgtaattacatccctgggggctttggagggggctgtccccgtgagctcaatcaacctctggattac
aaaatttgtgaaagattgactggtattcttaactatgttgctcctttttacgctatgtggatacgctgctttaatgcctttgtatcatgctattgctt
cccgtatggattcatttctcctccttgtataaatcctggttgctgtctctttatgaggagttgtggcccgttgtcaggcaacgtggcgtggt
gtgcactgtgtttgctgacgcaaccccccactggttggggcattgccaccacctgtcagctccttttccgggactttcgctttccccctcccta
ttgccacggcggaactcatcgccgctgccttgccccgctgctggacagggcctcggctgttgggcactgacaattccgtggtgttgtc
ggggaagctgacgtcctttccatggctgctcgcctgtgttgccacctggattctgcgcgggacgtccttctgctacgtcccttcggccct
caatccagcggaccttccttcccgcggcctgctgccggctctgcggcctcttccgcgtcttcgccttcgccctcagacgagtcggatct
ccctttgggccgcctccccgcctggaattaattctgcagtcagtcccctagaaaaacatgcagcaatcacaagtagcaatacagcagct
accaatgctgattgtgcctggctagaagcacaagaggaggaggtgggttttccagtcacacctcaggtaccttaagaccaatga
cttacaaggcagctgtagatcttagccacttttttaaaagaaaagaggggactggaagggctaattcactcccaacgaagacaagatatc
cttgatctgtggatctaccacacacaaggctacttccctgattagcagaactacacaccagggccaggggtcagatatccactgacctttt
ggatggtgctacaagctagtaccagttgagccagataaggtagaagaggccaataaaggagagaacaccagcttgttacccctgtg
agcctgcatgggatggatgacccgagagagaagtgttagagtggaggtttgacagccgcctagcatttcatcacgtggcccgagag
ctgcatccggagtacttcaagaactgctgatatcgagcttgctacaaggacttttccgctggggactttccaggaggcgtggcctggg
cgggactggggagtggcgagccctcagatcctgcatataagcagctgcttttttgcctgtactgggtctctctggttagaccagatctgag
cctgggagctctctggctaactagggaaccccactgcttaagcctcaataaagcttgccttgagtgcttcaagtagtgtgtgcccgtctgtt
gtgtgactctggtaactagagatccctcagacccttttagtcagtgtggaaaatctctagcagtagtagttcatgtcatcttattattcagtatt
tataacttgcaaagaaatgaatatcagagagtgagaggccttgacattgctagcgtttaccgtcgacctctagctagagcttggcgtaatc
atggtcatagctgtttcctgtgtgaaattgttatccgctcacaattccacacaacatacgagccggaagcataaagtgtaaagcctggggt
gcctaatgagtgagctaactcacattaattgcgttgcgctcactgcccgctttccagtcgggaaacctgtcgtgccagctgcattaatgaa
tcggccaacgcgcggggagaggcggtttgcgtattgggcgctcttccgcttcctcgctcactgactcgctgcgctcggtcgttcggctg
cggcgagcggtatcagctcactcaaaggcggtaatacggttatccacagaatcaggggataacgcaggaaagaacatgtgagcaaa
aggccagcaaaaggccaggaaccgtaaaaaggccgcgttgctggcgtttttccataggctccgcccccctgacgagcatcacaaaa
atcgacgctcaagtcagaggtggcgaaacccgacaggactataaagataccaggcgtttccccctggaagctccctcgtgcgctctc
tgttccgaccctgccgcttaccggatacctgtccgcctttctcccttcgggaagcgtggcgctttctcatagctcacgctgtaggtatctca
gttcggtgtaggtcgttcgctccaagctgggctgtgtgcacgaaccccccgttcagcccgaccgctgcgccttatccggtaactatcgt
cttgagtccaacccggtaagacacgacttatcgccactggcagcagccactggtaacaggattagcagagcgaggtatgtaggcggt
gctacagagttcttgaagtggtggcctaactacggctacactagaagaacagtatttggtatctgcgctctgctgaagccagttaccttcg
gaaaaagagttggtagctcttgatccggcaaacaaaccaccgctggtagcggtggtttttttgtttgcaagcagcagattacgcgcaga
aaaaaaggatctcaagaagatcctttgatcttttctacggggtctgacgctcagtggaacgaaaactcacgttaagggattttggtcatga
gattatcaaaaaggatcttcacctagatccttttaaattaaaaatgaagttttaaatcaatctaaagtatatatgagtaaacttggtctgacagt
taccaatgcttaatcagtgaggcacctatctcagcgatctgtctatttcgttcatccatagttgcctgactccccgtcgtgtagataactacg
atacgggagggcttaccatctggccccagtgctgcaatgataccgcgagacccacgctcaccggctccagatttatcagcaataaacc
agccagccggaagggccgagcgcagaagtggtcctgcaacttatccgcctccatccagtctattaattgttgccgggaagctagagt
aagtagttcgccagttaatagtttgcgcaacgttgttgccattgctacaggcatcgtggtgtcacgctcgtcgtttggtatggcttcattcag
ctccggttcccaacgatcaaggcgagttacatgatccccatgttgtgcaaaaaagcggttagctccttcggtcctccgatcgttgtcag
aagtaagttggccgcagtgttatcactcatggttatggcagcactgcataattctcttactgtcatgccatccgtaagatgcttttctgtgact
ggtgagtactcaaccaagtcattctgagaatagtgtatgcggcgaccgagttgctcttgcccggcgtcaatacgggataataccgcgcc
acatagcagaactttaaaagtgctcatcattggaaaacgttcttcggggcgaaaactctcaaggatcttaccgctgttgagatccagttcg
atgtaacccactcgtgcacccaactgatcttcagcatcttttactttcaccagcgtttctgggtgagcaaaaacaggaaggcaaaatgcc
gcaaaaaagggaataagggcgacacggaaatgttgaatactcatactcttcctttttcaatattattgaagcatttatcagggttattgtctc
atgagcggatacatatttgaatgtatttagaaaaataaacaaataggggttccgcgcacatttccccgaaaagtgccacctgacgtcgac
ggatcgggagatcaacttgtttattgcagcttataatggttacaaataaagcaatagcatcacaaatttcacaaataaagcatttttttcactg
cattctagttgtggtttgtccaaactcatcaatgtatcttatcatgtctggatcaactggataactcaagctaaccaaaatcatcccaaacttc
ccaccccataccctattaccactgccaattacctgtggtttcatttactctaaacctgtgattcctctgaattattttcattttaaagaaattgtat
ttgttaaatatgtactacaaacttagtagt (SEQ ID NO: 25)
``` pLVX-CMV-TCR1 (FIG. 8):
tggaagggctaattcactcccaaagaagacaagatatccttgatctgtggatctaccacacacaaggctacttccctgattagcagaact
acacaccagggccagggtcagatatccactgacctttggatggtgctacaagctagtaccagttgagccagataaggtagaagagg TABLE 2-continued Exemplary Vector Sequences

```
ccaataaaggagagaacaccagcttgttacaccctgtgagcctgcatgggatggatgacccggagagagaagtgttagagtggaggt
ttgacagccgcctagcatttcatcacgtggcccgagagctgcatccggagtacttcaagaactgctgatatcgagcttgctacaaggga
ctttccgctggggactttccagggaggcgtggcctgggcgggactggggagtggcgagccctcagatcctgcatataagcagctgct
ttttgcctgtactgggtctctctggttagaccagatctgagcctgggagctctctggctaactagggaacccactgcttaagcctcaataa
agcttgccttgagtgcttcaagtagtgtgtgcccgtctgttgtgtgactctggtaactagagatccctcagacccttttagtcagtgtggaa
aatctctagcagtggcgcccgaacagggacttgaaagcgaaagggaaaccagaggagctctctcgacgcaggactcggcttgctga
agcgcgcacggcaagaggcgaggggcggcgactggtgagtacgccaaaaattttgactagcggaggctagaaggagagagatgg
gtgcgagagcgtcagtattaagcgggggagaattagatcgcgatgggaaaaaattcggttaaggcgaggggaaagaaaaaatata
aattaaaacatatagtatgggcaagcagggagctagaacgattcgcagttaatcctggcctgttagaaacatcagaaggctgtagacaa
atactgggacagctacaaccatcccttcagacaggatcagaagaacttagatcattatataatacagtagcaaccctctattgtgtgcatc
aaaggatagagataaaagacaccaaggaagcttagacaagatagaggaagagcaaaacaaaagtaagaccaccgcacagcaag
cggccggccgctgatcttcagacctggaggaggagatatgagggacaattggagaagtgaattatataaatataaagtagtaaaaattg
aaccattaggagtagcacccaccaaggcaaagagaagagtggtgcagagagaaaaaagagcagtgggaataggagctttgttcctt
gggttcttgggagcagcaggaagcactatgggcgcagcgtcaatgacgctgacggtacaggccagacaattattgtctggtatagtgc
agcagcagaacaatttgctgagggctattgaggcgcaacagcatctgttgcaactcacagtctggggcatcaagcagctccaggcaa
gaatcctggctgtggaaagatacctaaaggatcaacagctcctggggatttggggttgctctggaaaactcatttgcaccactgctgtgc
cttggaatgctagttggagtaataaatctctggaacagatttggaatcacacgacctggatggagtgggacagagaaattaacaattaca
caagataatacactccttaattgaagaatcgcaaaaccagcaagaaaagaatgaacaagaattattggaattagataaatgggcaagtt
tgtggaattggtttaacataacaaattggctgtgtatataaaattattcataatgatagtaggaggcttggtaggtttaagaatagttttgct
gtactttctatagtgaatagagttaggcagggatattcaccattatcgtttcagacccacctcccaaccccgaggggacccgacaggcc
cgaaggaatagaagaagaaggtggagagagagacagagacagatccattcgattagtgaacggatctcgacggtatcgcctttaaaa
gaaaaggggggattgggggtacagtgcagggaaagaatagtagacataatagcaacagacatacaaactaaagaattacaaaaaa
caaattacaaaaattcaaaattttcgggtttattacagggacagcagagatccagtttatcgatcaagcttgggagttccgcgttacataactt
acggtaaatggcccgcctggctgaccgcccaacgacccccgcccattgacgtcaataatgacgtatgttcccatagtaacgccaatag
ggactttccattgacgtcaatgggtggagtatttacggtaaactgcccacttggcagtacatcaagtgtatcatatgccaagtacgcccc
tattgacgtcaatgacggtaaatggcccgcctggcattatgcccagtacatgaccttatgggactttcctacttggcagtacatctacgtat
tagtcatcgctattaccatggtgatgcggttttggcagtacatcaatgggcgtggatagcggtttgactcacggggatttccaagtctcca
ccccattgacgtcaatgggagtttgttttggcaccaaaatcaacggactttccaaaatgtcgtaacaactccgccccattgacgcaaat
gggcggtaggcgtgtacggtgggaggtctatataagcagagctcgtttagtgaaccgtcagatcgcctggagacgccatccacgctgt
tttgacctccatagaagacaccgactctactagaggatctatttccggtgAATTCGCCACCatgagcctcgggctcctgtgctg
tggggcctttctctcctgtgggcaggaccggtgGAAGCTGACATCTACCAGACCCCAAGATACCTTG
TTATAGGGACAGGAAAGAAGATCACTCTGGAATGTTCTCAAACCATGGGCCATG
ACAAAATGTACTGGTATCAACAAGATCCAGGAATGGAACTACACCTCATCCACT
ATTCCTATGGAGTTAATTCCACAGAGAAGGGAGATCTTTCCTCTGAGTCAACAGT
CTCCAGAATAAGGACGGAGCATTTTCCCTGACCCTGGAGTCTGCCAGGCCCTCA
CATACCTCTCAGTACCTCTGTGCCAGCAGTCGGACGCCCAACATTCAGTACTTCG
GCGCCGGGACCCGGCTCTCAGTGCTGGAGGACCTGAAAAACGTGTTCCCACCCG
AACTAGTCgtgtttgagccatcagaagcagagatctcccacacccaaaaggccacactggtgtgcctggccacaggcttctac
cccgaccacgtggagctgagctggtgggtgaatgggaaggaggtgcacagtggggtcagcacagacccgcagcccctcaaggag
cagcccgcccctcaatgactccagatactgcctgagcagccgcctgagggtctcggccacctctctggcagaacccccgcaaccacttc
cgctgtcaagtccagttctacgggctctcggagaatgacgagtggacccaggataggggccaaacctgtcacccagatcgtcagcgcc
gaggcctggggtagagcagactgtggatcacctccgagtataccagcaaggggtcctgtctgccaccatcctctatgagatcttgct
agggaaggccaccttgtatgccgtgctggtcagtgccctcgtgctgatggccatggtcaagagaaaggattccagaggcGGGAG
CGGAGCCACGAACTTCTCTCTGTTAAAGCAAGCAGGAGACTGGAAGAAAACCC
CGGTCCAtgacacgagttagcttgctgtgggcagtcgtggtctccacctgtctcgagtccggcatgGGTCAACAGCT
GAATCAGAGTCCTCAATCTATGTTTATCCAGGAAGGAGAAGATGTCTCCATGAAC
TGCACTTCTTCAAGCATATTTAACACCTGGCTATGGTACAAGCAGGAACCTGGGG
AAGGTCCTGTCCTCTTGATAGCCTTATATAAGGCTGGTGAATTGACCTCAAATGG
AAGACTGACTGCTCAGTTTGGTATAACCAGAAAGGACAGCTTCCTGAATATCTCA
GCATCCATACCTAGTGATGTAGGCATCTACTTCTGTGCTGGCACATACCAGAAAG
TTACCTTTGGAACTGGAACAAAGCTCCAAGTCATCCCAAATATCCAGAACCCTGA
CCCTGCCGTGTACCAGCTGAGAGACTCTAAATCCAGTGACAAGTCTGTCTGCctattc
accgatttgattctcaaacaaatgtgtcacaaagtaaggattctgatgtgtatatcacagacaaaactgtgctagacatgaggtctatgga
cttcaagagcaacagtgctgtggcctggagcaacaaatctgactttgcatgcgcaaacgccttcaacaacagcattattccagaagaca
ccttcttccccagcccagaaagttcctgtgatgtcaagctggtcgagaaaagctttgaaacagatacgaacctaaacttcaaaacctgtc
agtgattgggttccgaatcctcctcctgaaagtggccgggtttaatctgctcatgacgctgcggctgtggtccagcTGActcgaggga
tccgccctctccctccccccccccctaacgttactggccgaagccgcttggaataaggccggtgtgcgtttgtctatatgttattttccac
catattgccgtctttttggcaatgtgagggcccggaaacctggccctgtcttcttgacgagcattcctaggggtctttcccctctcgccaaa
ggaatgcaaggtctgttgaatgtcgtgaaggaagcagttcctctggaagcttcttgaagacaaacaacgtctgtagcgacccttgcag
gcagcggaaccccccacctggcgacaggtgcctctgcggccaaaagccacgtgtataagatacacctgcaaaggcggcacaaccc
cagtgccacgttgtgagttgtgagttgtggaaagagtcaaatggctctcctcaagcgtattcaacaaggggctgaaggatgcccaga
aggtaccccattgtatgggatctgatctggggcctcggtgcacatgattacataccgtgttagtcgaggttaaaaaacgtctaggccccccg
aaccacggggacgtggttttcctttgaaaaacacgatgataatatggtgagcaagggcgaggaggataacatggccatcatcaagga
gttcatgcgcttcaaggtgcacatggagggctccgtgaacggccacgagttcgagatcgagggcgagggcgagggccgccctac
gagggcacccagaccgccaagctgaaggtgaccaaggtgccccctgccttcgcctgggacatcctgtcccccagttcatgtac
ggctccaaggcctacgtgaagcacccgccgacatccccgactacttgaagctgtccttccccgagggcttcaagtgggagcgtg
atgaacttcgaggacggcggcgtggtgaccgtgacccaggactcctcctgcaggacggcgagttcatctacaaggtgaagctgcg
cggcaccaacttcccctccgacggccccgtaatgcagaagaagaccatgggctgggaggcctcctccgagcggatgtaccccgag
gacggcgcctcgaagggcgatcaagcagaggctgaaggtgaaggacggcggccactacgacgctgaggtcaagaccacctac
aaggccaagaagcccgtgcagctgcccggcgcctacaacgtcaacatcaagttggacatcacctcccacaacgaggactacaccat
cgtgaacagtacgaacgccgagggccgccactcaccggcggcatgacgagctgtacaagtgaacgcgtctgaacaatca
acctctggattacaaaatttgtgaaagattgactggtattcttaactatgttgctccttttacgctatgtggatacgctgctttaatgcctttgtat
catgctattgatcccgtatggctttcatttctcctccttgtataaatcctggttgctgtctctttatgaggagttgtggcccgttgtcaggcaa
cgtggcgtggtgtgcactgtgtttgctgacgcaacccccactggttggggcattgccaccacctgtcagctcctttccgggactttcgctt
tccccctccctattgccacggcggaactcatcgccgcctgccttgcccgctgctggacaggggctcggctgttgggcactgacaattc
cgtggtgttgtcggggaagctgacgtcctttccatggctgctcgcctgtgttgccacctggattctgcgcgggacgtccttctgctacgtc
ccttcggccctcaatccagcggaccttccttcccgcggcctgctgccggctctgcggcctcttccgcgtcttcgccttcgccctcagacg
agtcggatctccctttgggccgcctccccgcctggaattaattctgcagtcgagacctagaaaaacatggagcaatcacaagtagcaat
```

TABLE 2-continued

Exemplary Vector Sequences acagcagctaccaatgctgattgtgcctggctagaagcacaagaggaggaggaggtgggttttccagtcacacctcaggtacctttaa
gaccaatgacttacaaggcagctgtagatcttagccacttttttaaaagaaaagagggggactggaagggctaattcactcccaacgaag
acaagatatccttgatctgtggatctaccacacacaaggctacttccctgattagcagaactacacaccagggccaggggtcagatatc
cactgacctttggatggtgctacaagctagtaccagttgagccagataaggtagaagaggccaataaaggagagaacaccagcttgtt
acaccctgtgagcctgcatgggatggatgacccgagagagaagtgttagagtggaggtttgacagccgcctagcatttcatcacgtg
gcccgagagctgcatccggagtacttcaagaactgctgatatcgagcttgctacaagggactttccgctggggactttcagggaggc
gtggcctgggcgggactgggagtggcgagccctcagatcctgcatataagcagctgcttttttgcctgtactgggtctctctggttaga
ccagatctgagcctgggagctctctggctaactagggaacccactgcttaagcctcaataaagcttgccttgagtgcttcaagtagtgtg
tgcccgtctgttgtgtgactctggtaactagagatccctcagaccccttttagtcagtgtggaaaatctctagcagtagtagttcatgtcatctt
attattcagtatttataacttgcaaagaaatgaatatcagagagtgagaggccttgacattgctagcgtttaccgtcgacctctagctagag
cttggcgtaatcatggtcatagctgtttcctgtgtgaaattgttatccgctcacaattccacacaacatacgagccggaagcataaagtgta
aagcctggggtgcctaatgagtgagctaactcacattaattgcgttgcgctcactgcccgctttccagtcgggaaacctgtcgtgccagc
tgcattaatgaatcggccaacgcgcggggagaggcggtttgcgtattgggcgctcttccgcttcctcgctcactgactcgctgcgctcg
gtcgttcggctgcggcgagcggtatcagctcactcaaaggcggtaatacggttatccacagaatcaggggataacgcaggaaagaac
atgtgagcaaaaggccagcaaaaggccaggaaccgtaaaaaggccgcgttgctggcgtttttccataggctccgcccccctgacga
gcatcacaaaaatcgacgctcaagtcagaggtggcgaaacccgacaggactataaagataccaggcgtttccccctggaagctccct
cgtgcgctctcctgttccgaccctgccgcttaccggatacctgtccgcctttctcccttcgggaagcgtggcgctttctcatagctcacgc
tgtaggtatctcagttcggtgtaggtcgttcgctccaagctgggctgtgtgcacgaaccccccgttcagcccgaccgctgcgccttatcc
ggtaactatcgtcttgagtccaacccggtaagacacgacttatcgccactggcagcagccactggtaacaggattagcagagcgaggt
atgtaggcggtgctacagagttcttgaagtggtggcctaactacggctacactagaagaacagtatttggtatctgcgctctgctgaagc
cagttaccttcggaaaaagagttggtagctcttgatccggcaaacaaaccaccgctggtagcggtggtttttttgtttgcaagcagcagat
tacgcgcagaaaaaaaggatctcaagaagatcctttgatcttttctacggggtctgacgctcagtggaacgaaaactcacgttaaggga
ttttggtcatgagattatcaaaaaggatcttcacctagatccttttaaattaaaaatgaagttttaaatcaatctaaagtatatatgagtaaactt
ggtctgacagttaccaatgcttaatcagtgaggcacctatctcagcgatctgtctatttcgttcatccatagttgcctgactccccgtcgt
agataactacgatacgggagggcttaccatctggccccagtgctgcaatgataccgcgagacccacgctcaccggctccagatttatc
agcaataaaccagccagccggaagggccgagcgcagaagtggtcctgcaactttatccgcctccatccagtctattaattgttgccgg
gaagctagagtaagtagttcgccagttaatagtttgcgcaacgttgttgccattgctacaggcatcgtggtgtcacgctcgtcgtttggtat
ggcttcattcagctccggttcccaacgatcaaggcgagttacatgatcccccatgttgtgcaaaaaagcggttagctccttcggtcctcc
gatcgttgtcagaagtaagttggccgcagtgttatcactcatggttatggcagcactgcataattctcttactgtcatgccatccgtaagat
gcttttctgtgactggtgagtactcaaccaagtcattctgagaatagtgtatgcggcgaccgagttgctcttgcccggcgtcaatacggg
ataataccgcgccacatagcagaactttaaaagtgctcatcattggaaaacgttcttcggggcgaaaactctcaaggatcttaccgctgtt
gagatccagttcgatgtaacccactcgtgcacccaactgatcttcagcatcttttactttcaccagcgtttctgggtgagcaaaaacagga
aggcaaaatgccgcaaaaaagggaataagggcgacacggaaatgttgaatactcatactcttcctttttcaatattattgaagcatttatca
gggttattgtctcatgagcggatacatatttgaatgtatttagaaaaataaacaaataggggttccgcgcacatttccccgaaaagtgcca
cctgacgtcgacggatcgggagatcaacttgtttattgcagcttataatggttacaaataaagcaatagcatcacaaatttcacaaataaa
gcattttttcactgcattctagttgtggtttgtccaaactcatcaatgtatcttatcatgtctggatcaactggataactcaagctaaccaaaat
catcccaaacttcccaccccatacctattaccactgccaattacctgtgtttcatttactctaaacctgtgattcctctgaattattttcattttt
aaagaaattgtatttgttaaatatgtacaaacttagtagt (SEQ ID NO: 26)

pLVX-CMV-TCR2 (FIG. 9):
tggaagggctaattcactcccaaagaagacaagatatccttgatctgtggatctaccacacacaaggctacttccctgattagcagaact
acacaccagggccagggtcagatatccactgacctttggatggtgctacaagctagtaccagttgagccagataaggtagaagagg
ccaataaaggagagaacaccagcttgttacaccctgtgagcctgcatgggatggatgacccgagagagaagtgttagagtggaggt
ttgacagccgcctagcatttcatcacgtggcccgagagctgcatccggagtacttcaagaactgctgatatcgagcttgctacaaggga
ctttccgctggggactttccagggaggcgtggcctgggcgggactggggagtggcgagccctcagatcctgcatataagcagctgct
ttttgcctgtactgggtctctctggttagaccagatctgagcctgggagctctctggctaactagggaacccactgcttaagcctcaataa
agcttgccttgagtgcttcaagtagtgtgtgcccgtctgttgtgtgactctggtaactagagatccctcagacccttttagtcagtgtggaa
aatctctagcagtggcgcccgaacagggacttgaaagcgaaagggaaaccagaggagctctctcgacgcaggactcggcttgctga
agcgcgcacggcaagaggcgaggggcggcgactggtgagtacgccaaaaattttgactagcggaggctagaaggagagagatgg
gtgcgagagcgtcagtattaagcggggagaattagatcgcgatgggaaaaaattcggttaaggccagggggaaagaaaaaatata
aattaaaacatatagtatgggcaagcagggagctagaacgattcgcagttaatcctggcctgttagaaacatcagaaggctgtagacaa
atactgggacagctacaaccatcccttcagacaggatcagaagaacttagatcattatataatacagtagcaaccctctattgtgtgcatc
aaaggatagagataaaagacaccaaggaagctttagacaagatagaggaagagcaaaacaaaagtaagaccaccgcacagcaag
cggccggccgctgatcttcagacctggaggaggagatatgagggacaattggagaagtgaattatataaatataaagtagtaaaaattg
aaccattaggagtagcacccaccaaggcaaagagaagagtggtgcagagagaaaaaagagcagtgggaataggagctttgttcctt
gggttcttgggagcagcaggaagcactatgggcgcagcgtcaatgacgctgacggtacaggccagacaattattgtctggtatagtgc
agcagcagaacaatttgctgagggctattgaggcgcaacagcatctgttgcaactcacagtctggggcatcaagcagctccaggcaa
gaatcctggctgtggaaagatacctaaaggatcaacagctcctggggatttggggttgctctggaaaactcatttgcaccactgctgtgc
cttggaatgctagttggagtaataaatctctggaacagatttggaatcacacgacctggatggagtgggacagagaaattaacaattaca
caagcttaatacactccttaattgaagaatcgcaaaaccagcaagaaaagaatgaacaagaattattggaattagataaatgggcaagtt
tgtggaattggtttaacataacaaattggctgtggtatataaaattattcataatgatagtaggaggcttggtaggtttaagaatagtttttgct
gtactttctatagtgaatagagttaggcagggatattcaccattatcgtttcagacccacctcccaaccccgaggggacccgacaggcc
cgaaggaatagaagaagaaggtggagagagagacagagacagatccattcgattagtgaacggatctcgacggtatcgcctttaaaa
gaaagggggggattggggggtacagtgcaggggaaagaatagtagacataatagcaacagacatacaaactaaagaattacaaaaa
caaattacaaaaattcaaaattttcgggtttattacagggacagcagagatccagtttggttacgtaaatggcccgcctggctgaccgcccaacgacccccgcccattgacgtcaataatgacgtatgttcccatagtaacgccaatag
ggactttccattgacgtcaatgggtggagtatttacggtaaactgcccacttggcagtacatcaagtgtatcatatgccaagtacgcccc
tattgacgtcaatgacggtaaatggcccgcctggcattatgcccagtacatgaccttatgggactttcctacttggcagtacatctacgtat
tagtcatcgctattaccatggtgatgcggttttggcagtacatcaatgggcgtggatagcggtttgactcacggggatttccaagtctcca
ccccattgacgtcaatgggagtttgttttggcaccaaaatcaacgggactttccaaaatgtcgtaacaactccgccccattgacgcaaat
gggcggtaggcgtgtacggtgggaggtctatataagcagagctcgtttagtgaaccgtcagatcgcctggagacgccatccacgctgt
tttgacctccatagaagacaccgactctactagaggatctatttccggtgAATTCGCCACCatgggacccaggctcctatctg
ggcactgattgtctcctcggaaCCGGTCCGGTTGAAGCTGACATCTACCAGACCCCAAGATAC
CTTGTTATAGGGACAGGAAAGAAGATCACTCTGGAATGTTCTCAAACCATGGGC
CATGACAAAATGTACTGGTATCAACAAGATCCAGGAATGGAACTACACCTCATC
CACTATTCCTATGGAGTTAATTCCACAGAGAAGGGAGATCTTTCCTCTGAGTCAA
CAGTCTCCAGAATAAGGACGGAGCATTTTCCCCTGACCCTGGAGTCTGCCAGGCC
CTCACATACCTCTCAGTACCTCTGTGCCAGCAGTCGGACGCCCAACATTCAGTAC TABLE 2-continued Exemplary Vector Sequences

```
TTCGGCGCCGGGACCCGGCTCTCAGTGCTGGAGGACCTGAAAAACGTGTTCCCAC
CCGAgGCGGCCGCgtttgagccatcagaagcagagatctcccacacccaaaaggccacactggtgtgcctggccacagg
cttctaccccgaccacgtggagctgagctggtgggtgaatgggaaggaggtgcacagtggggtcagcacgaccgcagccccc
aaggagcagcccgccctcaatgactccagatactgcctgagcagccgcctgagggtctcggccaccttctggcagaaccccgcaa
ccacttccgctgtcaagtccagttctacgggctctcggagaatgacgagtggacccaggatagggccaaacctgtcacccagatcgtc
agcgccgaggcctggggtagagcagactgtggcttcacctccgagtcttaccagcaagggggtcctgtctgccaccatcctctatgaga
tcttgctagggaaggccaccttgtatgccgtgctggtcagtgccctcgtgctgatggccatggtcaagagaaaggattccagaggcG
GGAGCGGAGCCACGAACTTCTCTCTGTTAAAGCAAGCAGGAGACGTGGAAGAAA
ACCCCGGTCCTatgaactcctctctggactttctaattctgatcttaatgtttggaggaACTAGTGGTCAACAGC
TGAATCAGAGTCCTCAATCTATGTTTATCCAGGAAGGAGAAGATGTCTCCATGAA
CTGCACTTCTTCAAGCATATTTAACACCTGGCTATGGTACAAGCAGGAACCTGGG
GAAGGTCCTGTCCTCTTGATAGCCTTATATAAGGCTGGTGAATTGACCTCAAATG
GAAGACTGACTGCTCAGTTTGGTATAACCAGAAAGGACAGCTTCCTGAATATCTC
AGCATCCATACCTAGTGATGTAGGCATCTACTTCTGTGCTGGCACATACCAGAAA
GTTACCTTTGGAACTGGAACAAAGCTCCAAGTCATCCCAAATATCCAGAACCCTG
ACCCTGCCGTGTACCAGCTGAGAGACTCTAAATCCAGTGACAAGTCTGCATGCctat
tcaccgatttgattctcaaacaaatgtgtcacaaagtaaggattctgatgtgtatatcacagacaaaactgtgctagacatgaggtctatg
gacttcaagagcaacagtgctgtggcctggagcaacaaatctgactttgcatgtgcaaacgccttcaacaacagcattattccagaaga
cccttcttccccagcccagaaagttcctgtgatgtcaagctgtcgagaaaagcatacgaacctaaacttttcaaaacct
gtcagtgattgggttccgaatcctcctcctgaaagtggccgggtttaatctgctcatgacgctgcggctgtggtccagcTGActcgag
ggatcccgcccctctccctccccccccccctaacgttactggccgaagccgcttgaataaggccggtgtgcgtttgtctatatgttattttc
caccatattgccgtatttggcaatgtgagggcccggaaacctggccctgtatcttgacgagcattcctaggggtattcccctctcgcc
aaaggaatgcaaggtctgttgaatgtcgtgaaggaagcagttcctctggaagcttcttggaagacaaaacaacgtctgtagcgaccccttgc
aggcagcggaaccccccaccctggcgacaggtgcctctgccggccaaaagccacgtgtataagatacacctgcaaaggcggcacaac
cccagtgccacgttgtgagttggatagttgtggaaagagtcaaatggctcacctcaagcgtattcaacaaggggctgaaggatgccca
gaaggtaccccattgtatgggatctgatctggggcctcggtgcacatgctttacatgtgtttagtcgaggttaaaaaacgtctaggcccc
cgaaccacggggacgtggttttccttttgaaaaacacgatgataatatggtgagcaaggcgaggaggataacatggccatcatcaag
gagttcatgcgcttcaaggtgcacatggagggctccgtgaacggccacgagttcgagatcgaggcgagggcgagggccgcccct
acgagggcacccagaccgccaagctgaaggtgaccaagggtggccccctgcccttcgcctgggacatcctgtcccctcagttcatgt
acggctccaaggcctacgtgaagcacccgccgacatccccgactacttgaagctgtccttccccgagggcttcaagtgggagcgcg
tgatgaacttcgaggacggcggcgtggtgaccgtgacccaggactccccctgcaggacggcgagttcatctacaaggtgaagctgc
gcggcaccaacttccccctccgacggccccgtaatgcagaagaagaccatgggctgggagcctcctccgagcggatgtaccccga
ggacggcgccctgaagggcgagatcaagcagaggctgaagctgaaggacggcggccactacgacgctgaggtcaagaccaccta
caaggccaagaagcccgtgcagctgcccggcgcctacaacgtcaacatcaagttggacatcacctcccacaacgaggactacacca
tcgtggaacagtacgaacgcgccgagggccgccactccaccggcggcatggacgagctgtacaagtgaacgcgtctggaacaatc
aacctctggattacaaaatttgtgaaagattgactggtattcttaactatgttgctccttttacgctatgtggatacgctgattaatgcattgt
atcatgctattgatcccgtatggctttcatttctcctccttgtataaatcctggttgctgtctctttatgaggagttgtggcccgttgtcaggc
aacgtggcgtggtgtgcactgtgtttgctgacgcaacccccactggttggggcattgccaccacctgtcagctcctttccgggactttcg
ctttccccctccctattgccacggcggaactcatcgccgcctgccttgcccgctgctggacaggggctcggctgttgggcactgacaat
tccgtggtgttgtcggggaagctgacgtccttttccatggctgctccgcctgtgcttgccgggtgctcgcgggagctccttctctgctacg
tccatcggccctcaatccagcggaccttccttcccgcggcctgctgccggctctgcggcctatccgcgtatcgccttcgccctcaga
cgagtcggatctccctttgggccgcctccccgcctggaattaattctgcagtcgagacctagaaaaacatggagcaatcacaagtagc
aatacagcagctaccaatgctgattgtgcctggctagaagcacaagaggaggaggaggtgggttttccagtcacacctcaggtacctt
aagaccaatgacttacaaggcagctgtagatcttagccacttttttaaaagaaaaggggggactgaaagggctaattcactcccaacgaa
gacaagatatccttgatctgtggatctaccacacacaaggctacttccctgattagcagaactacacaccagggccagggtcagatat
ccactgacctttggatggtgctacaagctagtaccagttgagccagataaggtagaagaggccaataaaggagagaacaccagcttgt
tacaccctgtgagcctgcatgggatggatgacccggagagagaagtgttagagtggaggtttgacagccgcctagcatttcatcacgt
ggcccgagagctgcatccggagtacttcaagaactgctgatatcgagcttgctacaagggactttccgctggggactttccagggagg
cgtggcctgggcgggactggggagtggcgagccctcagatcctgcatataagcagctgcttttttgcctgtactgggtctctctggttag
accagatctgagcctgggagctctctggctaactagggaacccactgcttaagcctcaataaagcttgccttgagtgcttcaagtagtgt
gtgcccgtctgttgtgtgactctggtaactagagatccctcagacccttttagtcagtgtggaaaatctctagcagtagtagttcatgtcatc
ttattattcagtatttataacttgcaaagaaatgaatatcagagagtgagaggccttgacattgctagcgttttaccgtcgacctctagctaga
gcttggcgtaatcatggtcatagctgtttcctgtgtgaaattgttatccgctcacaattccacacaacatacgagccggaagcataaagtgt
aaagcctggggtgcctaatgagtgagctaactcacattaattgcgttgcgctcactgcccgctttccagtcgggaaacctgtcgtgccag
ctgcattaatgaatcggccaacgcgcggggagaggcggtttgcgtattgggcgctcttccgcttcctcgctcactgactcgctgcgctc
ggtcgttcggctgcggcgagcggtatcagctcactcaaaggcggtaatacggttatccacagaatcaggggataacgcaggaaaga
acatgtgagcaaaaggccagcaaaaggccaggaaccgtaaaaaggccgcgttgctggcgtttttccataggctccgcccccctgacg
agcatcacaaaaatcgacgctcaagtcagaggtggcgaaacccgacaggactataaagataccaggcgtttccccctggaagctccc
tcgtgcgctctcctgttccgaccctgccgcttaccggatacctgtccgcctttctcccttcgggaagcgtggcgctttctcatagctcacg
ctgtaggtatctcagttcggtgtaggtcgttcgctccaagctgggctgtgtgcacgaaccccccgttcagcccgaccgctgcgcctatc
cggtaactatcgtcttgagtccaacccggtaagacacgacttatcgccactggcagcagccactggtaacaggattagcagagcgagg
gtatgtaggcggtgctacagagttcttgaagtggtggcctaactacggctacactagaagaacagtatttggtatctgcgctctgctgaa
gccagttaccttcggaaaaagagttggtagctcttgatccggcaaacaaaccaccgctggtagcggtggtttttttgtttgcaagcagca
gattacgcgcagaaaaaaaggatctcaagaagatcctttgatcttttctacggggtctgacgctcagtggaacgaaaactcacgttaag
ggattttggtcatgagattatcaaaaaggatcttcacctagatccttttaaattaaaaatgaagttttaaatcaatctaaagtatatatgagtaa
acttggtctgacagttaccaatgcttaatcagtgaggcacctatctcagcgatctgtctatttcgttcatccatagttgcctgactccccgtc
gtgtagataactacgatacgggagggcttaccatctggccccagtgctgcaatgataccgcgagacccacgctcaccggctccagatt
tatcagcaataaaccagccagccggaagggccgagcgcagaagtggtcctgcaacttatccgcctccatccagtctattaattgttgc
cgggaagctagagtaagtagttcgccagttaatagtttgcgcaacgttgttgccattgctacaggcatcgtggtgtcacgctcgtcgtttg
gtatggcttcattcagctccggttcccaacgatcaaggcgagttacatgatcccccatgttgtgcaaaaaagcggttagctccttcggtcc
tccgatcgttgtcagaagtaagttggccgcagtgttatcactcatggttatggcagcactgcataattctcttactgtcatgccatccgtaag
atgcttttctgtgactggtgagtactcaaccaagtcattctgagaatagtgtatgcggcgaccgagttgctcttgcccggcgtcaatacgg
gataatacccgccacatagcagaactttaaaagtgctcatcattggaaaacgttcttcggggcgaaaactctcaaggatcttaccgctgtt
gagatccagttcgatgtaacccactcgtgcacccaactgatcttcagcatcttttactttcaccagcgtttctgggtgagcaaaaacagg
aaggcaaaatgccgcaaaaaagggaataagggcgacacggaaatgttgaatactcatactcttcctttttcaatattattgaagcatttatc
agggttattgtctcatgagcggatacatatttgaatgtatttagaaaaataaacaaataggggttccgcgcacatttccccgaaaagtgcc
acctgacgtcgacggatcgggagatcaacttgtttattgcagcttataatggttacaaataaagcaatagcatcacaaatttcacaaataa
agcatttttttcactgcattctagttgtggtttgtccaaactcatcaatgtatcttatcatgtctggatcaactggataactcaagctaaccaaa
```

TABLE 2-continued

Exemplary Vector Sequences atcatcccaaacttcccaccccatacccctattaccactgccaattacctgtggtttcatttactctaaacctgtgattcctctgaattattttcatt
ttaaagaaattgtatttgttaaatatgtactacaaacttagtagt (SEQ ID NO: 27)

pLVX-CMV-TCR3 (FIG. 10):
tggaagggctaattcactcccaaagaagacaagatatccttgatctgtggatctaccacacacaaggctacttccctgattagcagaact
acacaccagggccaggggtcagatatccactgacctttggatggtgctacaagctagtaccagttgagccagataaggtagaagagg
ccaataaaggagagaaccaccagcttgttacaccctgtgagcctgcatgggatggatgaccggagagagaagtgttagagtggaggt
ttgacagccgcctagcatttcatcacgtggcccgagagctgcatccggagtacttcaagaactgctgatatcgagcttgctacaaggga
ctttccgctggggactttccagggaggcgtggcctgggcgggactggggagtggcgagccctcagatcctgcatataagcagctgct
ttttgcctgtactgggtctctctggttagaccagatctgagcctgggagctctctggctaactagggaacccactgcttaagcctcaataa
agcttgccttgagtgcttcaagtagtgtgtgcccgtctgttgtcgtgactctgtaactagagatccctcagacccttttagtcagtgtggaa
aatctctagcagtggcgcccgaacagggacttgaaagcgaaagggaaaccagaggagctctctcgacgcaggactcggcttgctga
agcgcgcacggcaagaggcgaggggcggcgactggtgagtacgccaaaaattttgactagcggaggctagaaggagagagatgg
gtgcgagagcgtcagtattaagcggggggagaattagatcgcgatgggaaaaaattcggttaaggccaggggaaagaaaaaatata
aattaaaacatatagtatgggcaagcagggagctagaacgattcgcagttaatcctggcctgttagaaacatcagaaggctgtagacaa
atactgggacagctacaaccatcccttcagacaggatcagaagaacttagatcattatataatacagtagcaaccctctattgtgtgcatc
aaaggatagagataaaagacaccaaggaagctttagacaagatagaggaagagcaaaacaaaagtaagaccaccgcacagcaag
cggccggccgctgatcttcagacctggaggaggagatatgagggacaattggagaagtgaattatataaatataaagtagtaaaaattg
aaccattaggagtagcacccaccaaggcaaagagaagtggtgcagagagaaaaaagacagtgggaataggagctttgttccttt
gggttcttgggagcagcaggaagcactatgggcgcagcgtcaatgacgctgacggtacaggccagacaattattgtctggtatagtgc
agcagcagaacaatttgctgagggctattgaggcgcaacagcatctgttgcaactcacagtctggggcatcaagcagctccaggcaa
gaatcctggctgtgaaagataccctaaaggatcaacagctcctggggatttggggttgctctggaaaactcatttgcaccactgctgtgc
cttggaatgctagttggagtaataaatctctggaacagatttggaatcacacgacctggatggagtgggacagagaaattaacaattaca
caagataatacactccttaattgaagaatcgcaaaaccagcaagaaaagaatgaacaagaattattggaattagataaatgggcaagtt
tgtggaattggtttaacataacaaattggctgtggtatataaaattattcataatgatagtaggaggcttggtaggtttaagaatagttttgct
gtactttctatagtgaatagagttaggcagggatattcaccattatcgtttcagacccacctcccaaccccgaggggacccgacaggcc
cgaaggaatagaagaagaaggtggagagagagacagagacagatccattcgattagtgaacggatctcgacggtatcgccttaaaa
gaaaggggggattggggggtacagtgcaggggaaagaatagtagacataatagcaacagacatacaaactaaagaattacaaaaa
caaattacaaaaattcaaaattttcgggtttattacagggacagcagagatccagtttatcgataagcttgggagttccgcgttacataactt
acggtaaatggcccgcctggctgaccgcccaacgacccccgcccattgacgtcaataatgacgtatgttcccatagtaacgccaatag
ggactttccattgacgtcaatgggtggagtatttacggtaaactgcccacttggcagtacatcaagtgtatcatatgccaagtacgcccc
tattgacgtcaatgacggtaaatggcccgcctggcattatgcccagtacatgaccttatgggactttcctacttggcagtacatctacgtat
tagtcatcgctattaccatggtgatgcggttttggcagtacatcaatgggcgtggatagcggtttgactcacggggatttccaagtctcca
ccccattgacgtcaatgggagtttgttttggcaccaaaatcaacgggactttccaaaatgtcgtaacaactccgccccattgacgcaaat
gggcggtaggcgtgtacggtgggaggtctatataagcagagctcgtttagtgaaccgtcagatcgcctggagacgccatccacgctgt
tttgacctccatagaagacaccgactctactagaggatctatttccggtgAATTCGCCACCatgggcacaaggttgttcttctat
gtggccctttgtctcctgtggaccggtcacatgGAAGCTGACATCTACCAGACCCCAAGATACCTTGT
TATAGGGACAGGAAAGAAGATCACTCTGGAATGTTCTCAAACCATGGGCCATGA
CAAAATGTACTGGTATCAACAAGATCCAGGAATGGAACTACACCTCATCCACTAT
TCCTATGGAGTTAATTCCACAGAGAAGGGAGATCTTTCCTCTGAGTCAACAGTCT
CCAGAATAAGGACGGAGCATTTTCCCCTGACCCTGGAGTCTGCCAGGCCCTCACA
TACCTCTCAGTACCTCTGTGCCAGCAGTCGGACGCCCAACATTCAGTACTTCGGC
GCCGGGACCCGGCTCTCAGTGCTGgaggacctgaaaaacgtgttcccacccgaggtcgctgtgtttgagccatc
agaagcagagatctcccacaccaaaaggccacACTAGTgtgcctggcccacaggcttctaccccgaccacgtggagctgagct
ggtgggtgaatgggaaggaggtgcacagtgggtcagcacagacccgcagcccctcaaggagcagcccgccctcaatgactcca
gatactgcctgagcagccgcctgagggtctcggccaccttctggcagaaccccgcaaccacttccgctgtcaagtccagttctacgg
gctctcggagaatgacgagtggaccccaggatagggccaaacctgtcacccagatcgtcagcgccgaggcctggggtagagcagac
tgtgggttcacctccgagtcttaccagcaagggggtcctgtctgccaccatcctctatgagatcttgctagggaaggccaccttgtatgcc
gtgctggtcagtgccctcgtgctgatggccatggtcaagagaaaggattccagaggcGGGAGCGGAGCCACGAAC
TTCTCTCTGTTAAAGCAAGCAGGAGACGTGGAAGAAAACCCCGGTCCTatggcaggca
ttcgagctttatttatgtacttgtggctgcagctggactgggtctcgagaGGTCAACAGCTGAATCAGAGTCCTC
AATCTATGTTTATCCAGGAAGGAGAAGATGTCTCCATGAACTGCACTTCTTCAAG
CATATTTAACACCTGGCTATGGTACAAGCAGGAACCTGGGGAAGGTCCTGTCCTC
TTGATAGCCTTATATAAGGCTGGTGAATTGACCTCAAATGGAAGACTGACTGCTC
AGTTTGGTATAACCAGAAAGGACAGCTTCCTGAATATCTCAGCATCCATACCTAG
TGATGTAGGCATCTACTTCTGTGTGGCACATACCAGAAAGTTACCTTTGGAACT
GGAACAAAGCTCCAAGTCATCCCAaatatccagaaccctgaccctgccgtgtaccagctgagagactctaaatc
cagtgacaagtctgtctgcctattcaccgattttgattctcaaacaaatgtgtcacaaagtaaggattctgatgtgtatatcacagacaaaa
ctgtgctagacatgaggtctatggacttcaagagcaacagtGCGGCCgcctggagcaacaaatctgactttgcatgtgcaaacgc
cttcaacaacagcattattccagaagacaccttctccccagcccagaaagttcctgtgatgtcaagctggtcgagaaaagctttgaaac
agatacgaacctaaactttcaaaacctgtcagtgattggttccgaatcctctcctgaaagtggccgggttttaatctgctcatgacgctg
cggctgtggtccagcTGActcgagggatcccgcccctctccctcccccccccctaacgttactggccgaagccgcttggaataagg
ccggtgtgcgtttgtctatatgttattttccaccatattgccgtcttttggcaatgtgagggcccggaaacctggccctgtcttcttgacgag
cattcctaggggtattccctctcgccaaaggaatgcaaggtctgttgaatgtcgtgaaggaagcagttcctctggaagcttcttgaaga
caaacaacgtctgtagcgaccctttgcaggcagcggaaccccccacctggcgacaggtgcctctgcggccaaaagccacgtgtata
agatacacctgcaaaggcggcacaaccccagtgccacgttgtgagttggatagttgtggaaagagtcaaatggctcacctcaagcgta
ttcaacaaggggctgaaggatgcccagaaggtaccccattgtatgggatctgatctggggcctcggtgcacatgctttacatgtgtttag
tcgaggttaaaaaacgtctaggccccccgaaccacggggacgtggttttcctttgaaaaacacgatgataatatggtgagcaagggcg
aggaggataacatggccatcatcaaggagttcatgcgcttcaaggtgcacatggagggctccgtgaacggccacgagttcgagatcg
agggcgagggcgagggccgcccctacgagggcacccagaccgccaagctgaaggtgaccaaggcgcccctgcccttcgcct
gggacatcctgtccccctcagttcatgtacggctcaaggcctacgtgaagcaccccgccgacatccccgactacttgaagctgtccttc
cccgagggcttcaagtgggagcgcgtgatgaacttcgaggacggcggcgtggtgaccgtgacccaggactcctccctgcaggacg
gcgagttcatctacaaggtgaagctgcgcggcaccaacttccccccagatggccccaagcagaagagaccatgggctgggggag
gcctcctccgagcggatgtaccccgaggacggcgccctgaagggcgagatcaagcagaggctgaagctgaaggacggcggcca
ctacgacgctgaggtcaagaccacctacaaggccaagaagcccgtgcagctgcccggcgcctacaacgtcaacatcaagttggaca
tcacctcccacaacgaggactacaccatcgtggaacagtacgaacgcgccgagggccgccactccaccggcggcatggacgagct
gtacaagtgaacgcgtctgaacaatcaacctctggattacaaaatttgtgaaagattgactggtattcttaactatgttgctccttttacgct
atgtggatacgctgattaatgcattgtatcatgctattgatcccgtatggctttcattttctcctccttgtataaatcctggttgctgtctatta TABLE 2-continued Exemplary Vector Sequences tgaggagttgtggcccgttgtcaggcaacgtggcgtggtgtgcactgtgtttgctgacgcaaccccactggttggggcattgccacca
cctgtcagctccttccgggacttttcgctttccccctccctattgccacggcggaactcatcgccgcctgccttgcccgctgctggacag
gggctcggctgttgggcactgacaattccgtggtgttgtcggggaagctgacgtccttcccatggctgctcgcctgtgttgccacctgga
ttctgcgcgggacgtccttctgctacgtccctcggccctcaatccagcggaccttccttcccgcggcctgctgccggctctgcggcctc
ttccgcgtcttcgccttcgccctcagacgagtcggatctcccctttgggccgcctccccgcctggaattaattctgcagtcgagacctaga
aaaacatggagcaatcacaagtagcaatacagcagctaccaatgctgattgtgcctggctagaagcacaagaggaggaggaggtgg
gttttccagtcacacctcaggtaccttttaagaccaaatgacttacaaggcagctgtagatcttagccacttttttaaaagaaaagaggggact
ggaagggctaattcactcccaacgaagacaagatatccttgatctgtggatctaccacacacaaggctacttccctgattagcagaacta
cacaccagggccaggggtcagatatccactgacctttggatggtgctacaagctagtaccagttgagccagataaggtagaagaggc
caataaaggagagaacaccagcttgttacaccctgtgagcctgcatgggatggatgacccggagagagaagtgttagagtggaggtt
tgacagccgcctagcatttcatcacgtggcccgagagctgcatccggagtacttcaagaactgctgatatcgagcttgctacaagggac
tttccgctggggacttttccagggaggcgtggcctgggcggactggggagtggcgagccctcagatcctgcatataagcagctgcttt
ttgcctgtactgggtctctctggttagaccagatctgagcctgggagctctctggctaactagggaacccactgcttaagcctcaataaa
gcttgccttgagtgcttcaagtagtgtgtgcccgtctgttgtgtgactctggtaactagagatccctcagaccccttttagtcagtgtggaaa
atctctagcagtagtagttcatgtcatcttattattcagtatttataacttgcaaagaaatgaatatcagagagtgagaggccttgacattgct
agcgtttaccgtcgacctctagctagagactttggcgtaatcatggtcatagctgtttcctgtgtgaaattgttatccgctcacaattccacaca
acatacgagccggaagcataaagtgtaaagcctggggtgcctaatgagtgagctaactcacattaattgcgttgcgctcactgcccgct
ttccagtcgggaaacctgtcgtgccagctgcattaatgaatcggccaacgcgcggggagaggcggtttgcgtattgggcgctcttccg
cttcctcgctcactgactcgctgcgctcggtcgttcggctgcggcgagcggtatcagctcactcaaaggcggtaatacggttatccaca
gaatcaggggataacgcaggaaagaacatgtgagcaaaaggccagcaaaaggccaggaaccgtaaaaaggccgcgttgctggcg
tttttccataggctccgcccccctgacgagcatcacaaaaatcgacgctcaagtcagaggtggcgaaacccgacaggactataaagat
accaggcgtttccccctggaagctccctcgtgcgctctcctgttccgaccctgccgcttaccggatacctgtccgcctttctcccttcggg
aagcgtggcgctttctcatagctcacgctgtaggtatctcagttcggtgtaggtcgttcgctccaagctgggctgtgcacgaaccccc
cgttcagcccgaccgctgcgccttatccggtaactatcgtcttgagtccaacccggtaagacacgacttatcgccactggcagcagcca
ctggtaacaggattagcagagcgaggtatgtaggcggtgctacagagttcttgaagtggtggcctaactacggctacactagaagaac
agtatttggtatctgcgctctgctgaagccagttaccttcggaaaaagagttggtagctcttgatccggcaaacaaaccaccgctggtag
cggtggtttttttgtttgcaagcagcagattacgcgcagaaaaaaaggatctcaagaagatcctttgatcttttctacggggtctgacgctc
agtggaacgaaaactcacgttaagggattttggtcatgagattatcaaaaaggatcttcacctagatccttttaaattaaaaatgaagtttta
aatcaatctaaagtatatatgagtaaacttggtctgacagttaccaatgcttaatcagtgaggcacctatctcagcgatctgtctatttcgttc
atccatagttgcctgactccccgtcgtgtagataactacgatacgggagggcttaccatctggccccagtgctgcaatgataccgcgag
acccacgctcaccggctccagatttatcagcaataaaccagccagccggaagggccgagcgcagaagtggtcctgcaacttatccg
cctccatccagtctattaattgttgccgggaagctagagtaagtagttcgccagttaatagtttgcgcaacgttgttgccattgctacaggc
atcgtggtgtcacgctcgtcgtttggtatggcttcattcagctccggttcccaacgatcaaggcgagttacatgatccccatgttgtgcaa
aaaagcggttagctccttcggtcctccgatcgttgtcagaagtaagttggccgcagtgttatcactcatggttatggcagcactgcataatt
ctcttactgtcatgccatccgtaagatgcttttctgtgactggtgagtactcaaccaagtcattctgagaatagtgtatgcggcgaccgagt
tgctcttgcccggcgtcaatacgggataataccgcgccacatagcagaactttaaaagtgctcatcattggaaaacgttcttcggggcg
aaaactctcaaggatcttaccgctgttgagatccagttcgatgtaacccactcgtgcacccaactgatcttcagcatcttttactttcaccag
cgtttctgggtgagcaaaaacaggaaggcaaaatgccgcaaaaaagggaataagggcgacacggaaatgttgaatactcatactctt
cctttttcaatattattgaagcatttatcagggttattgtctcatgagcggatacatatttgaatgtatttagaaaaataaacaaataggggttc
cgcgcacatttccccgaaaagtgccacctgacgtcgacggatcgggagatcaacttgtttattgcagcttataatggttacaaataaagc
aatagcatcacaaatttcacaaataaagcatttttttcactgcattctagttgtggtttgtccaaactcatcaatgtatcttatcatgtctggatc
aactggataactcaagctaaccaaaatcatcccaaacttcccaccccataccctattaccactgccaatacctgtggtttcatttactctaa
acctgtgattcctctgaattattttcattttaaagaaattgtatttgttaaatatgtactacaaacttagtagt (SEQ ID NO: 28)

pLVX-CMV-TCR4 (FIG. 11):
tggaagggctaattcactcccaaagaagacaagatatccttgatctgtggatctaccacacacaaggctacttccctgattagcagaact
acacaccagggccaggggtcagatatccactgacctttggatggtgctacaagctagtaccagttgagccagataaggtagaagagg
ccaataaaggagagaacaccagcttgttacaccctgtgagcctgcatgggatggatgacccggagagagaagtgttagagtggaggt
ttgacagccgcctagcatttcatcacgtggcccgagagctgcatccgagtacttcaagaactgctgatatcgagcttgctacaagggga
ctttccgctggggactttccagggaggcgtggcctgggcgggactggggagtggcgagccctcagatcctgcatataagcagctgct
ttttgcctgtactgggtctctctggttagaccagatctgagcctgggagctctctggctaactagggaacccactgcttaagcctcaataa
agcttgccttgagtgcttcaagtagtgtgtgcccgtctgttgtgtgactctggtaactagagatccctcagacccctttagtcagtgtggaa
aatctctagcagtggcgcccgaacagggacttgaaagcgaaagggaaaccagaggagctctctcgacgcaggactcggcttgctga
agcgcgcacggcaagaggcgaggggcggcgactggtgagtacgccaaaaattttgactagcggaggctagaaggagagagatgg
gtgcgagagcgtcagtattaagcggggagaattagatcgcgatgggaaaaaattcggttaaggccagggggaaagaaaaaatata
aattaaaacatatagtatgggcaagcagggagctagaacgattcgcagttaatcctggcctgttagaaacatcagaaggctgtagacaa
atactgggacagctacaaccatcccttcagacaggatcagaagaacttagatcattatataatacagtagcaaccctctattgtgtgcatc
aaaggatagagataaaagacaccaaggaagctttagacaagatagaggaagagcaaaacaaaagtaagaccaccgcacagcaag
cggccggccgctgatcttcagacctggaggaggagatatgagggacaattggagaagtgaattatataaatataaagtagtaaaaattg
aaccattaggagtagcacccaccaaggcaaagagaagagtggtgcagagagaaaaaagagcagtgggaataggagctttgttcctt
gggttcttgggagcagcaggaagcactatgggcgcagcgtcaatgacgctgacggtacaggccagacaattattgtctggtatagtgc
agcagcagaacaatttgctgagggctattgaggcgcaacagcatctgttgcaactcacagtctggggcatcaagcagctccaggcaa
gaatcctggctgtggaaagatacctaaaggatcaacagctcctggggatttggggttgctctggaaaactcatttgcaccactgctgtgc
cttggaatgctagttggagtaataaatctctggaacagatttggaatcacacgacctggatggagtgggacagagaaattaacaattaca
caagcttaatacactccttaattgaagaatcgcaaaaccagcaagaaaagaatgaacaagaattattggaattagataaatgggcaagt
ttgtggaattggtttaacataacaaattggctgtggtatataaaattattcataatgatagtaggaggcttggtaggtttaagaatagtttttgct
gtactttctatagtgaatagagttaggcagggatattcaccattatcgtttcagacccacctcccaaccccgaggggacccgacaggcc
cgaaggaatagaagaagaaggtggagagagagacagagacagatccattcgattagtgaacggatctcgacggtatcgcctttaaaa
gaaaggggggactggaagggctacattggagcaggcaagatatccttgatcctgtggatctaccacacacaaggctacttccctgatt
ggcagaactacacaccagggccagggatcagatatccactgacctttggatggtgcttcaagctagtaccagttgagcaagagaagg
taggagaagccaacgaaggagagaacaaccgcttgttacaccctatgagcctgcatgggatggatgacccggagaaagaagtattag
tgtggaaatttgacagcagcctagcatttcatcacatggcccgagagctgcatccggagtactacaaagactgctgacatcgagctttc
taccagggactttccattgacgtcaatgggtggagtatttacggtaaactgcccacttggcagtacatcaagtgtatcatatgccaagtac
gccccctattgacgtcaatgacggtaaatggcccgcctggcattatgcccagtacatgaccttatgggactttcctacttggcagtacatctacgtat
tagtcatcgctattaccatggtgatgcggttttggcagtacatcaatgggcgtggatagcggtttgactcacggggatttccaagtctcca
ccccattgacgtcaatgggagtttgttttggcaccaaaatcaacgggactttccaaaatgtcgtaacaactccgccccattgacgcaaat
gggcggtaggcgtgtacggtgggaggtctatataagcagagctcgtttagtgaaccgtcagatcgcctggagacgccatccacgctgt
tttgacctccatagaagacaccgactctactagaggatctatttccggtgAATTCGCCACCatgggaatcaggctcctgtgtcg
tgtggccttttgtttcctggctgtaggactagtaGAAGCTGACATCTACCAGACCCCAAGATACCTTGT TABLE 2-continued Exemplary Vector Sequences

```
TATAGGGACAGGAAAGAAGATCACTCTGGAATGTTCTCAAACCATGGGCCATGA
CAAAATGTACTGGTATCAACAAGATCCAGGAATGGAACTACACCTCATCCACTAT
TCCTATGGAGTTAATTCCACAGAGAAGGGAGATCTTTCCTCTGAGTCAACAGTCT
CCAGAATAAGGACGGAGCATTTTCCCCTGACCCTGGAGTCTGCCAGGCCCTCACA
TACCTCTCAGTACCTCTGTGCCAGCAGTCGGACGCCCAACATTCAGTACTTCGGC
GCCGGGACCCGGCTCTCAGTGCTGgaggacctgaaaaacgtgttcccacccgaggtcgctgtgtttgagccatc
agaagcagagatctcccacacccaaaaggccacACTgGCAtgcctggccacaggcttctacccgaccacgtggagctgagc
tggtgggtgaatgggaaggaggtgcacagtggggtcagcacagacccgcagcccctcaaggagcagcccgccctcaatgactcca
gatactgcctgagcagccgcctgagggtctcggccaccttctggcagaaccccgcaaccacttccgctgtcaagtccagttctacgg
gctctcggagaatgacgagtggacccaggataggggccaaacctgtcacccagatcgtcagcgccgaggcctggggtagagcagac
tgtggcttcacctccgagtcttaccagcaagggtcctgtctgccaccatcctctatgagatcttgctagggaaggccaccttgtatgcc
gtgctggtcagtgccctcgtgctgatggccatggtcaagagaaaggattccagaggcGGGAGCGGAGCCACGAAC
TTCTCTCTGTTAAAGCAAGCAGGAGACGTGGAAGAAAACCCCGGTCCTatgacacgagt
tagcttgctgtgggcagtcgtggtctccacctgtctcgagtccggcatgGGTCAACAGCTGAATCAGAGTCCTC
AATCTATGTTTATCCAGGAAGGAGAAGATGTCTCCATGAACTGCACTTCTTCAAG
CATATTTAACACCTGGCTATGGTACAAGCAGGAACCTGGGGAAGGTCCTGTCCTC
TTGATAGCCTTATATAAGGCTGGTGAATTGACCTCAAATGGAAGACTGACTGCTC
AGTTTGGTATAACCAGAAAGGACAGCTTCCTGAATATCTCAGCATCCATACCTAG
TGATGTAGGCATCTACTTCTGTGCTGGCACATACCAGAAAGTTACCTTTGGAACT
GGAACAAAGCTCCAAGTCATCCCAaatatccagaaccctgaccctgccgtgtaccagctgagagactctaaatc
cagtgacaagtctgtctgcctattcaccgattttgattctcaaacaaatgtgtcacaaagtaaggattctgatgtgtatatcacagacaaaa
ctgtgctagacatgaggtctatggacttcaagagcaacagtGCGGCCgcctggagcaacaaatctgactttgcatgtgcaaacgc
cttcaacaacagcattattccagaagacaccttcttcccccagccccagaaagttcctgtgatgtcaagctggtcgagaaaagctttgaaac
agatacgaacctaaactttcaaaacctgtcagtgattgggttccgaatcctcctcctgaaagtggcgggttttaatctgctcatgacgctg
cggctgtggtccagcTGActcgagggatcccgcccctctccctccccccccccctaacgttactggcgaagccgcttggaataagg
ccggtgtgcgtttgtctatatgttatttcaccatattgccgtcttttggcaatgtgagggcccggaaacctggccctgtcttcttgacgag
cattcctaggggtattccctctcgccaaaggaatgcaaggtctgttgaatgtcgtgaaggaagcagttcctctggaagcttcttgaaga
caaacaacgtctgtagcgaccctttgcaggcagcggaacccccaacctggcgacaggtgcctctgcggccaaaagccacgtgtata
agatacacctgcaaaggcggcacaaccccagtgccacgttgtgagttggatagttgtggaaagagtcaaatggctcacctcaagcgta
ttcaacaaggggctgaaggatgcccagaaggtaccccattgtatgggatctgatctggggcctcggtgcacatgctttacatgtgtttag
tcgaggttaaaaaacgtctaggcccccgaaccacggggacgtggttttcctttgaaaaacacgatgataatatggtgagcaagggcg
aggaggataacatggccatcatcaaggagttcatgcgcttcaaggtgcacatggagggctccgtgaacggccacgagttcgagatcg
agggcgagggcgagggccgcccctacgagggcacccagaccgccaagctgaaggtgaccaagggtggccccctgcccttcgcct
gggacatcctgtcccctcagttcatgtacggctccaaggcctacgtgaagcaccccgccgacatccccgactacttgaagctgtccttc
cccgagggcttcaagtgggagcgcgtgatgaacttcgaggacggcggcgtggtgaccgtgacccaggactcctccctgcaggacg
gcgagttcatctacaaggtgaagctgcgcggcaccaacttccccctccgacgcccccgtgatgcagaagaagaccatgggctgggag
gcctcctccgagcggatgtaccccgaggacggcgccctgaaggcgagatcaagcagaggctgaagctgaaggacggcggcca
ctacgacgctgaggtcaagaccacctacaaggccaagaagcccgtgcagctgcccggcgcctacaacgtcaacatcaagttggaca
tcacctcccacaacgaggactacaccatcgtggaacagtacgaacgcgccgagggcgccactccaccggcggcatggacgagct
gtacaagtgaacgcgtctgaacaataccaacctctggattacaaaatttgtgaaagattgactggtattcttaactatgttgctccttttacgct
atgtggatacgctgcttaatgcctttgtatcatgctattgcttcccgtatggctttcatttctcctccttgtataaatcctggttgctgtctattta
tgaggagttgtggcccgttgtcaggcaacgtggcgtggtgtgcactgtgtttgctgacgcaaccccactggttggggcattgccacca
cctgtcagctcctttccgggactttcgctttccccctccctattgccacggcggaactcatcgccgcctgccttgcccgctgctggacag
gggctcggctgttgggcactgacaattccgtggtgttgtcggggaagctgacgtccttcccatggctgctcgcctgtgttgccacctgga
ttctgcgcgggacgtccttctgctacgtccctcggccctcaatccagcggaccttccttcccgcggcctgctgccgctctcggcctc
ttccgcgtcttcgccttcgccctcagacgagtcggatctccctttgggccgcctccccgcctggaattaattctgcagtcgagacctaga
aaaacatggagcaatcacaagtagcaatacagcagctaccaatgctgattgtgcctggctagaagcacaagaggaggaggaggtgg
gttttccagtcacacctcaggtaccttaagacagcacaggcttgtagatcttagccacttttttaaaagaaaaggggact
ggaagggctaattcactcccaacgaagacaagatatccttgatctgtggatctaccacacacaaggctacttccctgattagcagaacta
cacaccagggccaggggtcagatatccactgacctttggatggtgctacaagctagtaccagttgagccagataaggtagaagaggc
caataaaggagagaacaccagcttgttacaccctgtgagcctgcatgggatggatgacccggagagagaagtgttagagtggaggtt
tgacagccgcctagcatttcatcacgtggcccgagagctgcatccggagtacttcaagaactgctgatatcgagcttgctacaagggac
tttccgctggggactttccagggaggcgtggcctgggcgggactggggagtggcgagccctcagatcctgcatataagcagctgcttt
ttgcctgtactgggtctctctggttagaccagatctgagcctgggagctctctggctaactagggaacccactgcttaagcctcaataaa
gcttgccttgagtgcttcaagtagtgtgtgcccgtctgttgtgtgactctggtaactagagatccctcagacccttttagtcagtgtggaaa
atctctagcagtagtagttcatgtcatcttattattcagtatttataacttgcaaagaaatgaatatcagagagtgagaggccttgacattgct
agcgtttaccgtcgacctctagctagagcttggcgtaatcatggtcatagctgtttcctgtgtgaaattgttatccgctcacaattccacaca
acatacgagccggaagcataaagtgtaaagcctggggtgcctaatgagtgagctaactcacattaattgcgttgcgctcactgcccgct
ttccagtcgggaaacctgtcgtgccagctgcattaatgaatcggccaacgcgcggggagaggcggtttgcgtattgggcgctcttccg
cttcctcgctcactgactcgctgcgctcggtcgttcggctgcggcgagcggtatcagctcactcaaaggcggtaatacggttatccaca
gaatcaggggataacgcaggaaagaacatgtgagcaaaaggccagcaaaaggccaggaaccgtaaaaaggccgcgttgctggcg
tttttccataggctccgcccccctgacgagcatcacaaaaatcgacgctcaagtcagaggtggcgaaacccgacaggactataaagat
accaggcgtttccccctggaagctccctcgtgcgctctcctgttccgaccctgccgcttaccggatacctgtccgcctttctcccttcggg
aagcgtggcgctttctcatagctcacgctgtaggtatctcagttcggtgtaggtcgttcgctccaagctgggctgtgtgcacgaacccc
cgttcagcccgaccgctgcgccttatccggtaactatcgtcttgagtccaacccggtaagacacgacttatcgccactggcagcagcca
ctggtaacaggattagcagagcgaggtatgtaggcggtgctacagagttcttgaagtggtggcctaactacggctacactagaagaac
agtatttggtatctgcgctctgctgaagccagttaccttcggaaaaagagttggtagctcttgatccggcaaacaaaccaccgctggtag
cggtggtttttttgtttgcaagcagcagattacgcgcagaaaaaaggatctcaagaagatcctttgatcttttctacggggtctgacgctc
agtggaacgaaaactcacgttaagggattttggtcatgagattatcaaaaaggatcttcacctagatccttttaaattaaaaatgaagtttta
aatcaatctaaagtatatatgagtaaacttggtctgacagttaccaatgcttaatcagtgaggcacctatctcagcgatctgtctatttcgttc
atccatagttgcctgactccccgtcgtgtagataactacgatacgggagggcttaccatctggccccagtgctgcaatgataccgcgag
acccacgctcaccggctccagatttatcagcaataaaccagccagccggaagggccgagcgcagaagtggtcctgcaactttatccg
cctccatccagtctattaattgttgccgggaagctagagtaagtagttcgccagttaatagtttgcgcaacgttgttgccattgctacaggc
atcgtggtgtcacgctcgtcgtttggtatggcttcattcagctccggttcccaacgatcaaggcgagttacatgatcccccatgttgtgcaa
aaaagcggttagctccttcggtcctccgatcgttgtcagaagtaagttggccgcagtgttatcactcatggttatggcagcactgcataatt
ctcttactgtcatgccatccgtaagatgcttttctgtgactggtgagtactcaaccaagtcattctgagaatagtgtatgcggcgaccgagt
tgctcttgcccggcgtcaatacgggataataccgcgccacatagcagaactttaaaagtgctcatcattggaaaacgttcttcggggcg
aaaactctcaaggatcttaccgctgttgagatccagttcgatgtaacccactcgtgcacccaactgatcttcagcatcttttactttcaccag
```

TABLE 2-continued

Exemplary Vector Sequences cgtttctgggtgagcaaaaacaggaaggcaaaatgccgcaaaaaagggaataagggcgacacggaaatgttgaatactcatactctt
cctttttcaatattattgaagcatttatcagggttattgtctcatgagcggatacatatttgaatgtatttagaaaaataaacaaatagggttc
cgcgcacatttccccgaaaagtgccacctgacgtcgacggatcgggagatcaacttgtttattgcagcttataatggttacaaataaagc
aatagcatcacaaatttcacaaataaagcattttttttcactgcattctagttgtggtttgtccaaactcatcaatgtatcttatcatgtctggatc
aactggataactcaagctaaccaaaatcatcccaaacttcccaccccataccctattaccactgccaattacctgtggtttcatttactctaa
acctgtgattcctctgaattattttcattttaaagaaattgtatttgttaaatatgtactacaaacttagtagt (SEQ ID NO: 29)

pLVX-CMV-TCR5 (FIG. 12):
tggaagggctaattcactcccaaagaagaacaagatatccttgatctgtggatctaccacacacaaggctacttcctgattagcagaact
acacaccagggccaggggtcagatatccactgacctttggatggtgctacaagctagtaccagttgagccagataaggtagaagagg
ccaataaaggagagaacaccagcttgttacaccctgtgagcctgcatggaatggatgacccggagagagaagtgttagagtggaggt
ttgacagccgcctagcatttcatcacgtggcccgagagctgcatccggagtacttcaagaactgctgatatcgagcttgctacaaggga
ctttccgctggggactttccagggaggcgtggcctgggcgggactggggagtggcgagccctcagatcctgcatataagcagctgct
ttttgcctgtactgggtctctctggttagaccagatctgagcctgggagctctctggctaactagggaacccactgcttaagcctcaataa
agcttgccttgagtgcttcaagtagtgtgtgcccgtctgttgtgtgactctggtaactagagatccctcagacccctttagtcagtgtggaa
aatctctagcagtggcgcccgaacaggggacttgaaagcgaaagggaaaccagaggagctctctcgacgcaggactcggcttgctga
agcgcgcacggcaagaggcgaggggcggcgactggtgagtacgccaaaaattttgactagcggaggctagaaggagagagatgg
gtgcgagagcgtcagtattaagcggggagaattagatcgcgatgggaaaaaattcggttaaggccagggggaaagaaaaaatata
aattaaaacatatagtatgggcaagcagggagctagaacgattcgcagttaatcctggcctgttagaaacatcagaaggctgtagacaa
atactgggacagctacaaccatcccttcagacaggatcagaagaacttagatcattatataataacgtagcaaccctctattgtgtgcatc
aaaggatagagataaaagacaccaaggaagctttagacaagatagaggaagagcaaaacaaaagtaagaccaccgcacagcaag
cggccggccgctgatcttcagacctggaggaggagatatgagggacaattggagaagtgaattatataaatataaagtagtaaaaattg
aaccattaggagtagcacccaccaaggcaaaagaagactggtgcagagagaaaagcagtgggaataggagcttgttccttt
gggttcttgggagcagcaggaagcactatgggcgcagcgtcaatgacgctgacggtacaggccagacaattattgtctggtatagtgc
agcagcagaacaatttgctgagggctattgaggcgcaacagcatctgttgcaactcacagtctggggcatcaagcagctccaggcaa
gaatcctggctgtggaaagatacctaaaggatcaacagctcctggggatttggggttgctctggaaaactcatttgcaccactgctgtgc
cttggaatgctagttggagtaataaatctctggaacagatttggaatcacacgacctggatggagtgggacagagaaattaacaattaca
caagtaataacactccttaattgaagaatcgcaaaaccagcaagaaaagaatgaacaagaattattggaattagataaatgggcaagtt
tgtggaattggtttaacataacaaattggctgtggtatataaaattattcataatgatagtaggaggcttggtaggtttaagaatagttttgct
gtactttctatagtgaatagagttaggcagggatattcaccattatcgtttcagacccacctcccaaccccgaggggacccgacaggcc
cgaaggaatagaagaagaaggtggagagagagacagagacagatccattcgattagtgaacggatctcgacggtatcgccttttaaaa
gaaaagggggggactggggggtacagtgcaggggaaagatagcaataatagcaacaggacaataaaagaattacaaaaa
caaattacaaaaattcaaaattttcgggtttattacagggacagcagagatccagtttatcgataagcttgggagttccgcgttacataactt
acggtaaatggcccgcctggctgaccgcccaacgacccccgcccattgacgtcaataatgacgtatgttcccatagtaacgccaatag
ggactttccattgacgtcaatgggtggagtatttacggtaaactgcccacttggcagtacatcaagtgtatcatatgccaagtacgcccc
tattgacgtcaatgacggtaaatggcccgcctggcattatgcccagtacatgaccttatgggactttcctacttggcagtacatctacgtat
tagtcatcgctattaccatggtgatgcggttttggcagtacatcaatgggcgtggatagcggtttgactcacggggatttccaagtctcca
ccccattgacgtcaatgggagtttgttttggcaccaaaatcaacgggactttccaaaatgtcgtaacaactccgccccattgacgcaaat
gggcggtaggcgtgtacggtgggaggtctatataagcagagctcgtttagtgaaccgtcagatcgcctggagacgccatccacgctgt
tttgacctccatagaagacaccgactctactagaggatctatttccggtgAATTCGCCACCatggccctccctgctcttcttctgtg
gggccttttatctcctgggaaccggttccatgGAAGCTGACATCTACCAGACCCCAAGATACCTTGTT
ATAGGGACAGGAAAGAAGATCACTCTGGAATGTTCTCAAACCATGGGCCATGAC
AAAATGTACTGGTATCAACAAGATCCAGGAATGGAACTACACCTCATCCACTATT
CCTATGAGTTAATTCCACAGAGAAGGGAGATCTTTTCCTCTGAGTCAACAGTCTC
CAGAATAAGGACGGAGCATTTTCCCCTGACCCTGGAGTCTGCCAGGCCCTCACAT
ACCTCTCAGTACCTCTGTGCCAGCAGTCGGACGCCCAACATTCAGTACTTCGGCG
CCGGGACCCGGCTCTCAGTGCTGgaggacctgaaaaacgtgttcccacccgaggtcgctgtgtttgagccatca
gaagcagagatctcccacaccaaaaggccacACTAGTgtgcctggccacaggcttctacccccgaccacgtggagctgagct
ggtgggtgaatgggaaggaggtgcacagtggggtcagcacagacccgcagcccctcaaggagcagcccgccctcaatgactcca
gatactgcctgagcagccgcctgagggtctcggccaccttctggcagaaccccgcaaccacttccgctgtcaagtccagttctacgg
gctctcggagaatgacgagtggacccaggatagggccaaacctgtcacccagatcgtcagcgccgaggcctggggtagagcagac
tgtgccttcacctccgagtccttaccagcaaggggtcctgtctgccaccatcctctatgagatcttgctagggaaggccaccttgtatgcc
gtgctggtcagtgccctcgtgctgatggccatggtcaagagaaaggattccagaggcGGGAGCGGGAGCCACGAAC
TTCTCTCTGTTAAAGCAAGCAGGGACGTGGAAGAAAACCCCGGTCCTATgaactcctct
ctggactttctaattctgatcttaatgtttggaggaACTAGTGGTCAACAGCTGAATCAGAGTCCTCAAT
CTATGTTTATCCAGGAAGGAGAAGATGTCTCCATGAACTGCACTTCTTCAAGCAT
ATTTAACACCTGGCTATGGTACAAGCAGGAACCTGGGGAAGGTCCTGTCCTCTTG
ATAGCCTTATATAAGGCTGGTGAATTGACCTCAAATGGAAGACTGACTGCTCAGT
TTGGTATAACCAGAAAGGACAGCTTCCTGAATATCTCAGCATCCATACCTAGTGA
TGTAGGCATCTACTTCTGTGCTGGCACATACCAGAAAGTTACCTTTGGAACTGGA
ACAAAGCTCCAAGTCATCCCAAATATCCAGAACCCTGACCCTGCCGTGTACCAGC
TGAGAGACTCTAAATCCAGTGACAAGTCTGCATGCctattcaccgattttgattctcaaacaaatgtgtc
acaaagtaaggattctgatgtgtatatcacagacaaaactgtgctagacatgaggtctatggacttcaagagcaacagtgctgtggcctg
gagcaacaaatctgactttgcatgtgcaaacgccttcaacaacagcattattccagaagacaccttcttccccagcccagaaagttcctg
tgatgtcaagctggtcgagaaaagctttgaaacagatacgaacctaaactttcaaaacctgtcagtgattgggtctccgaatcctcctg
aaagtggccgggtttaatctgctcatgacgctgcggctgtggtccagcTGActcgagggatcccgccctctccctccccccccct
aacgttactggccgaagccgcttggaataaggccggtgtgcgtttgtctatatgttattttccaccatattgccgtcttttggcaatgtgagg
gcccggaaacctggccctgtcttcttgacgagcattcctaggggtctttcccctctcgccaaaggaatgcaaggtctgttgaatgtcgtg
aaggaagcagttcctctggaagcttcttgaagacaaacaacgtctgtagcgaccctttgcaggcagcggaaccccccacctggcgac
aggtgcctctgcggccaaaagccacgtgtataagatacacctgcaaaggcggcacaaccccagtgccacgttgtgagttggatagttg
tggaaagagtcaaatggctcacctcaagcgtattcaacaaggggctgaaggatgcccagaaggtaccccattgtatgggatctgatct
ggggcctcggtgcacatgctttacatgtgtttagtcgaggttaaaaaacgtctaggccccccgaaccacggggacgtggttttcctttga
aaaacacgatgataatatggttggagcaggtggaggagatcggcatcaaggcatatggcagatggcagaggtggttcggcttgatcgg
atgctttcgcgcgcaggccacaagctcgaaactgagtgcgcagtgggcgtgcatgcccagaccgccgtgcagtgcctgcaagcacgtgatca
aggtgaccaagggtggccccctgccctgccgtggccacatgtgtgccgcccagttccatgcctcctgcgccaaggcctacgtgaagcaccc
cgccgacatccccgactacttgaagctgtcttccccgagggctctgcaagtgggagcgcgtgatgaacttcgaggacggcggcgtggt
gaccgtgacccaggactcctccctgcaggacggcgagttcatctacaaggtgaagctgcgcggcaccaacttcccctccgacggcc
ccgtaatgcagaagaagaccatgggctgggaggcctcctccgagcggatgtaccccgaggacggcgccctgaagggcgagatca TABLE 2-continued Exemplary Vector Sequences

```
agcagaggctgaagctgaaggacggcggccactacgacgctgaggtcaagaccacctacaaggccaagaagcccgtgcagctgc
ccggcgcctacaacgtcaacatcaagttggacatcacctcccacaacgaggactacaccatcgtggaacagtacgaacgcgccgag
ggccgccactccaccggcggcatggacgagctgtacaagtgaacgcgtctggaacaatcaacctctggattacaaaatttgtgaaag
attgactggtattcttaactatgttgctccttttacgctatgtggatacgctgctttaatgcctttgtatcatgctattgcttcccgtatggctttca
ttttctcctccttgtataaatcctggttgctgtctctttatgaggagttgtggcccgttgtcaggcaacgtggcgtggtgtgcactgtgtttgct
gacgcaaccccccactggttggggcattgccaccacctgtcagctcctttccgggactttcgctttcccccctccctattgccacggcggaa
ctcatcgccgcctgccttgcccgctgctggacaggggctcggctgtcgggcactgacaattccgtggtgttgtcggggaagctgacgt
cctttccatggctgctcgcctgtgttgccacctggattctgcgcgggacgtccttctgctacgtccctccggccctcaatccagcggacct
tccttcccgcggcctgctgccggctctgcggcctcttccgcgtcttcgcttcgccctcagacgagtcggatctccctttgggccgcctc
cccgcctggaattaattctgcagtcgagacctagaaaaacatggagcaatcacaagtagcaatacagcagctaccaatgctgattgtgc
ctggctagaagcacaagaggaggaggaggtgggttttccagtcacaactcaggtacctttaagaccaatgacttacaaggcagctgta
gatcttagccactttttaaaagaaaagaggggactggaagggctaattcactcccaacgaagacaagatatccttgatctgtggatctac
cacacacaaggctacttccctgattagcagaactacacaccagggccaggggtcagatatccactgacattggatggtgctacaagct
agtaccagttgagccagataaggtagaagaggccaataaaggagagaacaccagcttgttacaccctgtgagcctgcatgggatgga
tgacccggagagagaagtgttagagtggaggtttgacagccgcctagcatttcatcacgtggcccgagagctgcatccggagtacttc
aagaactgctgatatcgagcttgctacaagggactttccgctggggactttccagggaggcgtggcctgggcgggactgggggagtgg
cgagccctcagatcctgcatataagcagctgcttttttgcctgtactgggtctctctggttagaccagatctgagcctgggagctctctggc
taactagggaacccactgataagcctcaataaagcttgccttgagtgatcaagtagtgtgtgcccgtctgttgtgtgactctggtaacta
gagatccctcagaccctttagtcagtgtggaaaatctctagcagtagtagttcatgtcatcttattattcagtatttataacttgcaaagaaat
gaatatcagagagtgagaggccttgacattgctagcgtttaccgtcgacctctagctagagcttggcgtaatcatggtcatagctgtttcc
tgtgtgaaattgttatccgctcacaattccacacaacatacgagccggaagcataaagtgtaaagcctggggtgcctaatgagtgagct
aactcacattaattgcgttgcgctcactgcccgctttccagtcgggaaacctgtcgtgccagctgcattaatgaatcggccaacgcgcg
gggagaggcggtttgcgtattgggcgctatcccgcttcctcgctcactgactcgctgcgctcggtcgttcggctgcggcgagcggtatc
agctcactcaaaggcggtaatacggttatccacagaatcagggataacgcaggaaagaacatgtgagcaaaaggccagcaaaag
gccaggaaccgtaaaaaggccgcgttgctggcgtttttccataggctccgcccccctgacgagcatcacaaaaatcgacgctcaagtc
agaggtggcgaaacccgacaggactataaagataccaggcgtttccccctggaagctccctcgtgcgctctcctgttccgaccctgcc
gcttaccggatacctgtccgcctttctcccttcgggaagcgtggcgctttctcatagctcacgctgtaggtatctcagttcggtgtaggtcg
ttcgctccaagctgggctgtgtgcacgaaccccccgttcagcccgaccgctgcgccttatccggtaactatcgtcttgagtccaacccg
gtaagacacgacttatcgccactggcagcagccactggtaacaggattagcagagcgaggtatgtaggcggtgctacagagttcttga
agtggtggcctaactacggctacactagaagaacagtatttggtatctgcgctctgctgaagccagttaccttcggaaaaagagttggta
gctcttgatccggcaaacaaaccaccgctggtagcggtggtttttttgtttgcaagcagcagattacgcgcagaaaaaaaggatctcaa
gaagatcctttgatcttttctcacggggtctgacgctcagtggaacgaaaactcacgttaaggggattttggtcatgagattatcaaaaaggat
cttcacctagatcctttttaaattaaaaatgaagttttaaatcaatctaaagtatatatgagtaaacttggtctgacagttaccaatgcttaatca
gtgaggcacctatctcagcgatctgtctatttcgttcatccatagttgcctgactccccgtcgtgtagataactacgatacgggagggctta
ccatctggccccagtgctgcaatgataccgcgagacccacgctcaccggctccagatttatcagcaataaaccagccagccggaagg
gccgagcgcagaagtggtcctgcaactttatccgcctccatccagtctattaagttgttgccgggaagctagagtaagtagttcgccagtt
aatagtttgcgcaacgttgttgccattgctacaggcatcgtggtgtcacgctcgtcgtttggtatggcttcattcagctccggttcccaacg
atcaaggcgagttacatgatccccccatgttgtgcaaaaaagcggttagctccttcggtcctccgatcgttgtcagaagtaagttggccgc
agtgttatcactcatggttatggcagcactgcataattctcttactgtcatgccatccgtaagatgcttttctgtgactggtgagtactcaacc
aagtcattctgagaatagtgtatgcggcgaccgagttgctcttgcccggcgtcaatacgggataataccgcgccacatagcagaactt
aaaagtgctcatcattggaaaacgttcttcggggcgaaaactctcaaggatcttaccgctgttgagatccagttcgatgtaacccactcgt
gcacccaactgatcttcagcatcttttactttcaccagcgtttctgggtgagcaaaaacaggaaggcaaaatgccgcaaaaaagggaat
aagggcgacacggaaatgttgaatactcatactatccttttttcaatattattgaagcatttatcaggggttattgtctcatgagcggatacata
tttgaatgtatttagaaaaataaacaaataggggttccgcgcacatttccccgaaaagtgccacctgacggtcgacggatcgggagatca
acttgtttattgcagatataatggttacaaataaagcaatagcatcacaaatttcacaaataaagcatttttttcactgcattctagttgtggttt
gtccaaactcatcaatgtatcttatcatgtctggatcaactggataactcaagctaaccaaaatcatcccaaacttcccacccatacccta
ttaccactgccaattacctgtggtttcatttactctaaacctgtgattcctctgaattattttcattttaaagaaattgtatttgttaaatatgtacta
caaacttagtagt (SEQ ID NO: 30)
```

In another aspect, the present technology provides a recombinant cell comprising a vector, wherein the vector comprises (a) a vector backbone; and (b) a first polynucleotide encoding a TCRα polypeptide and a second polynucleotide encoding a TCRβ polypeptide; or (b) a first polynucleotide encoding a TCRγ polypeptide and a second polynucleotide encoding a TCRδ polypeptide; wherein the first and second polynucleotides are a cognate pair, and wherein the first polynucleotide and the second polynucleotide are derived from mRNA of a single lysed T cell in a compartment. In some embodiments, the mRNA of the single lysed T cell is isolated using an mRNA capture reagent in a compartment, optionally wherein the recombinant cell is a bacterial cell, mammalian cell, or a yeast cell. In other embodiments, the polynucleotides encoding the paired T cell receptor polypeptides are derived from a single cell, without the use of an mRNA capture reagent. Additionally or alternatively, in some embodiments, the compartment containing the contents of the single lysed T cell is a microwell (e.g., a microwell within a 96-well plate) or a droplet.

In one aspect, the present technology provides a recombinant TCR vector library comprising a plurality of vectors each comprising (a) a vector backbone; and (b) a first polynucleotide encoding a TCRα polypeptide and a second polynucleotide encoding a TCRβ polypeptide; or (b) a first polynucleotide encoding a TCRγ polypeptide and a second polynucleotide encoding a TCRδ polypeptide; wherein the first and second polynucleotides are a cognate pair, and wherein the first polynucleotide and the second polynucleotide are derived from mRNA of a single lysed T cell in a compartment. In some embodiments, the mRNA of the single lysed T cell is isolated using an mRNA capture reagent in a compartment. In other embodiments, the polynucleotides encoding the paired T cell receptor polypeptides are derived from a single cell, without the use of an mRNA capture reagent. Additionally or alternatively, in some embodiments, the compartment containing the contents of the single lysed T cell is a microwell (e.g., a microwell within a 96-well plate) or a droplet.

In some embodiments, the TCR vector library comprises a TCR repertoire. Thus, in some embodiments, a TCR vector library is a full or partial collection of the different TCRs produced in a single donor or subject as a result of V(D)J rearrangement and/or T cell selection. In other embodiments, a TCR vector library of the present disclosure comprises a defined collection of TCRs specifically selected for their binding specificities or other desired characteristics. For example, the TCR vector library can comprise a subset of TCRs that specifically bind to a particular target cell, antigen, antigen:MHC complex, or combination thereof. In these embodiments, the TCRs can be derived from a single donor or subject, or more than one donor or subject.

In certain embodiments, each TCR in the TCR vector library is genetically distinct and comprises a distinct binding specificity. In some embodiments, the TCR vector comprises about 2 to about 5 different TCRs, about 2 to about 10 different TCRs, about 5 to about 10 different TCRs, about 5 to about 15 different TCRs, about 5 to about 20 different TCRs, about 10 to about 30 different TCRs, about 10 to about 40 different TCRs, about 10 to about 50 TCRs, about 20 to about 60 different TCRs, about 25 to about 75 different TCRs, about 50 to about 100 different TCRs, or greater than 100 different TCRs.

Precise molecular compositions can be advantageous for stability, efficacy, and/or safety of biotherapeutics. Thus, in certain embodiments, each vector and/or TCR in the TCR vector library is characterized to determine the nucleic acid and/or amino acid sequence of the TCR and/or its binding specificity. In some embodiments, molecular characterization is performed by nucleic acid sequencing the vector or a part of the vector (e.g., the first polynucleotide and the second polynucleotide). In certain embodiments, molecular characterization is performed by analysis of the TCR protein using mass spectrometry. In some embodiments, molecular characterization of the TCR vector library is performed by nucleic acid sequencing of 2 or more, or 3 or more, or 4 or more, or 5 or more, or 6 or more, or 7 or more, or 8 or more, or 9 or more, or 10 or more, or 15 or more, or 20 or more, or 30 or more, or 40 or more, or 50 or more isolated colonies, each comprising a recombinant cell transformed with the TCR vector library (e.g., a bacterial cell). In some embodiments, the TCR vector library is refined or selected by single-colony nucleic acid amplification and sequencing of transformed recombinant cells, followed by mixing of different vector colonies at a defined ratio to generate a defined molecular library composition. In some embodiments, the selection of individual vectors for inclusion in the library is informed by aspects of characterization and/or binding specificity of the starting library. Non-limiting examples of such aspects include TCR clonal prevalence, TCR enrichment characteristics from in vitro assays, TCR V segment sequence, TCR D segment sequence, TCR J segment sequence, TCR gene motifs, and/or CDR3 gene motifs.

In some embodiments, the ratio of vectors in the TCR vector library is adjusted or selected to optimize therapeutic activity of the library. For example, a TCR vector library comprising two TCRs may have a vector ratio of about 1:1, about 1:2, about 1:5, about 1:10, etc of each vector. In another non-limiting example, a library comprising three TCRs may have a vector ratio of about 1:1:1, about 2:1:1, about 2:2:1, etc of each vector.

In another aspect, the present technology provides an isolated immune cell comprising (a) a vector backbone; and (b) a first polynucleotide encoding a TCRα polypeptide and a second polynucleotide encoding a TCRβ polypeptide; or (b) a first polynucleotide encoding a TCRγ polypeptide and a second polynucleotide encoding a TCRδ polypeptide; wherein the first and second polynucleotides are a cognate pair, and wherein the first polynucleotide and the second polynucleotide are derived from mRNA of a single lysed T cell in a compartment. In some embodiments, the mRNA of the single lysed T cell is isolated using an mRNA capture reagent in a compartment. In other embodiments, the polynucleotides encoding the paired T cell receptor polypeptides are derived from a single cell, without the use of an mRNA capture reagent. Additionally or alternatively, in some embodiments, the compartment containing the contents of the single lysed T cell is a microwell (e.g., a microwell within a 96-well plate) or a droplet. In some embodiments the immune cell is a hematopoietic stem cell, a hematopoietic progenitor cell, a T cell, or an natural killer (NK) cell.

In one aspect, the present technology provides a cell population comprising a recombinant TCR vector library comprising a plurality of vectors each comprising (a) a vector backbone; and (b) a first polynucleotide encoding a TCRα polypeptide and a second polynucleotide encoding a TCRβ polypeptide; or (b) a first polynucleotide encoding a TCRγ polypeptide and a second polynucleotide encoding a TCRδ polypeptide; wherein the first and second polynucleotides are a cognate pair, and wherein the first polynucleotide and the second polynucleotide are derived from mRNA of a single lysed T cell in a compartment. In some embodiments, the mRNA of the single lysed T cell is isolated using an mRNA capture reagent in a compartment. In other embodiments, the polynucleotides encoding the paired T cell receptor polypeptides are derived from a single cell, without the use of an mRNA capture reagent. Additionally or alternatively, in some embodiments, the compartment containing the contents of the single lysed T cell is a microwell (e.g., a microwell within a 96-well plate) or a droplet. In some embodiments, the population comprises hematopoietic stem cells, hematopoietic progenitor cells, T cells, or NK cells. In some embodiments, the cell population comprises a full or partial TCR repertoire of a subject.

Additional aspects of the present technology relate to compositions comprising a carrier and one or more vectors of the present technology. Alternatively, the compositions comprise a carrier and one or more recombinant TCR vector libraries of the present technology. In another embodiment, the compositions comprise a carrier and one or more immune cells comprising one or more vectors of the present technology. In yet another embodiment, the compositions comprise a carrier and a cell population comprising a recombinant TCR vector library of the present technology. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the disclosure. Those skilled in the art will know of other suitable carriers for binding vectors, cells, cell populations, or vector libraries or will be able to ascertain such, using routine experimentation.

In some embodiments, the carrier is a pharmaceutically acceptable carrier. Pharmaceutical compositions of the present disclosure including but not limited to any one of the claimed compositions may comprise a vector, library, cell, or cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present disclosure can be formulated for oral, intravenous, topical, enteral, and/or parenteral administration. In certain embodiments, the compositions of the present disclosure are formulated for intravenous administration.

II. Methods of Preparing the Compositions of the Present Technology

Provided herein is a method for preparing a recombinant TCR library, the method comprising transforming a population of cells with a vector library comprising a plurality of vectors each comprising (a) a vector backbone; and (b) a first polynucleotide encoding a TCRα polypeptide and a second polynucleotide encoding a TCRβ polypeptide; or (b) a first polynucleotide encoding a TCRγ polypeptide and a second polynucleotide encoding a TCRδ polypeptide; wherein the first and second polynucleotides are a cognate pair, and wherein the first polynucleotide and the second polynucleotide are derived from mRNA of a single lysed T cell in a compartment. In some embodiments, the mRNA of the single lysed T cell is isolated using an mRNA capture reagent in a compartment. In other embodiments, the polynucleotides encoding the paired T cell receptor polypeptides are derived from a single cell, without the use of an mRNA capture reagent. Additionally or alternatively, in some embodiments, the compartment containing the contents of the single lysed T cell is a microwell (e.g., a microwell within a 96-well plate) or a droplet. In some embodiments, the population comprises hematopoietic stem cells, hematopoietic progenitor cells, T cells, or NK cells.

In some embodiments of the method, the library is screened for specific binding to a target cell. In certain embodiments, the target cell is a cancer cell, a cell infected with a virus, a cell derived from a subject infected with a virus, a tumor cell, or a tissue biopsy cell isolated from a subject suspected of having a viral infection or cancer.

In some embodiments of the method, the library is screened for specific binding to an antigen:MHC complex. In some embodiments the antigen of the antigen:MHC complex is a viral antigen derived from a virus selected from the group consisting of adenovirus, CMV, coronavirus, coxsackievirus, Dengue virus, Epstein-Barr virus (EBV), enterovirus 71 (EV71), Ebola virus, hepatitis A (HAV), hepatitis B (HBV), cytomegalovirus (CMV), hepatitis C (HCV), hepatitis D (HDV), hepatitis E (HEV), human immunodeficiency virus (HIV), human papillomavirus (HPV), herpes simplex virus (HSV), human T-lymphotropic virus (HTLV), influenza A virus, influenza B virus, Japanese encephalitis, leukemia virus, measles virus, molluscum contagiosum, orf virus, parvovirus, rabies virus, respiratory syncytial virus, rift valley fever virus, rubella virus, rotavirus, tick-borne encephalitis (TBEV), simian immunodeficiency virus, tobacco etch virus (TEV), varicella zoster virus, variola, West Nile virus, Zika virus, and Chikungunya virus. In other embodiments, the antigen of the antigen: MHC complex is a tumor antigen selected from the group consisting of CD45, glypican-3, IGF2B3, Kallikrein 4, KIF20A, Lengsin, Meloe, mucin 5AC (MUC5AC), survivin, cyclin-A1, MAGE-A1, MAGE-C1, MAGE-C2, SSX2, XAGE1b/GAGED2A, CD19, CD20, CD22, CD52, EGFR, HER2, TRAILR1, RANKL, IGF1R, EpCAM, and CEA.

In some embodiments of the method, the library is screened for T cell phenotypic markers. In certain embodiments, the T cell phenotypic markers identify expression of one or more TCR complex components, e.g., TCRalpha, TCRbeta, TCRgamma, TCRdelta, CD3δ/ε, CD37γ/ε, and CD247 ζ/ζ or/r. In some embodiments, the T cell phenotypic markers aid in the identification of specific T cell subsets such as naïve CD8+ T cells, naïve CD4+ T cells, CD4+ T cells, CD8+ Cytotoxic T cells, gamma/delta T cells, NKT cells, Th1 cells, Th2 cells, Th9 cells, Th22 cells, T follicular helper cells, Th17 cells, and regulatory T cells. Antibodies specific to cell surface markers suitable for identifying these T cell subsets are known in the art and are available, for example, from R&D Systems. Screening can be performed by any method known in the art including but not limited to ELISA, Western blot, Northern blot, PCR, qPCR, and flow cytometry.

In certain embodiments of the method, the library is screened for activity in a co-culture system, wherein the co-culture system comprises at least one of the following: (a) a cancer cell line; (b) a plurality of cells infected with a known virus; (c) a plurality of tumor cells isolated from a cancer patient; (d) an immortalized cell line; or (e) a plurality of cells derived from a patient tissue biopsy. In some embodiments, activity is measured by assaying co-engagement of the recombinant TCR/CD3 complex and a co-stimulatory receptor, e.g., CD28. Co-engagement of these receptors on the cell surface leads to intracellular signaling events and the activation of nuclear transcription factors such as Nuclear Factor of Activated T cells (NFAT), NF-kB and AP-1. Specifically, engagement of the TCR/CD3 complex leads to the phosphorylation and activation of PLC-g, intracellular calcium flux and transcriptional activation of NFAT pathway. In some embodiments, co-engagement of TCR/CD3 with the co-stimulatory receptor CD28 leads to activation of ERK/JNK and IkB kinase (IKK), which in turn regulates transcriptional activation of AP-1 and NF-kB pathways, respectively. The IL-2 promoter contains DNA binding sites for NFAT, NF-kB and AP-1. Therefore, co-engagement of TCR/CD3 and CD28 results in IL-2 production, which is commonly used as a functional readout for T cell activation. In some embodiments, other endpoints used to measure T cell activation include but are not limited to cell proliferation, cytotoxicity (death of the target cell), and production of additional cytokines such as IFNγ. Kits suitable for measuring or detecting T cell activity kits are available from, for example, Promega Corp. (T Cell Activation Bioassay (IL-2)(a,b) (Cat. #J1651 and J1655)).

In some embodiments of the method, the transformed cells are activated in vitro. In particular embodiments, activation is performed using one or more of the following stimulants: anti-CD3 antibody, anti-CD8 antibody, anti-CD27 antibody, IL-2, IL-4, IL-21, anti-PD1 antibody, anti-CTLA4 antibody, anti CD3/CD28 tetrameric antibody, tumor cell lysate, cellular co-culture with virus-infected cells, and tumor cell lines. T cell activation kits are available from, for example, Miltenyi Biotec (T cell Activation/Expansion Kit, human, cat #130-091-441).

In certain embodiments of the method, the population of cells is transformed with a transcription factor. In some embodiments, the transcription factor is selected from the group consisting of forkhead box P3 (FOXP3, Entrez gene: 50943, RefSeq mRNA: NM_001114377; NM_014009), PR domain zinc finger protein 1 (BLIMP-1, Entrez gene: 639, RefSeq mRNA: NM_001198; NM_182907), Helios (IKZF2, Entrez gene: 22807, RefSeq mRNA: NM_001079526.1; NM_016260.2, Uniprot: Q9UKS7), Ikaros (IKZF1, Entrez:gene: 10320, RefSeq mRNA: NM_001220765.2; NM_006060.6 etc.; Uniprot: Q13422) and transforming growth factor beta 1 (TGF-beta 1, Entrez gene: 7040, RefSeq mRNA: NM_000660). FOXP3 is a protein involved in immune system responses and is thought to function as a master regulator of the development and function of regulatory T cells. Regulatory T cells generally suppress the immune response. BLIMP-1 acts as a repressor of beta-interferon (0-IFN) gene expression. Regulatory T cells release TGF-β1 to inhibit the actions of other T cells. Interleukin 1- and interleukin 2-dependent proliferation of activated T cells, and the activation of quiescent helper T cells and cytotoxic T cells is prevented by the activity of TGF-β1. Similarly, TGF-β1 can inhibit the secretion and activity of many other cytokines including interferon-α, tumor necrosis factor-alpha (TNF-α) and various interleukins. It can also decrease the expression levels of cytokine receptors, such as the IL-2 receptor to down-regulate the activity of immune cells. Non-limiting examples of transcription factor amino acid sequences are provided herein:

FOXP3 (UniProt Q9BZS1):
(SEQ ID NO: 31)
MPNPRPGKPSAPSLALGPSPGASPSWRAAPKASDLLGARGPGGTFQGRDL

RGGAHASSSSLNPMPPSQLQLPTLPLVMVAPSGARLGPLPHLQALLQDRP

HFMHQLSTVDAHARTPVLQVHPLESPAMISLTPPTTATGVFSLKARPGLP

PGINVASLEWVSREPALLCTFPNPSAPRKDSTLSAVPQSSYPLLANGVCK

WPGCEKVFEEPEDFLKHCQADHLLDEKGRAQCLLQREMVQSLEQQLVLEK

EKLSAMQAHLAGKMALTKASSVASSDKGSCCIVAAGSQGPVVPAWSGPRE

APDSLFAVRRHLWGSHGNSTFPEFLHNMDYFKFHNMRPPFTYATLIRWAI

LEAPEKQRTLNEIYHWFTRMFAFFRNHPATWKNAIRHNLSLHKCFVRVES

EKGAVWTVDELEFRKKRSQRPSRCSNPTPGP

BLIMP-1 (UniProt O75626):
(SEQ ID NO: 32)
MLDICLEKRVGTTLAAPKCNSSTVRFQGLAEGTKGTMKMDMEDADMTLWT

EAEFEEKCTYIVNDHPWDSGADGGTSVQAEASLPRNLLFKYATNSEEVIG

VMSKEYIPKGTRFGPLIGEIYTNDTVPKNANRKYFWRIYSRGELHHFIDG

FNEEKSNWMRYVNPAHSPREQNLAACQNGMNIYFYTIKPIPANQELLVWY

CRDFAERLHYPYPGELTMMNLTQTQSSLKQPSTEKNELCPKNVPKREYSV

KEILKLDSNPSKGKDLYRSNISPLTSEKDLDDFRRRGSPEMPFYPRVVYP

IRAPLPEDFLKASLAYGIERPTYITRSPIPSSTTPSPSARSSPDQSLKSS

SPHSSPGNTVSPVGPGSQEHRDSYAYLNASYGTEGLGSYPGYAPLPHLPP

AFIPSYNAHYPKFLLPPYGMNCNGLSAVSSMNGINNFGLFPRLCPVYSNL

LGGGSLPHPMLNPTSLPSSLPSDGARRLLQPEHPREVLVPAPHSAFSFTG

AAASMKDKACSPTSGSPTAGTAATAEHVVQPKATSAAMAAPSSDEAMNLI

KNKRNMTGYKTLPYPLKKQNGKIKYECNVCAKTFGQLSNLKVHLRVHSGE

RPFKCQTCNKGFTQLAHLQKHYLVHTGEKPHECQVCHKRFSSTSNLKTHL

RLHSGEKPYQCKVCPAKFTQFVHLKLHKRLHTRERPHKCSQCHKNYIHLC

SLKVHLKGNCAAAPAPGLPLEDLTRINEEIEKFDISDNADRLEDVEDDIS

VISVVEKEILAVVRKEKEETGLKVSLQRNMGNGLLSSGCSLYESSDLPLM

KLPPSNPLPLVPVKVKQETVEPMDP

TGF-beta 1 (UniProt P01137):
(SEQ ID NO: 33)
MPPSGLRLLLLLLPLLWLLVLTPGRPAAGLSTCKTIDMELVKRKRIEAIR

GQILSKLRLASPPSQGEVPPGPLPEAVLALYNSTRDRVAGESAEPEPEPE

ADYYAKEVTRVLMVETHNEIYDKFKQSTHSIYMFFNTSELREAVPEPVLL

SRAELRLLRLKLKVEQHVELYQKYSNNSWRYLSNRLLAPSDSPEWLSFDV

TGVVRQWLSRGGEIEGFRLSAHCSCDSRDNTLQVDINGFTTGRRGDLATI

HGMNRPFLLLMATPLERAQHLQSSRHRRALDTNYCFSSTEKNCCVRQLYI

DFRKDLGWKWIHEPKGYHANFCLGPCPYIWSLDTQYSKVLALYNQHNPGA

SAAPCCVPQALEPLPIVYYVGRKPKVEQLSNMIVRSCKCS

In some embodiments, the method further comprises administering an effective amount of the recombinant TCR library prepared according to the methods described herein to a subject in need thereof. In some embodiments, the subject in need thereof is suffering from cancer or a viral infection.

In another aspect, provided herein is a recombinant TCR library prepared by a method comprising transforming a population of cells with a vector library comprising a plurality of vectors each comprising (a) a vector backbone; and (b) a first polynucleotide encoding a TCRα polypeptide and a second polynucleotide encoding a TCRβ polypeptide; or (b) a first polynucleotide encoding a TCRγ polypeptide and a second polynucleotide encoding a TCRδ polypeptide; wherein the first and second polynucleotides are a cognate pair, and wherein the first polynucleotide and the second polynucleotide are derived from mRNA of a single lysed T cell in a compartment. In some embodiments, the mRNA of the single lysed T cell is isolated using an mRNA capture reagent in a compartment. In other embodiments, the polynucleotides encoding the paired T cell receptor polypeptides are derived from a single cell, without the use of an mRNA capture reagent. Additionally or alternatively, in some embodiments, the compartment containing the contents of the single lysed T cell is a microwell (e.g., a microwell within a 96-well plate) or a droplet. In some embodiments, the population comprises hematopoietic stem cells, hematopoietic progenitor cells, T cells, or NK cells.

In one aspect, the present technology provides a composition comprising a carrier and the recombinant TCR library prepared by a method as described herein. In some embodiments, the carrier is a pharmaceutically acceptable carrier.

III. Methods of Use

The methods of treatment described herein provide a format for isolation and use of specific TCRs that can be rapidly discovered, amplified, and returned to the subject on a timescale that is relevant for bedside therapies (e.g., weeks, rather than months).

Accordingly, in one aspect, provided herein is a method of treating a subject in need thereof, the method comprising administering to the subject an effective amount of a recombinant TCR library or a composition comprising a recombinant TCR library, wherein the recombinant TCR library was prepared by a method comprising transforming a population of cells with a vector library comprising a plurality of vectors each comprising (a) a vector backbone; and (b) a first polynucleotide encoding a TCRα polypeptide and a second polynucleotide encoding a TCRβ polypeptide; or (b) a first polynucleotide encoding a TCRγ polypeptide and a second polynucleotide encoding a TCRδ polypeptide; wherein the first and second polynucleotides are a cognate pair, and wherein the first polynucleotide and the second polynucleotide are derived from mRNA of a single lysed T cell in a compartment. In some embodiments, the mRNA of the single lysed T cell is isolated using an mRNA capture reagent in a compartment. In other embodiments, the polynucleotides encoding the paired T cell receptor polypeptides are derived from a single cell, without the use of an mRNA capture reagent. Additionally or alternatively, in some embodiments, the compartment containing the contents of the single lysed T cell is a microwell (e.g., a microwell within a 96-well plate) or a droplet.

In another aspect, provided herein is a method of treating cancer in a subject in need thereof, the method comprising administering to the subject an effective amount of a recombinant TCR library or a composition comprising a recombinant TCR library, wherein the recombinant TCR library was prepared by a method comprising transforming a population of cells with a vector library comprising a plurality of vectors each comprising (a) a vector backbone; and (b) a first polynucleotide encoding a TCRα polypeptide and a second polynucleotide encoding a TCRβ polypeptide; or (b) a first polynucleotide encoding a TCRγ polypeptide and a second polynucleotide encoding a TCRδ polypeptide; wherein the first and second polynucleotides are a cognate pair, and wherein the first polynucleotide and the second polynucleotide are derived from mRNA of a single lysed T cell in a compartment. In some embodiments, the mRNA of the single lysed T cell is isolated using an mRNA capture reagent in a compartment. In other embodiments, the polynucleotides encoding the paired T cell receptor polypeptides are derived from a single cell, without the use of an mRNA capture reagent. Additionally or alternatively, in some embodiments, the compartment containing the contents of the single lysed T cell is a microwell (e.g., a microwell within a 96-well plate) or a droplet.

In some embodiments, the cancer is acute lymphoblastic leukemia (ALL); acute myeloid leukemia (AML); adrenocortical carcinoma; AIDS-related cancers; anal cancer; appendix cancer; astrocytomas; atypical teratoid/rhabdoid tumor, brain cancer; basal cell carcinoma of the skin; bile duct cancer; bladder cancer; bone cancer; breast cancer; bronchial tumors; Burkitt lymphoma; carcinoid tumor (gastrointestinal); germ cell tumor; primary CNS lymphoma; cervical cancer; cholangiocarcinoma; chordoma; chronic lymphocytic leukemia (CLL); chronic myelogenous leukemia (CML); chronic myeloproliferative neoplasms; colorectal cancer; craniopharyngioma; cutaneous T-cell lymphoma; ductal carcinoma in situ (DCIS); endometrial cancer; ependymoma; esophageal cancer; esthesioneuroblastoma; extracranial germ cell tumor; extragonadal germ cell tumor; eye cancer; intraocular melanoma; retinoblastoma; fallopian tube cancer; fibrous histiocytoma of bone, malignant, and osteosarcoma; gallbladder cancer; gastric cancer; gastrointestinal carcinoid tumor; gastrointestinal stromal tumors (GIST); germ cell tumors; gestational trophoblastic disease; hairy cell leukemia; head and neck cancer; heart tumors; hepatocellular cancer; histiocytosis, Langerhans cell; Hodgkin lymphoma; hypopharyngeal cancer; intraocular melanoma; islet cell tumors, pancreatic neuroendocrine tumors; kidney cancer; laryngeal cancer; leukemia; lip and oral cavity cancer; liver cancer; lung cancer; lymphoma; male breast cancer; malignant fibrous histiocytoma of bone and osteosarcoma; melanoma; Merkel cell carcinoma; mesothelioma; metastatic cancer; mouth cancer; multiple endocrine neoplasia syndrome; multiple myeloma/plasma cell neoplasms; mycosis fungoides; myelodysplastic syndrome, myeloproliferative neoplasm, chronic; nasopharyngeal cancer; neuroblastoma; Non-Hodgkin lymphoma; non-small cell lung cancer; oral cancer, oropharyngeal cancer; osteosarcoma; ovarian cancer; pancreatic cancer; pancreatic neuroendocrine tumors; papillomatosis; paraganglioma; paranasal sinus cancer; parathyroid cancer; pharyngeal cancer; pheochromocytoma; pituitary tumor; pleuropulmonary blastoma; prostate cancer; rectal cancer; recurrent cancer; renal cell cancer; retinoblastoma; rhabdomyosarcoma; salivary gland cancer; sarcoma, Ewing sarcoma; Kaposi sarcoma; osteosarcoma; uterine sarcoma; Sezary syndrome; skin cancer; small cell lung cancer; small intestine cancer; soft tissue sarcoma; squamous cell carcinoma of the skin; squamous neck cancer; stomach cancer; T cell lymphoma; testicular cancer; throat cancer; nasopharyngeal cancer; hypopharyngeal cancer; thymic carcinoma; thyroid cancer; urethral cancer; uterine cancer; vaginal cancer; vascular tumors; vulvar cancer; or Wilms tumor.

In one aspect, provided herein is a method of inhibiting tumor growth in a subject in need thereof, the method comprising administering to the subject an effective amount of a recombinant TCR library or a composition comprising a recombinant TCR library, wherein the recombinant TCR library was prepared by a method comprising transforming a population of cells with a vector library comprising a plurality of vectors each comprising (a) a vector backbone; and (b) a first polynucleotide encoding a TCRα polypeptide and a second polynucleotide encoding a TCRβ polypeptide; or (b) a first polynucleotide encoding a TCRγ polypeptide and a second polynucleotide encoding a TCRδ polypeptide; wherein the first and second polynucleotides are a cognate pair, and wherein the first polynucleotide and the second polynucleotide are derived from mRNA of a single lysed T cell in a compartment. In some embodiments, the mRNA of the single lysed T cell is isolated using an mRNA capture reagent in a compartment. In other embodiments, the polynucleotides encoding the paired T cell receptor polypeptides are derived from a single cell, without the use of an mRNA capture reagent. Additionally or alternatively, in some embodiments, the compartment containing the contents of the single lysed T cell is a microwell (e.g., a microwell within a 96-well plate) or a droplet. In some embodiments, the tumor is a solid tumor.

In another aspect, provided herein is a method of treating a viral infection in a subject in need thereof, the method comprising administering to the subject an effective amount of a recombinant TCR library or a composition comprising a recombinant TCR library, wherein the recombinant TCR library was prepared by a method comprising transforming a population of cells with a vector library comprising a plurality of vectors each comprising (a) a vector backbone; and (b) a first polynucleotide encoding a TCRα polypeptide and a second polynucleotide encoding a TCRβ polypeptide; or (b) a first polynucleotide encoding a TCRγ polypeptide and a second polynucleotide encoding a TCRδ polypeptide; wherein the first and second polynucleotides are a cognate pair, and wherein the first polynucleotide and the second polynucleotide are derived from mRNA of a single lysed T cell that was captured by an mRNA capture reagent in a compartment. In some embodiments, the viral infection is caused by a virus selected from the group consisting of adenovirus, CMV, coronavirus, coxsackievirus, Dengue virus, Epstein-Barr virus (EBV), enterovirus 71 (EV71), Ebola virus, hepatitis A (HAV), hepatitis B (HBV), cytomegalovirus (CMV), hepatitis C (HCV), hepatitis D (HDV), hepatitis E (HEV), human immunodeficiency virus (HIV), human papillomavirus (HPV), herpes simplex virus (HSV), human T-lymphotropic virus (HTLV), influenza A virus, influenza B virus, Japanese encephalitis, leukemia virus, measles virus, molluscum contagiosum, orf virus, parvovirus, rabies virus, respiratory syncytial virus, rift valley fever virus, rubella virus, rotavirus, tick-borne encephalitis (TBEV), simian immunodeficiency virus, tobacco etch virus (TEV), varicella zoster virus, variola, West Nile virus, Zika virus, and Chikungunya virus.

In some embodiments, the methods further comprise activating a suicide switch to kill the cells or cell population comprising a vector with a suicide switch (e.g., i-caspase9), thereby reducing the risk of harm to the patient. In some embodiments, the suicide switch is triggered following significant improvement or an apparent cure of the subject's cancer or infection, in order to reduce the risk of long-term side effects.

In certain embodiments, the methods further comprise pre-stimulating the cells in vitro prior to administration to achieve a desired TCR function or T cell identity in vivo, as described in the methods of preparation above.

In some embodiments, the methods further comprise co-expressing one or more transcription factors in the recombinant cells to influence T cell development into a potent anti-cancer or anti-viral phenotype, or to prevent the development of immunosuppressing Tregs, as described in the methods of preparation above.

Administration of the cells, libraries, cell populations, or compositions can be effected in one dose, continuously, or intermittently throughout the course of treatment. Methods of determining the most effective means and dosage of administration are known to those of skill in the art and will vary with the composition used for therapy, the purpose of the therapy and the subject being treated. Single or multiple administrations can be carried out with the dose level and pattern being selected by the treating physician. Suitable dosage formulations and methods of administering the agents are known in the art. In a further aspect, the cells and composition of the present disclosure can be administered in combination with other treatments. The cells and populations of cell are administered to the host using methods known in the art and described, for example, in PCT/US2011/064191. This administration of the cells or compositions of the present disclosure can be done to generate an animal model of the desired disease, disorder, or condition for experimental and screening assays.

Compositions of the present disclosure may be administered in a manner appropriate to the disease to be treated or prevented. The quantity and frequency of administration will be determined by such factors as the condition of the patient, and the type and severity of the patient's disease, although appropriate dosages may be determined by clinical trials.

In some embodiments, an effective dose of the recombinant TCR library comprises about 50 to about $10^2$ cells, about $10^2$ cells to about $10^3$ cells, about $10^2$ cells to about $10^4$ cells, about $10^3$ cells to about $10^5$ cells, about $10^4$ cells to about $10^6$ cells, about $10^5$ cells to about $10^7$ cells, about $10^6$ cells to about $10^1$ cells, about $10^7$ cells to about $10^9$ cells, or about $10^8$ cells to about $10^{10}$ cells. In particular embodiments, the effective dose comprises about $5\times10^5$ cells to about $1.5\times10^6$ cells or about $1\times10^4$ cells to about $5\times10^4$ cells, about $5\times10^4$ cells to about $5\times10^5$ cells, or about $2.5\times10^5$ cells to about $7.5\times10^5$ cells.

In certain embodiments, the administration is repeated and/or modified as needed in response to the subject's specific response to therapy administration. A repeat administration may be needed, for example, upon the re-appearance of a cancer cells or virus in the subject in need thereof (e.g., tumor immune "escape"). In some embodiments, repeated administration comprises cells, libraries, cell populations, or compositions prepared by a method that is distinct from the initial administration (e.g., the repeat dose comprises an additional step of pre-screening or pre-activating the T cells). In a particular embodiment, the methods of treatment provided herein further comprise administering a second, third, fourth, fifth, sixth, seventh, eighth, ninth, tenth dose of the recombinant TCR library or the composition.

In some embodiments, the recombinant TCR library comprises cells that are autologous or allogenic to the subject being treated.

Immunoassay and Imaging. In some aspects, the recombinant TCR library disclosed herein can be used to assay for the presence of target cells in a biological sample isolated from a subject (e.g. human plasma). The target cells (e.g., cancer cells) can be detected by exposing the recombinant TCR library to the biological sample and assaying for TCR activation and/or binding.

In addition to assaying for the presence of target cells, the recombinant TCR library disclosed herein can be used for in vivo imaging. Detectable labels that can be incorporated with the recombinant TCR library include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which can be incorporated into the TCR library. The TCR library which has been labeled with an appropriate detectable imaging moiety, such as a radioisotope (e.g., $^{131}$I, $^{112}$In, $^{99}$mTc), a radio-opaque substance, or a material detectable by nuclear magnetic resonance, is introduced (e.g., parenterally, subcutaneously, or intraperitoneally) into the subject. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}$mTc. The recombinant TCR library will then preferentially accumulate at the location of target cells. For example, in vivo tumor imaging is described in S. W. Burchiel et al., Tumor Imaging: The Radiochemical Detection of Cancer 13 (1982).

Diagnostic Uses. The recombinant TCR library disclosed herein can be used for diagnostic methods. As such, the present disclosure provides methods for using the recombinant TCR library disclosed herein in the diagnosis of cancer or viral infections in a subject. The diagnostic methods comprise contacting a biological sample isolated from a subject with a recombinant TCR library of the present disclosure. Biological samples can be obtained from any tissue (including biopsies), cell or body fluid of a subject. The activity or binding of the recombinant TCR library is assayed. If the recombinant TCR library is activated upon exposure to the biological sample, the subject's biological sample contains cells that are recognized by the TCR library. Accordingly, the subject is diagnosed with cancer or a viral infection.

Prognostic Uses. The recombinant TCR library disclosed herein can be used for prognostic methods. As such, the present disclosure provides methods for using the recombinant TCR library disclosed herein in predicting the prognosis of a subject with cancer or a viral infection. The prognostic methods comprise contacting a biological sample isolated from a subject with a recombinant TCR library of the present disclosure. Biological samples can be obtained from any tissue (including biopsies), cell or body fluid of a subject. The activity or binding of the recombinant TCR library is assayed. If the recombinant TCR library is activated upon exposure to the biological sample, the subject's biological sample contains cells that are recognized by the TCR library. Accordingly, the subject is identified as having or at risk for developing cancer and/or solid tumors, or a viral infection.

In some embodiments, the subject is a human, an animal, a non-human primate, a dog, cat, a sheep, a mouse, a horse, or a cow. In a particular embodiment, the subject is a human.

IV. Kits

As set forth herein, the present disclosure provides methods of TCR library preparation, methods of treatment, diagnostic methods, and prognostic methods. In one particular aspect, the present disclosure provides kits for performing these methods as well as instructions for carrying out the methods of the present disclosure such as collecting donor cells and/or performing a screen, and/or analyzing the results.

In some embodiments, the kit comprises, or alternatively consists essentially of, or yet further consists of the recombinant TCR library disclosed herein, and instructions for use. In some embodiments, the kit comprises, or alternatively consists essentially of, or yet further consists of one or more vectors disclosed herein, and instructions for use. In some embodiments, the kit comprises, or alternatively consists essentially of, or yet further consists of a pharmaceutical composition as disclosed herein, and instructions for use.

In some aspects, the kit can comprise: one or more vectors, cells, populations, or recombinant TCR libraries as disclosed herein; means for determining the amount of a reactive antigen or cell in a biological sample or means of assaying the activity of the TCR library; and means for comparison with a standard.

The kit components, (e.g., reagents) can be packaged in a suitable container. For example, these suggested kit components may be provided in solution or as a liquid dispersion or the like. The kit can also comprise, e.g., a buffering agent, a preservative or a protein-stabilizing agent. The kit can further comprise components necessary for detecting a detectable-label, e.g., an enzyme or a substrate. The kit can also contain a control sample or a series of control samples, which can be assayed and compared to the test sample. Each component of the kit can be enclosed within an individual container and all of the various containers can be within a single package, along with instructions for interpreting the results of the assays performed using the kit. The kits of the present disclosure may contain a written product on or in the kit container. The written product describes how to use the reagents contained in the kit.

EXAMPLES

The present technology is further illustrated by the following Examples, which should not be construed as limiting in any way.

Example 1: Paired Native TCRα:β Amplicon Generation and Cloning into Expression Vectors First, a population of human T cells were isolated for the collection of paired TCRα:β amplicons as a source of natively paired T cell receptor genes. Peripheral blood mononuclear cells (PBMC) were isolated from anticoagulated whole blood from healthy human patients using Histopaque®-1077 by centrifugation at 400×g for 30 minutes. After removing the upper plasma layer, the mononuclear cells between the plasma and Histopaque®-1077 were collected and resuspended in phosphate buffered saline. Cells were mixed gently and centrifuge at 250×g for 10 min for the removal of the platelets. Removed the supernatant and resuspended cell pellet with PBMCs culture media (RPMI with 10% fetal bovine serum) or cell freezing media (RPMI with 10% fetal bovine serum and 10% DMSO) for cryopreservation.

PBMCs were then cultured with RPMI-media supplied with 10% fetal bovine serum for 4 hours before the emulsion PCR for amplifying the full-length T cell receptor alpha and beta chain, Phorbol 12-myristate 13-acetate (PMA) and ionomycin were added to the PBMC culture media to a final concentration of 100 ng/mL for stimulation of T cells. A custom flow-focusing nozzle was used to isolate single PBMC cells into emulsion droplets with cell lysis buffer and poly(dT) beads which capture mRNA (Ref #1-4). The nozzle design ensured that cells are not exposed to lysis buffer until after they are isolated into single droplets. Within the droplet, cells were co-encapsulated with lysis reagents to release mRNA and poly(dT) magnetic beads for mRNA capture and purification. Emulsions were broken using diethyl ether, whereas poly(dT) beads were recovered and washed using first high-salt hybridization buffers and then PCR buffers. The beads were then re-emulsified in an overlap extension reverse transcription PCR OE-RTRT-PCR mix with primers adapted from Boria et al. (Ref #5) specific for the TCR alpha and beta chain sequences with the incorporation of restriction enzyme sequences and T cell receptor leader sequences for downstream cloning. The linker sequence was also included to enable the physical linkage of the TCR α and β chain during the TCR OE-RT-PCR. SuperScript™ III One-Step RT-PCR System with Platinum™ Taq DNA Polymerase was used for the emulsion PCR reagent. OE-PCR thermocycling conditions are provided in Table 3 and primer sequences are provided in Table 4.

TABLE 3

OE-PCR thermocycling conditions

| Cycle | Temperature | Time |
|---|---|---|
| 1 | 55° C. | 30 min |
| 1 | 94° C. | 2 min |
| 5 | 94° C. | 30 s |
|  | 50° C. | 30 s |
|  | 72° C. | 2 min |
| 5 | 94° C. | 30 s |
|  | 55° C. | 30 s |
|  | 72° C. | 2 min |
| 30 | 94° C. | 30 s |
|  | 60° C. | 30 s |
|  | 72° C. | 2 min |
| 1 | 72° C. | 7 min |

TABLE 4

Primers used for OE-PCR.

| Primer Name | Sequence | SEQ ID NO: |
|---|---|---|
| TRBV2for | CGCAGTAGCGGTAAACGGC GATGCTGAAGTCRCMCAGACTCC | 34 |
| TRBV3for | CGCAGTAGCGGTAAACGGC GATGCWGMTGTTWCCCAGAC | 35 |
| TRBV4for | CGCAGTAGCGGTAAACGGC GACACTGRAGTYACSCAGACACC | 36 |
| TRBV5for | CGCAGTAGCGGTAAACGGC GAGGCTGGAGTCACHCAAAS | 37 |
| TRBV6for | CGCAGTAGCGGTAAACGGC GAGCCTGGWGTCASYCAGAC | 38 |
| TRBV7for | CGCAGTAGCGGTAAACGGC GGTGCTGGAGTYKCCCAGW | 39 |
| TRBV10for | CGCAGTAGCGGTAAACGGC GATGCTGRRATCACCCAGR | 40 |
| TRBV11for | CGCAGTAGCGGTAAACGGC GAAGCTGAAGTTGCCCAGTC | 41 |
| TRBV13for | CGCAGTAGCGGTAAACGGC GATGCTGGAGTYATCCAGTC | 42 |
| TRBV14for | CGCAGTAGCGGTAAACGGC GAAGCTGGAGTKRYTCAGT | 43 |
| TRBV15for | CGCAGTAGCGGTAAACGGC GATGCCATGGTCATCCAGAA | 44 |
| TRBV18for | CGCAGTAGCGGTAAACGGC AATGCCGGCGTCATGCAGAA | 45 |
| TRBV19for | CGCAGTAGCGGTAAACGGC GATGGTGGAATCACTCAGTC | 46 |
| TRBV20for | CGCAGTAGCGGTAAACGGC AGTGCTGTCRTCTCTCAAMA | 47 |
| TRBV25for | CGCAGTAGCGGTAAACGGC GAAGCTGACATCTACCAGAC | 48 |
| TRBV27for | CGCAGTAGCGGTAAACGGC GATGTGAAAGTRACCCAGARCYC | 49 |
| TRBV30for | CGCAGTAGCGGTAAACGGC ACACTCCAGGCACAGAGATA | 50 |

After the OE-RT-PCR reaction, the PCR samples were purified by DNA-cleanup kit and subjected to DNA gel electrophoresis. As shown in FIG. 1, linked TCR alpha and beta amplicons were identified around 1000 b.p., indicating the successful OE-RT-PCR reaction.

After DNA gel electrophoresis, gel extraction was performed to obtain the TCR α:β amplicon. 5 ng purified PCR product was used as a template for performing semi-nested PCR. The nested PCR thermocycling conditions are provided in Table 5.

TABLE 5

Nested PCR thermocycling conditions

| Cycle | Temperature | Time |
|---|---|---|
| 1 | 95° C. | 2 min |
| 30 | 98° C. | 20 s |
|  | 63° C. | 30 s |
|  | 72° C. | 2 min |
| 1 | 72° C. | 7 min |

Figure 2:
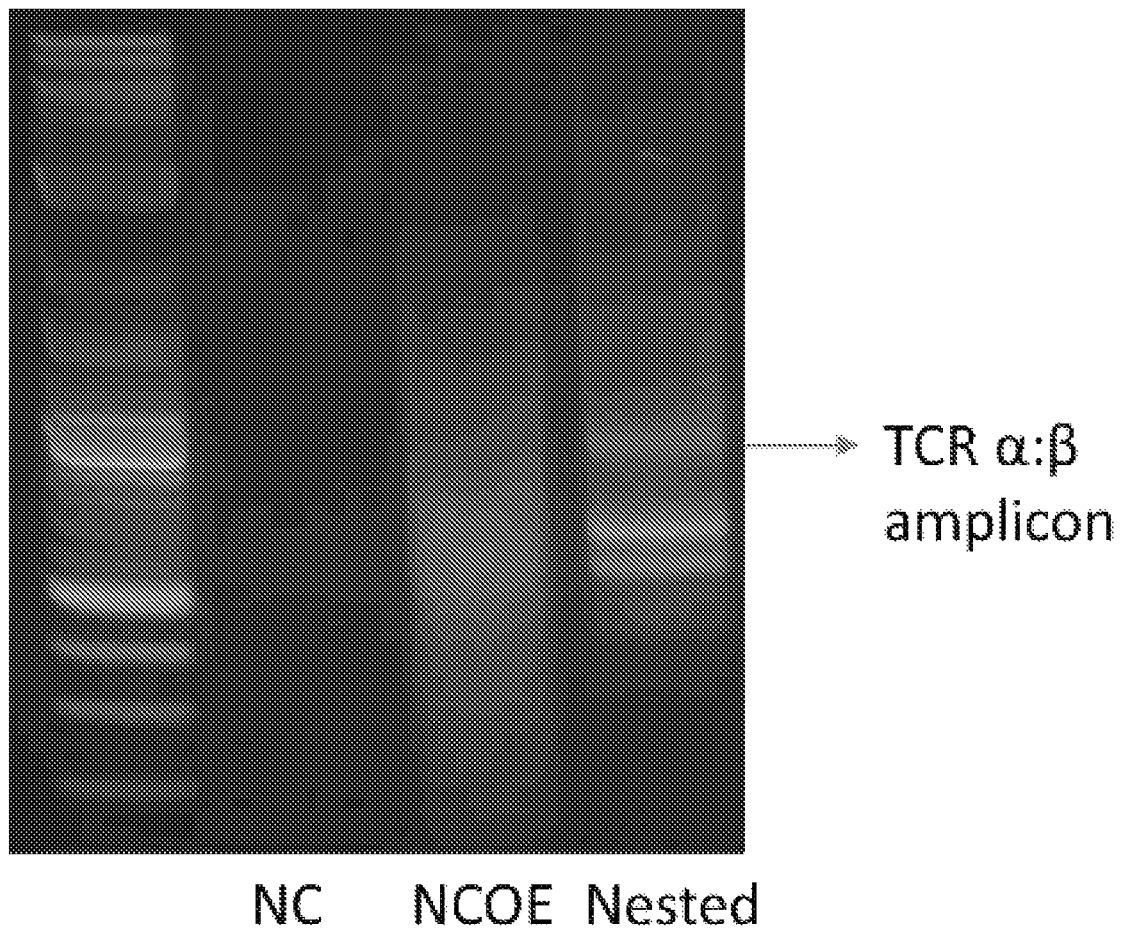
FIG. 2 shows gel electrophoresis of nested PCR products. After DNA electrophoresis, the TCR α:β amplicon was excised and gel purification was performed using Zymoclean™ Gel DNA Recovery Kits (Zymo Research). The purified amplicon was subjected to zero-blunt cloning (Thermo Fisher Scientific) to analyze TCR α:β amplicon sequences. The sequences were identified by the NCBI IGBLAST T cell receptor gene database.
Figure 3:
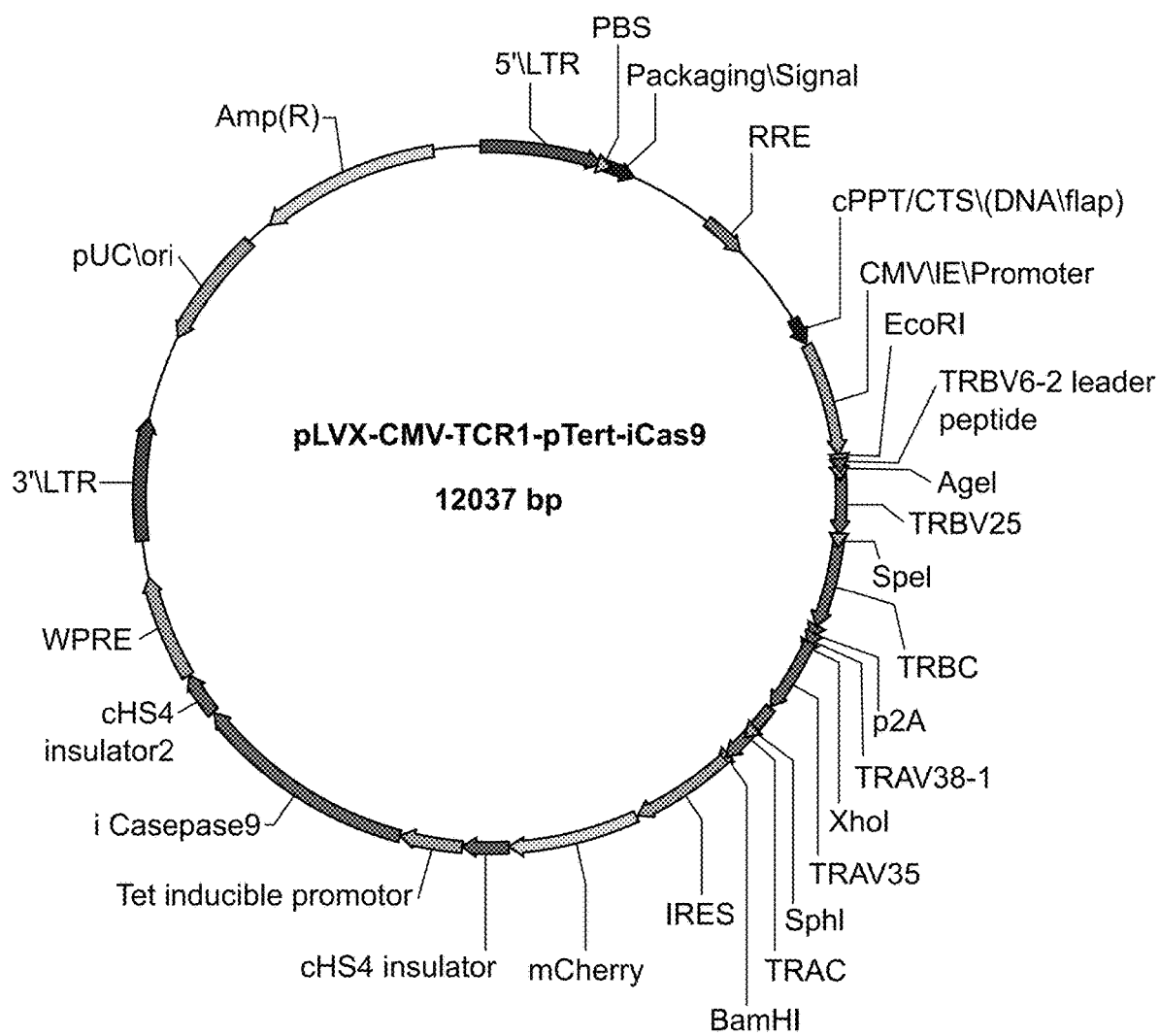
FIG. 3 shows a vector map for the exemplary pLVX-CMV-TCR1-pTert-iCas9 vector. The vector comprises an ampicillin resistance gene, 5' and 3' LTRs, a CMV promoter, TCR beta sequences (TRBV6-2 leader peptide, TRBV25, TRBC) and TCR alpha sequences (TRAV38-1, TRAV35, and TRAC), a p2A sequence inserted between TCR beta and TCR alpha, an IRES sequence inserted following the TCR alpha sequence, an mCherry fluorescent marker, an i-Caspase9 suicide switch controlled by a tet inducible promoter and flanked by cHS4 insulator sequences, and a WPRE enhancer.
Figure 4:
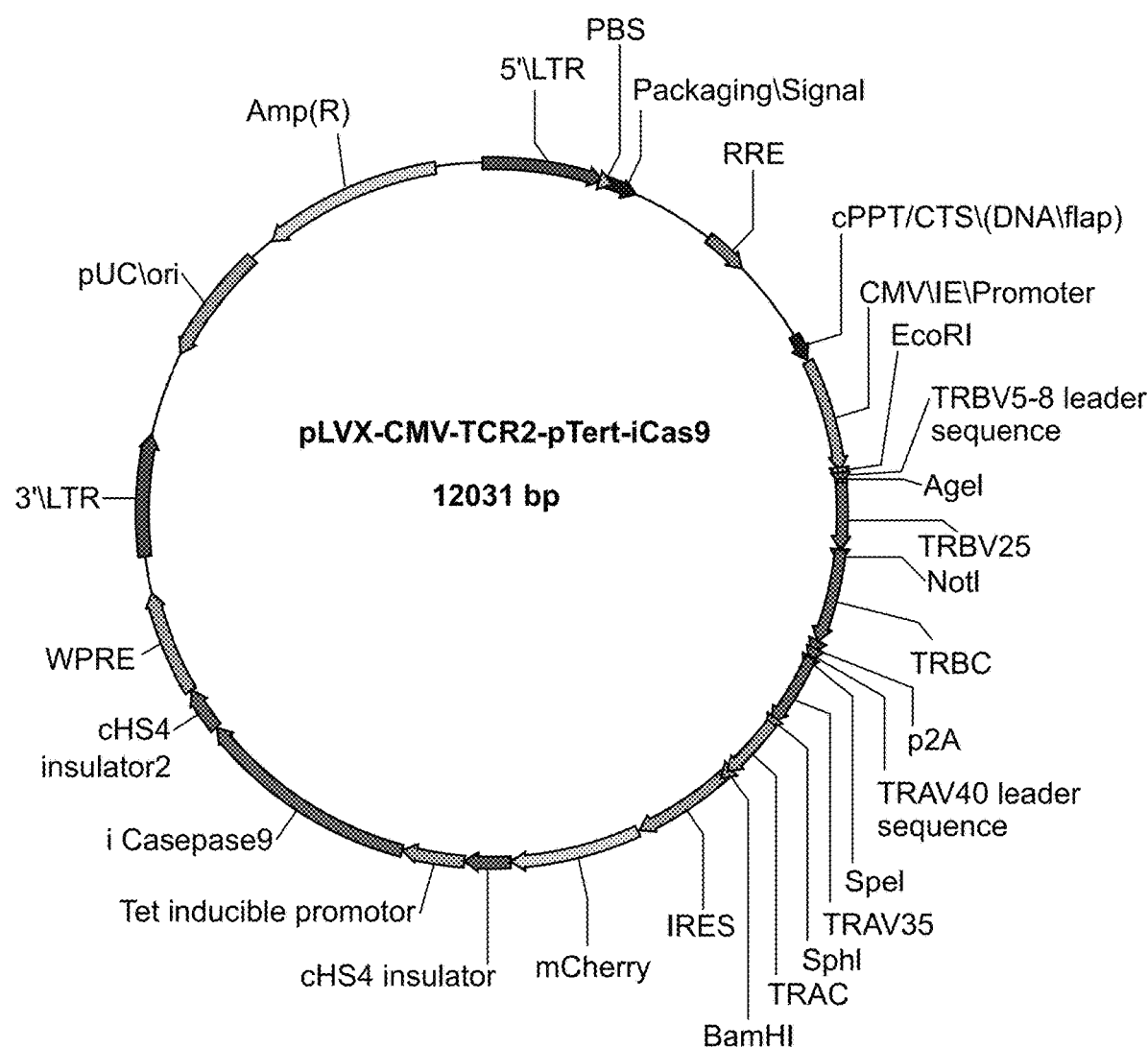
FIG. 4 shows a vector map for pLVX-CMV-TCR2-pTert-iCas9. The vector comprises an ampicillin resistance gene, 5' and 3' LTRs, a CMV promoter, TCR beta sequences (TRBV5-8 leader peptide, TRBV25, TRBC) and TCR alpha sequences (TRAV40, TRAV35, and TRAC), a p2A sequence inserted between TCR beta and TCR alpha, an IRES sequence inserted following the TCR alpha sequence, an mCherry fluorescent marker, an i-Caspase9 suicide switch controlled by a tet inducible promoter and flanked by cHS4 insulator sequences, and a WPRE enhancer.
Figure 5:
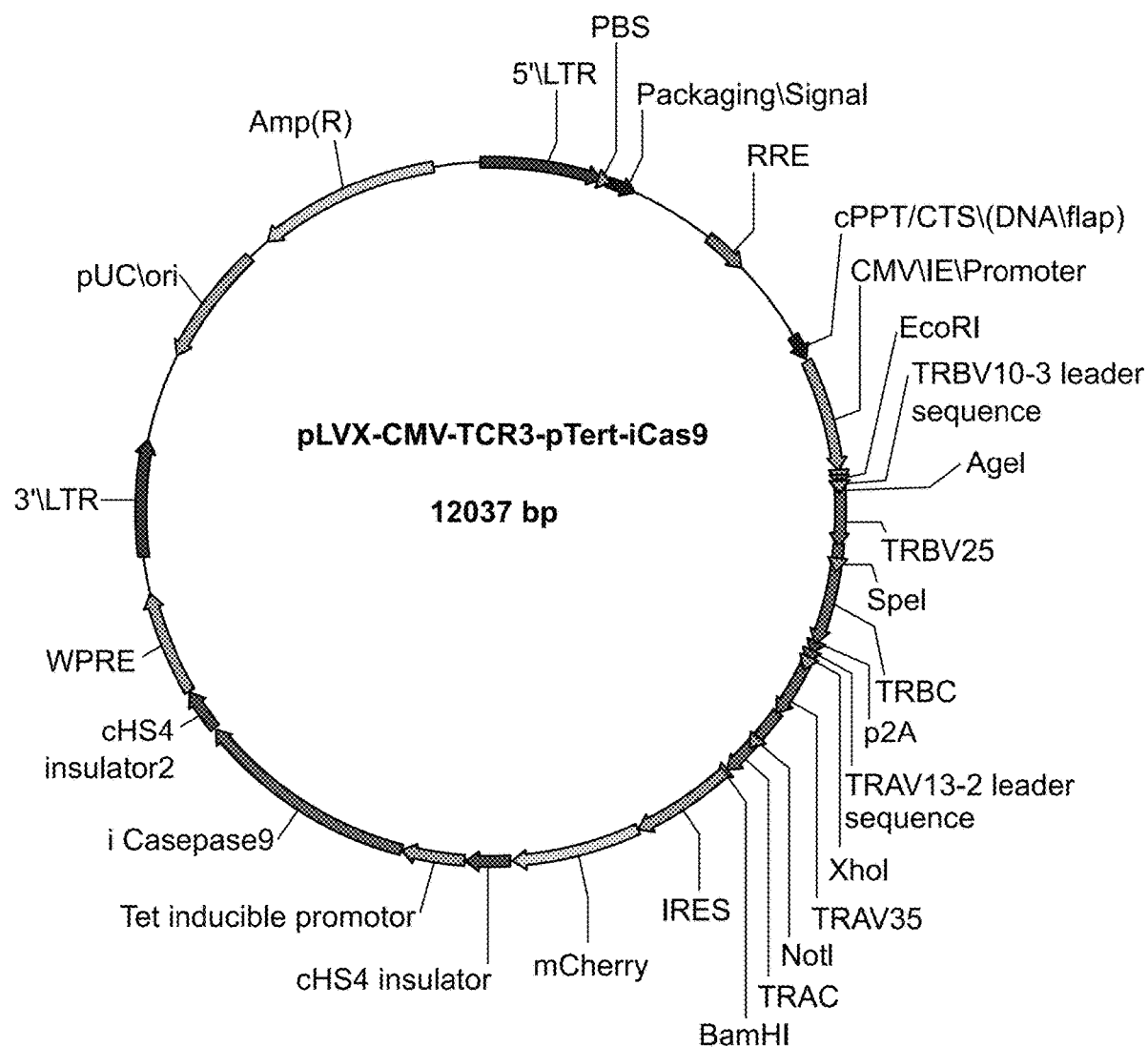
FIG. 5 shows a vector map for pLVX-CMV-TCR3-pTert-iCas9. The vector comprises an ampicillin resistance gene, 5' and 3' LTRs, a CMV promoter, TCR beta sequences (TRBV10-3 leader peptide, TRBV25, TRBC) and TCR alpha sequences (TRAV13-2, TRAV35, and TRAC), a p2A sequence inserted between TCR beta and TCR alpha, an IRES sequence inserted following the TCR alpha sequence, an mCherry fluorescent marker, an i-Caspase9 suicide switch controlled by a tet inducible promoter and flanked by cHS4 insulator sequences, and a WPRE enhancer.
Figure 6:
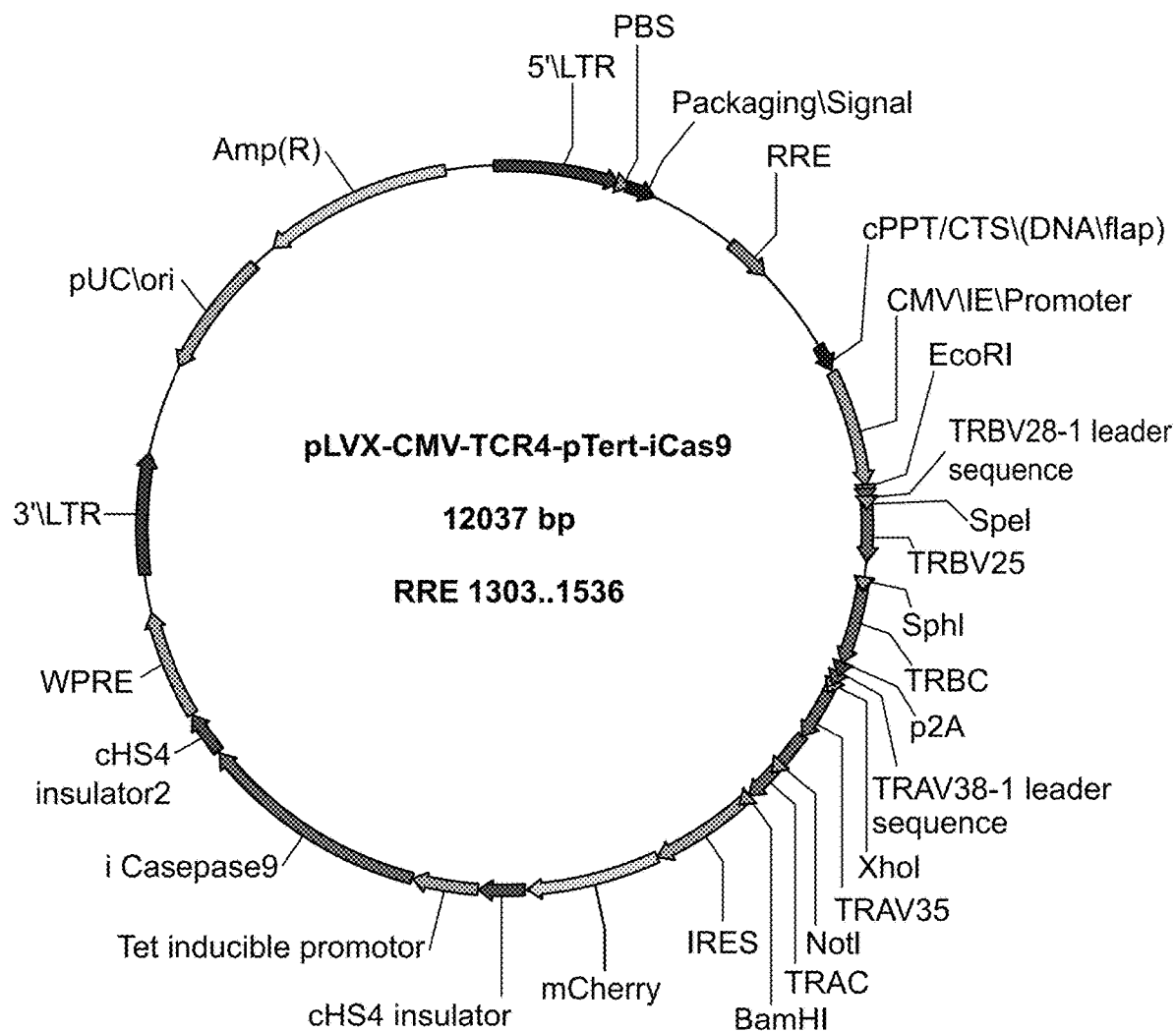
FIG. 6 shows a vector map for pLVX-CMV-TCR4-pTert-iCas9. The vector comprises an ampicillin resistance gene, 5' and 3' LTRs, a CMV promoter, TCR beta sequences (TRBV28-1 leader peptide, TRBV25, TRBC) and TCR alpha sequences (TRAV38-1, TRAV35, and TRAC), a p2A sequence inserted between TCR beta and TCR alpha, an IRES sequence inserted following the TCR alpha sequence, an mCherry fluorescent marker, an i-Caspase9 suicide switch controlled by a tet inducible promoter and flanked by cHS4 insulator sequences, and a WPRE enhancer.
Figure 7:
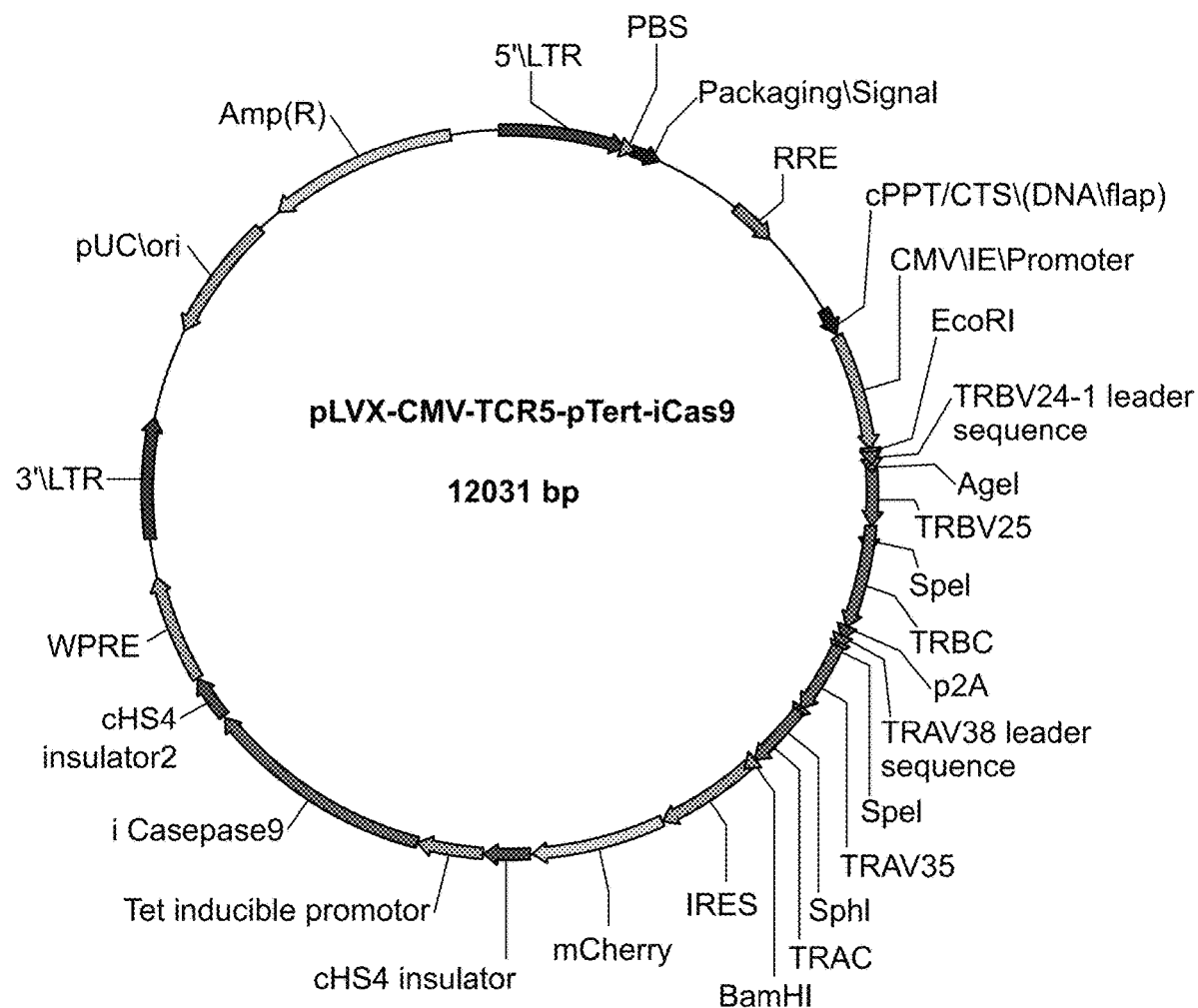
FIG. 7 shows a vector map for pLVX-CMV-TCR5-pTert-iCas9. The vector comprises an ampicillin resistance gene, 5' and 3' LTRs, a CMV promoter, TCR beta sequences (TRBV24-1 leader peptide, TRBV25, TRBC) and TCR alpha sequences (TRAV38, TRAV35, and TRAC), a p2A sequence inserted between TCR beta and TCR alpha, an IRES sequence inserted following the TCR alpha sequence, an mCherry fluorescent marker, an i-Caspase9 suicide switch controlled by a tet inducible promoter and flanked by cHS4 insulator sequences, and a WPRE enhancer.
Figure 8:
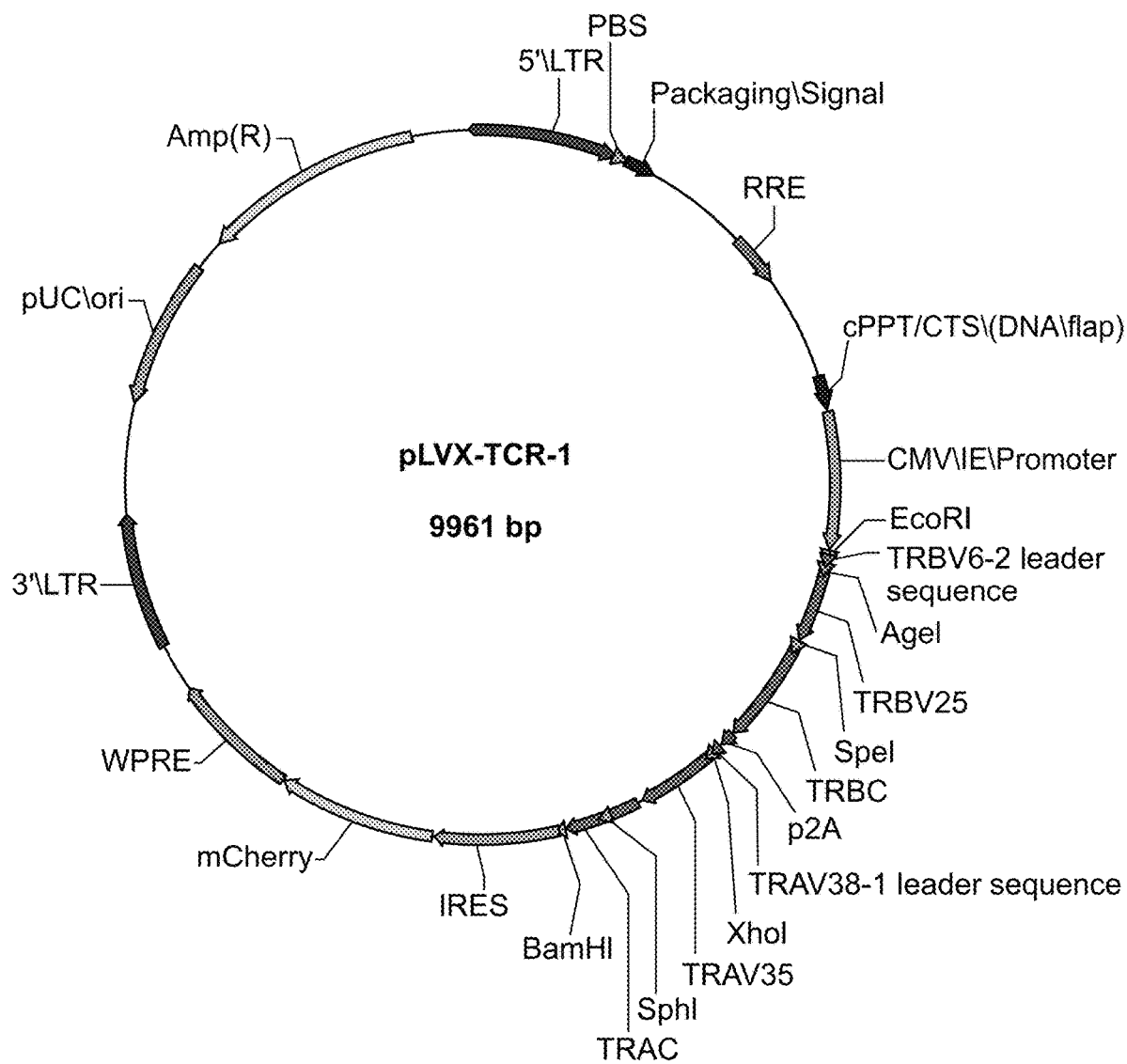
FIG. 8 shows a vector map for pLVX-TCR1-pTert-iCas9. The vector comprises an ampicillin resistance gene, 5' and 3' LTRs, a CMV promoter, TCR beta sequences (TRBV6-2 leader peptide, TRBV25, TRBC) and TCR alpha sequences (TRAV38-1, TRAV35, and TRAC), a p2A sequence inserted between TCR beta and TCR alpha, an IRES sequence inserted following the TCR alpha sequence, an mCherry fluorescent marker, and a WPRE enhancer.
Figure 9:
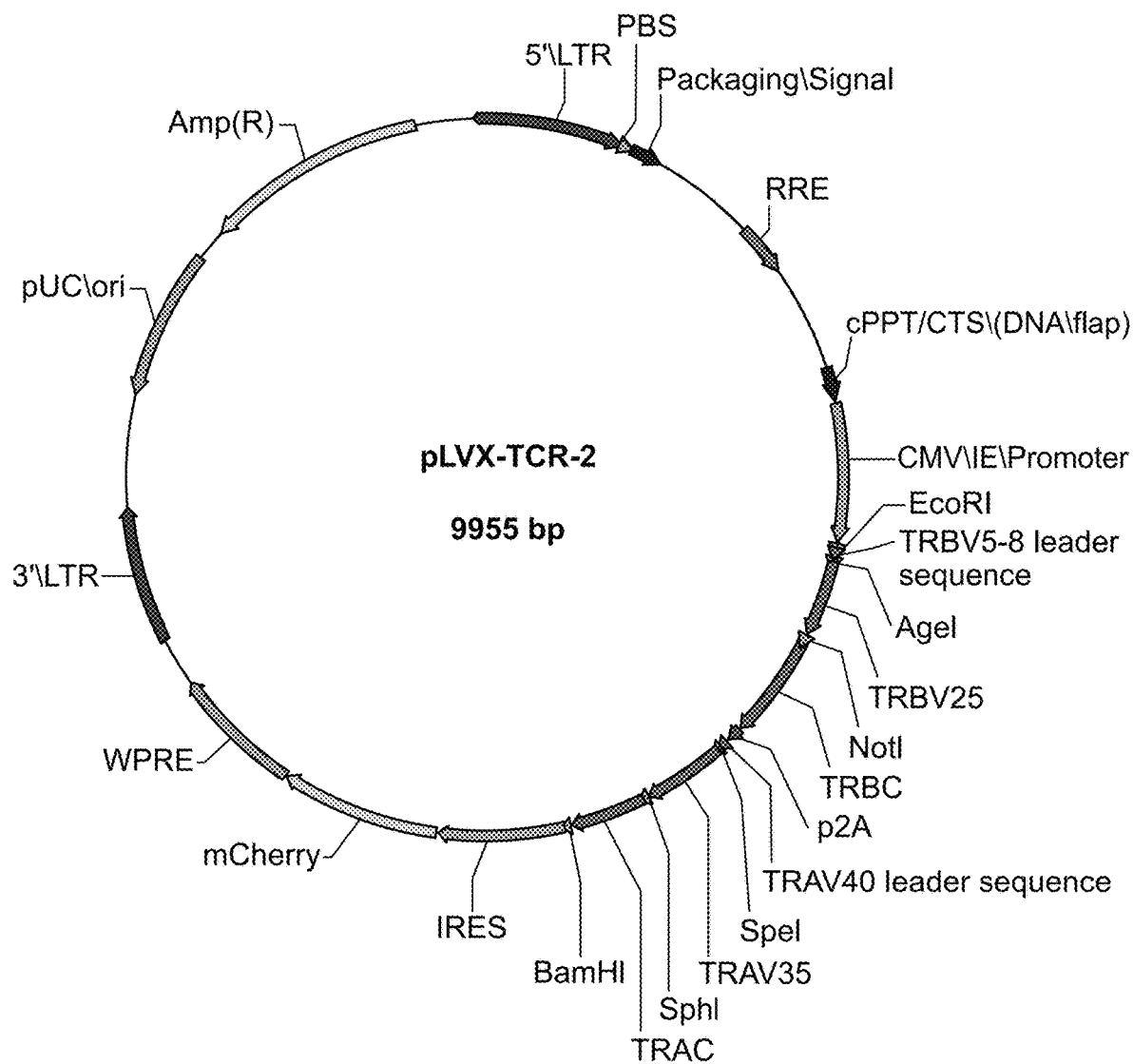
FIG. 9 shows a vector map for pLVX-TCR2-pTert-iCas9. The vector comprises an ampicillin resistance gene, 5' and 3' LTRs, a CMV promoter, TCR beta sequences (TRBV5-8 leader peptide, TRBV25, TRBC) and TCR alpha sequences (TRAV40, TRAV35, and TRAC), a p2A sequence inserted between TCR beta and TCR alpha, an IRES sequence inserted following the TCR alpha sequence, an mCherry fluorescent marker, and a WPRE enhancer.
Figure 10:
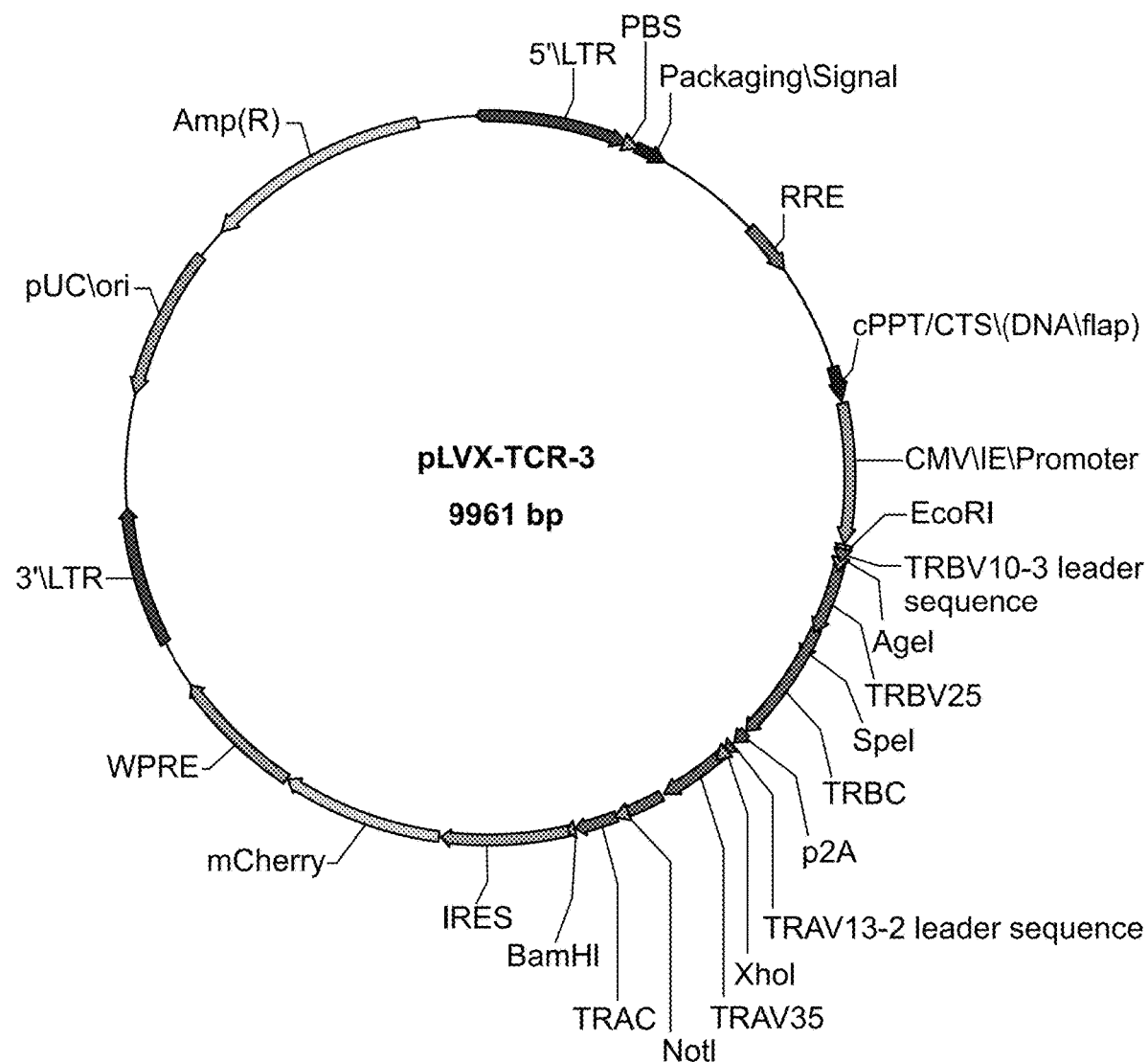
FIG. 10 shows a vector map for pLVX-TCR3-pTert-iCas9. The vector comprises an ampicillin resistance gene, 5' and 3' LTRs, a CMV promoter, TCR beta sequences (TRBV10-3 leader peptide, TRBV25, TRBC) and TCR alpha sequences (TRAV13-2, TRAV35, and TRAC), a p2A sequence inserted between TCR beta and TCR alpha, an IRES sequence inserted following the TCR alpha sequence, an mCherry fluorescent marker, and a WPRE enhancer.
Figure 11:
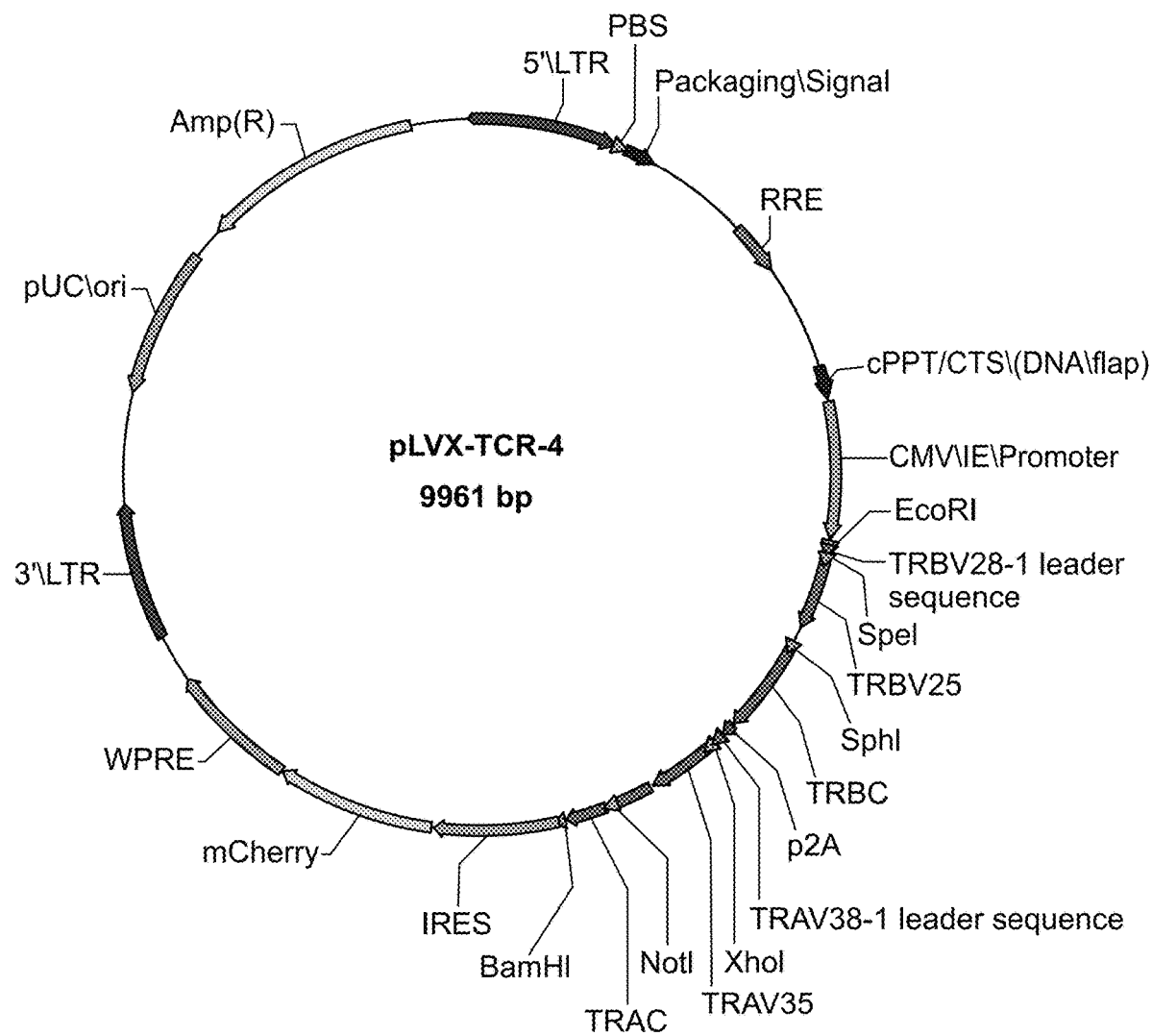
FIG. 11 shows a vector map for pLVX-TCR4-pTert-iCas9. vector comprises an ampicillin resistance gene, 5' and 3' LTRs, a CMV promoter, TCR beta sequences (TRBV28-1 leader peptide, TRBV25, TRBC) and TCR alpha sequences (TRAV38-1, TRAV35, and TRAC), a p2A sequence inserted between TCR beta and TCR alpha, an IRES sequence inserted following the TCR alpha sequence, an mCherry fluorescent marker, and a WPRE enhancer.
Figure 12:
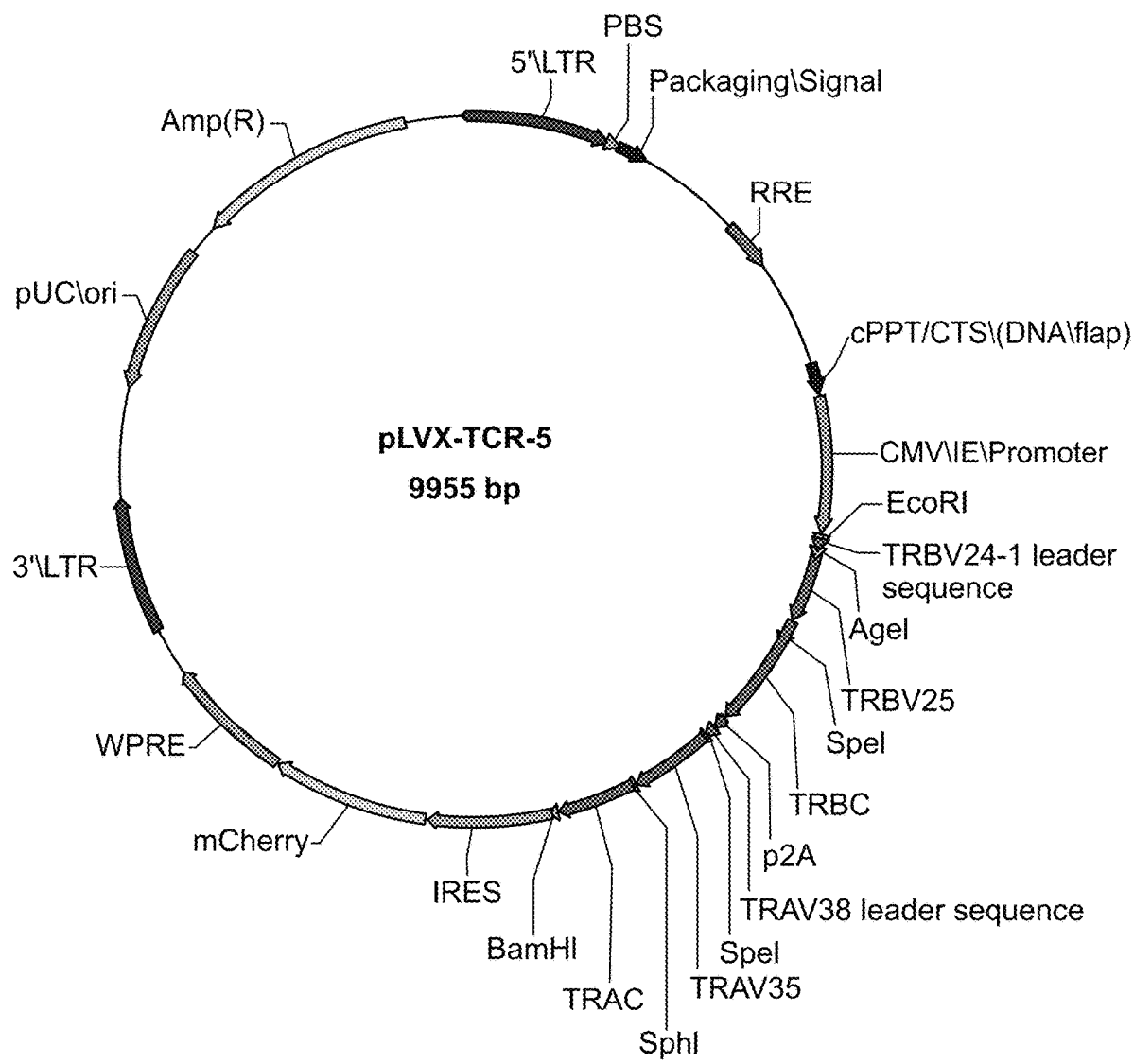
FIG. 12 shows a vector map for pLVX-TCR5-pTert-iCas9. The vector comprises an ampicillin resistance gene, 5' and 3' LTRs, a CMV promoter, TCR beta sequences (TRBV24-1 leader peptide, TRBV25, TRBC) and TCR alpha sequences (TRAV38, TRAV35, and TRAC), a p2A sequence inserted between TCR beta and TCR alpha, an IRES sequence inserted following the TCR alpha sequence, an mCherry fluorescent marker, and a WPRE enhancer.

DNA clean-up was performed using Zymo DNA Clean & Concentrator kit (Zymo Research) to purify the PCR products. The purified PCR products were analyzed by DNA electrophoresis. PCR results were showed in FIG. 2, and the band around 1000 b.p. indicated the successful amplification of the TCR α:β amplicon.

After the DNA electrophoresis, the TCR α:β amplicon was excised and gel purification was performed using Zymoclean™ Gel DNA Recovery Kits (Zymo Research). The purified amplicon was subjected to zero-blunt cloning (Thermo Fisher Scientific) to analyze TCR α:β amplicon sequences. The sequences were identified by the NCBI IGBLAST T cell receptor gene database (available at www.ncbi.nlm.nih.gov/igblast/). The sequencing results of the 8 TCR α:β amplicons and their respective TCR alpha and beta chain genes are listed in Table 6.

TABLE 6

Gene sequencing results TCR α:β amplicons cloned into plasmid vectors for single-colony sequencing.

| Amplicon | TRAV gene | TRBV gene |
|---|---|---|
| 1 | 26 | 28 |
| 2 | 35 | 4 |
| 3 | 2 | 2 |
| 4 | 21 | 19 |
| 5 | 12 | 11 |
| 6 | 13 | 19 |
| 7 | 12 | 25 |

The sequenced TCR α:β amplicon represented a diverse TCR α:β repertoire from the human PBMC which supported the conclusion that the TCR primer design described in this example can successfully amplify the TCR repertoire. The primer set forth in Table 4 with restriction endonucleases target cleavage sites was incorporated into the amplicon and OE-PCR and nested PCR was successfully performed. The restriction enzymes were chosen to select target cleavage sites which are rarely found (e.g., found in fewer than 5 segments) in T cell receptor genes (including the variable, diversity, joining and constant regions), allowing the expression of original TCR amino acid sequences without losing the TCR library diversity and reducing the TCR library bias due to cleavage during the restriction enzyme digestion and the afterward circulation of expression plasmid process. Several restriction sites were incorporated with silent and non-silent mutations to add additional restriction enzyme cut sites that are rarely found in native TCR genes (Tables 7 and 8).

TABLE 7

Silent mutations used to clone T cell receptors into lentiviral expression vectors without changing the amino acid sequence of the genes.

| Restriction enzyme | Amino acid sequence | Amino acid sites | TCR gene name | Original sequence | Mutated sequence |
| --- | --- | --- | --- | --- | --- |
| Age I | TG | 16-17 | TRBV 10-3 | acagga | accggt |
| Age I | TG | 16-17 | TRBV 15-1 | acaggt | accggt |
| Age I | TG | 16-17 | TRBV 24-1 | acaggg | accggt |
| Age I | TG | 10-11 | TRBV 24-2 | acaggg | accggt |
| Age I | TG | 16-17 | TRBV 24-3 | acaggg | accggt |
| Age I | TG | 16-17 | TRBV 5-8 | acaggc | accggt |
| Age I | GPV | 17-19 | TRBV5-1 | ggcccagta | ggaccggta |
| Age I | GPV | 17-19 | TRBV5-2 | ggcccagtg | ggaccggtg |
| Age I | GPV | 17-19 | TRBV5-3 | ggcccagtg | ggaccggtg |
| Age I | GPV | 17-19 | TRBV5-5 | ggcccagtg | ggaccggtg |
| Age I | GPV | 17-19 | TRBV5-7 | ggcccagtg | ggaccggtg |
| Age I | GPV | 17-19 | TRBV5-8 | ggcccagtg | ggaccggtg |
| Age I | GPV | 17-19 | TRBV6-2 | ggtccagtg | ggaccggtg |
| Age I | GPV | 17-19 | TRBV6-3 | ggtccagtg | ggaccggtg |
| Age I | GPV | 17-19 | TRBV6-4 | ggtccagtg | ggaccggtg |
| Age I | GPV | 17-19 | TRBV6-5 | ggtccagtg | ggaccggtg |
| Age I | GPV | 17-19 | TRBV6-6 | ggtccagtg | ggaccggtg |
| Age I | GPV | 17-19 | TRBV6-8 | ggtcccgtg | ggaccggtg |
| Age I | GPV | 17-19 | TRBV6-9 | ggtcccgtg | ggaccggtg |
| Age I | GPV | 17-19 | TRBV9-1 | ggcccagtg | ggaccggtg |
| Age I | GPV | 17-19 | TRBV9-2 | ggcccagtg | ggaccggtg |
| SpeI | GLV | 17-19 | TRBV 28-1 | ggcctcgta | ggactagta |
| SpeI | GLV | 17-19 | TRBV 5-6 | ggcttagtg | ggactagtg |
| SpeI | TS | 18-19 | TRAV40 | accagc | actagt |
| SpeI | TS | 18-19 | TRAV18 | accagt | actagt |
| XhoI | LE | 16-17 | TRAV38-1 | cttgaa | ctcgag |
| XhoI | LE | 16-17 | TRAV38-2 | cttgaa | ctcgag |
| XhoI | VSR | 18-20 | TRAV13-2 | gtgagcaga | gtctcgaga |
| NheI | QLA | 15-17 | TRAV17-1 | caactggct | caGctAgct |
| NheI | QLA | 13-15 | TRAV27-1 | cagttggca | cagCTAgca |
| BsiWI | RT | 16-17 | TRAV8-5 | agaact | CGTACG |
| BsiWI | RT | 17-18 | TRAV18-5 | aggacc | CGTACG |
| BsiWI | GVR | 15-17 | TRBV30-1 | ggggtcaga | GGCGTACGA |

TABLE 7-continued

Silent mutations used to clone T cell receptors into lentiviral expression vectors without changing the amino acid sequence of the genes.

| Restriction enzyme | Amino acid sequence | Amino acid sites | TCR gene name | Original sequence | Mutated sequence |
|---|---|---|---|---|---|
| BsiWI | GVR | 15-17 | TRBV30-2 | ggggtcaga | GGCGTACGA |
| BsiWI | GVR | 15-17 | TRBV30-3 | ggggtcaga | GGCGTACGA |
| MluI | TR | 18-19 | TRAV8-2 | accaga | ACGCGT |
| MluI | TR | 18-19 | TRAV8-4 | accaga | ACGCGT |
| MluI | TR | 18-19 | TRAV8-6 | accaga | ACGCGT |
| MluI | TR | 17-18 | TRAV8-7 | accaga | ACGCGT |
| MluI | TR | 18-19 | TRAV9-2 | acccgt | ACGCGT |
| MluI | TR | 18-19 | TRAV16-1 | acaaga | ACGCGT |
| SphI | AC | 72-73 | TRAC | gcatgt | gcatgC |
| BstZI7I | VY | 9-10 | TRAC | gtgtac | GTATAC |
| BstBI | DSK | 14-16 | TRAC | GACTCTAA | GATTCGAA |
| SpeI | TLV | 28-29 | TRBC1 | acactggtg | acACTAGTg |
| SpeI | TLV | 28-29 | TRBC2 | acactggtg | acACTAGTg |

TABLE 8

Non-silent mutations used to clone T cell receptors into lentiviral expression vectors with minimal modifications to native amino acid sequences.

| Restriction enzyme | Original amino acid sequence | Mutated amino acid sequence | Amino acid site | TCR gene name | Original DNA sequence | Mutated DNA seqence |
|---|---|---|---|---|---|---|
| NotI | VAV | AAA | 11-13 | TRBC1 | gtcgctgtg | CGGCCGCGT |
| NotI | VAV | AAA | 11-13 | TRBC2 | gtcgctgtg | CGGCCGCGT |
| SpeI | VAV | LVV | 11-13 | TRBC1 | gtcgctgtg | GAACTAGTC |
| SpeI | VAV | LVV | 11-13 | TRBC2 | gtcgctgtg | GAACTAGTC |
| sphI | VC | AC | 30-31 | TRBC1 | gtgtgc | GcaTGC |
| sphI | VC | AC | 30-31 | TRBC2 | gtgtgc | GcaTGC |
| XhoI | PE | LE | 9-10 | TRBC1 | CCCGAG | CTCGAG |
| XhoI | PE | LE | 9-10 | TRBC2 | CCCGAG | CTCGAG |
| XhoI | FE | LE | 14-15 | TRBC1 | tttgag | CTCGAG |
| XhoI | FE | LE | 14-15 | TRBC2 | tttgag | CTCGAG |
| XhoI | AE | LE | 19-20 | TRBC1 | GCAGAG | CTCGAG |
| XhoI | AE | LE | 19-20 | TRBC2 | GCAGAG | CTCGAG |
| NheI | TLV | TLA | 30 | TRBC1 | acactggtg | acGCTAGCC |
| NheI | TLV | TLA | 30 | TRBC2 | acactggtg | acGCTAGCC |
| NheI | AT | AS | 28 | TRBC1 | GCCACa | GCTAGC |
| NheI | AT | AS | 28 | TRBC2 | GCCACa | GCTAGC |
| NotI | AVA | AAA | 62-64 | TRAC | gctgtggcc | GCGGCCgcc |

TABLE 8-continued

Non-silent mutations used to clone T cell receptors into lentiviral expression vectors with minimal modifications to native amino acid sequences.

| Restriction enzyme | Original amino acid sequence | Mutated amino acid sequence | Amino acid site | TCR gene name | Original DNA sequence | Mutated DNA seqence |
|---|---|---|---|---|---|---|
| SphI | VC | AC | 22-23 | TRAC | gtctgc | GcaTGC |
| NheI | VS | AS | 34-35 | TRAC | gtgtca | gctagc |

The TCR α:β amplicon was subcloned into a Lentiviral expression vector, pLVX-EF1alpha-IRES-mCherry (Clontech). Co-transfection of the TCR containing lentiviral expression vector into HEK293T cells along with the lentivirus packaging vector and envelope vector was performed to generate lentiviral particles for TCR expression. HEK293T cells were transfected at the following ratios: 10 μg pLVX, 8 μg psPAX2 packaging plasmid, 3 μg pMID2.g envelope plasmid, 100 μl Fugene transfection reagent. The recombinant lentivirus encoding TCR were transduced into an in vitro display J.RT3 T cell line for the expression of TCR. J.RT3'5 endogenous TCR alpha and beta genes been knocked out allowing transgenic expression of foreign TCR alpha and beta chain. The transduction protocol was optimized to achieve an MOI≤0.2 so that the vast majority of cells are only expressing a single TCR paired alpha:beta amplicon. Finally, transduced cells were stained with anti-α chain, anti-β chain, anti-CD8, and anti-CD3 antibodies for flow cytometry analyses to determine the fraction of mCherry-expressing cells that display a fully assembled TCR complex ready for functional peptide-MHC binding analysis.

Figure 15:
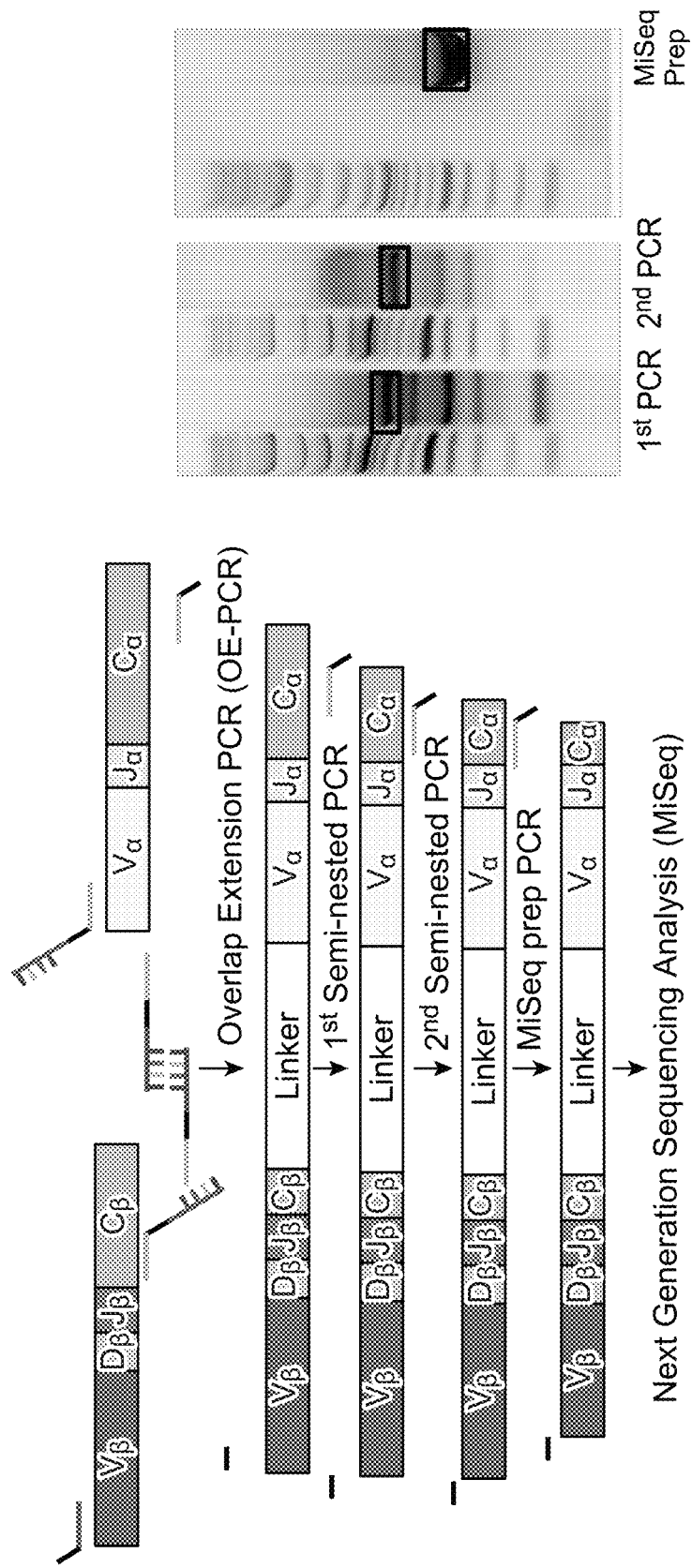
FIG. 15 shows DNA electrophoresis analysis of the T cell receptor (TCR) amplicon (alpha: beta chain) from single-cell emulsification overlap-extension RT-PCR. Left panel indicates PCR amplification scheme of the paired alpha: beta chain TCR amplicon. Right panel displays the DNA electrophoresis results of the $1^{st}$ semi-nested, $2^{nd}$ semi-nested and Mi-seq PCR. T cell receptor amplicons were highlighted in red square. The Miseq primers annealed at the FR3 region of the TRBV genes, yielding an ~550 bp paired alpha:beta PCR amplicon for natively paired DNA sequence analysis.

FIG. 15 shows DNA electrophoresis analysis of the T cell receptor (TCR) amplicon (alpha: beta chain) from single-cell emulsification overlap-extension RT-PCR. Briefly, T cells purified from PBMC using CD8 isolation kit were isolated into oil emulsion droplet with lysis buffer and poly(dT) beads to capture mRNA for cell lysis and RNA capture. The poly(dT) beads with T cell RNA were re-emulsified for cDNA synthesis and overlap-extension PCR (OE-PCR). Two semi-nested PCR ($1^{st}$ semi-nested and $2^{nd}$ semi-nested) were performed to increase the TCR pair α:β chain amplicon concentration. Mi-seq PCR was then performed to add the next-generation sequence barcode for high-throughput sequencing analysis.

Figure 16:
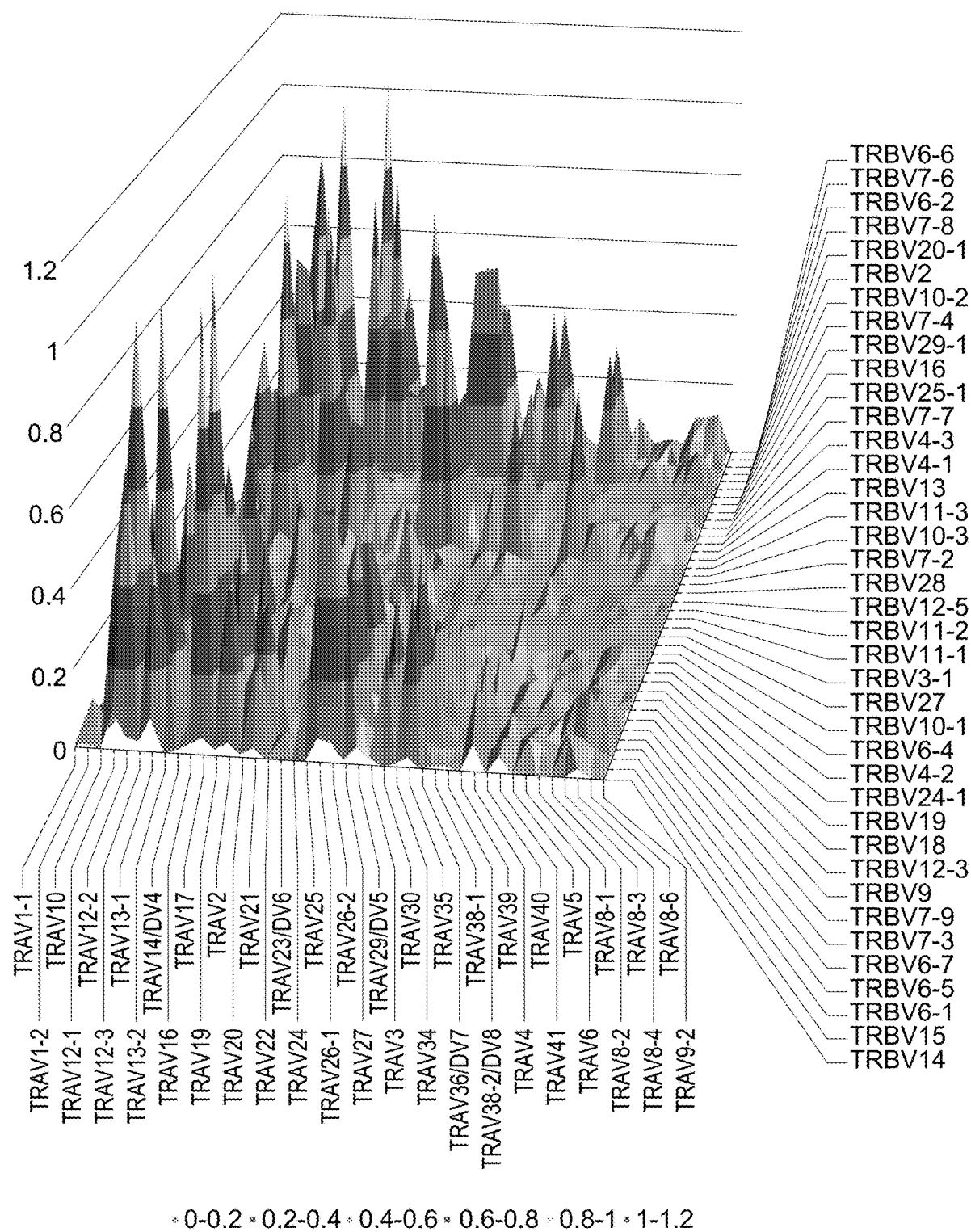
FIG. 16 shows a summary of linked alpha:beta T cell receptor gene distribution. After high-throughput sequencing, raw DNA sequences were quality-filtered and annotated for TCR gene usage via NCBI IgBLAST and a CDR3-motif algorithm, paired by α and β chains, and compiled into a TCR repertoire.

After high-throughput sequencing, raw DNA sequences were quality-filtered and annotated for TCR gene usage via NCBI IgBLAST and a CDR3-motif algorithm, paired by α and β chains, and compiled into a TCR repertoire. FIG. 16 shows a summary of linked alpha:beta T cell receptor gene distribution.

Example 2: Evaluation of TCR Clones Containing Silent or Non-Silent Mutations

To successfully clone in the TCR genes using restriction enzymes listed herein, the destination cloning vector pLVX-EF1α-IRES-mCherry was modified to remove the following four cutting sites via site-directed mutagenesis: AgeI (2415), SphI (2331), NheI (8192) and MluI (6669) cutting sites (numbers indicate the location of these cutting sites).

A previously identified TCR, anti-HIV-Nef-Rm9, was used as a model TCR for evaluation of the TCR genes with different mutations listed in Table 7 and Table 8. Wild-type anti-HIV-Nef-RM9 TCR gene fragment was subcloned into the Lentiviral vector, pLVX-EF1α-IRES-mCherry, for expression of active TCR. All anti-HIV-Nef-RM9 mutant clones (Table 7 and Table 8) were introduced by gene synthesis together with restriction enzymes digestion and ligation. Lentiviral expression vectors with Wild-type and mutant anti-HIV-Nef-Rm9 TCRs were transfected separately with envelope and packing plasmid (psPAX2 and pMD2.G) into HEK293FT cell for expression of lentiviruses. An engineered Jurkat cell line that was modified to have no active T cell receptor expression, JRT3/CD8, was used as a TCR expression platform. Lentiviruses encoding wild-type and mutant anti-HIV-Nef-RM9 TCR were transduced separately into JRT3/CD8 cells for TCR expression. The wild-type and mutant anti-HIV-Nef-Rm9 TCRs binding affinity to a HIV peptide, RPQVPLRPM (SEQ ID NO: 1), coupled onto the major histocompatibility complex (MHC) was evaluated. The RPQVPLRPM-MHC ("RPQVPLRPM" is disclosed as SEQ ID NO: 1) complexes were conjugated with Streptavidin-Allophycocyanin (SA-APC) for detection of the binding of TCR to peptide-MHC. In parallel, the transduced JRT3/CD8 cells were stained with anti-TCR antibody conjugated with a BV421 fluorescent marker for evaluation of T cell receptor expression of anti-HIV-Nef-Rm9 with different mutations.

Figure 17:
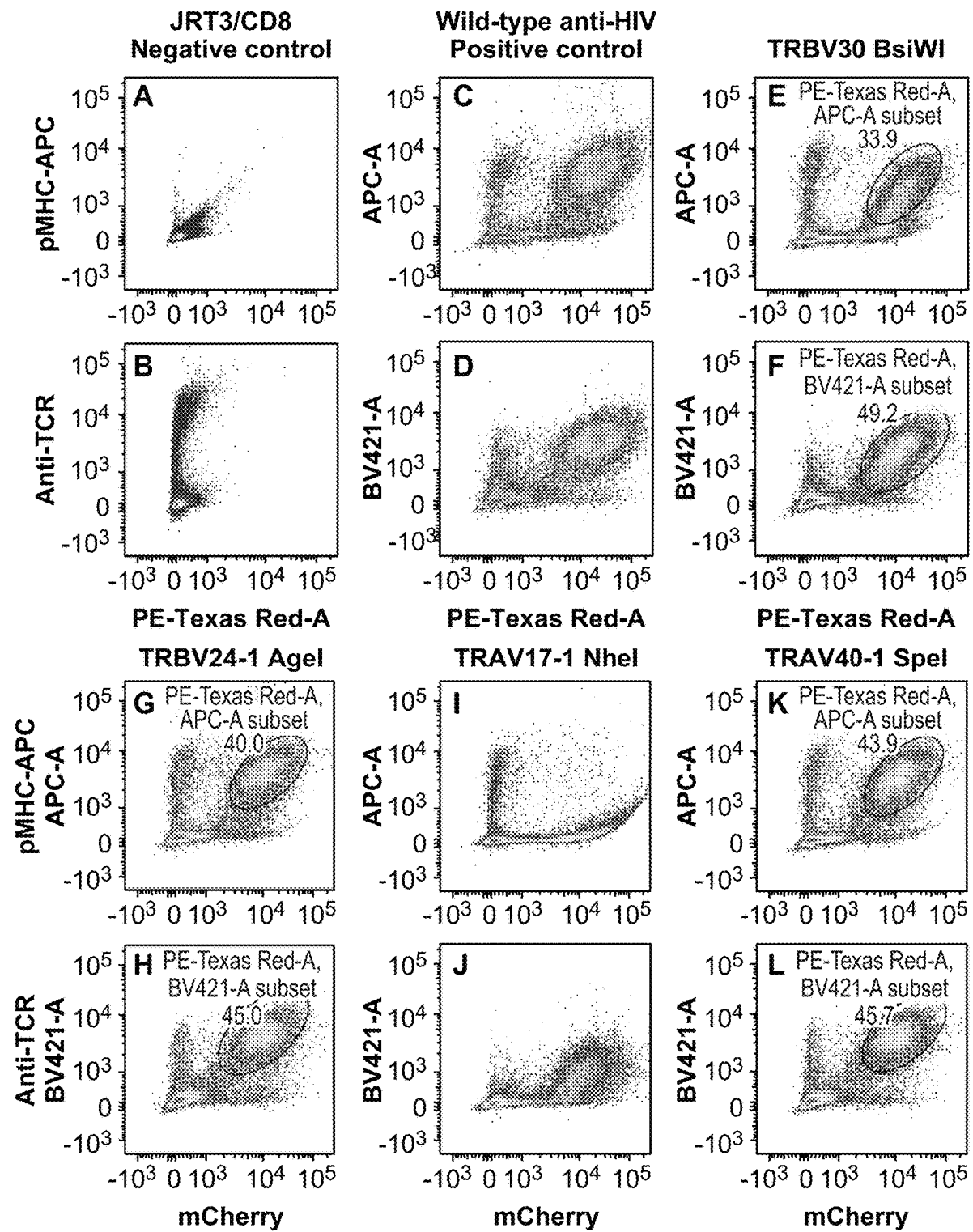
FIG. 17 shows the evaluation of the expression of mutant anti-HIV-Nef-Rm9 TCRs and their binding affinity to pMHC, where these mutant TCRs include a leader peptide different from the original wild-type anti-HIV-Nef-Rm9 leader peptide. These non-native leader peptides all have silent DNA mutation sequences in order to include restriction enzyme cutting sites (The original and non-silent mutant leader peptide DNA sequences and the introduced restriction cutting sites are summarized in Tables 7-8).
Figure 18:
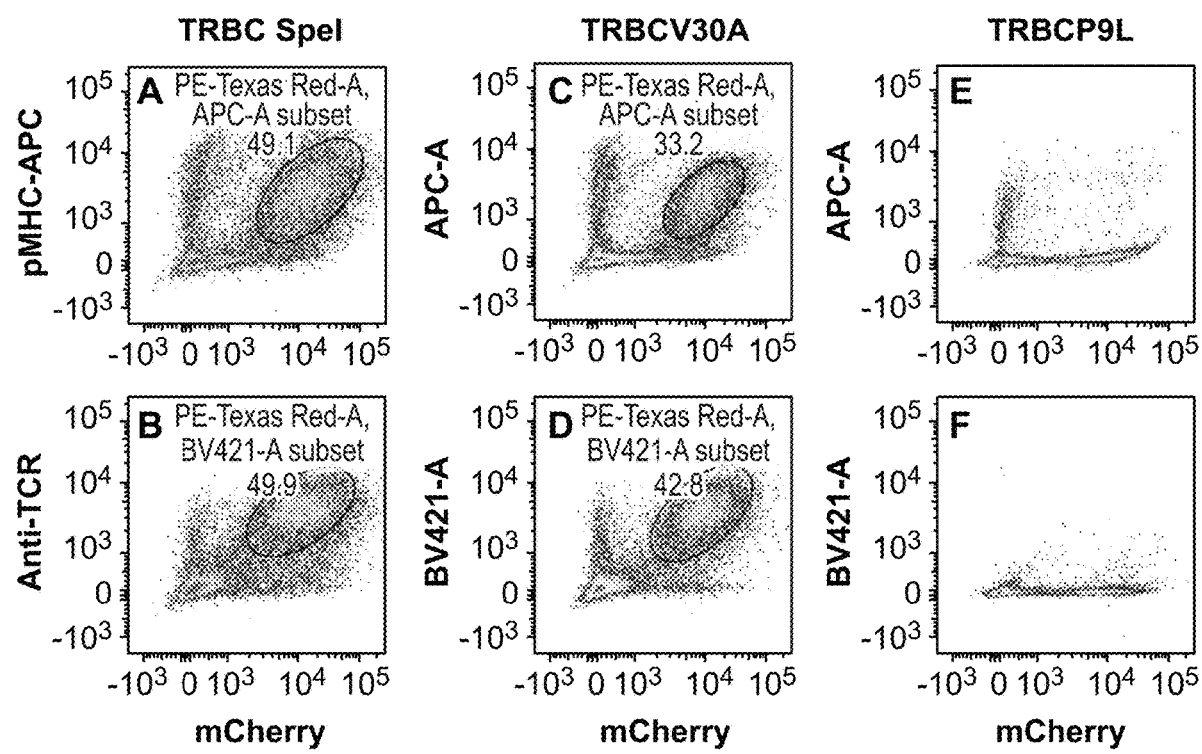
FIG. 18 shows the evaluation of the expression of mutant anti-HIV-Nef-Rm9 TCRs and their binding affinity to pMHC. These mutant TCRs include one non-silent or one silent mutation at the TCR constant region for incorporation of a restriction cutting site for TCR cloning (See all the silent mutations in Table 7 and non-silent mutations in Table 8).

FIG. 17 and FIG. 18 demonstrates that mutant anti-HIV-Nef-Rm9 TCRs with different non-native leader peptides can lead to different levels of TCR expression. Compared with the wild-type anti-HIV-TCR expression level and its binding affinity to the pMHC (FIG. 17 Panel C and D), mutant TCRs including a TRBV24-1 or a TRAV40-1 leader peptide showed comparable levels of TCR expression and pMHC binding affinities (FIG. 17 Panel G and H for TRBV24-1 and Panel K and L for TRAV40-1), whereas the mutant TCR with a TRBV30 leader peptide exhibited reduced TCR expression and pMHC binding capacity (FIG. 17 Panel E and F). Mutant anti-HIV TCR with TRAV17-1 leader peptide demonstrated no pMHC binding tendency and a low level of TCR expression (FIG. 17 Panel I and J). Compared with the wild-type anti-HIV-TCR expression level and its binding affinity to the pMHC (FIG. 17 Panel C and D), TCRs with a silent mutation (for incorporation of a SpeI restriction site) had a comparable level of TCR expression and pMHC binding affinities (FIG. 18 Panel A and B). The mutant TCR with a single amino acid mutation, TRBCV30A, exhibited a similar TCR expression and pMHC binding capacity to those of the wild-type anti-HIV TCR (FIG. 18 Panel C and D). Mutant anti-HIV TCR with a single amino acid mutation, TRBCP9L, demonstrated no pMHC binding tendency and no TCR expression (FIG. 18 Panel E and F).

Figure 19:
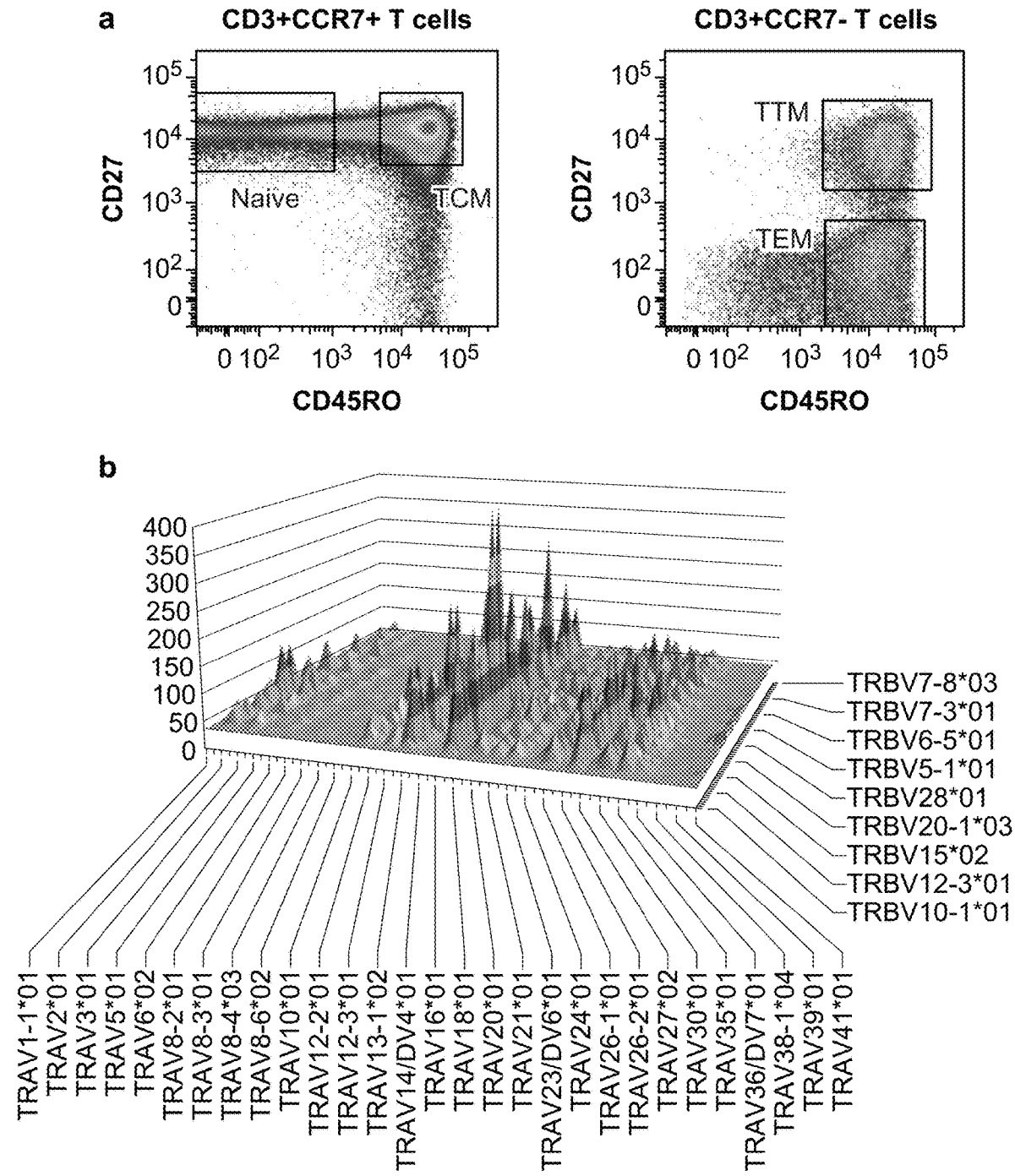
FIG. 19(a) shows isolation of human effector T cells for tumor-specific T cell analysis of humanized mouse models and cancer patients.
FIG. 19(b) shows Vα:Vβ gene usage in 31,718 human CD8+ TCR clusters that were isolated, RT-PCR amplified, analyzed via NGS.

FIG. 19(a) shows isolation of human effector T cells for tumor-specific T cell analysis of humanized mouse models and cancer patients. FIG. 19(b) shows Vα:Vβ gene usage in 31,718 human CD8+ TCR clusters that were isolated, RT-PCR amplified, analyzed via NGS.

Example 3: Screening Native TCRα:β for Binding to Known Peptide:MHC Combinations In this example, tetramer staining is performed using recombinant human leukocyte antigen (HLA) tetramer complexes loaded with known Epstein-Barr virus (EBV) peptide. The EBV reactive T cells with TCR on the cell surface will recognize the EBV peptide-HLA tetramer complexes. The HLA complexes were biotinylated and conjugated with streptavidin linked to a fluorophore permitting the sorting of the EBV-reactive T cells. The PBMC are isolated from an Epstein-Barr virus positive donor with known HLA alleles, and emulsion overlap reverse transcription extension PCR (OE-RT-PCR) is performed to isolate the donor's T cell receptor repertoire, as described in Example 1. The TCR amplicons were inserted into the developed TCR expression lentiviral vector constructed in Example 1. After generation of vectors for expressing natively paired T cell receptor libraries, J.RT3 cell lines are transduced with the lentiviral vectors at an MOI of ≤0.2, allowing the expression of TCR α and β chain on in vitro cell libraries.

Several previously characterized EBV TCR-peptide-MHC interactions are assessed (Ref #6-8). In particular, HLA B8 loaded with known immunodominant EBV peptide, HLA-B8-restricted epitope FLRGRAYGL (SEQ ID NO: 79) derived from the latent EBV antigen protein EBNA3A (Ref #9). The transgenic J.RT3 cells' response to an HLA-A*02.01-restricted epitopes from LMP2, a known EBV oncogenic protein, which is thought to have important, potentially protective effects for EBV protection but comprises a more measured EBV response is also tested (Ref #10). The biotinylated HLA tetramer is then conjugated with streptavidin allophycocyanin conjugate from Thermo Fisher Scientific (Catalog #S32362) with a 5:1 molar ratio of MHC monomer to streptavidin as cell sorting marker. The streptavidin-labeled MHC complex is incubated with the lentivirus-transduced J.RT3 cells with recombinant TCR on their cell surface and subjected to fluorescence-activated cell sorting as described in Altman et al (Ref #11).

The sorted J.RT3 cells that express EBV-reactive T cell receptor sequences (α:β chains) are sorted by flow cytometry and recovered in RPMI with 10% FBS overnight. TCR amplicon sequences re then identified by next generation sequencing analysis of the sorted T cell receptor libraries, as previously described (Refs #12-16). Alternatively, the EBV-reactive containing J.RT3 cells are seeded onto 96 well plate with a density of 1 cell/well to isolate single cell clones. Once the single cell is propagated into a colony, the RNA is extracted and the cDNA is synthesized by reverse transcriptase. PCR is performed to amply the TCR alpha:beta pair sequences, as previously described (Refs #17-19). Plasmids are extracted and the sequences are identified by Sanger sequencing.

Example 4: Screening Native TCRα:β for Activation and EBV-Infected Cell Killing by Cell Lines In Vitro Naïve T cells are isolated using EasySep™ Human Naïve CD8+ T Cell Isolation Kit (Stemcell Technology) from the PBMC of a healthy human donor. Sleeping Beauty transposon/transposase system is used to deliver the TCRα:β gene sequences as recovered in Examples 1 and 2 into the isolated naïve T cells. The TCR sequence libraries are subcloned in the pLVX vector from Example, 2 along with an EF1alpha promoter for gene expression, into the sleeping beauty transposon cloning vector pT2/BH, which contains the SB transposase (Ref #20). Naïve T cells are transfected with both pT2/BH vector and pCMV(CAT)T7-SB100 (Addgene Plasmid #34879). The pCMAT7-SB100 expressed hyperactive Sleeping Beauty transposase, allowing expression of full-length TCR. Gene delivery transposon plasmids containing the EBV TCR and SB100X transposase plasmids are transfected into T cell populations using a 4DNucleofector according to the manufacturer's instructions (Lonza, Cologne, Germany). In parallel, naïve T cells are transfected with a non-EBV responsive TCR identified in Example 2 as a negative control. Transduced T cell libraries are identified by staining for TCR surface markers that indicated stable TCR complex assembly (anti-α, anti-β, anti-CD8, anti-CD3) and analyzed via flow cytometry. The efficiency of productive TCR display on transduced cells is analyzed.

Next the transfected TCR libraries are analyzed for in vitro function by co-culturing with EBV infected B cells (Raji cells, a cancer cell line which has been tested positive for the presence of EBV), and also for activity against autologous donor B cells infected with EBV. T cells are seeded with EBV positive B cells at a ratio of 10:1 and co-cultured for 24 hours. After 24 hours of in vitro co-culture, the T cells are recovered, stained, and sorted for T cell markers and the expression of CD107/membrane TNF-α upregulation (Ref #21-23). The TCRs they encode are analyzed by NextGen sequence analysis to reveal EBV-targeting tumor infiltrating lymphocytes (TIL) sequences in the repertoire.

Monoclonal paired TCRα:β cDNAs are then recovered, transduced as monoclonal TCRs into naïve human T cells, and assayed by in vitro co-culture with the same populations of EBV-infected B cells to validate the ability of those TCRs to target EBV peptides. The co-culture assay is repeated and pro-inflammatory cytokines are measured using an ELISA kit for measuring IFN gamma, TNF-α, perforin and Granzyme. Compared to a negative control TCR transfected naïve T cells, the naïve T cells expressing EBV-specific TCRs demonstrate increased levels of all pro-inflammatory cytokines.

An in vitro cytotoxicity assay is also performed to evaluate the transformed naïve T cell's activity toward the EBV infected B cells or Raji cells. The Raji cells and the autologous B cells were diluted separately to a concentration of $5 \times 10^6$/mL and incubated with 0.25 μM carboxyfluorescein diacetate succinimidyl ester (CFSE) for 30 minutes at 37° C. $CO_2$ incubator, allowing the CFSE dye binds covalently to all free amines from cells. The CFSE dye enabled the evaluation of the viability and proliferation of the B cells. Stained B cells are washed three times with the RPMI media. The naïve T cells expressed EBV-reactive TCR alone with control TCR repertoire were then co-cultured with CFSE-stained B cells or Raji cells with a range of effector cell to target cells ratio. Cell cytotoxicity is evaluated by flow cytometry with excitation and emission wavelengths at 492 and 517 respectively. Compared to the naïve T cells in a control TCR experiment (TCR with no EBV peptide affinity), the EBV-reactive TCRs transduced into healthy naïve T cell populations exhibit superior cytotoxicity toward EBV-infected autologous B cells or Raji cells.

Example 5: Gene Transfer of Native TCRα:β Libraries for Treatment of Cancer

An animal model is used to demonstrate cancer-specific TCR isolation, recovery, and follow-up application of recovered TCR libraries as cell-based therapeutics. Human PBMC-engrafted CD34-NSG humanized mice are implanted with a human RKO colon carcinoma xenograft (Charles River Labs). CD34-NSG were first engrafted with human PBMC by intravenous injection (i.v.) and then engrafted with $1 \times 10^7$ RKO tumors in 50% Martigel® Matrix (Corning) by subcutaneous injection. The mice were then given two checkpoint inhibitors pembrolizumab (anti-PD-1) and ipilimumab (anti-CTLA-4) to enhance the anti-tumor TCR responses. Mice were given 100 μg of Pembrolizumab and 100 μg of Ipilimumab bi-weekly. On day 15, the spleen and tumor tissue was removed from the mice to isolate spleen and tumor-infiltrating T cells. The central memory (TCM) and transitional memory (TTM) T cells were obtained by FACS analysis for CD3+CD8+CD45RA CCR7 expression. TCM and TTM populations were then expanded and subjected to emulsion OE-PCR and nested PCR to obtain the TCR repertoire, as in Examples 1 and 2, and cloned into the Sleeping Beauty transposon/transposase transduction plasmids as described in Example 3.

The Illumina MiSeq 2×300 paired-end read platform was used to precisely define and determine the molecular features of the TCR libraries. Raw Illumina sequences were quality-filtered, mapped to V-, D-, and J-genes and CDR3's extracted using the International Immunogenetics Information System (IMGT, Ref #24). Sequence data is filtered for in-frame V(D)J junctions and productive TCRα and TCRβ sequences are paired by Illumina read ID and compiled by exact CDR3 nucleotide and V(D)J gene usage match. CDR-β3 nucleotide sequences were extracted and clustered to 96% nt identity with terminal gaps ignored (USEARCH v5.2.32, Ref #25) and resulting Vα:Vβ pairs with ≥2 reads comprised the list of Vα:Vβ clusters.

Alternatively, after performing the emulsion RT-PCR and nested PCR, the TCR α:β amplicon library can be ligated into sleeping beauty transposons vector (pT2/BH) and transformed into high efficacy competent *E. coli* cells such as XL-Gold (Agilent #200314) to clone the highly diverse TCR library. Paired alpha beta TCRs are then sequenced individually by bacterial colony Sanger sequencing. Approximately 100 colonies are combined with known TCR sequences to generate a precisely defined paired alpha beta TCR library for delivery into the naïve T cells. A TCR repertoire acquired from the TCM and TTM T cells derived from humanized mice without the engraft of RKO cancer cell line is used as a negative control group.

Next both TCR repertoires (derived from RKO xenograft TCR, or from mice without RKO xenograft TCR) are expressed in naïve T cells using the Sleeping Beauty transposon/transposase system as reported in Example 3. The transformed TCR libraries are separately administered to different RKO xenograft mice via i.v. injection. Tumor volume and body weight change of individual mouse is measured on a daily basis to track the tumor size and progression of disease. The RKO-xenograft mice treated with T cell populations transduced with TILs from other RKO-xenograft mice exhibit a delay in tumor growth as compared to mice treated with T cells transduced with TCR libraries from the control group (i.e., derived from human PBMC CD34-engrafted mice with no RKO xenograft). This demonstrates the applicability of precisely defined TCR libraries as cell-based therapeutics that could effectively reduce tumor progression.

Example 6: Gene Transfer of Native TCRα:β Libraries after Pre-Selection for Anti-Cancer Activity for Treatment of Cancer Similar procedures as Example 4 and the same mouse model (human PBMC-engrafted CD34-NSG humanized mice with RKO colon cancer xenograft model) is used in this example, but with an additional T cell pre-selection step to isolate anti-cancer TCRs by in vitro selection prior to use as a cell-based therapeutic. The splenocyte and tumor-infiltrating lymphocyte populations are isolated after the RKO colon cancer engraft. TCM and TTM are isolated by FACS with the markers CD3+CD8+CD45RA and CCR7. The TCR repertoire is isolated using emulsion OE-PCR, and nested PCR, and then subcloned into the Sleeping Beauty transposon vector and redelivered into the naïve T cells isolated from PBMC as described in Example 4. The transgenic naïve T cells are stimulated by co-culture with irradiated RKO colon cancer cell lines and isolated using flow cytometry for CD107 and membrane TNF-α, as described in Example 3.

Alternatively, dendritic cells (DCs) are isolated from the humanized mice using the blood dendritic cell isolation kit II (Miltenyi Biotec) and DCs are cultured in RPMI with 10% FBS supplemented with 50 ng/mL of granulocyte-macrophage colony-stimulating factor (GM-CSF). The dendritic cells are pulsed with RKO cancer cell lysates or human colon cancer cell lysates for two hours. Naïve T cells transduced with the TCR libraries that had been cloned into Sleeping Beauty transposon/transposase vectors are then co-cultured with the DC cells with a ratio of 10:1 for 4 days. The stimulated anti-cancer cytotoxic T cells are gated with membrane-bound CD107, membrane-bound TNF-α expression or CD137 (4-1BB) expression. CD107a is a marker for degranulation of activated CD8+ T cells (Refs #26-33). CD137 belongs to the TNFR family and is associated with T cells proliferation and survival (Ref #34-35). The sorted T cells (anti-cancer T cells) are delivered into the RKO colon cancer mouse model as described in Example 4. Compared to mice treated with naïve T cells transduced with TCR from the non-RKO xenograft mice, the mice treated with the naïve T cells transduced with RKO-targeting TCRs isolated from in vitro functional screening exhibited a higher survival rate and reduced tumor growth. The T cell are selected for activation in the anti-cancer co-culture assays and enriched for cancer-specific TCRs to increase the anti-cancer efficacy of the final cell-based therapeutics.

Example 7: Gene Transfer of Native TCRα:β Libraries after Pre-Selection for Anti-Cancer Activity and In Vitro Pre-Activation to Enhance Anti-Tumor Cell Killing The experiment procedures in Example 6 are performed as described in Example 5, with an additional T cell activation step after transduction of natively paired TCR libraries into naïve T cells. This activation step pre-primes the T cells and activates them for enhanced cancer cell killing. Briefly, after the OE-PCR and first nested PCR, the TCR libraries are cloned into the sleeping beauty transposon vector for transgenic expression of TCR. Next generation sequencing or Sanger sequencing of individual plasmids is performed to define TCR library size and diversity. The pooled TCR transposon plasmids are co-transfected with sleeping beauty transposase expression vector SB100 permitting the expression of TCR in naïve T cells. The transgenic T cells are first stimulated with RKO cell line or cancer antigen pulsed T cells and CD137/CD107/TFN-α expressing anti-cancer T cells are sorted by FACS. These cells are then activated in vitro prior to delivery as cell-based therapeutics into the RKO tumor mouse model. Gibco™ Dynabeads™ Human T-Activator CD3/CD28 (Thermo Fisher Scientific) are added to the TCR-transduced naïve T cell cultures at a final ratio of 1:1 of beads to cells and incubated in 37° C. C02 incubator for 3 days. The Dynabeads are conjugated with antiCD3 and antiCD28 antibody mimicking the in vivo interaction of T cell with antigen presenting cells (APC), allowing T cell clonal expansion and differentiation (Ref #36). Cell growth and viability are monitored daily after activation.

The expression of IFN-gamma and TNF-alpha is examined by ELISA, which indicates the differentiation of T cells. At day 3 post-bead addition, 20 U/mL of recombinant human interlukin2 (IL2) is added into the culture media to induce further T cell expansion. At day 7, the expanded T cells are counted and delivered into the RKO xenotransplant mice via tail vein i.v. injection. Tumor growth and individual mouse body weight was evaluated and compared to those obtained in Examples 4 and 5. RKO-engrafted mice treated with transgenic, RKO tumor-specific, stimulated, and activated T cells in this example exhibit superior anti-cancer efficiency as compared to the those from Example 4 (transgenic T cells without tumor selection or activation) and Example 5 (T cells screened for reactivity to RKO without in vitro pre-activation). The additional activation step described in this Example permits the differentiation of effector cytotoxic T cells prior to therapeutic delivery to enhance the speed and intensity of tumor immunosuppression in the mouse model.

Example 8: Gene Transfer of Native TCRα:β Libraries for the Induction of Antigen-Specific Immune Tolerance The CD34+ human PBMC-engrafted mouse model is known to induce Graft-versus-host disease (GvHD) in the mice. To alleviate this issue, regulatory T cells with TCRs isolated from mice suffering from GvHD were induced and used as therapeutics to induce immune tolerance.

T cells are isolated from the spleen and PBMC of mice that have been prepared as described in Example 4. T cells are isolated at 30 days post-engraftment, when GvHD onset begins. The TCR cloning primer set from the Example 1 is employed to perform overlap extension reverse transcriptase PCR to obtain TCR libraries from both the Treg cells (CD4+CD25+) as well as conventional T cells (CD4+CD25−). Next, the two TCR libraries are subcloned into thepT2/BH Sleeping Beauty transposon vector. Next generation sequencing is performed to analyze these two sets of T cells receptor libraries and to characterize the T cell receptor gene usage.

Naïve T cells are isolated from the PBMC with the following sorting marker setting: CD25-CD44$^{low}$CD62L$^{hi}$. The cells are transfected with TCR donor transposon plasmid containing two libraries described above along with Sleeping Beauty transposase plasmid (SB100) for TCR expression, using the TCR sequence libraries that had been isolated from GvHD mice. The transgenic naïve T cells are then induced to T reg cells by Dynabeads™ Human T-Activator CD3/CD28 along with 5 ng/mL of TGF-β1. TGF-β, a master regulator which has been shown to induce Foxp3 expression, allowing differentiation of naïve T cell into regulatory T cells (Ref #37-38). After 5 days of induction, the induced T regulatory cells (iTreg) are supplied with rIL-2 enabling T cell expansion for treatment of GvHD onset mice.

Alternatively, T cells are transduced directly with Foxp3 sequences as described previously (Ref #39-40). After 3 days post-expansion, the iTreg cells with transgenic TCR and without transgenic TCR are injected separately into the GvHD onset mice intravenously via tail vein injection (n=5); these mice had been engrafted with CD34+ human PBMCs from the same donor and time point of sampling as the earlier GvHD mice. The mice treated with iTregs with CD4+CD25+ transgenic TCR exhibit delayed GvHD disease onset as compared with those from the iTreg cells with transgenic CD4+CD25-TCR and iTreg without transgenic TCR.

Body weight changes and GvHD scores between the three groups (no transgenic TCR, CD4+CD25+ TCR and CD4+CD25-TCR) are analyzed. The mice injected with T cell expressing CD4+CD25+ transgenic TCR showed the lowest change in body weight and lowest GvHD score as compared with the mice infused with T cells only and T cells with CD4+CD25− transgenic TCR. Tolerogenic activities and T cell phenotype are monitored. 20 days post-T cell infusion, the splenocytes are isolated by sacrificing the humanized mice, harvesting spleen, and red blood cells lysis buffer digestion. The resultant leukocytes are stained with anti-CD25, anti-CD4+, anti-CD3 and Foxp3, and followed by flow cytometry analysis to evaluate the tolerogenic activities. The leukocytes from the mice with transgenic CD4+CD25+ TCR exhibit the most intense Foxp3 and CD25 signals from the flow cytometric staining analyses as compared with the leukocytes from the other two groups of mice (with no transgenic TCR and CD4+CD25− TCR).

Example 9: Application of Native TCRα:β Library Gene Transfer for Cancer Therapy in Mammalian or Human Patients In this example, a mammalian patient such as a human cancer patient is treated. In some embodiments, the cancer type is lung cancer, melanoma, renal cell carcinoma, breast cancer (including triple negative breast cancer), colon cancer, or prostate cancer. The therapeutic procedures may be performed similarly as described in Example 4. Briefly, T cells from a mammalian or human patient are recovered, which may derive from PBMC, tumor infiltrating lymphocytes, spleen tissue, affected organs, or other human tissue from the patient. Then, the TCR genes are recovered and cloned into expression vectors. In some embodiments, the T cell libraries are first pre-screened for anti-tumor activity. The screening can identify TCRs with reactivity against tumor peptide neoantigens, or alternatively reactivity against whole tumor cells in vitro. In some embodiments, the tumor cells may be derived from the cancer patient.

Next, the selected T cell libraries can be used as cell-based therapeutics. In some embodiments, the libraries are analyzed using high-throughput sequencing to precisely define the molecular composition of the cell-based TCR therapeutics. In other embodiments, the libraries are selected by sub-sampling a number of individual plasmid colonies in bacteria (ranging from 3 to 100,000 colonies derived from the library) and sequencing each plasmid colony individually after mini-prep. Then, those individual plasmids are mixed at a defined ratio to regenerate a precisely defined molecular library. These precisely defined molecular libraries can reduce the presence of PCR error variants that can occur when TCR libraries are originally generated by RT-PCR.

In some embodiments, mouse TCR constant region genes will be used to prevent TCR transgenes from associating with native human T cell receptor genes in gene recipient T cells. The libraries will be used to transfer the TCRs and any other plasmid genes to human T cells. In some embodiments, these T cells are derived from the patient. In some embodiments, these T cells will be patient-derived naïve T cells. In other embodiments, these T cells may be derived from other humans or from cell lines. In some embodiments, there may be an activation step to pre-prime the T cells and activate them for enhanced cancer cell killing as described in Example 6.

In some embodiments, transcription factors may be used to affect cell fate, as described in Example 7. The transformed T cells expressing the TCR transgene may be expanded in vitro to generate a cell bank, or they may be directly administered to the patient. In some embodiments, the T cells are injected directly into the tumor. In other embodiments, the T cells are administered intravenously or intrathecally.

The plasmid gene libraries can used again at any time to re-create a population of T cell transgenes for subsequent repeat administration; in other embodiments, the expanded cell banks may be used for repeat therapeutic administration. In the event of continued cancer progression and/or tumor growth, or an inadequate treatment of the tumor in any way, the entire therapeutic process can be repeated. In some embodiments, this may comprise capture the patient's T cell genes again, and repeating the screening and library generation process. In other embodiments, a repeat therapy could comprise re-screening the originally captured TCR gene libraries against a resistant tumor cell population to identify TCRs that target the evolved cancer cells. In other embodiments, a repeat therapy may comprise additional activation of the TCR gene libraries. In some embodiments, the in vitro cell activation process may change over the course of multiple treatment administrations, for example, as cancer progresses then more potently activating steps may be used for the cell-based therapeutics in vitro prior to therapeutic administration.

In some embodiments, an i-Caspase gene or other inducible suicide switch gene may be included in the transgene vectors to control the fate of the cell-based therapy after therapeutic administration.

Example 10: Application of Native TCRα:β Library Gene Transfer for Treatment of Viral Infections Post transplant lymphoproliferative disorder (PTLD) is a severe complication of solid organ transplantation. Primary Epstein-Barr virus (EBV) infection is a major risk factor, and around 60-80% of PTLD cases are EBV seropositive. T cell responses to EBV peptides are crucial to suppress malignancy (Llaurador, G. et al., Curr. Opin. Pediatr. 29, 34-40(2017)).

The TCRα:β library disclosed herein will be used to treat or prevent PTLD in mouse models as a model for antiviral TCR therapeutics (Ahmed, E. H. & Baiocchi, R. A, ILAR J. 57, 55-62 (2016); Ricciardelli, I. et al., Blood 124, 2514-2522 (2014)). Briefly, anti-EBV TCRs will be identified by single-cell isolation of paired alpha and beta genes, and will be cloned into TCR display vectors, and cell-based screening by FACS for anti-EBV peptide binding. In other embodiments, the anti-EBV TCRs may be discovered by identifying recognition, expansion, and/or in vitro killing activity of T cells transformed with transgenic TCRs. In other embodiments, T cell receptors are discovered that target other viruses to different antiviral therapies, including but not limited to human cytomegalovirus (HCMV), herpes simplex virus 1 or 2 (HSV-1/HSV-2), and yellow fever virus (YFV).

After the antiviral T cell receptor polynucleotides have been isolated, they will be cloned into DNA vectors and utilized for autologous gene therapy to treat PTLD. The transformed T cells might be used to treat other viral infections or for heterologous gene therapy. In other embodiments, they may be used as prophylactic cell therapy to prevent PTLD or other viral infections. In other embodiments, the vectors may be used for gene therapy as virally-associated preventive cancer vaccines.

Lentiviral gene transduction will be used to transform human pan-T cells with antiviral TCRs to evaluate in vitro killing efficacy of virally infected cells. Transformed T cells may be co-cultured with virally infected cells with any of the following stimulation conditions: none, IL-2, anti-CD3/anti-CD28 magnetic beads, or IL-2/anti-CD3/anti-CD28. In vitro virally infected cell killing will be assessed by the IncuCyte Live Cell assay, which measures the loss of fluorescently-labeled tumor cells due to cell killing (Single, A. et al., J. Biomol. Screen. 20, 1286-1293 (2015)).

Next, human pan-T cells will be transduced with antiviral TCRs under the optimized conditions and used to treat viral infections in mouse models. A mouse model of EBV infection and PTLD will be used (Johannessen, I. et al. J. Med. Virol. 83, 1585-1596 (2011)). In other embodiments, mice may be infected with a virus and treated with T cells specific to viral proteins. Transduced T cells will be isolated by flow cytometry for transgenic TCR expression to obtain pure transduced TCR libraries. Next, transformed cells will be stimulated using a T cell stimulation protocol, which could include the conditions described above, and stimulated T cells will be delivered to mice via intravenous tail vein injection (Kurtz, A. Mesenchymal Stem Cell Delivery Routes and Fate. Int. J. Stem Cells 1, 1-7 (2008)).

Mice will be followed for 30 days to record weight loss and PTLD tumor volume. Treated mice will be compared to non-treated mouse controls, as well as other controls treated with antiviral antibodies and antiviral small molecule inhibitors. Any delays in PTLD tumor growth will be quantified as the major study endpoint. It is expected that mice treated with transformed cells including anti-EBV TCRs of the present technology will show a delay in PTLD growth, delayed viral growth kinetics and/or faster disease recovery after viral infections compared to untreated controls. These results will demonstrate that the compositions of the present technology are useful in methods for treating or preventing viral infections and virally-associated cancers in a subject in need thereof.

Figure 22:
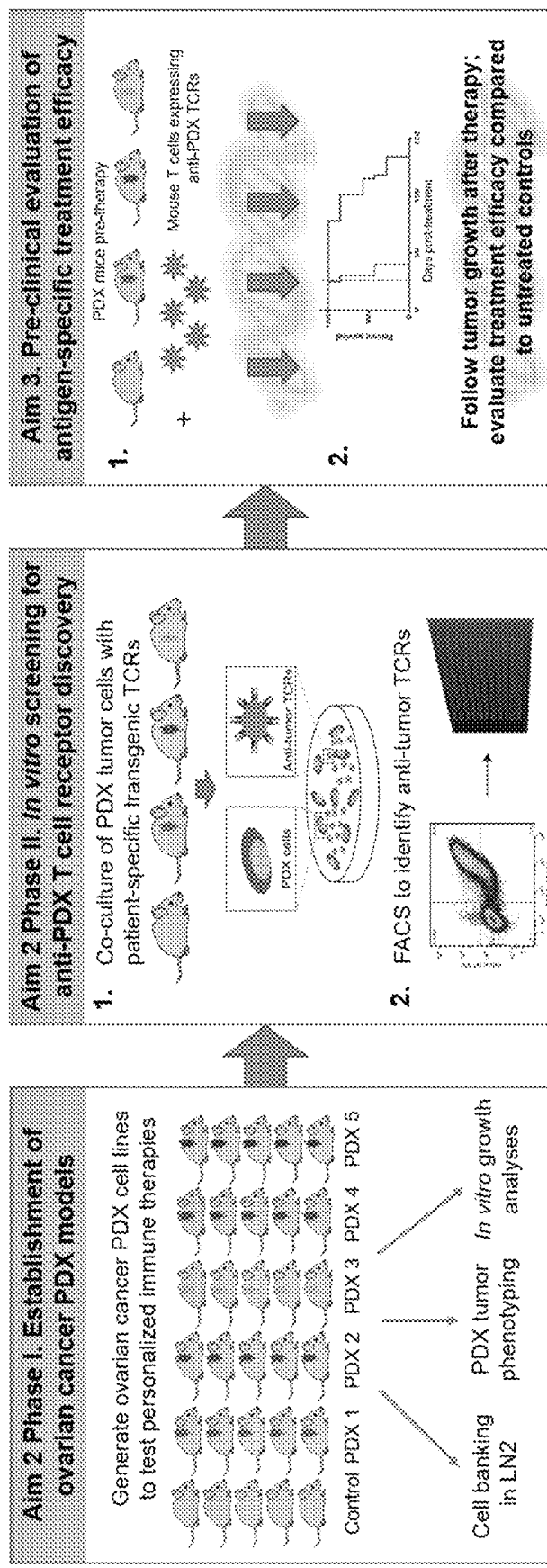
FIG. 22 shows the workflow for testing and optimizing antigen-specific cancer immunotherapy in PDX mouse models. (Left) Patient tumors were isolated and cultured as mouse xenografts, cryopreserved in LN2, and propagated in culture. (Center) TCR genes were collected and screened against PDX cells. (Right) Anti-tumor TCR genes were used as gene therapies in PDX models to test and optimize treatment efficacy.

Example 11: Evaluation of Antigen-Specific TCRα:β in Treating Cancer in PDX Mouse Models Patient-derived xenograft (PDX) mouse models from ovarian cancer patients will be established as a renewable cell source for anti-tumor T cell discovery (FIG. 22).

Human pan-T cells are transduced at a multiplicity of infection of less than 0.2 (i.e., one TCR transgene per cell) and transduced libraries are screened in vitro for TCR activation against co-cultured PDX tumor cells. Expansion and activator gene expression (CD69/CD107/membrane TNF-α) are quantified as hallmarks of anti-tumor TCR recognition. Illumina MiSeq 2×300 paired-end sequencing is utilized to analyze TCR library diversity and characterize Vβ and Vα genes at each step in the cloning and selection process (i.e., input cDNA, post-lentiviral particle generation, and mCherry+J.RT3 cells with surface-displayed TCR). 2×300 sequencing permits full coverage of CDRα3 and CDRβ3 regions. High-throughput sequencing will verify that TCR libraries maintain high diversity, and ≥105 native TCRα:βs displayed on mammalian T cells will be generated. NGS will also be used to identify PDX neoantigens and TCR molecular modeling will be performed to determine the neoantigen targets of anti-PDX TCRs.

Figure 20:
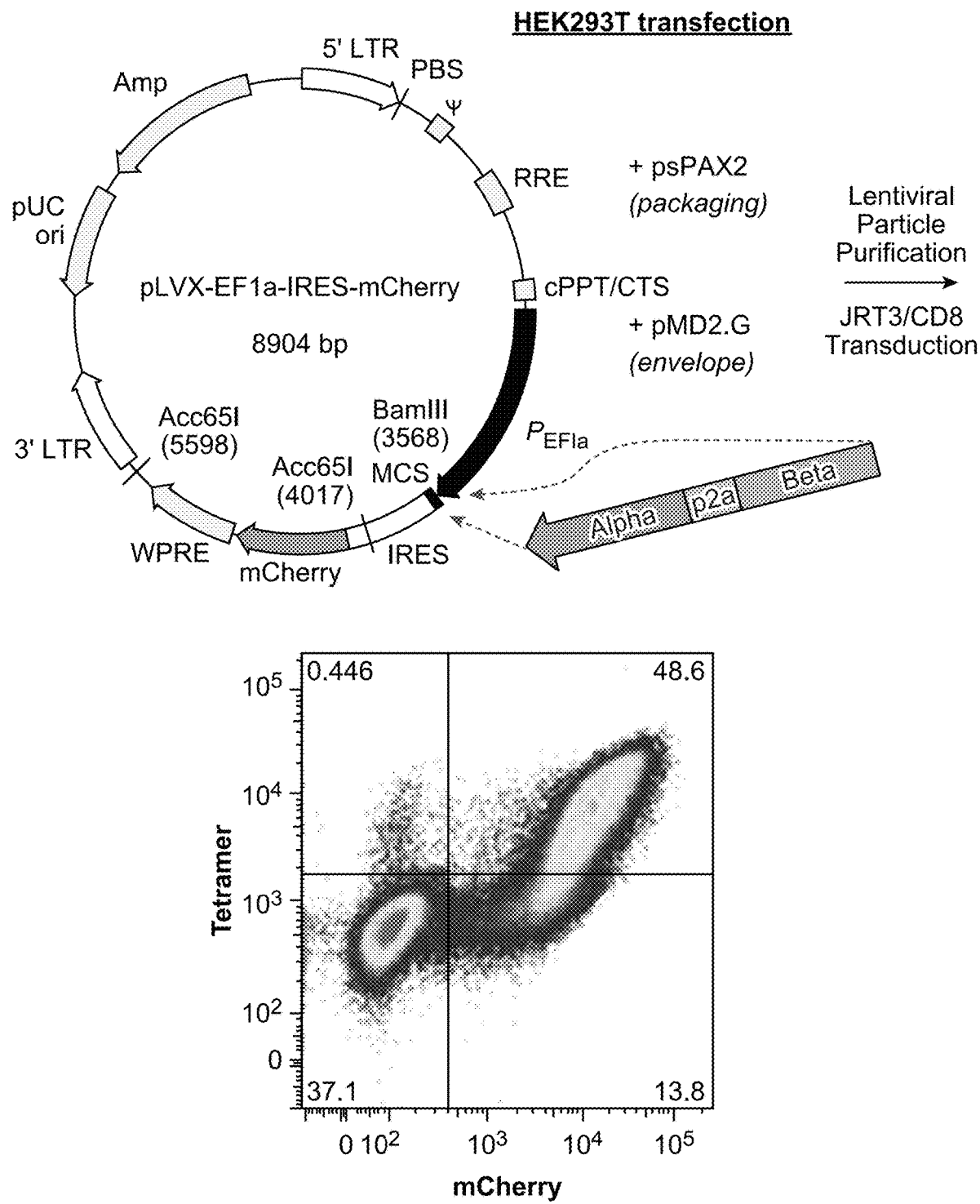
FIG. 20 shows a lentiviral TCR cell display platform of the present technology. TCRα:β genes separated by p2a were inserted into the multiple cloning site (MCS) of an IRES TCR expression vector. Co-transfection in HEK293T with packaging and envelope vectors generates lentiviral particles that transduce J.RT3/CD8 cell lines with TCR genes (which are expressed at the cell surface) and a mCherry reporter. Flow plot: J.RT3/CD8 with anti-B*0702 NEF TM9 TCR, stained with HIV Nef B*0702 RM9, RPQVPLRPM (SEQ ID NO: 1).

Once anti-PDX TCRs are identified by screening, autologous patient T cells will be transduced with those anti-tumor TCRs and their ability to kill PDX tumor cells in vitro will be assayed. Human T cells will be transfected with anti-tumor TCRα:β genes via lentiviral gene transduction (FIG. 20). Patient T cells are transduced with native human TCR constant region genes, including a cysteine modification to promote preferential expression of the transduced TCR. Transduced T cells are pre-activated with T cell stimulatory agents (as one example, anti-CD3/anti-CD28 magnetic beads/IL-2) and are incubated with IncuCyte-labeled tumor cells to assess TCR-based tumor cell killing in vitro. Autologous T cells that are transduced with linked TCRα:β genes that do not target tumor cells will serve as negative controls. ANOVA will be used for statistical analyses of tumor cell killing compared to negative control TCR genes.

Next, transgenic anti-PDX T cells will be delivered in PDX mice for antigen-specific tumor immunotherapy. Transduced T cells are isolated by flow cytometry to obtain pure transduced TCR libraries. Mouse pan-T cells are transduced with anti-PDX TCRs and pre-stimulated using the conditions determined in cell-killing assays; stimulated T cells are delivered to mice via intravenous tail vein injection. Mice are followed for 30 days and treated mice are compared to control groups and animals treated with checkpoint inhibitors. Delayed tumor growth is quantified as the major study endpoint, applying Kaplan-Meier survival analysis of survival to verify statistical significance. It is anticipated that animals treated with T cells comprising anti-PDX TCRs will match or exceed the therapeutic responses observed in animals receiving checkpoint immune therapy treatments. These results will demonstrate that the TCR libraries of the present technology are useful for personalized antigen-specific therapies in human patients.

Example 12: Evaluation of Antigen-Specific TCRα:β in Treating Cancer in PDX Mouse Models Renal cell carcinoma (RCC) is susceptible to immunotherapy and is typically clinically silent until the tumor is locally advanced or metastatic. Thus, late stage RCC diagnosis is common and surgical resection yields large tumors with substantial T cell infiltrates for laboratory study. Advanced RCC is also an FDA-approved indication for checkpoint inhibition and recombinant IL-2 therapies, and RCC can be highly immunogenic with a large T-cell infiltrate that can be reinvigorated with immunotherapy. High-throughput screening of TIL TCRs responding to RCC will be used to identify neoantigen-specific TCRs that can be leveraged for precision therapies.

First, TILs and cancer cells are isolated from tumors using flow cytometry; tumor cells are cryopreserved while TILs are the input for TCR repertoire isolation and cloning. Next, TCR repertoires are transformed into naïve T cells and the resulting display library is seeded in co-culture with autologous patient tumor cells. After 24 hours of co-culture, activated T cells are sorted by FACS for CD69/CD107/membrane TNF-α upregulation, and the encoded TCRs are analyzed by NextGen sequencing to reveal the tumor-targeting TCRs in the repertoire. Finally, monoclonal paired TCRα:β cDNAs are recovered, transduced into human pan-T cells, and assayed by tumor cell co-culture in order to identify anti-RCC TCRs. These results will demonstrate that the TCR libraries of the present technology are useful for personalized antigen-specific therapies in human patients.

Example 13: Application of Paired TCRα:β Gene Therapy to Treat Colon Carcinoma, Ovarian Cancer, and B Cell Cancers Colon cancer. Paired TCRα:β gene libraries against RKO cells (a human colon carcinoma cell line) are cloned into mouse T cells. Briefly, pan-T cells will be isolated from mouse spleens using magnetic beads and subjected to either lentiviral or transposase-based TCR gene delivery.

According to the lentiviral strategy illustrated in FIG. 20, human TCR constant region genes are used to prevent cross-dimerization with the native mouse TCRs. Next, T cells are stained with antibodies to evaluate surface expression of transgenic human α and β constant region proteins, and TCR expression is quantified by flow cytometry. Lentiviral gene transduction is used to transform mouse pan-T cells with anti-RKO TCRs to evaluate RKO killing efficacy. Transduced T cells are isolated by flow cytometry for human TCR expression to obtain pure transduced TCR libraries. Transformed cells may be co-cultured with RKO tumor cells with any of the following stimulation conditions: none, IL-2, anti-CD3/anti-CD28 magnetic beads, or IL-2/anti-CD3/anti-CD28. In vitro RKO cell killing was assessed by the IncuCyte Live Cell assay, which measures the loss of fluorescently-labeled tumor cells due to cell killing.

Figure 21:
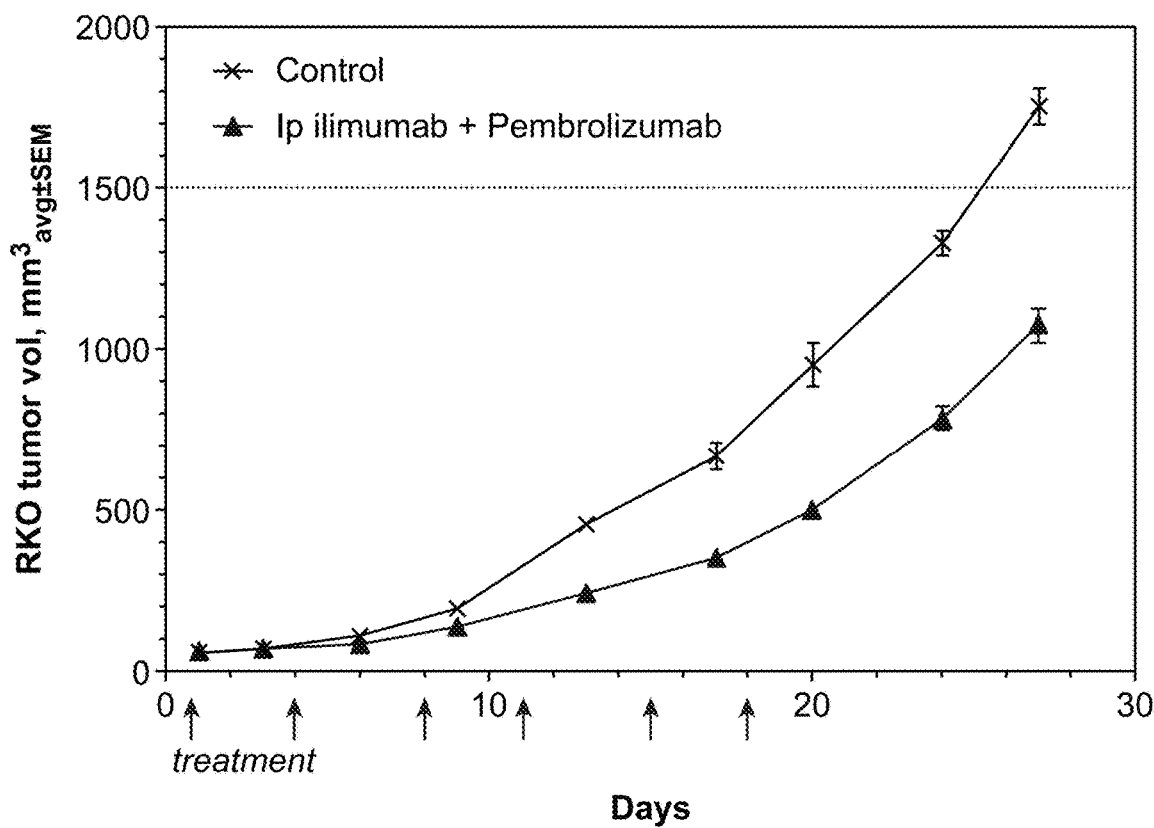
FIG. 21(a) shows RKO tumor size in humanized mice treated with immune checkpoint inhibitors. TCR screening will be performed to discover the antigen-specific TCRs targeting RKO cells.
FIG. 21(b) shows the treatment groups in a mouse colon cancer model that will be used evaluate identified TCRs for antigen-specific immunotherapy.

For in vivo studies, stimulated T cells are delivered to mice via intravenous tail vein injection. Mice are followed for 30 days to record weight loss and tumor volume. Treated mice are compared to non-treated mouse controls (Groups 1 and 4, FIG. 21(b)), as well as historical controls treated with currently approved antibody-based immunotherapies (FIG. 21(a)). Delays in tumor growth are quantified as a major study endpoint. Animals treated with T cells comprising anti-RKO TCRs are expected to match or exceed the delay in tumor growth observed in animals treated with antibody-based immunotherapies.

Ovarian Cancer. Human clinical PBMC and TIL samples are collected from excised tumors and/or patient blood. TCRα:β libraries from ovarian cancer patients are isolated. Clinical PBMC and/or TIL samples are obtained following surgical resection and/or blood draws. TCRα:β cloning is performed using a green fluorescent protein (GFP) reporter system for retroviral TCR transduction into J.RT3 T cells. J.RT3 cells do not express an endogenous TCR and provide stabilizing proteins and co-expression factors (including CD3 and CD8) for TCR expression, making J.RT3 an ideal mammalian host for TCR display. Natively paired α:β variable region genes are cloned into the pLVX lentiviral expression vector using restriction sites at the ends of the linked amplicon. Vector libraries are amplified in E. coli. and TCRα:β expression libraries are co-transfected into HEK293T cells along with packaging and envelope vectors (psPax2 and pMD2.g) to generate lentiviral TCRα:β transduction particles (FIG. 20).

B cell cancers. B cell lineage cancers include lymphoma and multiple myeloma that express antibody genes as tumor-specific neoantigens that are targeted by TCRs. Paired TCRα:β gene libraries are isolated from B cell lineage cancer patients. Paired TCRα:β cloning is performed using a green fluorescent protein (GFP) reporter system for retroviral transduction of TCR expression plasmids into J.RT3 T cells. J.RT3 cells do not express an endogenous TCR and also provide the stabilizing proteins and co-expression factors (including CD3 and CD8) needed for stable TCR expression, making J.RT3 a suitable mammalian host for TCR library display. Natively paired α:β variable region genes are cloned into the pLVX lentiviral expression vector using restriction sites at the ends of the linked amplicon (as shown in FIG. 20).

Vector libraries are amplified in *E. coli.* using strains designed for stable lentiviral plasmid replication (e.g., Stbl3[12]), and then TCRα:β expression libraries are co-transfected into HEK293T cells along with packaging and envelope vectors (psPax2 and pMD2.g) to generate lentiviral TCRα:β transduction particles. In parallel, tumor-specific BCRs are sequenceed from PBMC clinical samples. J.RT3 T cells are transduced at a multiplicity of infection (MOI) of less than 0.2 (i.e., one TCR transgene per cell) to assay TCR binding to BCR neoantigens. Transduced cells will be screened against overlapping peptide-MHC from CDR-H3−, CDR-L3−, and somatic mutation-derived neoantigens from the patient-sequenced tumor-encoded antibody genes.

The Illumina MiSeq 2×300 paired-end NGS system is used to analyze library diversity and characterize Vβ and Vα libraries at each step in the cloning process (i.e., input cDNA, post-lentiviral particle generation, and mCherry+ J.RT3/CD8 cells with surface-displayed TCR). 2×300 sequencing permits full coverage of CDRα3 and CDRβ3 regions. High-throughput sequencing will verify that TCR libraries maintain high diversity throughout the library cloning process and that ≥10$^6$ native TCRα:βs displayed on mammalian cells will be generated. TCRα:βs discovered by peptide:MHC neoantigen screening are tested for affinity using surface plasmon resonance (SPR). These results will demonstrate that the TCR libraries of the present technology are useful for personalized antigen-specific therapies in human patients.

All publications, patent applications, patents, and other references mentioned herein are expressly incorporated by reference in their entirety, to the same extent as if each were incorporated by reference individually. In case of conflict, the present specification, including definitions, will control.

REFERENCES

1. DeKosky, B. Decoding the Antibody Repertoire: High Throughput Sequencing of Multiple Transcripts from Single B Cells. (Springer, 2017).
2. Hunicke-Smith, S., Dekosky, B., Ellington, A. & Georgiou, G. High throughput sequencing of multiple transcripts of a single cell. (2015), US20150141261A1.
3. McDaniel, J. R., DeKosky, B. J., Tanno, H., Ellington, A. D. & Georgiou, G. Ultra-high-throughput sequencing of the immune receptor repertoire from millions of lymphocytes. *Nat Protoc* 11, 429-42 (2016).
4. DeKosky, B. J., Kojima, T., Rodin, A., Charab, W., Ippolito, G. C., Ellington, A. D. & Georgiou, G. In-depth determination and analysis of the human paired heavy- and light-chain antibody repertoire. *Nat Med* 21, 86-91 (2015).
5. Primer sets for cloning the human repertoire of T cell Receptor Variable regions Ilenia Boria doi: 10.1186/1471-2172-9-50
6. Catalina, M. D., Sullivan, J. L., Brody, R. M. & Luzuriaga, K. Phenotypic and Functional Heterogeneity of EBV Epitope-Specific CD8+ T Cells. *J. Immunol.* 168, 4184-4191 (2002).
7. Hislop, A. D. & Taylor, G. S. in *Epstein Barr Virus Volume 2* (ed. Münz, C.) 391, 325-353 (Springer International Publishing, 2015).
8. Ibisch, C., Saulquin, X., Gallot, G., Vivien, R., Ferrand, C., Tiberghien, P., Houssaint, E. & Vié, H. The TCR repertoire Selected In vitro Against EBV: Diversity, Specificity, and Improved Purification Through Early IL-2 Receptor α-Chain (CD25)-Positive Selection. *J. Immunol.* 164, 4924-4932 (2000).
9. *J Immunol* Jan. 1, 2012, 188 (1) 311-321; DOI: doi.org/10.4049/jimmunol.1102686
10. Jones, K., Wockner, L., Brennan, R. M., Keane, C., Chattopadhyay, P. K., Roederer, M., Price, D. A., Cole, D. K., Hassan, B., Beck, K., Gottlieb, D., Ritchie, D. S., Seymour, J. F., Vari, F., Crooks, P., Burrows, S. R. & Gandhi, M. K. The impact of HLA class I and EBV latency-II antigen-specific CD8+ T cells on the pathogenesis of EBV+ Hodgkin lymphoma. *Clin. Exp. Immunol.* 183, 206-220 (2016).
11. *Science.* 1996 Oct. 4; 274(5284):94-6. Phenotypic analysis of antigen-specific T lymphocytes. Altman J D I, Moss P A, Goulder P J, Barouch D H, McHeyzer-Williams M G, Bell J I, McMichael A J, Davis M M.
12. Golding, A., Darko, S., Wylie, W. H., Douek, D. C. & Shevach, E. M. Deep sequencing of the TCRB repertoire of human Foxp3+ and Foxp3− T cells suggests that they are completely distinct and non-overlapping. *Clin Exp Immunol* n/a-n/a (2016). doi:10.1111/cei.12904
13. Lee, E. S., Thomas, P. G., Mold, J. E. & Yates, A. J. Identifying T Cell Receptors from High-Throughput Sequencing: Dealing with Promiscuity in TCRα and TCRβ Pairing. *PLOS Computational Biology* 13, e1005313 (2017).
14. Poschke, I., Flossdorf, M. & Offringa, R. Next-generation TCR sequencing—a tool to understand T-cell infiltration in human cancers. J. Pathol. n/a-n/a (2016). doi: 10.1002/path.4800
15. Marrero, I., Aguilera, C., Hamm, D. E., Quinn, A. & Kumar, V. High-throughput sequencing reveals restricted TCR V usage and public TCRβ clonotypes among pancreatic lymph node memory CD4+ T cells and their involvement in autoimmune diabetes. Molecular Immunology 74, 82-95 (2016).
16. Lossius, A. et al. High-throughput sequencing of TCR repertoires in multiple sclerosis reveals intrathecal enrichment of EBV-reactive CD8+ T cells. *Eur. J. Immunol.* 44, 3439-3452(2014)
17. Sprouse, M. L. et al. Streamlined Single Cell TCR Isolation and Generation of Retroviral Vectors for In vitro and In vivo Expression of Human TCRs. *JoVE (Journal of Visualized Experiments)* e55379-e55379 (2017). doi: 10.3791/55379
18. Dash, P., Wang, G. C. & Thomas, P. G. Single-Cell Analysis of T-Cell Receptor αβ Repertoire. in *Immunosenecence* (ed. Shaw, A. C.) 1343, 181-197 (Springer New York, 2015).
19. Guo, X. J. et al. Rapid cloning, expression, and functional characterization of paired αβ and γδ T-cell receptor chains from single-cell analysis. *Molecular Therapy—Methods & Clinical Development* 3, 15054 (2016).

20. JUNG, S. et al. Sleeping Beauty transposon system harboring HRAS, c-Myc and shp53 induces sarcomatoid carcinomas in mouse skin. *Oncol Rep* 29, 1293-1298 (2013).
21. Aktas, E., Kucuksezer, U. C., Bilgic, S., Erten, G. & Deniz, G. Relationship between CD107a expression and cytotoxic activity. *Cell. Immunol.* 254, 149-154 (2009).
22. Betts, M. R., Brenchley, J. M., Price, D. A., De Rosa, S. C., Douek, D. C., Roederer, M. & Koup, R. A. Sensitive and viable identification of antigen-specific CD8+ T cells by a flow cytometric assay for degranulation. *J. Immunol. Methods* 281, 65-78 (2003).
23. Haney, D., Quigley, M. F., Asher, T. E., Ambrozak, D. R., Gostick, E., Price, D. A., Douek, D. C. & Betts, M. R. Isolation of viable antigen-specific CD8+ T cells based on membrane-bound tumor necrosis factor (TNF)-α expression. *J. Immunol. Methods* 369, 33-41(2011).
24. Brochet, X., Lefranc, M.-P. & Giudicelli, V. IMGT/V-QUEST: the highly customized and integrated system for IG and TR standardized V-J and V-D-J sequence analysis. *Nucleic Acids Res.* 36, W503-W508 (2008)
25. Edgar, R. C. Search and clustering orders of magnitude faster than BLAST. *Bioinformatics* 26, 2460-2461 (2010).
26. Betts, M. R., Brenchley, J. M., Price, D. A., De Rosa, S. C., Douek, D. C., Roederer, M. & Koup, R. A. Sensitive and viable identification of antigen-specific CD8+ T cells by a flow cytometric assay for degranulation. *J. Immunol. Methods* 281, 65-78 (2003).
27. Haney, D., Quigley, M. F., Asher, T. E., Ambrozak, D. R., Gostick, E., Price, D. A., Douek, D. C. & Betts, M. R. Isolation of viable antigen-specific CD8+ T cells based on membrane-bound tumor necrosis factor (TNF)-α expression. *J. Immunol. Methods* 369, 33-41(2011).
28. Chattopadhyay, P. K., Yu, J. & Roederer, M. A live-cell assay to detect antigen-specific CD4+ T cells with diverse cytokine profiles. *Nat. Med.* 11, 1113-1117 (2005).
29. Boswell, K. L., Paris, R., Boritz, E., Ambrozak, D., Yamamoto, T., Darko, S., Wloka, K., Wheatley, A., Narpala, S., McDermott, A., Roederer, M., Haubrich, R., Connors, M., Ake, J., Douek, D. C., Kim, J., Petrovas, C. & Koup, R. A. Loss of Circulating CD4 T Cells with B Cell Helper Function during Chronic HIV Infection. *PLoS Pathog* 10, e1003853 (2014)
30. Isolation of T-Cell Receptors Specifically Reactive with Mutated Tumor-Associated Antigens from Tumor-Infiltrating Lymphocytes Based on CD137 Expression Maria Parkhurst, Alena Gros, Anna Pasetto, Todd Prickett, Jessica S. Crystal, Paul Robbins and Steven A. Rosenberg
31. Activation-induced expression of CD137 permits detection, isolation, and expansion of the full repertoire of CD8+ T cells responding to antigen without requiring knowledge of epitope specificities Matthias Wolfl,1 Jürgen Kuball,1 William Y. Ho,1 Hieu Nguyen,1 Thomas J. Manley,1 Marie Bleakley,1 and Philip D. Greenberg1,2
32. CD137 Accurately Identifies and Enriches for Naturally Occurring Tumor-Reactive T Cells in Tumor Qunrui Ye, De-Gang Song, Mathilde Poussin, Tori Yamamoto, Andrew Best, Chunsheng Li, George Coukos and Daniel J. Powell Jr. DOI: 10.1158/1078-0432.CCR-13-0945 Published January 2014
33. *Cell Immunol.* 2009; 254(2):149-54. doi: 10.1016/j.cellimm.2008.08.007. Epub 2008 Oct. 5. Relationship between CD107a expression and cytotoxic activity. Aktas E1, Kucuksezer U C, Bilgic S, Erten G, Deniz G.
34. Cannons J L, Lau P, Ghumman B, et al. 4-1BB ligand induces cell division, sustains survival, and enhances effector function of CD4 and CD8 T cells with similar efficacy. *J Immunol.* 2001; 167:1313-1324.]
35. Lee H W, Park S J, Choi B K, Kim H H, Nam K O, Kwon B S. 4-1BB promotes the survival of CD8+T lymphocytes by increasing expression of Bcl-xL and Bfl-1. *J Immunol.* 2002; 169:4882-4888.
36. Ex vivo expansion protocol for human tumor specific T cells for adoptive T cell therapy. *Journal of Immunological Methods* Volume 355, Issues 1-2, 15 Apr. 2010, Pages 52-60
37. *Am J Transplant.* 2004 October; 4(10):1614-27 TGF-beta induces Foxp3+T-regulatory cells from CD4+CD25− precursors. Fu S[1], Zhang N, Yopp A C, Chen D, Mao M, Chen D, Zhang H, Ding Y, Bromberg J S.
38. *Science.* 2003 Feb. 14; 299(5609):1057-61. Epub 2003 Jan. 9. Control of regulatory T cell development by the transcription factor Foxp3. Hori S1, Nomura T, Sakaguchi S.
39. Wang, Y. et al. *J Am Soc Nephrol.* 2006 March; 17(3): 697-706.
40. Dons, E. et al. *Hum Immunol.* 2012 April; 73(4):328-34.
41. *Nat Immunol.* 2014 Nov.; 15(11):1070-8. doi: 10.1038/ni.3004. Epub 2014 Sep. 28. Continuous requirement for the TCR in regulatory T cell function. Levine AG1, Arvey A1, Jin W1, Rudensky AY2.
42. *Nat Immunol.* 2014 Nov.; 15(11):1070-8. doi: 10.1038/ni.3004. Epub 2014 Sep. 28. Continuous requirement for the TCR in regulatory T cell function. Levine AG1, Arvey A1, Jin W I, Rudensky AY2.
43. Boyd, D., Florent, G., Kim, P. & Brattain, M. Determination of the Levels of Urokinase and Its Receptor in Human Colon Carcinoma Cell Lines. *Cancer Res.* 48, 3112-3116 (1988).
44. Lorz, A., Botesteanu, D.-A. & Levy, D. Universal response in the RKO colon cancer cell line to distinct antimitotic therapies. *Sci. Rep.* 8, 8979 (2018).
45. June, C. H., O'Connor, R. S., Kawalekar, O. U., Ghassemi, S. & Milone, M. C. CAR T cell immunotherapy for human cancer. *Science* 359, 1361-1365 (2018).
46. Kebriaei, P. et al. Phase I trials using Sleeping Beauty to generate CD19-specific CAR T cells. *J. Clin. Invest.* 126, 3363-3376 (2016).
47. Levine, B. L., Miskin, J., Wonnacott, K. & Keir, C. Global Manufacturing of CAR T Cell Therapy. *Mol. Ther.—Methods Clin. Dev.* 4, 92-101 (2017).
48. Wang, X. & Riviere, I. Clinical manufacturing of CAR T cells: foundation of a promising therapy. *Mol. Ther.—Oncolytics* 3, 16015 (2016).
49. Single, A., Beetham, H., Telford, B. J., Guilford, P. & Chen, A. A Comparison of Real-Time and Endpoint Cell Viability Assays for Improved Synthetic Lethal Drug Validation. *J. Biomol. Screen.* 20, 1286-1293 (2015).
50. Kurtz, A. Mesenchymal Stem Cell Delivery Routes and Fate. *Int. J. Stem Cells* 1, 1-7 (2008).
51. Khodadoust, M. S. et al. Antigen presentation profiling reveals recognition of lymphoma immunoglobulin neoantigens. *Nature* 543, 723-727 (2017).
52. Gonzlez, S., Volkova, N., Beer, P. & Gerstung, M. Immuno-oncology from the perspective of somatic evolution. *Semin. Cancer Biol.* (2017). doi:10.1016/j.semcancer.2017.12.001
53. J.RT3-T3.5 ATCC® TIB-153™ *Homo sapiens* peripheral blood ac. Available at: https://www.atcc.org/Products/All/TIB-153.aspx. (Accessed: 3 Apr. 2017)
54. Al-Allaf, F. A., Tolmachov, O. E., Zambetti, L. P., Tchetchelnitski, V. & Mehmet, H. Remarkable stability of an instability-prone lentiviral vector plasmid in *Escherichia coli* Stbl3. *3 Biotech* 3, 61-70 (2013).
55. Descours, B. et al. SAMHD1 restricts HIV-1 reverse transcription in quiescent CD4+ T-cells. *Retrovirology* 9, 87 (2012).
56. DeKosky, B. J. et al. High-throughput sequencing of the paired human immunoglobulin heavy and light chain repertoire. *Nat Biotech* 31, 166-169 (2013).
57. DeKosky, B. J. et al. In-depth determination and analysis of the human paired heavy- and light-chain antibody repertoire. *Nat. Med* 21, 86-91 (2015).
58. McDaniel, J. R., DeKosky, B. J., Tanno, H., Ellington, A. D. & Georgiou, G. Ultra-high-throughput sequencing of the immune receptor repertoire from millions of lymphocytes. *Nat. Protoc.* 11, 429-42 (2016).
59. DeKosky, B. J. et al. Large-scale sequence and structural comparisons of human naive and antigen-experienced antibody repertoires. *Proc. Natl. Acad Sci.* 113, E2636-E2645 (2016).
60. Tian, M. et al. Induction of HIV Neutralizing Antibody Lineages in Mice with Diverse Precursor Repertoires. *Cell* 166, 1471-1484.e18 (2016).
61. Wang, B. et al. Functional interrogation and mining of natively paired human $V_H:V_L$ antibody repertoires. *Nat. Biotechnol.* 36, 152-155 (2018).
62. Wu, L. C., Tuot, D. S., Lyons, D. S., Garcia, K. C. & Davis, M. M. Two-step binding mechanism for T-cell receptor recognition of peptide-MHC. *Nature* 418, 552-556 (2002).
63. Zhang, S.-Q. et al. Direct measurement of T cell receptor affinity and sequence from naïve antiviral T cells. *Sci. Transl. Med* 8, 341ra77-341ra77 (2016).
64. Vargas, J. E. et al. Retroviral vectors and transposons for stable gene therapy: advances, current challenges and perspectives. *J. Transl. Med* 14, 288 (2016).
65. Cohen, C. J. et al. Enhanced Antitumor Activity of T Cells Engineered to Express T-*Cell* Receptors with a Second Disulfide Bond. *Cancer Res.* 67, 3898-3903 (2007).
66. Dudley,1, W. N., Wickham,2, R. & COOMBS,3, N. An Introduction to Survival Statistics: Kaplan-Meier Analysis. *J. Adv. Pract. Oncol.* 7, 91-100 (2016).
67. Birnbaum, M. E. et al. Deconstructing the Peptide-MHC Specificity of T *Cell* Recognition. *Cell* 157, 1073-1087 (2014).
68. Glanville, J. et al. Identifying specificity groups in the T cell receptor repertoire. *Nature* advance online publication, (2017).
69. Han, A., Glanville, J., Hansmann, L. & Davis, M. M. Linking T-cell receptor sequence to functional phenotype at the single-cell level. *Nat. Biotechnol.* 32, 684-692 (2014).
70. Atkins, M. Clinical manifestations, evaluation, and staging of renal cell carcinoma. *UpToDate* 18, (2017).
71. Betts, M. R. et al. Sensitive and viable identification of antigen-specific CD8+ T cells by a flow cytometric assay for degranulation. *J. Immunol. Methods* 281, 65-78 (2003).
72. Aktas, E., Kucuksezer, U. C., Bilgic, S., Erten, G. & Deniz, G. Relationship between CD107a expression and cytotoxic activity. *Cell. Immunol.* 254, 149-154 (2009).
73. Haney, D. et al. Isolation of viable antigen-specific CD8+ T cells based on membrane-bound tumor necrosis factor (TNF)-α expression. *J. Immunol. Methods* 369, 33-41(2011).
74. Roybal, K. T. et al. Precision Tumor Recognition by T Cells With Combinatorial Antigen-Sensing Circuits. *Cell* 164, 770-779 (2016).

EQUIVALENTS

The present technology is not to be limited in terms of the particular embodiments described in this application, which are intended as single illustrations of individual aspects of the present technology. Many modifications and variations of this technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the appended claims. The present technology is to be limited only by the terms of the appended claims, along with the full scope of equivalents to which such claims are entitled. It is to be understood that this technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

The present technology may include, but is not limited to, the features and combinations of features recited in the following lettered paragraphs, it being understood that the following paragraphs should not be interpreted as limiting the scope of the claims as appended hereto or mandating that all such features must necessarily be included in such A. A recombinant T cell receptor (TCR) library vector comprising:

(a) a vector backbone; and (b) (i) a first polynucleotide encoding a TCRα polypeptide and a second polynucleotide encoding a TCRβ polypeptide; or (ii) a first polynucleotide encoding a TCRγ polypeptide and a second polynucleotide encoding a TCRδ polypeptide;

wherein the first and second polynucleotides are a cognate pair, and wherein the first polynucleotide and the second polynucleotide are derived from mRNA isolated from a single lysed T cell that is present in a compartment.

B. The vector of Paragraph A, wherein the mRNA of the single lysed T cell is isolated using an mRNA capture reagent or reverse transcription-PCR (RT-PCR).

C. The vector of Paragraph A or Paragraph B, wherein the first polynucleotide and the second polynucleotide are operably linked, optionally via a linker polynucleotide, and optionally wherein the first polynucleotide and the second polynucleotide are operably linked by reverse transcription and PCR amplification of the T cell mRNA.

D. The vector of any one of the previous Paragraphs, wherein the first polynucleotide and the second polynucleotide have been cloned into the vector backbone by cleavage at a target restriction endonuclease site that is natively found in TCR genes.

E. The vector of Paragraph D, wherein the target restriction endonuclease site occurs in TCR genes with low frequency.

F. The vector of Paragraph D or Paragraph E, wherein the first polynucleotide and the second polynucleotide have been altered to incorporate at least one target restriction endonuclease site disclosed in Table 7 or 8.

G. The vector of any one of Paragraphs D-F, wherein the target restriction endonuclease site comprises a silent mutation.

H. The vector of any one of Paragraphs D-G, wherein the mRNA capture reagent is selected from the group consisting of a poly(dT) coated bead, an oligonucleotide-coated bead, a hydrogel bead, and a printed oligo on the surface of a microarray well.

I. The vector of any one of the previous Paragraphs, wherein the compartment is an emulsion droplet or a well.

J. The vector of Paragraph I, wherein the well is located in a printed polymer slide, a plastic plate, a microtiter plate, or a gel. K. The vector of any one of the previous Paragraphs, wherein the compartment has a volume of 5 nL or less.

L. The vector of any one of the previous Paragraphs, further comprising at least one polynucleotide encoding an expression control element operably linked to the first polynucleotide and/or the second polynucleotide.

M. The vector of Paragraph L, wherein the expression control element is selected from the group consisting of: a promoter, a p2A sequence, and an IRES sequence.

N. The vector of Paragraph M, wherein the promoter is an EF1α promoter or a CMV promoter.

o. The vector of any one of Paragraphs L-N, wherein the polynucleotide encoding the expression control element is located between the first polynucleotide and the second polynucleotide.

P. The vector of any one of the previous Paragraphs, wherein the vector is circularized.

Q. The vector of any one of Paragraphs L-P, wherein the vector has been circularized prior to incorporation of the expression control element into the vector.

R. The vector of any one of Paragraphs L-P, wherein the vector has been circularized after incorporation of the expression control element into the vector.

S. The vector of any one of Paragraphs L-R, wherein the expression control element has been incorporated near a protospacer adjacent motif (PAM).

T. The vector of any one of Paragraphs L-R, wherein the expression control element has been incorporated into the vector using a DNA-modifying enzyme selected from a restriction enzyme or a TALEN.

U. The vector of any one of the previous Paragraphs, further comprising one or more polynucleotides encoding a transposon linked to at least one of the first polynucleotide and the second polynucleotide.

V. The vector of any one of the previous Paragraphs, further comprising a polynucleotide encoding a detectable marker.

W. The vector of any one of the previous Paragraphs, further comprising a polynucleotide encoding a selectable marker.

X. The vector of any one of the previous Paragraphs, further comprising a polynucleotide encoding a switch mechanism for controlling expression and/or activation of the first polynucleotide and the second polynucleotide.

Y. The vector of any one of the previous Paragraphs, further comprising a polynucleotide encoding a Kozak consensus sequence or an enhancer.

Z. The vector of any one of the previous Paragraphs, wherein the vector backbone is selected from a group consisting of a retroviral, a lentiviral, an adenoviral, and an adeno-associated viral vector backbone.

AA. The vector of any one of the previous Paragraphs, wherein the vector encodes a TCR that has binding specificity for a target cell or a disease antigen.

BB. The vector of Paragraph AA, wherein the target cell is a cancer cell or a cell infected with a virus, optionally wherein the target cell was isolated from a subject.

CC. The vector of Paragraph AA, wherein the disease antigen is a viral antigen or a tumor antigen, optionally wherein the antigen is loaded into an antigen:MHC complex.

DD. The vector of Paragraph CC, wherein the disease antigen is a viral antigen derived from a virus selected from the group consisting of adenovirus, CMV, coronavirus, coxsackievirus, Dengue virus, Epstein-Barr virus (EBV), enterovirus 71 (EV71), Ebola virus, hepatitis A (HAV), hepatitis B (HBV), cytomegalovirus (CMV), hepatitis C (HCV), hepatitis D (HDV), hepatitis E (HEV), human immunodeficiency virus (HIV), human papillomavirus (HPV), herpes simplex virus (HSV), human T-lymphotropic virus (HTLV), influenza A virus, influenza B virus, Japanese encephalitis, leukemia virus, measles virus, molluscum contagiosum, orf virus, parvovirus, rabies virus, respiratory syncytial virus, rift valley fever virus, rubella virus, rotavirus, tick-borne encephalitis (TBEV), simian immunodeficiency virus, tobacco etch virus (TEV), varicella zoster virus, variola, West Nile virus, Zika virus, and Chikungunya virus.

EE. The vector of Paragraph CC, wherein the disease antigen is a tumor antigen selected from the group consisting of CD45, glypican-3, IGF2B3, Kallikrein 4, KIF20A, Lengsin, Meloe, mucin 5AC (MUC5AC), survivin, cyclin-A1, MAGE-A1, MAGE-C1, MAGE-C2, SSX2, XAGE1b/GAGED2A, CD19, CD20, CD22, CD52, epidermal growth factor receptor (EGFR), human epidermal growth factor receptor 2 (HER2), tumor necrosis factor receptor superfamily, member 10a (TRAILR1), receptor activator of nuclear factor kappa-B ligand (RANKL), insulin-like growth factor 1 receptor (IGF1R), epithelial cell adhesion molecule (EpCAM), and carcinoembryonic antigen (CEA).

FF. A recombinant cell comprising the vector of any one of the previous Paragraphs, optionally wherein the recombinant cell is a bacterial cell, mammalian cell, or a yeast cell.

GG. A recombinant TCR vector library comprising a plurality of vectors according to any one of Paragraphs A-EE.

HH. The recombinant TCR vector library of Paragraph GG, wherein the plurality of vectors comprises a TCR repertoire.

II. The recombinant TCR vector library of Paragraph GG or Paragraph HH, wherein each vector in the plurality of vectors has been selected on the basis of one or more of the following characteristics: TCR clonal prevalence, TCR enrichment characteristics from in vitro assays, TCR binding specificity, TCR V segment sequence, TCR D segment sequence, TCR J segment sequence, TCR gene motifs, and/or CDR3 gene motifs.

JJ. The recombinant TCR vector library of any one of Paragraphs GG-II, wherein the TCR vector library has been characterized by nucleic acid sequencing of the first polynucleotide and the second polynucleotide.

KK. An isolated immune cell comprising the vector of any one of Paragraphs A-EE.

LL. The isolated immune cell of Paragraph KK, wherein the immune cell is a hematopoietic stem cell, a hematopoietic progenitor cell, a T cell, or a natural killer (NK) cell.

MM. A cell population comprising the vector of any one of Paragraphs A-EE, or the vector library of any one of Paragraphs GG-JJ.

NN. The cell population of Paragraph MM, wherein the population comprises hematopoietic stem cells, hematopoietic progenitor cells, T cells, and/or NK cells.

OO. A method for preparing a recombinant TCR library, the method comprising transforming a population of cells with the vector library of any one of Paragraphs GG-JJ.

PP. The method of Paragraph OO, wherein the cells are hematopoietic stem cells, hematopoietic progenitor cells, T cells, or NK cells.

QQ. The method of Paragraph OO or Paragraph PP, further comprising screening the library for specific binding to a target cell.

RR. The method of Paragraph QQ, wherein the target cell is a cancer cell or a cell infected with a virus, optionally wherein the cell was isolated from a subject.

SS. The method of Paragraph OO or Paragraph PP, further comprising screening the library for specific binding to an antigen:MHC complex.

TT. The method of Paragraph SS, wherein the antigen of the antigen:MHC complex is a viral antigen derived from a virus selected from the group consisting of adenovirus, CMV, coronavirus, coxsackievirus, Dengue virus, Epstein-Barr virus (EBV), enterovirus 71 (EV71), Ebola virus, hepatitis A (HAV), hepatitis B (HBV), cytomegalovirus (CMV), hepatitis C (HCV), hepatitis D (HDV), hepatitis E (HEV), human immunodeficiency virus (HIV), human papillomavirus (HPV), herpes simplex virus (HSV), human T-lymphotropic virus (HTLV), influenza A virus, influenza B virus, Japanese encephalitis, leukemia virus, measles virus, molluscum contagiosum, orf virus, parvovirus, rabies virus, respiratory syncytial virus, rift valley fever virus, rubella virus, rotavirus, tick-borne encephalitis (TBEV), simian immunodeficiency virus, tobacco etch virus (TEV), varicella zoster virus, variola, West Nile virus, Zika virus, and Chikungunya virus.

UU. The method of Paragraph SS, wherein the antigen of the antigen:MHC complex is a tumor antigen selected from the group consisting of CD45, glypican-3, IGF2B3, Kallikrein 4, KIF20A, Lengsin, Meloe, mucin 5AC (MUC5AC), survivin, cyclin-A1, MAGE-A1, MAGE-C1, MAGE-C2, SSX2, XAGE1b/GAGED2A, CD19, CD20, CD22, CD52, EGFR, HER2, TRAILR1, RANKL, IGF1R, EpCAM, and CEA.

VV. The method of any one of Paragraphs OO-UU, further comprising screening the library for T cell phenotypic markers.

WW. The method of any one of Paragraphs OO-VV, further comprising screening the library for activity in a co-culture system, wherein the co-culture system comprises at least one of the following:
 (a) a cancer cell line;
 (b) a plurality of cells infected with a known virus;
 (c) a plurality of tumor cells isolated from a cancer patient;
 (d) an immortalized cell line; or
 (e) a plurality of cells derived from a patient tissue biopsy.

XX. The method of any one of Paragraphs OO-WW, further comprising in vitro activation of the transformed population of cells.

YY. The method of Paragraph XX, wherein in vitro activation is performed using one or more of the following stimulants: anti-CD3 antibody, anti-CD8 antibody, anti-CD27 antibody, IL-2, IL-4, IL-21, anti-PD1 antibody, anti-CTLA4 antibody, tumor cell lysate, cellular co-culture with virus-infected cells, and tumor cell lines.

ZZ. The method of any one of Paragraphs OO-YY, further comprising transforming the population of cells with a polynucleotide encoding a transcription factor.

AAA. The method of Paragraph ZZ, wherein the transcription factor is selected from the group consisting of FOXP3, BLIMP-1, Ikaros, Helios and TGF-beta.

BBB. The method of any one of Paragraphs OO-AAA, further comprising selecting individual vectors for inclusion in the recombinant TCR library on the basis of one or more of the following characteristics: TCR clonal prevalence, TCR enrichment characteristics from in vitro assays, TCR binding specificity, TCR V segment sequence, TCR D segment sequence, TCR J segment sequence, TCR gene motifs, and/or CDR3 gene motifs.

CCC. The method of Paragraph BBB, wherein selection comprises mixing individual vectors at a defined ratio to generate a synthetically-derived TCR library.

DDD. A recombinant TCR library prepared by a method according to any one of Paragraphs OO-CCC.

EEE. A composition comprising the recombinant TCR library of Paragraph DDD and a carrier.

FFF. The composition of Paragraph EEE, wherein the carrier is a pharmaceutically acceptable carrier.

GGG. A method of treating a subject in need thereof, the method comprising administering to the subject an effective amount of the recombinant TCR library of Paragraph DDD or the composition of Paragraph EEE or Paragraph FFF to the subject.

HHH. A method of treating cancer in a subject in need thereof, the method comprising administering to the subject an effective amount of the recombinant TCR library Paragraph DDD or the composition of Paragraph EEE or Paragraph FFF to the subject.

III. The method of Paragraph HHH, wherein the cancer is acute lymphoblastic leukemia (ALL); acute myeloid leukemia (AML); adrenocortical carcinoma; AIDS-related cancers; anal cancer; appendix cancer; astrocytomas; atypical teratoid/rhabdoid tumor, brain cancer; basal cell carcinoma of the skin; bile duct cancer; bladder cancer; bone cancer; breast cancer; bronchial tumors; Burkitt lymphoma; carcinoid tumor (gastrointestinal); germ cell tumor; primary CNS lymphoma; cervical cancer; cholangiocarcinoma; chordoma; chronic lymphocytic leukemia (CLL); chronic myelogenous leukemia (CML); chronic myeloproliferative neoplasms; colorectal cancer; craniopharyngioma; cutaneous T-cell lymphoma; ductal carcinoma in situ (DCIS); endometrial cancer; ependymoma; esophageal cancer; esthesioneuroblastoma; extracranial germ cell tumor; extragonadal germ cell tumor; eye cancer; intraocular melanoma; retinoblastoma; fallopian tube cancer; fibrous histiocytoma of bone, malignant, and osteosarcoma; gallbladder cancer; gastric cancer; gastrointestinal carcinoid tumor; gastrointestinal stromal tumors (GIST); germ cell tumors; gestational trophoblastic disease; hairy cell leukemia; head and neck cancer; heart tumors; hepatocellular cancer; histiocytosis, Langerhans cell; Hodgkin lymphoma; hypopharyngeal cancer; intraocular melanoma; islet cell tumors, pancreatic neuroendocrine tumors; kidney cancer; laryngeal cancer; leukemia; lip and oral cavity cancer; liver cancer; lung cancer; lymphoma; male breast cancer; malignant fibrous histiocytoma of bone and osteosarcoma; melanoma; Merkel cell carcinoma; mesothelioma; metastatic cancer; mouth cancer; multiple endocrine neoplasia syndrome; multiple myeloma/plasma cell neoplasms; mycosis fungoides; myelodysplastic syndrome, myeloproliferative neoplasm, chronic; nasopharyngeal cancer; neuroblastoma; Non-Hodgkin lymphoma; non-small cell lung cancer; oral cancer, oropharyngeal cancer; osteosarcoma; ovarian cancer; pancreatic cancer; pancreatic neuroendocrine tumors; papillomatosis; paraganglioma; paranasal sinus cancer; parathyroid cancer; pharyngeal cancer; pheochromocytoma; pituitary tumor; pleuropulmonary blastoma; prostate cancer; rectal cancer; recurrent cancer; renal cell cancer; retinoblastoma; rhabdomyosarcoma; salivary gland cancer; sarcoma; Ewing sarcoma; Kaposi sarcoma; osteosarcoma; uterine sarcoma; Sezary syndrome; skin cancer; small cell lung cancer; small intestine cancer; soft tissue sarcoma; squamous cell carcinoma of the skin; squamous neck cancer; stomach cancer; T cell lymphoma; testicular cancer; throat cancer; nasopharyngeal cancer; hypopharyngeal cancer; thymic carcinoma; thyroid cancer; urethral cancer; uterine cancer; vaginal cancer; vascular tumors; vulvar cancer; or Wilms tumor.

JJJ. A method of inhibiting tumor growth in a subject in need thereof, the method comprising administering to the subject an effective amount of the recombinant TCR library of Paragraph DDD or the composition of Paragraph EEE or Paragraph FFF to the subject.

KKK. The method of Paragraph JJJ, wherein the tumor is a solid tumor.

LLL. A method of treating a viral infection in a subject in need thereof, the method comprising administering to the subject an effective amount of the recombinant TCR library of Paragraph DDD or the composition of Paragraph EEE or Paragraph FFF to the subject.

MMM. The method of Paragraph LLL, wherein the viral infection is caused by a virus selected from the group consisting of adenovirus, CMV, coronavirus, coxsackievirus, Dengue virus, Epstein-Barr virus (EBV), enterovirus 71 (EV71), Ebola virus, hepatitis A (HAV), hepatitis B (HBV), cytomegalovirus (CMV), hepatitis C (HCV), hepatitis D (HDV), hepatitis E (HEV), human immunodeficiency virus (HIV), human papillomavirus (HPV), herpes simplex virus (HSV), human T-lymphotropic virus (HTLV), influenza A virus, influenza B virus, Japanese encephalitis, leukemia virus, measles virus, molluscum contagiosum, orf virus, parvovirus, rabies virus, respiratory syncytial virus, rift valley fever virus, rubella virus, rotavirus, tick-borne encephalitis (TBEV), simian immunodeficiency virus, tobacco etch virus (TEV), varicella zoster virus, variola, West Nile virus, Zika virus, and Chikungunya virus.

NNN. The method of any one of Paragraphs GGG-MMM, further comprising administering a second dose of the recombinant TCR library of Paragraph DDD or the composition of Paragraph EEE or Paragraph FFF to the subject.

OOO. The method of any one of Paragraphs GGG-NNN, wherein the recombinant TCR library comprises cells that are autologous or allogenic to the subject being treated.

PPP. The method of anyone of Paragraphs GGG-OO, wherein the subject is a human, an animal, a non-human primate, a dog, cat, a sheep, a mouse, a horse, or a cow.

QQQ. The method of Paragraph PPP, wherein the subject is a human.

Other embodiments are set forth within the following claims.

What is claimed is:

1. A method for preparing a recombinant TCR library, the method comprising
   (a) lysing a single T cell in a compartment having a volume of 5 nL or less,
   (b) isolating mRNA of the lysed single T cell in the compartment using an mRNA capture reagent;
   (c) reverse transcribing the mRNA into cDNA in the compartment by overlap extension reverse transcription PCR (OE-RT-PCR) to generate linked cDNA products, wherein the linked cDNA products comprise
      (i) a first polynucleotide encoding a T cell receptor (TCR) a polypeptide and a second polynucleotide encoding a TCRβ polypeptide; or
      (ii) a first polynucleotide encoding a TCRγ polypeptide and a second polynucleotide encoding a TCRδ polypeptide,
   wherein the first and second polynucleotides are a cognate pair and are operably linked via a linker polynucleotide;
   (d) amplifying the linked cDNA products using nested PCR to generate TCR amplicons;
   (e) generating a recombinant TCR library by introducing the TCR amplicons into an expression vector or a population of cells.

2. The method of claim 1, further comprising screening the library for specific binding to a target cell, optionally wherein
   the target cell is a cancer cell or a cell infected with a virus, or
   the cell was isolated from a subject.

3. The method of claim 1, further comprising screening the library for specific binding to an antigen: MHC complex, optionally wherein
   the antigen of the antigen: MHC complex is a viral antigen derived from a virus selected from the group consisting of adenovirus, CMV, coronavirus, coxsackievirus, Dengue virus, Epstein-Barr virus (EBV), enterovirus 71 (EV71), Ebola virus, hepatitis A (HAV), hepatitis B (HBV), cytomegalovirus (CMV), hepatitis C (HCV), hepatitis D (HDV), hepatitis E (HEV), human immunodeficiency virus (HIV), human papillomavirus (HPV), herpes simplex virus (HSV), human T-lymphotropic virus (HTLV), influenza A virus, influenza B virus, Japanese encephalitis, leukemia virus, measles virus, molluscum contagiosum, orf virus, parvovirus, rabies virus, respiratory syncytial virus, rift valley fever virus, rubella virus, rotavirus, tick-borne encephalitis (TBEV), simian immunodeficiency virus, tobacco etch virus (TEV), varicella zoster virus, variola, West Nile virus, Zika virus, and Chikungunya virus, or
   the antigen of the antigen: MHC complex is a tumor antigen selected from the group consisting of CD45, glypican-3, IGF2B3, Kallikrein 4, KIF20A, Lengsin, Meloe, mucin 5AC (MUC5AC), survivin, cyclin-A1, MAGE-A1, MAGE-C1, MAGE-C2, SSX2, XAGE1b/GAGED2A, CD19, CD20, CD22, CD52, EGFR, HER2, TRAILR1, RANKL, IGF1R, EpCAM, and CEA.

4. The method of claim 1, further comprising
   screening the library for T cell phenotypic markers; or
   screening the library for activity in a co-culture system, wherein the co-culture system comprises at least one of the following:
   (a) a cancer cell line;
   (b) a plurality of cells infected with a known virus;
   (c) a plurality of tumor cells isolated from a cancer patient;
   (d) an immortalized cell line; or
   (e) a plurality of cells derived from a patient tissue biopsy; or
   performing in vitro activation of the transformed population of cells, optionally wherein in vitro activation is performed using one or more of the following stimulants: anti-CD3 antibody, anti-CD8 antibody, anti-CD27 antibody, IL-2, IL-4, IL-21, anti-PD1 antibody, anti-CTLA4 antibody, tumor cell lysate, cellular co-culture with virus-infected cells, and tumor cell lines; or
   transforming the population of cells with a polynucleotide encoding a transcription factor, optionally wherein the transcription factor is selected from the group consisting of FOXP3, BLIMP-1, Ikaros, Helios and TGF-beta; or
   selecting individual vectors for inclusion in the recombinant TCR library on the basis of one or more of the following characteristics: TCR clonal prevalence, TCR enrichment characteristics from in vitro assays, TCR binding specificity, TCR V segment sequence, TCR D segment sequence, TCR J segment sequence, TCR gene motifs, and/or CDR3 gene motifs, optionally wherein selection comprises mixing individual vectors at a defined ratio to generate a synthetically-derived TCR library.

5. The method of claim 1, wherein the first polynucleotide and the second polynucleotide have been altered to incorporate at least one target restriction endonuclease site selected from the group consisting of: Age I, SpeI, XhoI, NheI, BsiWI, BstZ17I, BstBI, and SphI or wherein the target restriction endonuclease site comprises a silent mutation; or
   wherein step (e) is performed by cleaving at a target restriction endonuclease site, optionally wherein the target restriction endonuclease site is natively found in TCR genes at low frequency; or
   wherein the population of cells are hematopoietic stem cells, hematopoietic progenitor cells, T cells, or NK cells.

* * * * *

SEQUENCE LISTING

```
<160> NUMBER OF SEQ ID NOS: 79

<210> SEQ ID NO 1
<211> LENGTH: 9
<212> TYPE: PRT
<213> ORGANISM: Human immunodeficiency virus

<400> SEQUENCE: 1

Arg Pro Gln Val Pro Leu Arg Pro Met
1               5

<210> SEQ ID NO 2
<211> LENGTH: 142
<212> TYPE: PRT
<213> ORGANISM: Homo sapiens

<400> SEQUENCE: 2

Pro Asn Ile Gln Asn Pro Asp Pro Ala Val Tyr Gln Leu Arg Asp Ser
1               5                   10                  15

Lys Ser Ser Asp Lys Ser Val Cys Leu Phe Thr Asp Phe Asp Ser Gln
            20                  25                  30

Thr Asn Val Ser Gln Ser Lys Asp Ser Asp Val Tyr Ile Thr Asp Lys
        35                  40                  45

Thr Val Leu Asp Met Arg Ser Met Asp Phe Lys Ser Asn Ser Ala Val
```

```
                    50                  55                  60
Ala Trp Ser Asn Lys Ser Asp Phe Ala Cys Ala Asn Ala Phe Asn Asn
 65                  70                  75                  80

Ser Ile Ile Pro Glu Asp Thr Phe Phe Pro Ser Pro Glu Ser Ser Cys
                     85                  90                  95

Asp Val Lys Leu Val Glu Lys Ser Phe Glu Thr Asp Thr Asn Leu Asn
                    100                 105                 110

Phe Gln Asn Leu Ser Val Ile Gly Phe Arg Ile Leu Leu Leu Lys Val
                115                 120                 125

Ala Gly Phe Asn Leu Leu Met Thr Leu Arg Leu Trp Ser Ser
                130                 135                 140
```

<210> SEQ ID NO 3
<211> LENGTH: 177
<212> TYPE: PRT
<213> ORGANISM: Homo sapiens

<400> SEQUENCE: 3

```
Glu Asp Leu Asn Lys Val Phe Pro Pro Glu Val Ala Val Phe Glu Pro
  1               5                  10                  15

Ser Glu Ala Glu Ile Ser His Thr Gln Lys Ala Thr Leu Val Cys Leu
                 20                  25                  30

Ala Thr Gly Phe Phe Pro Asp His Val Glu Leu Ser Trp Trp Val Asn
                 35                  40                  45

Gly Lys Glu Val His Ser Gly Val Ser Thr Asp Pro Gln Pro Leu Lys
             50                  55                  60

Glu Gln Pro Ala Leu Asn Asp Ser Arg Tyr Cys Leu Ser Ser Arg Leu
 65                  70                  75                  80

Arg Val Ser Ala Thr Phe Trp Gln Asn Pro Arg Asn His Phe Arg Cys
                     85                  90                  95

Gln Val Gln Phe Tyr Gly Leu Ser Glu Asn Asp Glu Trp Thr Gln Asp
                100                 105                 110

Arg Ala Lys Pro Val Thr Gln Ile Val Ser Ala Glu Ala Trp Gly Arg
            115                 120                 125

Ala Asp Cys Gly Phe Thr Ser Val Ser Tyr Gln Gln Gly Val Leu Ser
        130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Phe
```

<210> SEQ ID NO 4
<211> LENGTH: 178
<212> TYPE: PRT
<213> ORGANISM: Homo sapiens

<400> SEQUENCE: 4

```
Asp Leu Lys Asn Val Phe Pro Pro Glu Val Ala Val Phe Glu Pro Ser
  1               5                  10                  15

Glu Ala Glu Ile Ser His Thr Gln Lys Ala Thr Leu Val Cys Leu Ala
                 20                  25                  30

Thr Gly Phe Tyr Pro Asp His Val Glu Leu Ser Trp Trp Val Asn Gly
                 35                  40                  45

Lys Glu Val His Ser Gly Val Ser Thr Asp Pro Gln Pro Leu Lys Glu
             50                  55                  60
```

Gln Pro Ala Leu Asn Asp Ser Arg Tyr Cys Leu Ser Arg Leu Arg
 65                  70                  75                  80

Val Ser Ala Thr Phe Trp Gln Asn Pro Arg Asn His Phe Arg Cys Gln
                 85                  90                  95

Val Gln Phe Tyr Gly Leu Ser Glu Asn Asp Glu Trp Thr Gln Asp Arg
            100                 105                 110

Ala Lys Pro Val Thr Gln Ile Val Ser Ala Glu Ala Trp Gly Arg Ala
        115                 120                 125

Asp Cys Gly Phe Thr Ser Glu Ser Tyr Gln Gln Gly Val Leu Ser Ala
    130                 135                 140

Thr Ile Leu Tyr Glu Ile Leu Leu Gly Lys Ala Thr Leu Tyr Ala Val
145                 150                 155                 160

Leu Val Ser Ala Leu Val Leu Met Ala Met Val Lys Arg Lys Asp Ser
                165                 170                 175

Arg Gly

<210> SEQ ID NO 5
<211> LENGTH: 173
<212> TYPE: PRT
<213> ORGANISM: Homo sapiens

<400> SEQUENCE: 5

Asp Lys Gln Leu Asp Ala Asp Val Ser Pro Lys Pro Thr Ile Phe Leu
 1               5                  10                  15

Pro Ser Ile Ala Glu Thr Lys Leu Gln Lys Ala Gly Thr Tyr Leu Cys
             20                  25                  30

Leu Leu Glu Lys Phe Phe Pro Asp Val Ile Lys Ile His Trp Gln Glu
         35                  40                  45

Lys Lys Ser Asn Thr Ile Leu Gly Ser Gln Glu Gly Asn Thr Met Lys
     50                  55                  60

Thr Asn Asp Thr Tyr Met Lys Phe Ser Trp Leu Thr Val Pro Glu Lys
 65                  70                  75                  80

Ser Leu Asp Lys Glu His Arg Cys Ile Val Arg His Glu Asn Asn Lys
                 85                  90                  95

Asn Gly Val Asp Gln Glu Ile Ile Phe Pro Pro Ile Lys Thr Asp Val
            100                 105                 110

Ile Thr Met Asp Pro Lys Asp Asn Cys Ser Lys Asp Ala Asn Asp Thr
        115                 120                 125

Leu Leu Leu Gln Leu Thr Asn Thr Ser Ala Tyr Tyr Met Tyr Leu Leu
    130                 135                 140

Leu Leu Leu Lys Ser Val Val Tyr Phe Ala Ile Ile Thr Cys Cys Leu
145                 150                 155                 160

Leu Arg Arg Thr Ala Phe Cys Cys Asn Gly Glu Lys Ser
                165                 170

<210> SEQ ID NO 6
<211> LENGTH: 189
<212> TYPE: PRT
<213> ORGANISM: Homo sapiens

<400> SEQUENCE: 6

Asp Lys Gln Leu Asp Ala Asp Val Ser Pro Lys Pro Thr Ile Phe Leu
 1               5                  10                  15

Pro Ser Ile Ala Glu Thr Lys Leu Gln Lys Ala Gly Thr Tyr Leu Cys
             20                  25                  30

Leu Leu Glu Lys Phe Phe Pro Asp Ile Ile Lys Ile His Trp Gln Glu
             35                  40                  45

Lys Lys Ser Asn Thr Ile Leu Gly Ser Gln Glu Gly Asn Thr Met Lys
 50                  55                  60

Thr Asn Asp Thr Tyr Met Lys Phe Ser Trp Leu Thr Val Pro Glu Glu
 65                  70                  75                  80

Ser Leu Asp Lys Glu His Arg Cys Ile Val Arg His Glu Asn Asn Lys
                 85                  90                  95

Asn Gly Ile Asp Gln Glu Ile Ile Phe Pro Pro Ile Lys Thr Asp Val
                100                 105                 110

Thr Thr Val Asp Pro Lys Asp Ser Tyr Ser Lys Asp Ala Asn Asp Val
                115                 120                 125

Ile Thr Met Asp Pro Lys Asp Asn Trp Ser Lys Asp Ala Asn Asp Thr
                130                 135                 140

Leu Leu Leu Gln Leu Thr Asn Thr Ser Ala Tyr Tyr Met Tyr Leu Leu
145                 150                 155                 160

Leu Leu Leu Lys Ser Val Val Tyr Phe Ala Ile Ile Thr Cys Cys Leu
                165                 170                 175

Leu Gly Arg Thr Ala Phe Cys Cys Asn Gly Glu Lys Ser
                180                 185

<210> SEQ ID NO 7
<211> LENGTH: 153
<212> TYPE: PRT
<213> ORGANISM: Homo sapiens

<400> SEQUENCE: 7

Ser Gln Pro His Thr Lys Pro Ser Val Phe Val Met Lys Asn Gly Thr
1                5                  10                  15

Asn Val Ala Cys Leu Val Lys Glu Phe Tyr Pro Lys Asp Ile Arg Ile
                 20                  25                  30

Asn Leu Val Ser Ser Lys Lys Ile Thr Glu Phe Asp Pro Ala Ile Val
                 35                  40                  45

Ile Ser Pro Ser Gly Lys Tyr Asn Ala Val Lys Leu Gly Lys Tyr Glu
 50                  55                  60

Asp Ser Asn Ser Val Thr Cys Ser Val Gln His Asp Asn Lys Thr Val
 65                  70                  75                  80

His Ser Thr Asp Phe Glu Val Lys Thr Asp Ser Thr Asp His Val Lys
                 85                  90                  95

Pro Lys Glu Thr Glu Asn Thr Lys Gln Pro Ser Lys Ser Cys His Lys
                100                 105                 110

Pro Lys Ala Ile Val His Thr Glu Lys Val Asn Met Met Ser Leu Thr
                115                 120                 125

Val Leu Gly Leu Arg Met Leu Phe Ala Lys Thr Val Ala Val Asn Phe
                130                 135                 140

Leu Leu Thr Ala Lys Leu Phe Phe Leu
145                 150

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

```
Gly Gly Gly Gly Ser Gly Gly Gly Gly Ser Gly Gly Gly Ser
1               5                   10                  15

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Gly Gly Gly Ser
1               5

<210> SEQ ID NO 10
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Gly Gly Gly Ser Gly Gly Gly Gly Ser Gly Gly Gly Gly
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Glu Phe Gly Ala Gly Leu Val Leu Gly Gly Gln Phe Met
1               5                   10

<210> SEQ ID NO 12
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(3)
<223> OTHER INFORMATION: This region may or may not be present

<400> SEQUENCE: 12

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 13
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(3)
<223> OTHER INFORMATION: This region may or may not be present
```

-continued

<400> SEQUENCE: 13

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 14
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(3)
<223> OTHER INFORMATION: This region may or may not be present

<400> SEQUENCE: 14

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 15
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(3)
<223> OTHER INFORMATION: This region may or may not be present

<400> SEQUENCE: 15

Gly Ser Gly Val Lys Gln Thr Leu Asn Phe Asp Leu Leu Lys Leu Ala
1               5                   10                  15

Gly Asp Val Glu Ser Asn Pro Gly
            20

<210> SEQ ID NO 16
<211> LENGTH: 355
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
tatgctagta cgtctctcaa ggataagtaa gtaatattaa ggtacgggag gtattggaca      60
ggccgcaata aaatatcttt attttcatta catctgtgtg ttggttttt gtgtgaatcg      120 atagtactaa catacgctct ccatcaaaac aaaacgaaac aaaacaaact agcaaaatag     180
gctgtcccca gtgcaagtgc aggtgccaga acatttctct ggcctaactg gccggtacct    240
gagctctagt ttcactttcc ctagtttcac ttccctagt ttcactttcc ctagtttcac     300
tttccctagt ttcactttcc cctcgaggat atcaagatct ggcctcggcg gccag         355

<210> SEQ ID NO 17
<211> LENGTH: 80
<212> TYPE: DNA
<213> ORGANISM: Woodchuck hepatitis virus

```
<400> SEQUENCE: 17
gccacggcgg aactcatcgc cgcctgcctt gcccgctgct ggacaggggc tcggctgttg    60
ggcactgaca attccgtggt                                                80

<210> SEQ ID NO 18
<211> LENGTH: 592
<212> TYPE: DNA
<213> ORGANISM: Woodchuck hepatitis virus

<400> SEQUENCE: 18
aatcaacctc tggattacaa aatttgtgaa agattgactg gtattcttaa ctatgttgct    60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt ttgctgacgc aacccccact   240
ggttggggca ttgccaccac ctgtcagctc ctttccggga ctttcgcttt ccccctccct   300
attgccacgg cggaactcat cgccgcctgc cttgcccgct gctggacagg ggctcggctg   360
ttgggcactg acaattccgt ggtgttgtcg gggaagctga cgtcctttcc atggctgctc   420
gcctgtgttg ccacctggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc ctttgggccg cctccccgcc tg           592

<210> SEQ ID NO 19
<211> LENGTH: 8904
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
tggaagggct aattcactcc caagaagac aagatatcct tgatctgtgg atctaccaca    60
cacaaggcta cttccctgat tagcagaact acacaccagg gccaggggtc agatatccac   120
tgacctttgg atggtgctac aagctagtac cagttgagcc agataaggta gaagaggcca   180
ataaaggaga gaacaccagc ttgttacacc ctgtgagcct gcatgggatg gatgacccgg   240
agagagaagt gttagagtgg aggtttgaca gccgcctagc atttcatcac gtggcccgag   300
agctgcatcc ggagtacttc aagaactgct gatatcgagc ttgctacaag gactttccg    360 ctggggactt tccagggagg cgtggcctgg gcgggactgg ggagtggcga gccctcagat   420
cctgcatata agcagctgct ttttgcctgt actgggtctc tctggttaga ccagatctga   480
gcctgggagc tctctggcta actagggaac ccactgctta agcctcaata aagcttgcct   540
tgagtgcttc aagtagtgtg tgcccgtctg ttgtgtgact ctggtaacta gagatccctc   600
agaccctttt agtcagtgtg gaaaatctct agcagtggcg cccgaacagg gacttgaaag   660
cgaaagggaa accagaggag ctctctcgac gcaggactcg gcttgctgaa gcgcgcacgg   720
caagaggcga ggggcggcga ctggtgagta cgccaaaaat tttgactagc ggaggctaga   780
aggagagaga tgggtgcgag agcgtcagta ttaagcgggg gagaattaga tcgcgatggg   840
aaaaaattcg gttaaggcca gggggaaaga aaaatataa attaaaacat atagtatggg   900
caagcaggga gctagaacga ttcgcagtta atcctggcct gttagaaaca tcagaaggct   960
gtagacaaat actgggacag ctacaaccat cccttcagac aggatcagaa gaacttagat  1020
```

-continued

```
cattatataa tacagtagca accctctatt gtgtgcatca aaggatagag ataaaagaca    1080
ccaaggaagc tttagacaag atagaggaag agcaaaacaa aagtaagacc accgcacagc    1140
aagcggccgg ccgctgatct tcagacctgg aggaggagat atgagggaca attggagaag    1200
tgaattatat aaatataaag tagtaaaaat tgaaccatta ggagtagcac ccaccaaggc    1260
aaagagaaga gtggtgcaga gagaaaaaag agcagtggga ataggagctt tgttccttgg    1320
gttcttggga gcagcaggaa gcactatggg cgcagcgtca atgacgctga cggtacaggc    1380
cagacaatta ttgtctggta tagtgcagca gcagaacaat ttgctgaggg ctattgaggc    1440
gcaacagcat ctgttgcaac tcacagtctg gggcatcaag cagctccagg caagaatcct    1500
ggctgtggaa agatacctaa aggatcaaca gctcctgggg atttggggtt gctctggaaa    1560
actcatttgc accactgctg tgccttggaa tgctagttgg agtaataaat ctctggaaca    1620
gatttggaat cacacgacct ggatggagtg ggacagagaa attaacaatt acacaagctt    1680
aatacactcc ttaattgaag aatcgcaaaa ccagcaagaa aagaatgaac aagaattatt    1740
ggaattagat aaatgggcaa gtttgtggaa ttggtttaac ataacaaatt ggctgtggta    1800
tataaaatta ttcataatga tagtaggagg cttggtaggt ttaagaatag ttttgctgt     1860 actttctata gtgaatagag ttaggcaggg atattcacca ttatcgtttc agacccacct    1920
cccaaccccg aggggacccg acaggcccga aggaatagaa gaagaaggtg gagagagaga    1980
cagagacaga tccattcgat tagtgaacgg atctcgacgg tatcgccttt aaaagaaaag    2040
gggggattgg ggggtacagt gcaggggaaa gaatagtaga cataatagca acagacatac    2100
aaactaaaga attacaaaaa caaattacaa aaattcaaaa ttttcgggtt tattacaggg    2160
acagcagaga tccagtttat cgatgagtaa ttcatacaaa aggactcgcc cctgccttgg    2220
ggaatcccag ggaccgtcgt taaactccca ctaacgtaga acccagagat cgctgcgttc    2280
ccgccccctc acccgcccgc tctcgtcatc actgaggtgg agaagagcat gcgtgaggct    2340
ccggtgcccg tcagtgggca gagcgcacat cgcccacagt ccccgagaag ttgggggggag   2400 gggtcggcaa ttgaaccggt gcctagagaa ggtggcgcgg ggtaaactgg gaaagtgatg    2460
tcgtgtactg gctccgcctt ttttcccgagg gtgggggaga accgtatata agtgcagtag   2520
tcgccgtgaa cgttcttttt cgcaacgggt ttgccgccag aacacaggta agtgccgtgt    2580
gtggttcccg cgggcctggc ctctttacgg gttatggccc ttgcgtgcct tgaattactt    2640
ccacgcccct ggctgcagta cgtgattctt gatcccgagc ttcgggttgg aagtgggtgg    2700
gagagttcga ggccttgcgc ttaaggagcc ccttcgcctc gtgcttgagt tgaggcctgg    2760
cttgggcgct ggggccgccg cgtgcgaatc tggtggcacc ttcgcgcctg tctcgctgct    2820
ttcgataagt ctctagccat ttaaaatttt tgatgacctg ctgcgacgct ttttttctgg    2880
caagatagtc ttgtaaatgc gggccaagat ctgcacactg gtatttcggt ttttggggcc    2940
gcgggcggcg acgggcccg tgcgtcccag cgcacatgtt cggcgaggcg gggcctgcga    3000
gcgcggccac cgagaatcgg acgggggtag tctcaagctg gccggcctgc tctggtgcct    3060
ggcctcgcgc cgccgtgtat cgccccgccc tgggcggcaa ggctggcccg tcggcacca    3120 gttgcgtgag cggaaagatg gccgcttccc ggccctgctg cagggagctc aaaatggagg    3180
acgcggcgct cgggagagcg ggcgggtgag tcacccacac aaaggaaaag ggcctttccg    3240
tcctcagccg tcgcttcatg tgactccacg gagtaccggg cgccgtccag gcacctcgat    3300
tagttctcga gcttttggag tacgtcgtct ttaggttggg gggagggggtt ttatgcgatg    3360 gagtttcccc acactgagtg ggtggagact gaagttaggc cagcttggca cttgatgtaa    3420
```

```
ttctccttgg aatttgccct ttttgagttt ggatcttggt tcattctcaa gcctcagaca    3480
gtggttcaaa gttttttttct tccatttcag gtgtcgtgag gatctatttc cggtgaattc   3540
ctcgagacta gttctagagc ggccgcggat cccgcccctc tccctccccc ccccctaacg    3600
ttactggccg aagccgcttg gaataaggcc ggtgtgcgtt tgtctatatg ttattttcca    3660
ccatattgcc gtcttttggc aatgtgaggg cccggaaacc tggccctgtc ttcttgacga    3720
gcattcctag gggtctttcc cctctcgcca aggaatgca aggtctgttg aatgtcgtga     3780
aggaagcagt tcctctggaa gcttcttgaa gacaaacaac gtctgtagcg acccttttgca  3840 ggcagcggaa cccccccacct ggcgacaggt gcctctgcgg ccaaaagcca cgtgtataag  3900
atacacctgc aaaggcggca aaccccagt gccacgttgt gagttggata gttgtggaaa    3960
gagtcaaatg gctcacctca agcgtattca acaaggggct gaaggatgcc cagaaggtac   4020
cccattgtat gggatctgat ctggggcctc ggtgcacatg ctttacatgt gtttagtcga   4080
ggttaaaaaa cgtctaggcc ccccgaacca cggggacgtg gttttccttt gaaaaacacg   4140
atgataatat ggtgagcaag ggcgaggagg ataacatggc catcatcaag gagttcatgc   4200
gcttcaaggt gcacatggag ggctccgtga acggccacga gttcgagatc gagggcgagg  4260
gcgagggccg cccctacgag ggcacccaga ccgccaagct gaaggtgacc aagggtggcc   4320
ccctgccctt cgcctgggac atcctgtccc ctcagttcat gtacggctcc aaggcctacg   4380
tgaagcaccc cgccgacatc cccgactact tgaagctgtc cttccccgag ggcttcaagt   4440
gggagcgcgt gatgaacttc gaggacggcg gcgtggtgac cgtgacccag gactcctccc   4500
tgcaggacgg cgagttcatc tacaaggtga agctgcgcgg caccaacttc ccctccgacg   4560
gccccgtaat gcagaagaag accatgggct gggaggcctc ctccgagcgg atgtaccccg   4620
aggacggcgc cctgaagggc gagatcaagc agaggctgaa gctgaaggac ggcggccact   4680
acgacgctga ggtcaagacc acctacaagg ccaagaagcc cgtgcagctg cccggcgcct   4740
acaacgtcaa catcaagttg gacatcacct cccacaacga ggactacacc atcgtggaac   4800
agtacgaacg cgccgagggc cgccactcca ccggcggcat ggacgagctg tacaagtgaa   4860
cgcgtctgga acaatcaacc tctggattac aaaatttgtg aaagattgac tggtattctt   4920
aactatgttg ctccttttac gctatgtgga tacgctgctt taatgccttt gtatcatgct   4980
attgcttccc gtatggcttt cattttctcc tccttgtata aatcctggtt gctgtctctt   5040
tatgaggagt tgtggcccgt tgtcaggcaa cgtggcgtgg tgtgcactgt gtttgctgac   5100
gcaaccccca ctggttgggg cattgccacc acctgtcagc tcctttccgg gactttcgct   5160
ttccccctcc ctattgccac ggcggaactc atcgccgcct gccttgcccg ctgctggaca   5220
ggggctcggt tgtgggcac tgacaattcc gtggtgttgt cggggaagct gacgtccttt    5280
ccatggctgc tcgcctgtgt tgccacctgg attctgcgcg gacgtccttt ctgctacgtc   5340
ccttcggccc tcaatccagc ggaccttcct tcccgcggcc tgctgccggc tctgcggcct   5400
cttccgcgtc ttcgccttcg ccctcagacg agtcggatct cccttttgggc cgcctccccg   5460 cctggaatta ttctgcagt cgagacctag aaaaacatgg agcaatcaca agtagcaata   5520
cagcagctac caatgctgat tgtgcctggc tagaagcaca agaggaggag gaggtggggtt 5580 ttccagtcac acctcaggta cctttaagac caatgactta caaggcagct gtagatctta   5640 gccactttt aaaagaaaag aggggactgg aagggctaat tcactcccaa cgaagacaag   5700
atatccttga tctgtggatc taccacacac aaggctactt ccctgattag cagaactaca   5760
```

```
caccagggcc aggggtcaga tatccactga cctttggatg gtgctacaag ctagtaccag   5820
ttgagccaga taaggtagaa gaggccaata aaggagagaa caccagcttg ttacaccctg   5880
tgagcctgca tgggatggat gacccggaga gagaagtgtt agagtggagg tttgacagcc   5940
gcctagcatt tcatcacgtg gcccgagagc tgcatccgga gtacttcaag aactgctgat   6000
atcgagcttg ctacaaggga cttttccgctg gggactttcc agggaggcgt ggcctgggcg   6060
ggactgggga gtggcgagcc ctcagatcct gcatataagc agctgctttt tgcctgtact   6120
gggtctctct ggttagacca gatctgagcc tgggagctct ctggctaact agggaaccca   6180
ctgcttaagc ctcaataaag cttgccttga gtgcttcaag tagtgtgtgc ccgtctgttg   6240
tgtgactctg gtaactagag atccctcaga ccctttttagt cagtgtggaa aatctctagc   6300
agtagtagtt catgtcatct tattattcag tatttataac ttgcaaagaa atgaatatca   6360
gagagtgaga ggccttgaca ttgctagcgt ttaccgtcga cctctagcta gagcttggcg   6420
taatcatggt catagctgtt tcctgtgtga aattgttatc cgctcacaat tccacacaac   6480
atacgagccg gaagcataaa gtgtaaagcc tggggtgcct aatgagtgag ctaactcaca   6540
ttaattgcgt tgcgctcact gcccgctttc cagtcgggaa acctgtcgtg ccagctgcat   6600
taatgaatcg gccaacgcgc ggggagaggc ggtttgcgta ttgggcgctc ttccgcttcc   6660
tcgctcactg actcgctgcg ctcggtcgtt cggctgcggc gagcggtatc agctcactca   6720
aaggcggtaa tacggttatc cacagaatca ggggataacg caggaaagaa catgtgagca   6780
aaaggccagc aaaaggccag gaaccgtaaa aaggccgcgt tgctggcgtt tttccatagg   6840
ctccgccccc ctgacgagca tcacaaaaat cgacgctcaa gtcagaggtg gcgaaacccg   6900
acaggactat aaagatacca ggcgtttccc cctggaagct ccctcgtgcg ctctcctgtt   6960
ccgaccctgc cgcttaccgg atacctgtcc gcctttctcc cttcgggaag cgtggcgctt   7020
tctcatagct cacgctgtag gtatctcagt tcggtgtagg tcgttcgctc caagctgggc   7080
tgtgtgcacg aaccccccgt tcagcccgac cgctgcgcct tatccggtaa ctatcgtctt   7140
gagtccaacc cggtaagaca cgacttatcg ccactggcag cagccactgg taacaggatt   7200
agcagagcga ggtatgtagg cggtgctaca gagttcttga agtggtggcc taactacggc   7260
tacactagaa gaacagtatt tggtatctgc gctctgctga agccagttac cttcggaaaa   7320
agagttggta gctcttgatc cggcaaacaa accaccgctg gtagcggtgg tttttttgtt   7380
tgcaagcagc agattacgcg cagaaaaaaa ggatctcaag aagatccttt gatcttttct   7440
acggggtctg acgctcagtg gaacgaaaac tcacgttaag ggattttggt catgagatta   7500
tcaaaaagga tcttcaccta gatccttttta aattaaaaat gaagttttaa atcaatctaa   7560
agtatatatg agtaaacttg gtctgacagt taccaatgct taatcagtga ggcacctatc   7620
tcagcgatct gtctatttcg ttcatccata gttgcctgac tccccgtcgt gtagataact   7680
acgatacggg agggcttacc atctggcccc agtgctgcaa tgataccgcg agacccacgc   7740
tcaccggctc cagatttatc agcaataaac cagccagccg gaagggccga gcgcagaagt   7800
ggtcctgcaa ctttatccgc ctccatccag tctattaatt gttgccggga agctagagta   7860
agtagttcgc cagttaatag tttgcgcaac gttgttgcca ttgctacagg catcgtggtg   7920
tcacgctcgt cgtttggtat ggcttcattc agctccggtt cccaacgatc aaggcgagtt   7980
acatgatccc ccatgttgtg caaaaaagcg gttagctcct tcggtcctcc gatcgttgtc   8040
agaagtaagt tggccgcagt gttatcactc atggttatgg cagcactgca taattctctt   8100
actgtcatgc catccgtaag atgcttttct gtgactggtg agtactcaac caagtcattc   8160
```

```
tgagaatagt gtatgcggcg accgagttgc tcttgcccgg cgtcaatacg ggataatacc    8220
gcgccacata gcagaacttt aaaagtgctc atcattggaa acgttcttc ggggcgaaaa     8280 ctctcaagga tcttaccgct gttgagatcc agttcgatgt aacccactcg tgcacccaac    8340
tgatcttcag catcttttac tttcaccagc gtttctgggt gagcaaaaac aggaaggcaa    8400
aatgccgcaa aaagggaat aagggcgaca cggaaatgtt gaatactcat actcttcctt    8460
tttcaatatt attgaagcat ttatcagggt tattgtctca tgagcggata catatttgaa    8520
tgtatttaga aaaataaaca atagggggtt ccgcgcacat ttccccgaaa agtgccacct    8580
gacgtcgacg gatcgggaga tcaacttgtt tattgcagct tataatggtt acaaataaag    8640
caatagcatc acaaatttca caaataaagc attttttttca ctgcattcta gttgtggttt    8700
gtccaaactc atcaatgtat cttatcatgt ctggatcaac tggataactc aagctaacca    8760
aaatcatccc aaacttccca ccccataccc tattaccact gccaattacc tgtggtttca    8820
tttactctaa acctgtgatt cctctgaatt attttcattt taaagaaatt gtatttgtta    8880
aatatgtact acaaacttag tagt                                           8904

<210> SEQ ID NO 20
<211> LENGTH: 8904
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
tggaagggct aattcactcc caagaagac aagatatcct tgatctgtgg atctaccaca       60
cacaaggcta cttccctgat tagcagaact acacaccagg gccagggtc agatatccac      120 tgacctttgg atggtgctac aagctagtac cagttgagcc agataaggta gaagaggcca     180
ataaaggaga gaacaccagc ttgttacacc ctgtgagcct gcatgggatg gatgacccgg     240
agagagaagt gttagagtgg aggtttgaca gccgcctagc atttcatcac gtggcccgag     300
agctgcatcc ggagtacttc aagaactgct gatatcgagc ttgctacaag ggactttccg     360
ctggggactt tccagggagg cgtggcctgg gcgggactgg ggagtggcga gccctcagat     420
cctgcatata agcagctgct ttttgcctgt actgggtctc tctggttaga ccagatctga     480
gcctgggagc tctctggcta actagggaac ccactgctta agcctcaata agcttgcct     540 tgagtgcttc aagtagtgtg tgcccgtctg ttgtgtgact ctggtaacta gagatccctc     600 agacccttttt agtcagtgtg gaaaatctct agcagtggcg cccgaacagg gacttgaaag     660
cgaaagggaa accagaggag ctctctcgac gcaggactcg gcttgctgaa gcgcgcacgg     720
caagaggcga ggggcggcga ctggtgagta cgccaaaaat tttgactagc ggaggctaga     780
aggagagaga tgggtgcgag agcgtcagta ttaagcgggg gagaattaga tcgcgatggg     840
aaaaaattcg gttaaggcca gggggaaaga aaaaatataa attaaaacat atagtatggg     900
caagcaggga gctagaacga ttcgcagtta atcctggcct gttagaaaca tcagaaggct     960
gtagacaaat actgggacag ctacaaccat cccttcagac aggatcagaa gaacttagat    1020
cattatataa tacagtagca accctctatt gtgtgcatca aaggatagag ataaaagaca    1080
ccaaggaagc tttagacaag atagaggaag agcaaaacaa agtaagacc accgcacagc    1140 aagcggccgc ccgctgatct tcagacctgg aggaggagat atgagggaca attggagaag    1200
tgaattatat aaatataaag tagtaaaaat tgaaccatta ggagtagcac ccaccaaggc    1260
```

-continued

```
aaagagaaga gtggtgcaga gagaaaaaag agcagtggga ataggagctt tgttccttgg    1320
gttcttggga gcagcaggaa gcactatggg cgcagcgtca atgacgctga cggtacaggc    1380
cagacaatta ttgtctggta tagtgcagca gcagaacaat ttgctgaggg ctattgaggc    1440
gcaacagcat ctgttgcaac tcacagtctg gggcatcaag cagctccagg caagaatcct    1500
ggctgtggaa agatacctaa aggatcaaca gctcctgggg atttggggtt gctctggaaa    1560
actcatttgc accactgctg tgccttggaa tgctagttgg agtaataaat ctctggaaca    1620
gatttggaat cacacgacct ggatggagtg ggacagagaa attaacaatt acacaagctt    1680
aatacactcc ttaattgaag aatcgcaaaa ccagcaagaa aagaatgaac aagaattatt    1740
ggaattagat aaatgggcaa gtttgtggaa ttggtttaac ataacaaatt ggctgtggta    1800
tataaaatta ttcataatga tagtaggagg cttggtaggt ttaagaatag ttttttgctgt    1860 actttctata gtgaatagag ttaggcaggg atattcacca ttatcgtttc agacccacct    1920
cccaaccccg aggggacccg acaggcccga aggaataaga agaaggtg gagagagaga     1980 cagagacaga tccattcgat tagtgaacgg atctcgacgg tatcgccttt aaaagaaaag    2040
gggggattgg ggggtacagt gcaggggaaa gaatagtaga cataatagca acagacatac    2100
aaactaaaga attacaaaaa caaattacaa aaattcaaaa ttttcgggtt tattacaggg    2160
acagcagaga tccagtttat cgatgagtaa ttcatacaaa aggactcgcc cctgccttgg    2220
ggaatcccag ggaccgtcgt taaactccca ctaacgtaga acccagagat cgctgcgttc    2280 ccgcccctc acccgcccgc tctcgtcatc actgaggtgg agaagagcaa gcgtgaggct    2340
ccggtgcccg tcagtgggca gagcgcacat cgcccacagt ccccgagaag ttggggggag    2400
gggtcggcaa ttgatccgga gcctagaaa ggtggcgcgg ggtaaactgg gaaagtgatg     2460
tcgtgtactg gctccgcctt tttcccgagg gtgggggaga accgtatata agtgcagtag    2520
tcgccgtgaa cgttcttttt cgcaacgggt ttgccgccag aacacaggta agtgccgtgt    2580
gtggttcccg cgggcctggc ctctttacgg gttatggccc ttgcgtgcct tgaattactt    2640
ccacgcccct ggctgcagta cgtgattctt gatcccgagc ttcgggttgg aagtgggtgg    2700
gagagttcga ggccttgcgc ttaaggagcc ccttcgcctc gtgcttgagt tgaggcctgg    2760
cttgggcgct ggggccgccg cgtgcgaatc tggtggcacc ttcgcgcctg tctcgctgct    2820
ttcgataagt ctccagccat ttaaaatttt tgatgacctg ctgcgacgct tttttctgg    2880 caagatagtc ttgtaaatgc gggccaagat ctgcacactg gtatttcggt ttttggggcc    2940
gcgggcggcg acggggcccg tgcgtcccag cgcacatgtt cggcgaggcg gggcctgcga    3000
gcgcggccac cgagaatcgg acggggtag tctcaagctg gccggcctgc tctggtgcct     3060
ggcctcgcgc cgccgtgtat cgccccgccc tgggcggcaa ggctggcccg gtcggcacca    3120
gttgcgtgag cggaaagatg gccgcttccc ggccctgctg cagggagctc aaaatggagg    3180
acgcggcgct cggagagcg ggcgggtgag tcacccacac aaaggaaaag gcctttccg      3240 tcctcagccg tcgcttcatg tgactccacg gagtaccggg cgccgtccag gcacctcgat    3300
tagttctcga gcttttggag tacgtcgtct ttaggttggg gggaggggtt ttatgcgatg    3360
gagtttcccc acactgagtg ggtggagact gaagttaggc cagcttggca cttgatgtaa    3420
ttctccttgg aatttgccct ttttgagttt ggatcttggt tcattctcaa gcctcagaca    3480
gtggttcaaa gttttttttct tccatttcag gtgtcgtgag gatctatttc cggtgaattc    3540
ctcgagacta gttctagagc ggccgcggat cccgcccctc tccctccccc cccctaacg    3600
```

```
ttactggccg aagccgcttg aataaggcc ggtgtgcgtt tgtctatatg ttattttcca    3660
ccatattgcc gtcttttggc aatgtgaggg cccggaaacc tggccctgtc ttcttgacga    3720
gcattcctag gggtctttcc cctctcgcca aaggaatgca aggtctgttg aatgtcgtga    3780
aggaagcagt tcctctggaa gcttcttgaa gacaaacaac gtctgtagcg accctttgca    3840
ggcagcggaa ccccccacct ggcgacaggt gcctctgcgg ccaaaagcca cgtgtataag    3900
atacacctgc aaaggcggca aaccccagt gccacgttgt gagttggata gttgtggaaa     3960
gagtcaaatg gctcacctca agcgtattca acaaggggct gaaggatgcc cagaaggtac    4020
cccattgtat gggatctgat ctggggcctc ggtgcacatg ctttacatgt gtttagtcga    4080
ggttaaaaaa cgtctaggcc ccccgaacca cggggacgtg gttttccttt gaaaaacacg    4140
atgataatat ggtgagcaag ggcgaggagg ataacatggc catcatcaag gagttcatgc    4200
gcttcaaggt gcacatggag ggctccgtga acggccacga gttcgagatc gagggcgagg    4260
gcgagggccg cccctacgag ggcacccaga ccgccaagct gaaggtgacc aagggtggcc    4320
ccctgccctt cgcctgggac atcctgtccc ctcagttcat gtacggctcc aaggcctacg    4380
tgaagcaccc cgccgacatc cccgactact gaagctgtc cttccccgag ggcttcaagt     4440
gggagcgcgt gatgaacttc gaggacggcg gcgtggtgac cgtgacccag gactcctccc    4500
tgcaggacgg cgagttcatc tacaaggtga agctgcgcgg caccaacttc ccctccgacg    4560
gccccgtaat gcagaagaag accatgggct gggaggcctc ctccgagcgg atgtaccccg    4620
aggacggcgc cctgaagggc gagatcaagc agaggctgaa gctgaaggac ggcggccact    4680
acgacgctga ggtcaagacc acctacaagg ccaagaagcc cgtgcagctg cccggcgcct    4740
acaacgtcaa catcaagttg gacatcacct cccacaacga ggactacacc atcgtggaac    4800
agtacgaacg cgccgagggc cgccactcca ccggcggcat ggacgagctg tacaagtgaa    4860
cccgtctgga acaatcaacc tctggattac aaaatttgtg aaagattgac tggtattctt    4920
aactatgttg ctccttttac gctatgtgga tacgctgctt taatgccttt gtatcatgct    4980
attgcttccc gtatggcttt cattttctcc tccttgtata atcctggtt gctgtctctt     5040
tatgaggagt tgtggcccgt tgtcaggcaa cgtggcgtgg tgtgcactgt gtttgctgac    5100
gcaaccccca ctggttgggg cattgccacc acctgtcagc tcctttccgg gactttcgct    5160
ttccccctcc ctattgccac ggcggaactc atcgccgcct gccttgcccg ctgctggaca    5220
ggggctcggc tgttgggcac tgacaattcc gtggtgttgt cggggaagct gacgtccttt    5280
ccatggctgc tcgcctgtgt tgccacctgg attctgcgcg gacgtccctt ctgctacgtc    5340
ccttcggccc tcaatccagc ggaccttcct tcccgcggcc tgctgccggc tctgcggcct    5400
cttccgcgtc ttcgccttcg ccctcagacg agtcggatct ccctttgggc cgcctccccg    5460
cctggaatta attctgcagt cgagacctag aaaaacatgg agcaatcaca gtagcaata     5520
cagcagctac caatgctgat tgtgcctggc tagaagcaca agaggaggag gaggtgggtt    5580
ttccagtcac acctcaggta cctttaagac caatgactta caaggcagct gtagatctta    5640
gccactttt aaaagaaaag aggggactgg aagggctaat tcactcccaa cgaagacaag     5700
atatccttga tctgtggatc taccacacac aaggctactt ccctgattag cagaactaca    5760
caccagggcc aggggtcaga tatccactga cctttggatg gtgctacaag ctagtaccag    5820
ttgagccaga taaggtagaa gaggccaata aggagagaa caccagcttg ttacaccctg     5880
tgagcctgca tgggatggat gacccggaga gagaagtgtt agagtggagg tttgacagcc    5940
gcctagcatt tcatcacgtg gcccgagagc tgcatccgga gtacttcaag aactgctgat    6000
```

```
atcgagcttg ctacaaggga ctttccgctg gggactttcc agggaggcgt ggcctgggcg    6060
ggactgggga gtggcgagcc ctcagatcct gcatataagc agctgctttt tgcctgtact    6120
gggtctctct ggttagacca gatctgagcc tgggagctct ctggctaact agggaaccca    6180
ctgcttaagc ctcaataaag cttgccttga gtgcttcaag tagtgtgtgc ccgtctgttg    6240
tgtgactctg gtaactagag atccctcaga ccctttagt cagtgtggaa aatctctagc     6300
agtagtagtt catgtcatct tattattcag tatttataac ttgcaaagaa atgaatatca    6360
gagagtgaga ggccttgaca ttgcttgcgt ttaccgtcga cctctagcta gagcttggcg    6420
taatcatggt catagctgtt tcctgtgtga aattgttatc cgctcacaat tccacacaac    6480
atacgagccg aagcataaa gtgtaaagcc tggggtgcct aatgagtgag ctaactcaca     6540
ttaattgcgt tgcgctcact gcccgctttc cagtcgggaa acctgtcgtg ccagctgcat    6600
taatgaatcg gccaacgcgc ggggagaggc ggtttgcgta ttgggcgctc ttccgcttcc    6660
tcgctcactg actcgctgcg ctcggtcgtt cggctgcggc gagcggtatc agctcactca    6720
aaggcggtaa tacggttatc cacagaatca ggggataacg caggaaagaa catgtgagca    6780
aaaggccagc aaaaggccag gaaccgtaaa aaggccgcgt tgctggcgtt tttccatagg    6840
ctccgccccc ctgacgagca tcacaaaaat cgacgctcaa gtcagaggtg gcgaaacccg    6900
acaggactat aaagatacca ggcgtttccc cctggaagct ccctcgtgcg ctctcctgtt    6960
ccgaccctgc cgcttaccgg atacctgtcc gcctttctcc cttcgggaag cgtggcgctt    7020
tctcatagct cacgctgtag gtatctcagt tcggtgtagg tcgttcgctc caagctgggc    7080
tgtgtgcacg aaccccccgt tcagcccgac cgctgcgcct tatccggtaa ctatcgtctt    7140
gagtccaacc cggtaagaca cgacttatcg ccactggcag cagccactgg taacaggatt    7200
agcagagcga ggtatgtagg cggtgctaca gagttcttga agtggtggcc taactacggc    7260
tacactagaa gaacagtatt tggtatctgc gctctgctga agccagttac cttcggaaaa    7320
agagttggta gctcttgatc cggcaaacaa accaccgctg gtagcggtgg tttttttgtt    7380
tgcaagcagc agattacgcg cagaaaaaaa ggatctcaag aagatccttt gatcttttct    7440
acggggtctg acgctcagtg gaacgaaaac tcacgttaag ggattttggt catgagatta    7500
tcaaaaagga tcttcaccta gatccttta aattaaaaat gaagttttaa atcaatctaa    7560
agtatatatg agtaaacttg gtctgacagt taccaatgct taatcagtga ggcacctatc    7620
tcagcgatct gtctatttcg ttcatccata gttgcctgac tccccgtcgt gtagataact    7680
acgatacggg agggcttacc atctggcccc agtgctgcaa tgataccgcg agacccacgc    7740
tcaccggctc cagatttatc agcaataaac cagccagccg aagggccga gcgcagaagt     7800 ggtcctgcaa ctttatccgc ctccatccag tctattaatt gttgccggga agctagagta    7860
agtagttcgc cagttaatag tttgcgcaac gttgttgcca ttgctacagg catcgtggtg    7920
tcacgctcgt cgtttggtat ggcttcattc agctccggtt cccaacgatc aaggcgagtt    7980
acatgatccc ccatgttgtg caaaaaagcg gttagctcct tcggtcctcc gatcgttgtc    8040
agaagtaagt tggccgcagt gttatcactc atggttatgg cagcactgca taattctctt    8100
actgtcatgc catccgtaag atgcttttct gtgactggtg agtactcaac caagtcattc    8160
tgagaatagt gtatgcggcg accgagttgc tcttgcccgg cgtcaatacg ggataatacc    8220
gcgccacata gcagaacttt aaaagtgctc atcattggaa aacgttcttc ggggcgaaaa    8280
ctctcaagga tcttaccgct gttgagatcc agttcgatgt aacccactcg tgcacccaac    8340
```

| | |
|---|---|
| tgatcttcag catcttttac tttcaccagc gtttctgggt gagcaaaaac aggaaggcaa | 8400 |
| aatgccgcaa aaaagggaat aagggcgaca cggaaatgtt gaatactcat actcttcctt | 8460 |
| tttcaatatt attgaagcat ttatcagggt tattgtctca tgagcggata catatttgaa | 8520 |
| tgtatttaga aaaataaaca aatagggggtt ccgcgcacat ttccccgaaa agtgccacct | 8580 |
| gacgtcgacg gatcgggaga tcaacttgtt tattgcagct tataatggtt acaaataaag | 8640 |
| caatagcatc acaaatttca caaataaagc atttttttca ctgcattcta gttgtggttt | 8700 |
| gtccaaactc atcaatgtat cttatcatgt ctggatcaac tggataactc aagctaacca | 8760 |
| aaatcatccc aaacttccca ccccataccc tattaccact gccaattacc tgtggtttca | 8820 |
| tttactctaa acctgtgatt cctctgaatt attttcattt taaagaaatt gtatttgtta | 8880 |
| aatatgtact acaaacttag tagt | 8904 |

<210> SEQ ID NO 21
<211> LENGTH: 12037
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 21

| | |
|---|---|
| tggaagggct aattcactcc caaagaagac aagatatcct tgatctgtgg atctaccaca | 60 |
| cacaaggcta cttccctgat tagcagaact acacaccagg gccagggggtc agatatccac | 120 |
| tgacctttgg atggtgctac aagctagtac cagttgagcc agataaggta gaagaggcca | 180 |
| ataaaggaga gaacaccagc ttgttacacc ctgtgagcct gcatgggatg gatgacccgg | 240 |
| agagagaagt gttagagtgg aggtttgaca gccgcctagc atttcatcac gtggcccgag | 300 |
| agctgcatcc ggagtacttc aagaactgct gatatcgagc ttgctacaag ggactttccg | 360 |
| ctggggactt tccagggagg cgtggcctgg gcgggactgg ggagtggcga gccctcagat | 420 |
| cctgcatata agcagctgct ttttgcctgt actgggtctc tctggttaga ccagatctga | 480 |
| gcctgggagc tctctggcta actagggaac ccactgctta agcctcaata aagcttgcct | 540 |
| tgagtgcttc aagtagtgtg tgcccgtctg ttgtgtgact ctggtaacta gagatccctc | 600 |
| agacccttttt agtcagtgtg gaaaatctct agcagtggcg cccgaacagg gacttgaaag | 660 |
| cgaaagggaa accagaggag ctctctcgac gcaggactcg gcttgctgaa gcgcgcacgg | 720 |
| caagaggcga ggggcggcga ctggtgagta cgccaaaaat tttgactagc ggaggctaga | 780 |
| aggagagaga tgggtgcgag agcgtcagta ttaagcgggg gagaattaga tcgcgatggg | 840 |
| aaaaaattcg gttaaggcca ggggggaaaga aaaatataa attaaaacat atagtatggg | 900 |
| caagcaggga gctagaacga ttcgcagtta atcctggcct gttagaaaca tcagaaggct | 960 |
| gtagacaaat actgggacag ctacaaccat cccttcagac aggatcagaa gaacttagat | 1020 |
| cattatataa tacagtagca accctctatt gtgtgcatca aaggatagag ataaaagaca | 1080 |
| ccaaggaagc tttagacaag atagaggaag agcaaaacaa aagtaagacc accgcacagc | 1140 |
| aagcggccgg ccgctgatct tcagacctgg aggaggagat atgagggaca attggagaag | 1200 |
| tgaattatat aaatataaag tagtaaaaat tgaaccatta ggagtagcac ccaccaaggc | 1260 |
| aaagagaaga gtggtgcaga gagaaaaaag agcagtggga ataggagctt tgttccttgg | 1320 |
| gttcttggga gcagcaggaa gcactatggg cgcagcgtca atgacgctga cggtacaggc | 1380 |
| cagacaatta ttgtctggta tagtgcagca gcagaacaat ttgctgaggg ctattgaggc | 1440 |

```
gcaacagcat ctgttgcaac tcacagtctg gggcatcaag cagctccagg caagaatcct    1500
ggctgtggaa agatacctaa aggatcaaca gctcctgggg atttggggtt gctctggaaa    1560
actcatttgc accactgctg tgccttggaa tgctagttgg agtaataaat ctctggaaca    1620
gatttggaat cacacgacct ggatggagtg ggacagagaa attaacaatt acacaagctt    1680
aatacactcc ttaattgaag aatcgcaaaa ccagcaagaa aagaatgaac aagaattatt    1740
ggaattagat aaatgggcaa gtttgtggaa ttggtttaac ataacaaatt ggctgtggta    1800
tataaaatta ttcataatga tagtaggagg cttggtaggt ttaagaatag tttttgctgt    1860
actttctata gtaatagag ttaggcaggg atattcacca ttatcgtttc agacccacct    1920
cccaaccccg aggggacccg acaggcccga aggaatagaa gaagaaggtg agagagaga    1980 cagagacaga tccattcgat tagtgaacgg atctcgacgg tatcgccttt aaaagaaaag    2040
gggggattgg ggggtacagt gcaggggaaa gaatagtaga cataatagca acagacatac    2100
aaactaaaga attacaaaaa caaattacaa aaattcaaaa ttttcgggtt tattacaggg    2160
acagcagaga tccagtttat cgataagctt gggagttccg cgttacataa cttacggtaa    2220
atggcccgcc tggctgaccg cccaacgacc cccgcccatt gacgtcaata atgacgtatg    2280
ttcccatagt aacgccaata gggactttcc attgacgtca atgggtggag tatttacggt    2340
aaactgccca cttggcagta catcaagtgt atcatatgcc aagtacgccc cctattgacg    2400
tcaatgacgg taaatggccc gcctggcatt atgcccagta catgacctta tgggactttc    2460
ctacttggca gtacatctac gtattagtca tcgctattac catggtgatg cggttttggc    2520
agtacatcaa tgggcgtgga tagcggtttg actcacgggg atttccaagt ctccacccca    2580
ttgacgtcaa tgggagtttg ttttggcacc aaaatcaacg ggactttcca aaatgtcgta    2640
acaactccgc cccattgacg caaatgggcg gtaggcgtgt acggtgggag gtctatataa    2700
gcagagctcg tttagtgaac cgtcagatcg cctggagacg ccatccacgc tgttttgacc    2760
tccatagaag acaccgactc tactagagga tctatttccg gtgaattcgc caccatgagc    2820
ctcgggctcc tgtgctgtgg ggccttttct ctcctgtggg caggaccggt ggaagctgac    2880
atctaccaga ccccaagata ccttgttata gggacaggaa agaagatcac tctggaatgt    2940
tctcaaacca tgggccatga caaaatgtac tggtatcaac aagatccagg aatggaacta    3000
cacctcatcc actattccta tggagttaat tccacagaga agggagatct ttcctctgag    3060
tcaacagtct ccagaataag gacggagcat tttcccctga ccctggagtc tgccaggccc    3120
tcacatacct ctcagtacct ctgtgccagc agtcggacgc ccaacattca gtacttcggc    3180
gccgggaccc ggctctcagt gctggaggac ctgaaaaacg tgttcccacc cgaactagtc    3240
gtgtttgagc atcagaagc agagatctcc cacacccaaa aggccacact ggtgtgcctg    3300
gccacaggct tctaccccga ccacgtggag ctgagctggt gggtgaatgg gaaggaggtg    3360
cacagtgggg tcagcacaga cccgcagccc ctcaaggagc agcccgccct caatgactcc    3420
agatactgcc tgagcagccg cctgagggtc tcggccacct tctggcagaa ccccgcaac    3480 cacttccgct gtcaagtcca gttctacggg ctctcggaga atgacgagtg gacccaggat    3540
agggccaaac ctgtcaccca gatcgtcagc gccgaggcct ggggtagagc agactgtggc    3600
ttcacctccg agtcttacca gcaaggggtc ctgtctgcca ccatcctcta tgagatcttg    3660
ctagggaagg ccaccttgta tgccgtgctg gtcagtgccc tcgtgctgat ggccatggtc    3720
aagagaaagg attccagagg cgggagcgga gccacgaact tctctctgtt aaagcaagca    3780
ggagacgtgg aagaaaaccc cggtcctatg acacgagtta gcttgctgtg ggcagtcgtg    3840
```

```
gtctccacct gtctcgagtc cggcatgggt caacagctga atcagagtcc tcaatctatg   3900
tttatccagg aaggagaaga tgtctccatg aactgcactt cttcaagcat atttaacacc   3960
tggctatggt acaagcagga acctggggaa ggtcctgtcc tcttgatagc cttatataag   4020
gctggtgaat tgacctcaaa tggaagactg actgctcagt ttggtataac cagaaaggac   4080
agcttcctga atatctcagc atccatacct agtgatgtag gcatctactt ctgtgctggc   4140
acataccaga aagttacctt tggaactgga acaaagctcc aagtcatccc aaatatccag   4200
aaccctgacc ctgccgtgta ccagctgaga gactctaaat ccagtgacaa gtctgtctgc   4260
ctattcaccg attttgattc tcaaacaaat gtgtcacaaa gtaaggattc tgatgtgtat   4320
atcacagaca aaactgtgct agacatgagg tctatggact tcaagagcaa cagtgctgtg   4380
gcctggagca caaatctga ctttgcatgc gcaaacgcct tcaacaacag cattattcca   4440
gaagacacct tcttccccag cccagaaagt tcctgtgatg tcaagctggt cgagaaaagc   4500
tttgaaacag atacgaacct aaactttcaa aacctgtcag tgattgggtt ccgaatcctc   4560
ctcctgaaag tggccgggtt taatctgctc atgacgctgc ggctgtggtc cagctgactc   4620
gagggatccc gcccctctcc ctccccccccc cctaacgtta ctggccgaag ccgcttggaa   4680
taaggccggt gtgcgtttgt ctatatgtta ttttccacca tattgccgtc ttttggcaat   4740
gtgagggccc ggaaacctgg ccctgtcttc ttgacgagca ttcctagggg tctttcccct   4800
ctcgccaaag gaatgcaagg tctgttgaat gtcgtgaagg aagcagttcc tctggaagct   4860
tcttgaagac aaaacaacgtc tgtagcgacc ctttgcaggc agcggaaccc cccacctggc   4920
gacaggtgcc tctgcggcca aaagccacgt gtataagata cacctgcaaa ggcggcacaa   4980
ccccagtgcc acgttgtgag ttggatagtt gtggaaagag tcaaatggct cacctcaagc   5040
gtattcaaca aggggctgaa ggatgcccag aaggtacccc attgtatggg atctgatctg   5100 gggcctcgt gcacatgctt tacatgtgtt tagtcgaggt taaaaaacgt ctaggccccc   5160
cgaaccacgg ggacgtggtt ttcctttgaa aaacacgatg ataatatggt gagcaagggc   5220
gaggaggata acatggccat catcaaggag ttcatgcgct tcaaggtgca catggagggc   5280
tccgtgaacg gccacgagtt cgagatcgag ggcgagggcg agggccgccc ctacgagggc   5340
acccagaccg ccaagctgaa ggtgaccaag ggtggccccc tgcccttcgc ctgggacatc   5400
ctgtcccctc agttcatgta cggctccaag gcctacgtga agcaccccgc cgacatcccc   5460
gactacttga agctgtcctt ccccgagggc ttcaagtggg agcgcgtgat gaacttcgag   5520
gacggcggcg tggtgaccgt gacccaggac tcctccctgc aggacggcga gttcatctac   5580
aaggtgaagc tgcgcggcac caacttcccc tccgacggcc ccgtaatgca gaagaagacc   5640
atgggctggg aggcctcctc cgagcggatg taccccgagg acggcgccct gaagggcgag   5700
atcaagcaga ggctgaagct gaaggacggc ggccactacg acgctgaggt caagaccacc   5760
tacaaggcca agaagcccgt gcagctgccc ggcgcctaca acgtcaacat caagttggac   5820
atcacctccc acaacgagga ctacaccatc gtggaacagt acgaacgcgc cgagggccgc   5880
cactccaccg gcggcatgga cgagctgtac aagtgaacgc gtctggaaca agctttttcc   5940
ccgtatcccc ccaggtgtct gcaggctcaa agagcagcga gaagcgttca gaggaaagcg   6000
atcccgtgcc accttccccg tgcccgggct gtcccgcac gctgccggct cggggatgcg   6060
gggggagcgc cggaccggag cggagcccg gcggctcgc tgctgccccc tagcggggga   6120
gggacgtaat tacatccctg ggggctttgg ggggggggctg tccccgtgag ctcttactcc   6180
```

```
ctatcagtga tagagaacgt atgaagagtt tactccctat cagtgataga gaacgtatgc    6240
agactttact ccctatcagt gatagagaac gtataaggag tttactccct atcagtgata    6300
gagaacgtat gaccagttta ctccctatca gtgatagaga acgtatctac agtttactcc    6360
ctatcagtga tagagaacgt atatccagtt tactccctat cagtgataga gaacgtatgt    6420
cgaggtaggc gtgtacggtg ggcgcctata aaagcagagc tcgtttagtg aaccgtcaga    6480
tcgcctggag caattccaca acacttttgt cttatactta tgctcgaggg agtgcaggtg    6540
gagactatct ccccaggaga cgggcgcacc ttccccaagc gcggcagac ctgcgtggtg     6600 cactacaccg ggatgcttga agatggaaag aaagttgatt cctcccggga cagaaacaag    6660 cccctttaagt ttatgctagg caagcaggag gtgatccgag gctgggaaga aggggttgcc    6720
cagatgagtg tgggtcagag agccaaactg actatatctc cagattatgc ctatggtgcc    6780
actgggcacc caggcatcat cccaccacat gccactctcg tcttcgatgt ggagcttcta    6840
aaactggaat ctggcggtgg atccggagtc gacggatttg gtgatgtcgg tgctcttgag    6900
agtttgaggg gaaatgcaga tttggcttac atcctgagca tggagccctg tggccactgc    6960
ctcattatca acaatgtgaa cttctgccgt gagtccgggc tccgcacccg cactggctcc    7020
aacatcgact gtgagaagtt gcggcgtcgc ttctcctcgc tgcatttcat ggtggaggtg    7080
aagggcgacc tgactgccaa gaaaatggtg ctggctttgc tggagctggc gcggcaggac    7140
cacggtgctc tggactgctg cgtggtggtc attctctctc acggctgtca ggccagccac    7200
ctgcagttcc caggggctgt ctacggcaca gatggatgcc ctgtgtcggt cgagaagatt    7260
gtgaacatct tcaatgggac cagctgcccc agcctgggag ggaagcccaa gctcttttc    7320 atccaggcct gtggtgggga gcagaaagac catgggtttg aggtggcctc cacttcccct    7380
gaagacgagt cccctggcag taaccccgag ccagatgcca cccgttcca ggaaggtttg     7440 aggaccttcg accagctgga cgccatatct agtttgccca cccagtga catctttgtg      7500 tcctactcta ctttcccagg ttttgttccc tggagggacc ccaagagtgg ctcctggtac    7560
gttgagaccc tggacgacat cttttgagcag tgggctcact ctgaagacct gcagtccctc   7620
ctgcttaggg tcgctaatgc tgtttcggtg aaagggattt ataaacagat gcctggttgc    7680
tttaatttcc tccggaaaaa acttttcttt aaaacatcag tcgactatcc gtacgacgta    7740
ccagactacg cactcgacta aaagcttttt cccgtatcc ccccaggtgt ctgcaggctc     7800
aaagagcagc gagaagcgtt cagaggaaag cgatcccgtg ccaccttccc cgtgcccggg    7860
ctgtccccgc acgctgccgg ctcggggatg cgggggagc gccggaccgg agcggagccc     7920
cgggcggctc gctgctgccc cctagcgggg gagggacgta attacatccc tggggggcttt   7980 gggagggggc tgtccccgtg agctcaatca acctctggat tacaaaattt gtgaaagatt    8040
gactggtatt cttaactatg ttgctccttt tacgctatgt ggatacgctg ctttaatgcc    8100
tttgtatcat gctattgctt cccgtatggc tttcattttc tcctccttgt ataaatcctg    8160
gttgctgtct ctttatgagg agttgtggcc cgttgtcagg caacgtggcg tggtgtgcac    8220
tgtgtttgct gacgcaaccc ccactggttg gggcattgcc accacctgtc agctccttc     8280 cgggactttc gctttccccc tccctattgc cacggcggaa ctcatcgccg cctgccttgc    8340
ccgctgctgg acagggctc ggctgttggg cactgacaat tccgtggtgt tgtcggggaa     8400
gctgacgtcc tttccatggc tgctcgcctg tgttgccacc tggattctgc gcgggacgtc    8460
cttctgctac gtcccttcgg ccctcaatcc agcggacctt ccttcccgcg gcctgctgcc    8520
ggctctgcgg cctcttccgc gtcttcgcct tcgccctcag acgagtcgga tctccctttg    8580
```

```
ggccgcctcc  ccgcctggaa  ttaattctgc  agtcgagacc  tagaaaaaca  tggagcaatc   8640
acaagtagca  atacagcagc  taccaatgct  gattgtgcct  ggctagaagc  acaagaggag   8700
gaggaggtgg  gttttccagt  cacacctcag  gtacctttaa  gaccaatgac  ttacaaggca   8760
gctgtagatc  ttagccactt  tttaaaagaa  aagaggggac  tggaagggct  aattcactcc   8820
caacgaagac  aagatatcct  tgatctgtgg  atctaccaca  cacaaggcta  cttccctgat   8880
tagcagaact  acacaccagg  gccagggggtc  agatatccac  tgacctttgg  atggtgctac   8940
aagctagtac  cagttgagcc  agataaggta  gaagaggcca  ataaaggaga  gaacaccagc   9000
ttgttacacc  ctgtgagcct  gcatgggatg  gatgacccgg  agagaagt    gttagagtgg   9060 aggtttgaca  gccgcctagc  atttcatcac  gtggcccgag  agctgcatcc  ggagtacttc   9120
aagaactgct  gatatcgagc  ttgctacaag  ggactttccg  ctggggactt  tccaggggagg   9180 cgtggcctgg  gcgggactgg  ggagtggcga  gccctcagat  cctgcatata  agcagctgct   9240
ttttgcctgt  actgggtctc  tctggttaga  ccagatctga  gcctgggagc  tctctggcta   9300
actagggaac  ccactgctta  agcctcaata  aagcttgcct  tgagtgcttc  aagtagtgtg   9360
tgcccgtctg  ttgtgtgact  ctggtaacta  gagatccctc  agaccctttt  agtcagtgtg   9420
gaaaatctct  agcagtagta  gttcatgtca  tcttattatt  cagtatttat  aacttgcaaa   9480
gaaatgaata  tcagagagtg  agaggccttg  acattgctag  cgtttaccgt  cgacctctag   9540
ctagagcttg  gcgtaatcat  ggtcatagct  gtttcctgtg  tgaaattgtt  atccgctcac   9600
aattccacac  aacatacgag  ccggaagcat  aaagtgtaaa  gcctggggtg  cctaatgagt   9660
gagctaactc  acattaattg  cgttgcgctc  actgcccgct  ttccagtcgg  gaaacctgtc   9720
gtgccagctg  cattaatgaa  tcggccaacg  cgcggggaga  ggcggtttgc  gtattgggcg   9780
ctcttccgct  tcctcgctca  ctgactcgct  gcgctcggtc  gttcggctgc  ggcgagcggt   9840
atcagctcac  tcaaaggcgg  taatacggtt  atccacagaa  tcaggggata  acgcaggaaa   9900
gaacatgtga  gcaaaaggcc  agcaaaaggc  caggaaccgt  aaaaaggccg  cgttgctggc   9960
gtttttccat  aggctccgcc  ccctgacga  gcatcacaaa  aatcgacgct  caagtcagag   10020
gtggcgaaac  ccgacaggac  tataaagata  ccaggcgttt  ccccctggaa  gctccctcgt   10080
gcgctctcct  gttccgaccc  tgccgcttac  cggatacctg  tccgcctttc  tcccttcggg   10140
aagcgtggcg  ctttctcata  gctcacgctg  taggtatctc  agttcggtgt  aggtcgttcg   10200
ctccaagctg  ggctgtgtgc  acgaacccccc  cgttcagccc  gaccgctgcg  ccttatccgg   10260
taactatcgt  cttgagtcca  acccggtaag  acacgactta  tcgccactgg  cagcagccac   10320
tggtaacagg  attagcagag  cgaggtatgt  aggcggtgct  acagagttct  tgaagtggtg   10380
gcctaactac  ggctacacta  gaagaacagt  atttggtatc  tgcgctctgc  tgaagccagt   10440
taccttcgga  aaaagagttg  gtagctcttg  atccggcaaa  caaaccaccg  ctggtagcgg   10500
tggttttttt  gtttgcaagc  agcagattac  gcgcagaaaa  aaaggatctc  aagaagatcc   10560
tttgatcttt  tctacggggt  ctgacgctca  gtggaacgaa  aactcacgtt  aagggatttt   10620
ggtcatgaga  ttatcaaaaa  ggatcttcac  ctagatcctt  ttaaattaaa  aatgaagttt   10680
taaatcaatc  taaagtatat  atgagtaaac  ttggtctgac  agttaccaat  gcttaatcag   10740
tgaggcacct  atctcagcga  tctgtctatt  tcgttcatcc  atagttgcct  gactccccgt   10800
cgtgtagata  actacgatac  gggagggctt  accatctggc  cccagtgctg  caatgatacc   10860
gcgagaccca  cgctcaccgg  ctccagattt  atcagcaata  aaccagccag  ccggaagggc   10920
```

```
cgagcgcaga agtggtcctg caactttatc cgcctccatc cagtctatta attgttgccg  10980
ggaagctaga gtaagtagtt cgccagttaa tagtttgcgc aacgttgttg ccattgctac  11040
aggcatcgtg gtgtcacgct cgtcgtttgg tatggcttca ttcagctccg gttcccaacg  11100
atcaaggcga gttacatgat cccccatgtt gtgcaaaaaa gcggttagct ccttcggtcc  11160
tccgatcgtt gtcagaagta agttggccgc agtgttatca ctcatggtta tggcagcact  11220
gcataattct cttactgtca tgccatccgt aagatgcttt tctgtgactg gtgagtactc  11280
aaccaagtca ttctgagaat agtgtatgcg gcgaccgagt tgctcttgcc cggcgtcaat  11340
acgggataat accgcgccac atagcagaac tttaaaagtg ctcatcattg gaaaacgttc  11400 ttcgggcga aaactctcaa ggatcttacc gctgttgaga tccagttcga tgtaacccac  11460
tcgtgcaccc aactgatctt cagcatcttt tactttcacc agcgtttctg ggtgagcaaa  11520
aacaggaagg caaaatgccg caaaaaaggg aataagggcg acacggaaat gttgaatact  11580
catactcttc cttttttcaat attattgaag catttatcag ggttattgtc tcatgagcgg  11640
atacatattt gaatgtattt agaaaaataa acaaataggg gttccgcgca catttccccg  11700
aaaagtgcca cctgacgtcg acggatcggg agatcaactt gtttattgca gcttataatg  11760
gttacaaata aagcaatagc atcacaaatt tcacaaataa agcatttttt tcactgcatt  11820
ctagttgtgg tttgtccaaa ctcatcaatg tatcttatca tgtctggatc aactggataa  11880
ctcaagctaa ccaaaatcat cccaaacttc caccccata ccctattacc actgccaatt  11940
acctgtggtt tcatttactc taaacctgtg attcctctga attattttca ttttaaagaa  12000
attgtatttg ttaaatatgt actacaaact tagtagt                           12037
```

<210> SEQ ID NO 22
<211> LENGTH: 12031
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22

```
tggaagggct aattcactcc caaagaagac aagatatcct tgatctgtgg atctaccaca    60
cacaaggcta cttccctgat tagcagaact acacaccagg gccagggggtc agatatccac   120 tgacctttgg atggtgctac aagctagtac cagttgagcc agataaggta gaagaggcca   180
ataaaggaga gaacaccagc ttgttacacc ctgtgagcct gcatgggatg gatgacccgg   240
agagagaagt gttagagtgg aggtttgaca gccgcctagc atttcatcac gtgggccgag   300
agctgcatcc ggagtacttc aagaactgct gatatcgagc ttgctacaag ggactttccg   360
ctggggactt tccagggagg cgtggcctgg gcgggactgg ggagtggcga gccctcagat   420
cctgcatata agcagctgct ttttgcctgt actgggtctc tctggttaga ccagatctga   480
gcctgggagc tctctggcta actagggaac ccactgctta agcctcaata aagcttgcct   540
tgagtgcttc aagtagtgtg tgcccgtctg ttgtgtgact ctggtaacta gagatccctc   600 agacccttt agtcagtgtg gaaaatctct agcagtggcg cccgaacagg gacttgaaag   660 cgaaaggaa accagaggag ctctctcgac gcaggactcg gcttgctgaa gcgcgcacgg   720
caagaggcga ggggcggcga ctggtgagta cgccaaaaat tttgactagc ggaggctaga   780
aggagagaga tgggtgcgag agcgtcagta ttaagcgggg gagaattaga tcgcgatggg   840
aaaaaattcg gttaaggcca gggggaaaga aaaaatataa attaaaacat atagtatggg   900
```

```
caagcaggga gctagaacga ttcgcagtta atcctggcct gttagaaaca tcagaaggct    960
gtagacaaat actgggacag ctacaaccat cccttcagac aggatcagaa gaacttagat   1020
cattatataa tacagtagca accctctatt gtgtgcatca aaggatagag ataaaagaca   1080
ccaaggaagc tttagacaag atagaggaag agcaaaacaa aagtaagacc accgcacagc   1140
aagcggccgg ccgctgatct tcagacctgg aggaggagat atgagggaca attggagaag   1200
tgaattatat aaatataaag tagtaaaaat tgaaccatta ggagtagcac ccaccaaggc   1260
aaagagaaga gtggtgcaga gagaaaaaag agcagtggga ataggagctt tgttccttgg   1320
gttcttggga gcagcaggaa gcactatggg cgcagcgtca atgacgctga cggtacaggc   1380
cagacaatta ttgtctggta tagtgcagca gcagaacaat ttgctgaggg ctattgaggc   1440
gcaacagcat ctgttgcaac tcacagtctg gggcatcaag cagctccagg caagaatcct   1500
ggctgtggaa agatacctaa aggatcaaca gctcctgggg atttggggtt gctctggaaa   1560
actcatttgc accactgctg tgccttggaa tgctagttgg agtaataaat ctctggaaca   1620
gatttggaat cacacgacct ggatggagtg ggacagagaa attaacaatt acacaagctt   1680
aatacactcc ttaattgaag aatcgcaaaa ccagcaagaa aagaatgaac aagaattatt   1740
ggaattagat aaatgggcaa gtttgtggaa ttggtttaac ataacaaatt ggctgtggta   1800
tataaaatta ttcataatga tagtaggagg cttggtaggt ttaagaatag ttttgctgt   1860
actttctata gtgaatagag ttaggcaggg atattcacca ttatcgtttc agacccacct   1920
cccaaccccg aggggacccg acaggcccga aggaatagaa gaagaaggtg gagagagaga   1980
cagagacaga tccattcgat tagtgaacgg atctcgacgg tatcgccttt aaaagaaaag   2040
gggggattgg ggggtacagt gcaggggaaa gaatagtaga cataatagca acagacatac   2100
aaactaaaga attacaaaaa caaattacaa aaattcaaaa ttttcgggtt tattacaggg   2160
acagcagaga tccagtttat cgataagctt gggagttccg cgttacataa cttacggtaa   2220
atggcccgcc tggctgaccg cccaacgacc cccgcccatt gacgtcaata atgacgtatg   2280
ttcccatagt aacgccaata gggactttcc attgacgtca atgggtggag tatttacggt   2340
aaactgccca cttggcagta catcaagtgt atcatatgcc aagtacgccc cctattgacg   2400
tcaatgacgg taaatggccc gcctggcatt atgcccagta catgacctta tgggactttc   2460
ctacttggca gtacatctac gtattagtca tcgctattac catggtgatg cggttttggc   2520
agtacatcaa tgggcgtgga tagcggtttg actcacgggg atttccaagt ctccacccca   2580
ttgacgtcaa tgggagtttg ttttggcacc aaaatcaacg ggactttcca aaatgtcgta   2640
acaactccgc cccattgacg caaatgggcg gtaggcgtgt acggtgggag gtctatataa   2700
gcagagctcg tttagtgaac cgtcagatcg cctggagacg ccatccacgc tgttttgacc   2760
tccatagaag acaccgactc tactagagga tctatttccg gtgaattcgc caccatggga   2820
cccaggctcc tcttctgggc actgctttgt ctcctcggaa ccgtccggt tgaagctgac   2880
atctaccaga ccccaagata ccttgttata gggacaggaa agaagatcac tctggaatgt   2940
tctcaaacca tgggccatga caaaatgtac tggtatcaac aagatccagg aatggaacta   3000
cacctcatcc actattccta tggagttaat tccacagaga agggagatct ttcctctgag   3060
tcaacagtct ccagaataag gacggagcat tttcccctga ccctggagtc tgccaggccc   3120
tcacatacct ctcagtacct ctgtgccagc agtcggacgc ccaacattca gtacttcggc   3180
gccgggaccc ggctctcagt gctggaggac ctgaaaaacg tgttcccacc cgaggcggcc   3240
gcgtttgagc catcagaagc agagatctcc cacacccaaa aggccacact ggtgtgcctg   3300
```

-continued

```
gccacaggct tctaccccga ccacgtggag ctgagctggt gggtgaatgg aaggaggtg    3360 cacagtgggg tcagcacaga cccgcagccc ctcaaggagc agcccgccct caatgactcc    3420
agatactgcc tgagcagccg cctgagggtc tcggccacct tctggcagaa ccccgcaac    3480 cacttccgct gtcaagtcca gttctacggg ctctcggaga atgacgagtg gacccaggat    3540
agggccaaac ctgtcaccca gatcgtcagc gccgaggcct ggggtagagc agactgtggc    3600
ttcacctccg agtcttacca gcaaggggtc ctgtctgcca ccatcctcta tgagatcttg    3660
ctagggaagg ccaccttgta tgccgtgctg gtcagtgccc tcgtgctgat ggccatggtc    3720
aagagaaagg attccagagg cgggagcgga gccacgaact tctctctgtt aaagcaagca    3780
ggagacgtgg aagaaaaccc cggtcctatg aactcctctc tggactttct aattctgatc    3840
ttaatgtttg gaggaactag tggtcaacag ctgaatcaga gtcctcaatc tatgtttatc    3900
caggaaggag aagatgtctc catgaactgc acttcttcaa gcatatttaa cacctggcta    3960
tggtacaagc aggaacctgg ggaaggtcct gtcctcttga tagccttata taaggctggt    4020
gaattgacct caaatggaag actgactgct cagtttggta taaccagaaa ggacagcttc    4080
ctgaatatct cagcatccat acctagtgat gtaggcatct acttctgtgc tggcacatac    4140
cagaaagtta cctttggaac tggaacaaag ctccaagtca tcccaaatat ccagaaccct    4200
gaccctgccg tgtaccagct gagagactct aaatccagtg acaagtctgc atgcctattc    4260
accgattttg attctcaaac aaatgtgtca caaagtaagg attctgatgt gtatatcaca    4320
gacaaaactg tgctagacat gaggtctatg gacttcaaga gcaacagtgc tgtggcctgg    4380
agcaacaaat ctgactttgc atgtgcaaac gccttcaaca acagcattat tccagaagac    4440
accttcttcc ccagcccaga aagttcctgt gatgtcaagc tggtcgagaa aagctttgaa    4500
acagatacga acctaaactt tcaaaacctg tcagtgattg ggttccgaat cctcctcctg    4560
aaagtggccg ggtttaatct gctcatgacg ctgcggctgt ggtccagctg actgagggaa    4620 tccccgcccct ctccctcccc ccccctaac gttactggcc gaagccgctt ggaataaggc    4680
cggtgtgcgt ttgtctatat gttatttttcc accatattgc cgtctttttgg caatgtgagg    4740 gcccggaaac ctggccctgt cttcttgacg agcattccta ggggtctttc ccctctcgcc    4800
aaaggaatgc aaggtctgtt gaatgtcgtg aaggaagcag ttcctctgga agcttcttga    4860
agacaaacaa cgtctgtagc gacccttttgc aggcagcgga accccccacc tggcgacagg    4920
tgcctctgcg gccaaaagcc acgtgtataa gatacacctg caaaggcggc acaaccccag    4980
tgccacgttg tgagttggat agttgtggaa agagtcaaat ggctcacctc aagcgtattc    5040 aacaagggc tgaaggatgc ccagaaggta ccccattgta tgggatctga tctgggggcct    5100 cggtgcacat gctttacatg tgtttagtcg aggttaaaaa acgtctaggc cccccgaacc    5160
acggggacgt ggttttcctt tgaaaaacac gatgataata tggtgagcaa gggcgaggag    5220
gataacatgg ccatcatcaa ggagttcatg cgcttcaagg tgcacatgga gggctccgtg    5280
aacggccacg agttcgagat cgagggcgag ggcgagggcc gcccctacga gggcacccag    5340
accgccaagc tgaaggtgac caagggtggc cccctgccct tcgcctggga catcctgtcc    5400
cctcagttca tgtacggctc caaggcctac gtgaagcacc ccgccgacat ccccgactac    5460
ttgaagctgt ccttccccga gggcttcaag tgggagcgcg tgatgaactt cgaggacggc    5520
ggcgtggtga ccgtgaccca ggactcctcc ctgcaggacg gcgagttcat ctacaaggtg    5580
aagctgcgcg gcaccaactt cccctccgac ggccccgtaa tgcagaagaa gaccatgggc    5640
```

```
tgggaggcct cctccgagcg gatgtacccc gaggacggcg ccctgaaggg cgagatcaag    5700
cagaggctga agctgaagga cggcggccac tacgacgctg aggtcaagac cacctacaag    5760
gccaagaagc ccgtgcagct gcccggcgcc tacaacgtca acatcaagtt ggacatcacc    5820
tcccacaacg aggactacac catcgtggaa cagtacgaac gcgccgaggg ccgccactcc    5880
accggcggca tggacgagct gtacaagtga acgcgtctgg aacaagcttt ttccccgtat    5940
ccccccaggt gtctgcaggc tcaaagagca gcgagaagcg ttcagaggaa agcgatcccg    6000
tgccaccttc cccgtgcccg ggctgtcccc gcacgctgcc ggctcgggga tgcgggggga    6060
gcgccggacc ggagcggagc cccggccggc tcgctgctgc ccctagcgg gggagggacg    6120 taattacatc cctgggggct tggggggggg gctgtccccg tgagctctta ctccctatca    6180
gtgatagaga acgtatgaag agtttactcc ctatcagtga tagagaacgt atgcagactt    6240
tactccctat cagtgataga gaacgtataa ggagtttact ccctatcagt gatagagaac    6300
gtatgaccag tttactccct atcagtgata gagaacgtat ctacagttta ctccctatca    6360
gtgatagaga acgtatatcc agtttactcc ctatcagtga tagagaacgt atgtcgaggt    6420
aggcgtgtac ggtgggcgcc tataaaagca gagctcgttt agtgaaccgt cagatcgcct    6480
ggagcaattc cacaacactt ttgtcttata cttatgctcg agggagtgca ggtggagact    6540
atctccccag gagacgggcg caccttcccc aagcgcggcc agacctgcgt ggtgcactac    6600
accgggatgc ttgaagatgg aaagaaagtt gattcctccc gggacagaaa caagcccttt    6660
aagtttatgc taggcaagca ggaggtgatc cgaggctggg aagaaggggt tgcccagatg    6720
agtgtgggtc agagagccaa actgactata tctccagatt atgcctatgg tgccactggg    6780
cacccaggca tcatcccacc acatgccact ctcgtcttcg atgtggagct tctaaaactg    6840
gaatctggcg gtggatccgg agtcgacgga tttggtgatg tcggtgctct tgagagtttg    6900
aggggaaatg cagatttggc ttacatcctg agcatggagc cctgtggcca ctgcctcatt    6960
atcaacaatg tgaacttctg ccgtgagtcc ggctccgca cccgcactgg ctccaacatc    7020
gactgtgaga agttgcggcg tcgcttctcc tcgctgcatt tcatggtgga ggtgaagggc    7080
gacctgactg ccaagaaaat ggtgctggct ttgctggagc tggcgcggca ggaccacggt    7140
gctctggact gctgcgtggt ggtcattctc tctcacggct gtcaggccag ccacctgcag    7200
ttcccagggg ctgtctacgg cacagatgga tgccctgtgt cggtcgagaa gattgtgaac    7260
atcttcaatg ggaccagctg ccccagcctg ggagggaagc ccaagctctt tttcatccag    7320
gcctgtggtg gggagcagaa agaccatggg tttgaggtgg cctccacttc ccctgaagac    7380
gagtcccctg gcagtaaccc cgagccagat gccacccccgt tccaggaagg tttgaggacc    7440
ttcgaccagc tggacgccat atctagtttg cccacaccca gtgacatctt tgtgtcctac    7500
tctactttcc caggttttgt ttcctggagg accccaagga gtggctcctg gtacgttgag    7560
accctggacg acatctttga gcagtgggct cactctgaag acctgcagtc cctcctgctt    7620
agggtcgcta atgctgtttc ggtgaaaggg atttataaac agatgcctgg ttgctttaat    7680
ttcctccgga aaaacttttt ctttaaaaca tcagtcgact atccgtacga cgtaccagac    7740
tacgcactcg actaaaagct ttttcccgt atccccccag gtgtctgcag gctcaaagag    7800
cagcgagaag cgttcagagg aaagcgatcc cgtgccacct tccccgtgcc cgggctgtcc    7860
ccgcacgctg ccggctcggg gatgcggggg gagcgccgga ccggagcgga gccccgggcg    7920
gctcgctgct gccccctagc gggggaggga cgtaattaca tccctgggggg cttttgggagg    7980 gggctgtccc cgtgagctca atcaacctct ggattacaaa atttgtgaaa gattgactgg    8040
```

```
tattcttaac tatgttgctc cttttacgct atgtggatac gctgctttaa tgcctttgta   8100
tcatgctatt gcttcccgta tggctttcat tttctcctcc ttgtataaat cctggttgct   8160
gtctctttat gaggagttgt ggcccgttgt caggcaacgt ggcgtggtgt gcactgtgtt   8220
tgctgacgca accccactg gttggggcat tgccaccacc tgtcagctcc tttccgggac    8280
tttcgctttc cccctcccta ttgccacggc ggaactcatc gccgcctgcc ttgcccgctg   8340
ctggacaggg gctcggctgt tgggcactga caattccgtg gtgttgtcgg ggaagctgac   8400
gtcctttcca tggctgctcg cctgtgttgc cacctggatt ctgcgcggga cgtccttctg   8460
ctacgtccct tcggccctca atccagcgga ccttccttcc cgcggcctgc tgccggctct   8520
gcggcctctt ccgcgtcttc gccttcgccc tcagacgagt cggatctccc tttgggccgc   8580
ctcccccgcct ggaattaatt ctgcagtcga cctagaaaa acatggagc aatcacaagt    8640
agcaatacag cagctaccaa tgctgattgt gcctggctag aagcacaaga ggaggaggag   8700
gtgggttttc cagtcacacc tcaggtacct ttaagaccaa tgacttacaa ggcagctgta   8760
gatcttagcc acttttttaaa agaaaagagg ggactggaag ggctaattca ctcccaacga  8820
agacaagata tccttgatct gtggatctac cacacacaag gctacttccc tgattagcag   8880
aactacacac cagggccagg ggtcagatat ccactgacct ttggatggtg ctacaagcta   8940
gtaccagttg agccagataa ggtagaagag gccaataaag agagaacac cagcttgtta    9000
caccctgtga gcctgcatgg gatggatgac ccggagagag aagtgttaga gtggaggttt   9060
gacagccgcc tagcatttca tcacgtggcc cgagagctgc atccggagta cttcaagaac   9120
tgctgatatc gagcttgcta caagggactt tccgctgggg actttccagg gaggcgtggc   9180
ctgggcggga ctggggagtg gcgagccctc agatcctgca tataagcagc tgcttttgc    9240
ctgtactggg tctctctggt tagaccagat ctgagcctgg gagctctctg gctaactagg   9300
gaacccactg cttaagcctc aataaagctt gccttgagtg cttcaagtag tgtgtgcccg   9360
tctgttgtgt gactctggta actagagatc cctcagaccc ttttagtcag tgtggaaaat   9420
ctctagcagt agtagttcat gtcatcttat tattcagtat ttataacttg caaagaaatg   9480
aatatcagag agtgagaggc cttgacattg ctagcgttta ccgtcgacct ctagctagag   9540
cttggcgtaa tcatggtcat agctgttttcc tgtgtgaaat tgttatccgc tcacaattcc   9600
acacaacata cgagccggaa gcataaagtg taaagcctgg ggtgcctaat gagtgagcta   9660
actcacatta attgcgttgc gctcactgcc cgctttccag tcgggaaacc tgtcgtgcca   9720
gctgcattaa tgaatcggcc aacgcgcggg gagaggcggt ttgcgtattg ggcgctcttc   9780
cgcttcctcg ctcactgact cgctgcgctc ggtcgttcgg ctgcggcgag cggtatcagc   9840
tcactcaaag gcggtaatac ggttatccac agaatcaggg gataacgcag gaaagaacat   9900
gtgagcaaaa ggccagcaaa aggccaggaa ccgtaaaaag gccgcgttgc tggcgttttt   9960
ccataggctc cgcccccctg acgagcatca caaaaatcga cgctcaagtc agaggtggcg   10020
aaacccgaca ggactataaa gataccaggc gtttccccct ggaagctccc tcgtgcgctc   10080
tcctgttccg accctgccgc ttaccggata cctgtccgcc tttctccctt cgggaagcgt   10140
ggcgctttct catagctcac gctgtaggta tctcagttcg gtgtaggtcg ttcgctccaa   10200
gctgggctgt gtgcacgaac cccccgttca gcccgaccgc tgcgccttat ccggtaacta   10260
tcgtcttgag tccaacccgg taagacacga cttatcgcca ctggcagcag ccactggtaa   10320
caggattagc agagcgaggt atgtaggcgg tgctacagag ttcttgaagt ggtggcctaa   10380
```

| | | | |
|---|---|---|---|
| ctacggctac | actagaagaa | cagtatttgg tatctgcgct ctgctgaagc cagttacctt | 10440 |
| cggaaaaaga | gttggtagct | cttgatccgg caaacaaacc accgctggta gcggtggttt | 10500 |
| ttttgtttgc | aagcagcaga | ttacgcgcag aaaaaaagga tctcaagaag atcctttgat | 10560 |
| cttttctacg | gggtctgacg | ctcagtggaa cgaaaactca cgttaaggga ttttggtcat | 10620 |
| gagattatca | aaaaggatct | tcacctagat ccttttaaat taaaaatgaa gttttaaatc | 10680 |
| aatctaaagt | atatatgagt | aaacttggtc tgacagttac caatgcttaa tcagtgaggc | 10740 |
| acctatctca | gcgatctgtc | tatttcgttc atccatagtt gcctgactcc ccgtcgtgta | 10800 |
| gataactacg | atacgggagg | gcttaccatc tggccccagt gctgcaatga taccgcgaga | 10860 |
| cccacgctca | ccggctccag | atttatcagc aataaaccag ccagccggaa gggccgagcg | 10920 |
| cagaagtggt | cctgcaactt | tatccgcctc catccagtct attaattgtt gccgggaagc | 10980 |
| tagagtaagt | agttcgccag | ttaatagttt gcgcaacgtt gttgccattg ctacaggcat | 11040 |
| cgtggtgtca | cgctcgtcgt | ttggtatggc ttcattcagc tccggttccc aacgatcaag | 11100 |
| gcgagttaca | tgatccccca | tgttgtgcaa aaaagcggtt agctccttcg gtcctccgat | 11160 |
| cgttgtcaga | agtaagttgg | ccgcagtgtt atcactcatg gttatggcag cactgcataa | 11220 |
| ttctcttact | gtcatgccat | ccgtaagatg cttttctgtg actggtgagt actcaaccaa | 11280 |
| gtcattctga | gaatagtgta | tgcggcgacc gagttgctct tgcccggcgt caatacggga | 11340 |
| taataccgcg | ccacatagca | gaactttaaa agtgctcatc attggaaaac gttcttcggg | 11400 |
| gcgaaaactc | tcaaggatct | taccgctgtt gagatccagt tcgatgtaac ccactcgtgc | 11460 |
| acccaactga | tcttcagcat | cttttacttt caccagcgtt tctgggtgag caaaaacagg | 11520 |
| aaggcaaaat | gccgcaaaaa | agggaataag ggcgacacgg aaatgttgaa tactcatact | 11580 |
| cttcctttt | caatattatt | gaagcattta tcagggttat tgtctcatga gcggatacat | 11640 |
| atttgaatgt | atttagaaaa | ataaacaaat aggggttccg cgcacatttc cccgaaaagt | 11700 |
| gccacctgac | gtcgacggat | cgggagatca acttgtttat tgcagcttat aatggttaca | 11760 |
| aataaagcaa | tagcatcaca | aatttcacaa ataaagcatt ttttcactg cattctagtt | 11820 |
| gtggtttgtc | caaactcatc | aatgtatctt atcatgtctg gatcaactgg ataactcaag | 11880 |
| ctaaccaaaa | tcatcccaaa | cttcccaccc catacctat taccactgcc aattacctgt | 11940 |
| ggtttcattt | actctaaacc | tgtgattcct ctgaattatt tcattttaa agaaattgta | 12000 |
| tttgttaaat | atgtactaca | aacttagtag t | 12031 |

<210> SEQ ID NO 23
<211> LENGTH: 12037
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 23

| | | | |
|---|---|---|---|
| tggaagggct | aattcactcc | caaagaagac aagatatcct tgatctgtgg atctaccaca | 60 |
| cacaaggcta | cttccctgat | tagcagaact acacaccagg gccagggtc agatatccac | 120 |
| tgacctttgg | atggtgctac | aagctagtac cagttgagcc agataaggta gaagaggcca | 180 |
| ataaaggaga | gaacaccagc | ttgttacacc ctgtgagcct gcatgggatg gatgacccgg | 240 |
| agagagaagt | gttagagtgg | aggtttgaca gccgcctagc atttcatcac gtggcccgag | 300 |
| agctgcatcc | ggagtacttc | aagaactgct gatatcgagc ttgctacaag ggactttccg | 360 |

```
ctggggactt tccagggagg cgtggcctgg gcgggactgg ggagtggcga gccctcagat    420
cctgcatata agcagctgct ttttgcctgt actgggtctc tctggttaga ccagatctga    480
gcctgggagc tctctggcta actagggaac ccactgctta agcctcaata aagcttgcct    540
tgagtgcttc aagtagtgtg tgcccgtctg ttgtgtgact ctggtaacta gagatccctc    600
agacccttt agtcagtgtg gaaaatctct agcagtggcg cccgaacagg gacttgaaag    660
cgaaagggaa accagaggag ctctctcgac gcaggactcg gcttgctgaa gcgcgcacgg    720
caagaggcga gggcggcga ctggtgagta cgccaaaaat tttgactagc ggaggctaga    780
aggagagaga tgggtgcgag agcgtcagta ttaagcgggg gagaattaga tcgcgatggg    840
aaaaaattcg gttaaggcca gggggaaaga aaaaatataa attaaaacat atagtatggg    900
caagcaggga gctagaacga ttcgcagtta atcctggcct gttagaaaca tcagaaggct    960
gtagacaaat actgggacag ctacaaccat cccttcagac aggatcagaa gaacttagat   1020
cattatataa tacagtagca accctctatt gtgtgcatca aaggatagag ataaaagaca   1080
ccaaggaagc tttagacaag atagaggaag agcaaaacaa aagtaagacc accgcacagc   1140
aagcggccgg ccgctgatct tcagacctgg aggaggagat atgagggaca attggagaag   1200
tgaattatat aaatataaag tagtaaaaat tgaaccatta ggagtagcac ccaccaaggc   1260
aaagagaaga gtggtgcaga gagaaaaaag agcagtggga ataggagctt tgttccttgg   1320
gttcttggga gcagcaggaa gcactatggg cgcagcgtca atgacgctga cggtacaggc   1380
cagacaatta ttgtctggta tagtgcagca gcagaacaat ttgctgaggg ctattgaggc   1440
gcaacagcat ctgttgcaac tcacagtctg gggcatcaag cagctccagg caagaatcct   1500
ggctgtggaa agatacctaa aggatcaaca gctcctgggg atttggggtt gctctggaaa   1560
actcatttgc accactgctg tgccttggaa tgctagttgg agtaataaat ctctggaaca   1620
gatttggaat cacacgacct ggatggagtg ggacagagaa attaacaatt acacaagctt   1680
aatacactcc ttaattgaag aatcgcaaaa ccagcaagaa aagaatgaac aagaattatt   1740
ggaattagat aaatgggcaa gtttgtggaa ttggtttaac ataacaaatt ggctgtggta   1800
tataaaatta ttcataatga tagtaggagg cttggtaggt ttaagaatag ttttttgctgt   1860
actttctata gtgaatagag ttaggcaggg atattcacca ttatcgtttc agacccacct   1920
cccaaccccg aggggacccg acaggcccga aggaataga gaagaaggtg gagagagaga   1980
cagagacaga tccattcgat tagtgaacgg atctcgacgg tatcgccttt aaaagaaaag   2040
ggggattgg ggggtacagt gcaggggaaa gaatagtaga cataatagca acagacatac   2100
aaactaaaga attacaaaa caaattacaa aaattcaaaa ttttcgggtt tattacaggg   2160
acagcagaga tccagtttat cgataagctt gggagttccg cgttacataa cttacggtaa   2220
atggcccgcc tggctgaccg cccaacgacc cccgcccatt gacgtcaata atgacgtatg   2280
ttcccatagt aacgccaata gggactttcc attgacgtca atgggtggag tatttacggt   2340
aaactgccca cttggcagta catcaagtgt atcatatgcc aagtacgccc cctattgacg   2400
tcaatgacgg taaatggccc gcctggcatt atgcccagta catgacctta tgggactttc   2460
ctacttggca gtacatctac gtattagtca tcgctattac catggtgatg cggttttggc   2520
agtacatcaa tgggcgtgga tagcggtttg actcacgggg atttccaagt ctccacccca   2580
ttgacgtcaa tgggagtttg ttttggcacc aaaatcaacg ggactttcca aatgtcgta   2640
acaactccgc cccattgacg caaatgggcg gtaggcgtgt acggtgggag gtctatataa   2700
gcagagctcg tttagtgaac cgtcagatcg cctggagacg ccatccacgc tgttttgacc   2760
```

```
tccatagaag acaccgactc tactagagga tctatttccg gtgaattcgc caccatgggc   2820
acaaggttgt tcttctatgt ggcccttttgt ctcctgtgga ccggtcacat ggaagctgac   2880
atctaccaga ccccaagata ccttgttata gggacaggaa agaagatcac tctggaatgt   2940
tctcaaacca tgggccatga caaaatgtac tggtatcaac aagatccagg aatggaacta   3000
cacctcatcc actattccta tggagttaat tccacagaga agggagatct ttcctctgag   3060
tcaacagtct ccagaataag gacggagcat tttcccctga ccctggagtc tgccaggccc   3120
tcacatacct ctcagtacct ctgtgccagc agtcggacgc ccaacattca gtacttcggc   3180
gccgggaccc ggctctcagt gctggaggac ctgaaaaacg tgttcccacc cgaggtcgct   3240
gtgtttgagc catcagaagc agagatctcc cacacccaaa aggccacact agtgtgcctg   3300
gccacaggct tctaccccga ccacgtggag ctgagctggt gggtgaatgg gaaggaggtg   3360
cacagtgggg tcagcacaga cccgcagccc ctcaaggagc agcccgccct caatgactcc   3420
agatactgcc tgagcagccg cctgagggtc tcggccacct tctggcagaa cccccgcaac   3480
cacttccgct gtcaagtcca gttctacggg ctctcggaga atgacgagtg gacccaggat   3540
agggccaaac ctgtcaccca gatcgtcagc gccgaggcct ggggtagagc agactgtggc   3600
ttcacctccg agtcttacca gcaaggggtc ctgtctgcca ccatcctcta tgagatcttg   3660
ctagggaagg ccaccttgta tgccgtgctg gtcagtgccc tcgtgctgat ggccatggtc   3720
aagagaaagg attccagagg cgggagcgga gccacgaact tctctctgtt aaagcaagca   3780
ggagacgtgg aagaaaaccc cggtcctatg gcaggcattc gagctttatt tatgtacttg   3840
tggctgcagc tggactgggt ctcgagaggt caacagctga atcagagtcc tcaatctatg   3900
tttatccagg aaggagaaga tgtctccatg aactgcactt cttcaagcat atttaacacc   3960
tggctatggt acaagcagga acctgggaaa ggtcctgtcc tcttgatagc cttatataag   4020
gctggtgaat tgacctcaaa tggaagactg actgctcagt ttggtataac cagaaaggac   4080
agcttcctga atatctcagc atccatacct agtgatgtag gcatctactt ctgtgctggc   4140
acataccaga aagttacctt tggaactgga caaagctcc aagtcatccc aaatatccag   4200
aaccctgacc ctgccgtgta ccagctgaga gactctaaat ccagtgacaa gtctgtctgc   4260
ctattcaccg attttgattc tcaaacaaat gtgtcacaaa gtaaggattc tgatgtgtat   4320
atcacagaca aaactgtgct agacatgagg tctatggact tcaagagcaa cagtgcggcc   4380
gcctggagca caaaatctga ctttgcatgt gcaaacgcct tcaacaacag cattattcca   4440
gaagacacct tcttccccag cccagaaagt tcctgtgatg tcaagctggt cgagaaaagc   4500
tttgaaacag atacgaacct aaactttcaa aacctgtcag tgattgggtt ccgaatcctc   4560
ctcctgaaag tggccgggtt taatctgctc atgacgctgc ggctgtggtc cagctgactc   4620
gagggatccc gcccctctcc ctccccccc cctaacgtta ctggccgaag ccgcttggaa   4680
taaggccggt gtgcgtttgt ctatatgtta ttttccacca tattgccgtc ttttggcaat   4740
gtgagggccc ggaaacctgg ccctgtcttc ttgacgagca ttcctagggg tctttcccct   4800
ctcgccaaag gaatgcaagg tctgttgaat gtcgtgaagg aagcagttcc tctggaagct   4860
tcttgaagac aaacaacgtc tgtagcgacc cttttgcagg agcggaaccc cccacctggc   4920
gacaggtgcc tctgcggcca aaagccacgt gtataagata cacctgcaaa ggcggcacaa   4980
ccccagtgcc acgttgtgag ttggatagtt gtggaaagag tcaaatggct cacctcaagc   5040
gtattcaaca aggggctgaa ggatgcccag aaggtacccc attgtatggg atctgatctg   5100
```

```
gggcctcggt gcacatgctt tacatgtgtt tagtcgaggt taaaaaacgt ctaggccccc    5160
cgaaccacgg ggacgtggtt ttcctttgaa aaacacgatg ataatatggt gagcaagggc    5220
gaggaggata acatggccat catcaaggag ttcatgcgct tcaaggtgca catggagggc    5280
tccgtgaacg gccacgagtt cgagatcgag ggcgagggcg agggccgccc ctacgagggc    5340
acccagaccg ccaagctgaa ggtgaccaag ggtggcccc tgcccttcgc ctgggacatc     5400
ctgtcccctc agttcatgta cggctccaag gcctacgtga agcacccgc cgacatcccc     5460 gactacttga agctgtcctt ccccgagggc ttcaagtggg agcgcgtgat gaacttcgag    5520
gacggcggcg tggtgaccgt gacccaggac tcctccctgc aggacggcga gttcatctac    5580
aaggtgaagc tgcgcggcac caacttcccc tccgacggcc ccgtaatgca gaagaagacc    5640
atgggctggg aggcctcctc cgagcggatg taccccgagg acggcgccct gaagggcgag    5700
atcaagcaga ggctgaagct gaaggacggc ggccactacg acgctgaggt caagaccacc    5760
tacaaggcca agaagcccgt gcagctgccc ggcgcctaca acgtcaacat caagttggac    5820
atcacctccc acaacgagga ctacaccatc gtggaacagt acgaacgcgc cgagggccgc    5880
cactccaccg gcggcatgga cgagctgtac aagtgaacgc gtctggaaca gcttttttcc    5940
ccgtatcccc ccaggtgtct gcaggctcaa agagcagcga gaagcgttca gaggaaagcg    6000
atcccgtgcc accttccccg tgcccgggct gtcccgcac gctgccggct cggggatgcg     6060
gggggagcgc cggaccggag cggagccccg ggcggctcgc tgctgccccc tagcggggga    6120
gggacgtaat tacatccctg ggggctttgg ggggggggctg tccccgtgag ctcttactcc    6180
ctatcagtga tagagaacgt atgaagagtt tactccctat cagtgataga gaacgtatgc    6240
agactttact ccctatcagt gatagagaac gtataaggag tttactccct atcagtgata    6300
gagaacgtat gaccagttta ctccctatca gtgatagaga acgtatctac agtttactcc    6360
ctatcagtga tagagaacgt atatccagtt tactccctat cagtgataga gaacgtatgt    6420
cgaggtaggc gtgtacggtg gcgcctata aaagcagagc tcgtttagtg aaccgtcaga    6480
tcgcctggag caattccaca acacttttgt cttatactta tgctcgaggg agtgcaggtg    6540
gagactatct ccccaggaga cgggcgcacc ttccccaagc gcggccagac ctgcgtggtg    6600
cactacaccg ggatgcttga agatggaaag aaagttgatt cctcccggga cagaaacaag    6660
ccctttaagt ttatgctagg caagcaggag gtgatccgag gctgggaaga aggggttgcc    6720
cagatgagtg tgggtcagag agccaaactg actatatctc cagattatgc ctatggtgcc    6780
actgggcacc caggcatcat cccaccacat gccactctcg tcttcgatgt ggagcttcta    6840
aaactggaat ctggcggtgg atccggagtc gacggatttg gtgatgtcgg tgctcttgag    6900
agtttgaggg gaaatgcaga tttggcttac atcctgagca tggagccctg tggccactgc    6960
ctcattatca acaatgtgaa cttctgccgt gagtccgggc tccgcacccg cactggctcc    7020
aacatcgact gtgagaagtt gcggcgtcgc ttctcctcgc tgcatttcat ggtggaggtg    7080
aagggcgacc tgactgccaa gaaaatggtg ctggcttttg ctggagctgg cgcggcagga    7140
cacggtgctc tggactgctg cgtggtggtc attctctctc acggctgtca ggccagccac    7200
ctgcagttcc caggggctgt ctacggcaca gatggatgcc ctgtgtcggt cgagaagatt    7260
gtgaacatct tcaatgggac cagctgcccc agcctgggag ggaagcccaa gctctttttc    7320
atccaggcct gtggtgggga gcagaaagac catgggtttg aggtggcctc cacttcccct    7380
gaagacgagt cccctggcag taaccccgag ccagatgcca cccgttcca ggaaggtttg     7440 aggaccttcg accagctgga cgccatatct agtttgccca cacccagtga catctttgtg    7500
```

```
tcctactcta ctttcccagg ttttgtttcc tggagggacc ccaagagtgg ctcctggtac    7560
gttgagaccc tggacgacat ctttgagcag tgggctcact ctgaagacct gcagtccctc    7620
ctgcttaggg tcgctaatgc tgtttcggtg aaagggattt ataaacagat gcctggttgc    7680
tttaatttcc tccggaaaaa acttttcttt aaaacatcag tcgactatcc gtacgacgta    7740
ccagactacg cactcgacta aaagcttttt ccccgtatcc ccccaggtgt ctgcaggctc    7800
aaagagcagc gagaagcgtt cagaggaaag cgatcccgtg ccaccttccc cgtgcccggg    7860
ctgtccccgc acgctgccgg ctcggggatg cgggggagc gccggaccgg agcggagccc    7920
cgggcggctc gctgctgccc cctagcgggg gagggacgta attcatccc tggggctttt   7980 gggaggggc tgtccccgtg agctcaatca acctctggat tacaaaattt gtgaaagatt    8040
gactggtatt cttaactatg ttgctccttt tacgctatgt ggatacgctg ctttaatgcc    8100
tttgtatcat gctattgctt cccgtatggc tttcattttc tcctccttgt ataaatcctg    8160
gttgctgtct ctttatgagg agttgtggcc cgttgtcagg caacgtggcg tggtgtgcac    8220
tgtgtttgct gacgcaaccc ccactggttg gggcattgcc accacctgtc agctcctttc    8280
cgggactttc gctttccccc tccctattgc cacggcggaa ctcatcgccg cctgccttgc    8340
ccgctgctgg acagggctc ggctgttggg cactgacaat tccgtggtgt tgtcgggaa    8400 gctgacgtcc tttccatggc tgctcgcctg tgttgccacc tggattctgc gcggacgtc    8460 cttctgctac gtcccttcgg ccctcaatcc agcggacctt ccttcccgcg gcctgctgcc    8520
ggctctgcgg cctcttccgc gtcttcgcct tcgccctcag acgagtcgga tctccctttg    8580
ggccgcctcc ccgcctggaa ttaattctgc agtcgagacc tagaaaaaca tggagcaatc    8640
acaagtagca atacagcagc taccaatgct gattgtgcct ggctagaagc acaagaggag    8700
gaggaggtgg gttttccagt cacacctcag gtacctttaa gaccaatgac ttacaaggca    8760
gctgtagatc ttagccactt tttaaaagaa aagaggggac tggaagggct aattcactcc    8820
caacgaagac aagatatcct tgatctgtgg atctaccaca caaggcta cttccctgat    8880 tagcagaact acacaccagg gccagggtc agatatccac tgacctttgg atggtgctac    8940
aagctagtac cagttgagcc agataaggta gaagaggcca ataaggaga gaacaccagc    9000 ttgttacacc ctgtgagcct gcatgggatg gatgacccgg agagagaagt gttagagtgg    9060
aggtttgaca gccgcctagc atttcatcac gtgcccgag agctgcatcc ggagtacttc    9120
aagaactgct gatatcgagc ttgctacaag ggactttccg ctggggactt tccagggagg    9180
cgtggcctgg gcgggactgg ggagtggcga gccctcagat cctgcatata agcagctgct    9240
ttttgcctgt actgggtctc tctggttaga ccagatctga gcctgggagc tctctggcta    9300
actagggaac ccactgctta agcctcaata aagcttgcct tgagtgcttc aagtagtgtg    9360
tgcccgtctg ttgtgtgact ctggtaacta gagatccctc agacccttt agtcagtgtg    9420 gaaaatctct agcagtagta gttcatgtca tcttattatt cagtatttat aacttgcaaa    9480
gaaatgaata tcagagagtg agaggccttg acattgctag cgtttaccgt cgacctctag    9540
ctagagcttg gcgtaatcat ggtcatagct gtttcctgtg tgaaattgtt atccgctcac    9600
aattccacac aacatacgag ccggaagcat aaagtgtaaa gcctggggtg cctaatgagt    9660
gagctaactc acattaattg cgttgcgctc actgcccgct ttccagtcgg gaaacctgtc    9720
gtgccagctg cattaatgaa tcggccaacg cgcgggaga gcggttttgc gtattgggcg    9780
ctcttccgct tcctcgctca ctgactcgct gcgctcggtc gttcggctgc ggcgagcggt    9840
```

```
atcagctcac tcaaaggcgg taatacggtt atccacagaa tcaggggata acgcaggaaa    9900
gaacatgtga gcaaaaggcc agcaaaaggc caggaaccgt aaaaaggccg cgttgctggc    9960
gttttttccat aggctccgcc cccctgacga gcatcacaaa aatcgacgct caagtcagag   10020
gtggcgaaac ccgacaggac tataaagata ccaggcgttt ccccctggaa gctccctcgt   10080
gcgctctcct gttccgaccc tgccgcttac cggatacctg tccgcctttc tcccttcggg   10140
aagcgtggcg ctttctcata gctcacgctg taggtatctc agttcggtgt aggtcgttcg   10200
ctccaagctg ggctgtgtgc acgaaccccc cgttcagccc gaccgctgcg ccttatccgg   10260
taactatcgt cttgagtcca acccggtaag acacgactta tcgccactgg cagcagccac   10320
tggtaacagg attagcagag cgaggtatgt aggcggtgct acagagttct tgaagtggtg   10380
gcctaactac ggctacacta agaacagt atttggtatc tgcgctctgc tgaagccagt   10440
taccttcgga aaagagttg gtagctcttg atccggcaaa caaccaccg ctggtagcgg   10500
tggttttttt gtttgcaagc agcagattac gcgcagaaaa aaggatctc aagaagatcc   10560
tttgatcttt tctacggggt ctgacgctca gtggaacgaa aactcacgtt aagggatttt   10620
ggtcatgaga ttatcaaaaa ggatcttcac ctagatcctt ttaaattaaa aatgaagttt   10680
taaatcaatc taaagtatat atgagtaaac ttggtctgac agttaccaat gcttaatcag   10740
tgaggcacct atctcagcga tctgtctatt tcgttcatcc atagttgcct gactccccgt   10800
cgtgtagata actacgatac gggagggctt accatctggc cccagtgctg caatgatacc   10860
gcgagaccca cgctcaccgg ctccagattt atcagcaata aaccagccag ccggaagggc   10920
cgagcgcaga agtggtcctg caactttatc cgcctccatc cagtctatta attgttgccg   10980
ggaagctaga gtaagtagtt cgccagttaa tagtttgcgc aacgttgttg ccattgctac   11040
aggcatcgtg gtgtcacgct cgtcgtttgg tatggcttca ttcagctccg gttcccaacg   11100
atcaaggcga gttacatgat cccccatgtt gtgcaaaaaa gcggttagct ccttcggtcc   11160
tccgatcgtt gtcagaagta agttggccgc agtgttatca ctcatggtta tggcagcact   11220
gcataattct cttactgtca tgccatccgt aagatgcttt tctgtgactg gtgagtactc   11280
aaccaagtca ttctgagaat agtgtatgcg gcgaccgagt tgctcttgcc cggcgtcaat   11340
acgggataat accgcgccac atagcagaac tttaaaagtg ctcatcattg gaaaacgttc   11400
ttcggggcga aaactctcaa ggatcttacc gctgttgaga tccagttcga tgtaacccac   11460
tcgtgcaccc aactgatctt cagcatcttt tactttcacc agcgtttctg ggtgagcaaa   11520
aacaggaagg caaaatgccg caaaaaaggg aataagggcg acacggaaat gttgaatact   11580
catactcttc ctttttcaat attattgaag catttatcag ggttattgtc tcatgagcgg   11640
atacatattt gaatgtattt agaaaaataa acaaataggg gttccgcgca catttccccg   11700
aaaagtgcca cctgacgtcg acggatcggg agatcaactt gtttattgca gcttataatg   11760
gttacaaata aagcaatagc atcacaaatt tcacaaataa agcatttttt tcactgcatt   11820
ctagttgtgg tttgtccaaa ctcatcaatg tatcttatca tgtctggatc aactggataa   11880
ctcaagctaa ccaaaatcat cccaaacttc ccaccccata ccctattacc actgccaatt   11940
acctgtggtt tcatttactc taaacctgtg attcctctga attattttca ttttaaagaa   12000
attgtatttg ttaaatatgt actacaaact tagtagt                             12037
```

<210> SEQ ID NO 24
<211> LENGTH: 12037
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 24

| | | | | | |
|---|---|---|---|---|---|
| tggaagggct | aattcactcc | caaagaagac | aagatatcct | tgatctgtgg | atctaccaca | 60 |
| cacaaggcta | cttccctgat | tagcagaact | acacaccagg | gccagggggtc | agatatccac | 120 |
| tgacctttgg | atggtgctac | aagctagtac | cagttgagcc | agataaggta | gaagaggcca | 180 |
| ataaaggaga | gaacaccagc | ttgttacacc | ctgtgagcct | gcatgggatg | gatgacccgg | 240 |
| agagagaagt | gttagagtgg | aggtttgaca | gccgcctagc | atttcatcac | gtggcccgag | 300 |
| agctgcatcc | ggagtacttc | aagaactgct | gatatcgagc | ttgctacaag | ggactttccg | 360 |
| ctggggactt | tccagggagg | cgtggcctgg | gcgggactgg | ggagtggcga | gccctcagat | 420 |
| cctgcatata | agcagctgct | ttttgcctgt | actgggtctc | tctggttaga | ccagatctga | 480 |
| gcctgggagc | tctctggcta | actagggaac | ccactgctta | agcctcaata | aagcttgcct | 540 |
| tgagtgcttc | aagtagtgtg | tgcccgtctg | ttgtgtgact | ctggtaacta | gagatccctc | 600 |
| agaccctttt | agtcagtgtg | gaaaatctct | agcagtggcg | cccgaacagg | gacttgaaag | 660 |
| cgaaaggaaa | accagaggag | ctctctcgac | gcaggactcg | gcttgctgaa | gcgcgcacgg | 720 |
| caagaggcga | ggggcggcga | ctggtgagta | cgccaaaaat | tttgactagc | ggaggctaga | 780 |
| aggagagaga | tgggtgcgag | agcgtcagta | ttaagcgggg | gagaattaga | tcgcgatggg | 840 |
| aaaaaattcg | gttaaggcca | gggggaaaga | aaaaatataa | attaaaacat | atagtatggg | 900 |
| caagcaggga | gctagaacga | ttcgcagtta | atcctggcct | gttagaaaca | tcagaaggct | 960 |
| gtagacaaat | actgggacag | ctacaaccat | cccttcagac | aggatcagaa | gaacttagat | 1020 |
| cattatataa | tacagtagca | accctctatt | gtgtgcatca | aaggatagag | ataaaagaca | 1080 |
| ccaaggaagc | tttagacaag | atagaggaag | agcaaaacaa | aagtaagacc | accgcacagc | 1140 |
| aagcggccgg | ccgctgatct | tcagacctgg | aggaggagat | atgagggaca | attggagaag | 1200 |
| tgaattatat | aaatataaag | tagtaaaaat | tgaaccatta | ggagtagcac | ccaccaaggc | 1260 |
| aaagagaaga | gtggtgcaga | gagaaaaaag | agcagtggga | ataggagctt | tgttccttgg | 1320 |
| gttcttggga | gcagcaggaa | gcactatggg | cgcagcgtca | atgacgctga | cggtacaggc | 1380 |
| cagacaatta | ttgtctggta | tagtgcagca | gcagaacaat | ttgctgaggg | ctattgaggc | 1440 |
| gcaacagcat | ctgttgcaac | tcacagtctg | gggcatcaag | cagctccagg | caagaatcct | 1500 |
| ggctgtggaa | agatacctaa | aggatcaaca | gctcctgggg | atttggggtt | gctctggaaa | 1560 |
| actcatttgc | accactgctg | tgccttggaa | tgctagttgg | agtaataaat | ctctggaaca | 1620 |
| gatttggaat | cacacgacct | ggatggagtg | ggacagagaa | attaacaatt | acacaagctt | 1680 |
| aatacactcc | ttaattgaag | aatcgcaaaa | ccagcaagaa | aagaatgaac | aagaattatt | 1740 |
| ggaattagat | aaatgggcaa | gtttgtggaa | ttggtttaac | ataacaaatt | ggctgtggta | 1800 |
| tataaaatta | ttcataatga | tagtaggagg | cttggtaggt | ttaagaatag | tttttgctgt | 1860 |
| actttctata | gtgaatagag | ttaggcaggg | atattcacca | ttatcgtttc | agacccacct | 1920 |
| cccaaccccg | aggggacccg | acaggcccga | aggaatagaa | gaagaaggtg | gagagagaga | 1980 |
| cagagacaga | tccattcgat | tagtgaacgg | atctcgacgg | tatcgccttt | aaaagaaaag | 2040 |
| gggggattgg | ggggtacagt | gcaggggaaa | gaatagtaga | cataatagca | acagacatac | 2100 |
| aaactaaaga | attacaaaaa | caaattacaa | aaattcaaaa | ttttcgggtt | tattacaggg | 2160 |
| acagcagaga | tccagtttat | cgataagctt | gggagttccg | cgttacataa | cttacggtaa | 2220 |

```
atggcccgcc tggctgaccg cccaacgacc cccgcccatt gacgtcaata atgacgtatg   2280
ttcccatagt aacgccaata gggactttcc attgacgtca atgggtggag tatttacggt   2340
aaactgccca cttggcagta catcaagtgt atcatatgcc aagtacgccc cctattgacg   2400
tcaatgacgg taaatggccc gcctggcatt atgcccagta catgacctta tgggactttc   2460
ctacttggca gtacatctac gtattagtca tcgctattac catggtgatg cggttttggc   2520
agtacatcaa tgggcgtgga tagcggtttg actcacgggg atttccaagt ctccacccca   2580
ttgacgtcaa tgggagtttg ttttggcacc aaaatcaacg ggactttcca aaatgtcgta   2640
acaactccgc cccattgacg caaatgggcg taggcgtgt acgtgggag gtctatataa   2700 gcagagctcg tttagtgaac cgtcagatcg cctggagacg ccatccacgc tgttttgacc   2760
tccatagaag acaccgactc tactagagga tctatttccg gtgaattcgc accatggga   2820 atcaggctcc tgtgtcgtgt ggccttttgt ttcctggctg taggactagt agaagctgac   2880
atctaccaga ccccaagata ccttgttata gggacaggaa agaagatcac tctggaatgt   2940
tctcaaacca tgggccatga caaaatgtac tggtatcaac aagatccagg aatggaacta   3000
cacctcatcc actattccta tggagttaat tccacagaga agggagatct ttcctctgag   3060
tcaacagtct ccagaataag gacggagcat tttcccctga ccctggagtc tgccaggccc   3120
tcacatacct ctcagtacct ctgtgccagc agtcggacgc ccaacattca gtacttcggc   3180
gccgggaccc ggctctcagt gctggaggac ctgaaaaacg tgttcccacc cgaggtcgct   3240
gtgtttgagc catcagaagc agagatctcc cacacccaaa aggccacact ggcatgcctg   3300
gccacaggct tctaccccga ccacgtggag ctgagctggt gggtgaatgg gaaggaggtg   3360
cacagtgggg tcagcacaga cccgcagccc tcaaggagc agcccgccct caatgactcc   3420
agatactgcc tgagcagccg cctgagggtc tcggccacct tctggcagaa ccccgcaac   3480 cacttccgct gtcaagtcca gttctacggg ctctcggaga tgacgagtg gacccaggat   3540 agggccaaac ctgtcaccca gatcgtcagc gccgaggcct ggggtagagc agactgtggc   3600
ttcacctccg agtcttacca gcaagggtc ctgtctgcca ccatcctcta tgagatcttg   3660
ctagggaagg ccaccttgta tgccgtgctg gtcagtgccc tcgtgctgat ggccatggtc   3720
aagagaaagg attccagagg cgggagcgga gccacgaact tctctctgtt aaagcaagca   3780
ggagacgtgg aagaaaaccc cggtcctatg acacagttta gcttgctgtg ggcagtcgtg   3840
gtctccacct gtctcgagtc cggcatgggt caacagctga atcagagtcc tcaatctatg   3900
tttatccagg aaggagaaga tgtctccatg aactgcactt cttcaagcat atttaacacc   3960
tggctatggt acaagcagga acctgggaa ggtcctgtcc tcttgatagc cttatataag   4020
gctggtgaat tgacctcaaa tggaagactg actgctcagt ttggtataac agaaaaggac   4080
agcttcctga atatctcagc atccatacct agtgatgtag gcatctactt ctgtgctggc   4140
acataccaga aagttacctt tggaactgga acaaagctcc aagtcatccc aaatatccag   4200
aaccctgacc ctgccgtgta ccagctgaga gactctaaat ccagtgacaa gtctgtctgc   4260
ctattcaccg attttgattc tcaaacaaat gtgtcacaaa gtaaggattc tgatgtgtat   4320
atcacagaca aaactgtgct agacatgagg tctatggact tcaagagcaa cagtgcggcc   4380
gcctggagca caaatctgac tttgcatgt gcaaacgcct tcaacaacag cattattcca   4440
gaagacacct tcttccccag cccagaaagt tcctgtgatg tcaagctggt cgagaaaagc   4500
tttgaaacag atacgaacct aaactttcaa aacctgtcag tgattgggtt ccgaatcctc   4560
```

```
ctcctgaaag tggccgggtt taatctgctc atgacgctgc ggctgtggtc cagctgactc    4620
gagggatccc gccccctctcc ctcccccccc cctaacgtta ctggccgaag ccgcttggaa    4680
taaggccggt gtgcgtttgt ctatatgtta ttttccacca tattgccgtc ttttggcaat    4740
gtgagggccc ggaaacctgg ccctgtcttc ttgacgagca ttcctagggg tctttcccct    4800
ctcgccaaag gaatgcaagg tctgttgaat gtcgtgaagg aagcagttcc tctggaagct    4860
tcttgaagac aaacaacgtc tgtagcgacc ctttgcaggc agcggaaccc cccacctggc    4920
gacaggtgcc tctgcggcca aaagccacgt gtataagata cacctgcaaa ggcggcacaa    4980
ccccagtgcc acgttgtgag ttggatagtt gtggaaagag tcaaatggct cacctcaagc    5040
gtattcaaca aggggctgaa ggatgcccag aaggtacccc attgtatggg atctgatctg    5100
gggcctcggt gcacatgctt tacatgtgtt tagtcgaggt taaaaaacgt ctaggccccc    5160
cgaaccacgg ggacgtggtt ttcctttgaa aaacacgatg ataatatggt gagcaagggc    5220
gaggaggata acatggccat catcaaggag ttcatgcgct tcaaggtgca catggagggc    5280
tccgtgaacg gccacgagtt cgagatcgag ggcgagggcg agggccgccc ctacgagggc    5340
acccagaccg ccaagctgaa ggtgaccaag ggtggccccc tgcccttcgc ctgggacatc    5400
ctgtcccctc agttcatgta cggctccaag gcctacgtga agcaccccgc cgacatcccc    5460
gactacttga agctgtcctt ccccgagggc ttcaagtggg agcgcgtgat gaacttcgag    5520
gacggcggcg tggtgaccgt gacccaggac tcctccctgc aggacggcga gttcatctac    5580
aaggtgaagc tgcgcggcac caacttcccc tccgacggcc ccgtaatgca gaagaagacc    5640
atgggctggg aggcctcctc cgagcggatg taccccgagg acggcgccct gaagggcgag    5700
atcaagcaga ggctgaagct gaaggacggc ggccactacg acgctgaggt caagaccacc    5760
tacaaggcca gaagcccgt gcagctgccc ggcgcctaca cgtcaacat caagttggac    5820
atcacctccc acaacgagga ctacaccatc gtggaacagt acgaacgcgc cgagggccgc    5880
cactccaccg gcggcatgga cgagctgtac aagtgaacgc gtctggaaca agcttttttcc    5940
ccgtatcccc ccaggtgtct gcaggctcaa agagcagcga gaagcgttca gaggaaagcg    6000
atcccgtgcc acctttcccccg tgccggggct gtccccgcac gctgccggct cggggatgcg    6060
gggggagcgc cggaccggag cggagccccg ggcggctcgc tgctgccccc tagcggggga    6120
gggacgtaat tacatccctg ggggctttgg ggggggctg tccccgtgag ctcttactcc    6180
ctatcagtga tagagaacgt atgaagagtt tactccctat cagtgataga gaacgtatgc    6240
agactttact ccctatcagt gatagagaac gtataaggag tttactccct atcagtgata    6300
gagaacgtat gaccagttta ctccctatca gtgatagaga acgtatctac agtttactcc    6360
ctatcagtga tagagaacgt atatccagtt tactccctat cagtgataga gaacgtatgt    6420
cgaggtaggc gtgtacggtg ggcgcctata aaagcagagc tcgtttagtg aaccgtcaga    6480
tcgcctggag caattccaca cacttttgt cttatactta tgctcgaggg agtgcaggtg    6540
gagactatct ccccaggaga cgggcgcacc ttccccaagc gcggcagac ctgcgtggtg    6600
cactacaccg ggatgcttga agatggaaag aaagttgatt cctcccggga cagaaacaag    6660
cccttaagt ttatgctagg caagcaggag gtgatccgag gctgggaaga aggggttgcc    6720
cagatgagtg tgggtcagag agccaaactg actatatctc cagattatgc ctatggtgcc    6780
actgggcacc caggcatcat cccaccacat gccactctcg tcttcgatgt ggagcttcta    6840
aaactggaat ctggcggtgg atccggagtc gacggatttg gtgatgtcgg tgctcttgag    6900
agtttgaggg gaaatgcaga tttggcttac atcctgagca tggagccctg tggccactgc    6960
```

```
ctcattatca acaatgtgaa cttctgccgt gagtccgggc tccgcacccg cactggctcc    7020
aacatcgact gtgagaagtt gcggcgtcgc ttctcctcgc tgcatttcat ggtggaggtg    7080
aagggcgacc tgactgccaa gaaaatggtg ctggctttgc tggagctggc gcggcaggac    7140
cacggtgctc tggactgctg cgtggtggtc attctctctc acggctgtca ggccagccac    7200
ctgcagttcc cagggctgt ctacggcaca gatggatgcc ctgtgtcggt cgagaagatt    7260
gtgaacatct tcaatgggac cagctgcccc agcctgggag ggaagcccaa gctctttttc    7320
atccaggcct gtggtgggga cagaaagac catgggtttg aggtggcctc cacttcccct    7380
gaagacgagt cccctggcag taaccccgag ccagatgcca ccccgttcca ggaaggtttg    7440
aggaccttcg accagctgga cgccatatct agtttgccca cacccagtga catctttgtg    7500
tcctactcta ctttcccagg ttttgtttcc tggaggggacc ccaagagtgg ctcctggtac    7560
gttgagaccc tggacgacat ctttgagcag tgggctcact ctgaagacct gcagtccctc    7620
ctgcttaggg tcgctaatgc tgtttcggtg aaagggattt ataaacagat gcctggttgc    7680
tttaatttcc tccggaaaaa acttttcttt aaaacatcag tcgactatcc gtacgacgta    7740
ccagactacg cactcgacta aaagcttttt ccccgtatcc ccccaggtgt ctgcaggctc    7800
aaagagcagc gagaagcgtt cagaggaaag cgatcccgtg ccaccttccc cgtgcccggg    7860
ctgtccccgc acgctgccgg ctcggggatg cggggggagc gccggaccgg agcggagccc    7920
cgggcggctc gctgctgccc cctagcgggg gagggacgta attacatccc tgggggcttt    7980 gggaggggc tgtccccgtg agctcaatca acctctggat tacaaaatt gtgaaagatt    8040 gactggtatt cttaactatg ttgctccttt tacgctatgt ggatacgctg ctttaatgcc    8100
tttgtatcat gctattgctt cccgtatggc tttcattttc tcctccttgt ataaatcctg    8160
gttgctgtct ctttatgagg agttgtggcc cgttgtcagg caacgtggcg tggtgtgcac    8220
tgtgtttgct gacgcaaccc ccactggttg gggcattgcc accacctgtc agctcctttc    8280
cgggactttc gctttccccc tccctattgc cacggcggaa ctcatcgccg cctgccttgc    8340
ccgctgctgg acaggggctc ggctgttggg cactgacaat tccgtggtgt tgtcggggaa    8400
gctgacgtcc tttccatggc tgctcgcctg tgttgccacc tggattctgc gcgggacgtc    8460
cttctgctac gtcccttcgg ccctcaatcc agcggacctt ccttcccgcg gcctgctgcc    8520
ggctctgcgg cctcttccgc gtcttcgcct tcgccctcag acgagtcgga tctccctttg    8580
ggccgcctcc ccgcctggaa ttaattctgc agtcgagacc tagaaaaaca tggagcaatc    8640
acaagtagca atacagcagc taccaatgct gattgtgcct ggctagaagc acaagaggag    8700
gaggaggtgg gttttccagt cacacctcag gtacctttaa gaccaatgac ttacaaggca    8760
gctgtagatc ttagccactt tttaaaagaa aagaggggac tggaagggct aattcactcc    8820
caacgaagac aagatatcct tgatctgtgg atctaccaca caaaggcta cttccctgat    8880 tagcagaact acacaccagg ccagggggtc agatatccac tgacctttgg atggtgctac    8940
aagctagtac cagttgagcc agataaggta gaagaggcca ataaggaga gaacaccagc    9000 ttgttacacc ctgtgagcct gcatgggatg gatgacccgg agagaaagt gttagagtgg    9060 aggtttgaca gccgcctagc atttcatcac gtgcccgag agctgcatcc ggagtacttc    9120
aagaactgct gatatcgagc ttgctacaag ggactttccg ctggggactt tccagggagg    9180
cgtggcctgg gcgggactgg ggagtggcga gccctcagat cctgcatata agcagctgct    9240
ttttgcctgt actgggtctc tctggttaga ccagatctga gcctgggagc tctctggcta    9300
```

```
actagggaac ccactgctta agcctcaata aagcttgcct tgagtgcttc aagtagtgtg    9360
tgcccgtctg ttgtgtgact ctggtaacta gagatccctc agaccctttt agtcagtgtg    9420
gaaaatctct agcagtagta gttcatgtca tcttattatt cagtatttat aacttgcaaa    9480
gaaatgaata tcagagagtg agaggccttg acattgctag cgtttaccgt cgacctctag    9540
ctagagcttg gcgtaatcat ggtcatagct gtttcctgtg tgaaattgtt atccgctcac    9600
aattccacac aacatacgag ccggaagcat aaagtgtaaa gcctggggtg cctaatgagt    9660
gagctaactc acattaattg cgttgcgctc actgcccgct ttccagtcgg gaaacctgtc    9720
gtgccagctg cattaatgaa tcggccaacg cgcggggaga ggcggtttgc gtattgggcg    9780
ctcttccgct tcctcgctca ctgactcgct gcgctcggtc gttcggctgc ggcgagcggt    9840
atcagctcac tcaaaggcgg taatacggtt atccacagaa tcaggggata acgcaggaaa    9900
gaacatgtga gcaaaaggcc agcaaaaggc caggaaccgt aaaaaggccg cgttgctggc    9960
gtttttccat aggctccgcc cccctgacga gcatcacaaa aatcgacgct caagtcagag   10020
gtggcgaaac ccgacaggac tataaagata ccaggcgttt ccccctggaa gctccctcgt   10080
gcgctctcct gttccgaccc tgccgcttac cggatacctg tccgcctttc tcccttcggg   10140
aagcgtggcg ctttctcata gctcacgctg taggtatctc agttcggtgt aggtcgttcg   10200
ctccaagctg ggctgtgtgc acgaaccccc cgttcagccc gaccgctgcg ccttatccgg   10260
taactatcgt cttgagtcca acccggtaag acacgactta tcgccactgg cagcagccac   10320
tggtaacagg attagcagag cgaggtatgt aggcggtgct acagagttct tgaagtggtg   10380
gcctaactac ggctacacta agaacagt atttggtatc tgcgctctgc tgaagccagt   10440
taccttcgga aaagagttg gtagctcttg atccggcaaa caaaccaccg ctggtagcgg   10500 tggtttttt gtttgcaagc agcagattac gcgcagaaaa aaggatctc aagaagatcc   10560 tttgatcttt tctacggggt ctgacgctca gtggaacgaa aactcacgtt aagggatttt   10620
ggtcatgaga ttatcaaaaa ggatcttcac ctagatcctt ttaaattaaa aatgaagttt   10680
taaatcaatc taaagtatat atgagtaaac ttggtctgac agttaccaat gcttaatcag   10740
tgaggcacct atctcagcga tctgtctatt tcgttcatcc atagttgcct gactccccgt   10800
cgtgtagata actacgatac gggagggctt accatctggc cccagtgctg caatgatacc   10860
gcgagaccca cgctcaccgg ctccagattt atcagcaata aaccagccag ccggaagggc   10920
cgagcgcaga agtggtcctg caactttatc cgcctccatc cagtctatta attgttgccg   10980
ggaagctaga gtaagtagtt cgccagttaa tagtttgcgc aacgttgttg ccattgctac   11040
aggcatcgtg gtgtcacgct cgtcgtttgg tatggcttca ttcagctccg gttcccaacg   11100
atcaaggcga gttacatgat cccccatgtt gtgcaaaaaa gcggttagct ccttcggtcc   11160
tccgatcgtt gtcagaagta agttggccgc agtgttatca ctcatggtta tggcagcact   11220
gcataattct cttactgtca tgccatccgt aagatgcttt tctgtgactg gtgagtactc   11280
aaccaagtca ttctgagaat agtgtatgcg gcgaccgagt tgctcttgcc cggcgtcaat   11340
acgggataat accgcgccac atagcagaac tttaaaagtg ctcatcattg gaaaacgttc   11400
ttcggggcga aaactctcaa ggatcttacc gctgttgaga tccagttcga tgtaacccac   11460
tcgtgcaccc aactgatctt cagcatcttt tactttcacc agcgtttctg ggtgagcaaa   11520
aacaggaagg caaaatgccg caaaaaaggg aataagggcg acacggaaat gttgaatact   11580
catactcttc cttttttcaat attattgaag catttatcag ggttattgtc tcatgagcgg   11640
atacatattt gaatgtattt agaaaaataa acaaataggg gttccgcgca catttccccg   11700
```

```
aaaagtgcca cctgacgtcg acggatcggg agatcaactt gtttattgca gcttataatg    11760
gttacaaata aagcaatagc atcacaaatt tcacaaataa agcattttt tcactgcatt     11820 ctagttgtgg tttgtccaaa ctcatcaatg tatcttatca tgtctggatc aactggataa    11880
ctcaagctaa ccaaaatcat cccaaacttc cacccata ccctattacc actgccaatt      11940
acctgtggtt tcatttactc taaacctgtg attcctctga attattttca ttttaaagaa    12000
attgtatttg ttaaatatgt actacaaact tagtagt                             12037
```

<210> SEQ ID NO 25  
<211> LENGTH: 12031  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 25

```
tggaagggct aattcactcc caagaagac aagatatcct tgatctgtgg atctaccaca     60
cacaaggcta cttccctgat tagcagaact acacaccagg gccagggggtc agatatccac    120 tgacctttgg atggtgctac aagctagtac cagttgagcc agataaggta gaagaggcca   180
ataaaggaga gaacaccagc ttgttacacc ctgtgagcct gcatgggatg gatgacccgg    240
agagagaagt gttagagtgg aggtttgaca gccgcctagc atttcatcac gtggcccgag   300
agctgcatcc ggagtacttc aagaactgct gatatcgagc ttgctacaag ggactttccg    360
ctggggactt tccagggagg cgtggcctgg gcgggactgg ggagtggcga gccctcagat    420
cctgcatata agcagctgct ttttgcctgt actgggtctc tctggttaga ccagatctga    480
gcctgggagc tctctggcta actagggaac ccactgctta agcctcaata aagcttgcct    540
tgagtgcttc aagtagtgtg tgcccgtctg ttgtgtgact ctggtaacta gagatccctc    600
agaccctttt agtcagtgtg aaaatctct agcagtggcg cccgaacagg gacttgaaag    660
cgaaagggaa accagaggag ctctctcgac gcaggactcg gcttgctgaa gcgcgcacgg   720
caagaggcga gggcggcga ctggtgagta cgccaaaaat tttgactagc ggaggctaga    780
aggagagaga tgggtgcgag agcgtcagta ttaagcgggg gagaattaga tcgcgatggg    840
aaaaaattcg gttaaggcca gggggaaaga aaaaatataa attaaaacat atagtatggg    900
caagcaggga gctagaacga ttcgcagtta atcctggcct gttagaaaca tcagaaggct    960
gtagacaaat actgggacag ctacaaccat cccttcagac aggatcagaa gaacttagat    1020
cattatataa tacagtagca accctctatt gtgtgcatca aaggatagag ataaaagaca   1080
ccaaggaagc tttagacaag atagaggaag agcaaaacaa aagtaagacc accgcacagc   1140
aagcggccgg ccgctgatct tcagacctgg aggaggagat atgagggaca attggagaag    1200
tgaattatat aaatataaag tagtaaaaat tgaaccatta ggagtagcac ccaccaaggc    1260
aaagagaaga gtggtgcaga gagaaaaaag agcagtggga ataggagctt tgttccttgg    1320
gttcttggga gcagcaggaa gcactatggg cgcagcgtca atgacgctga cggtacaggc    1380
cagacaatta ttgtctggta tagtgcagca gcagaacaat ttgctgaggg ctattgaggc    1440
gcaacagcat ctgttgcaac tcacagtctg ggcatcaag cagctccagg caagaatcct     1500
ggctgtggaa agatacctaa aggatcaaca gctcctgggg atttggggtt gctctggaaa    1560
actcatttgc accactgctg tgccttgaa tgctagttgg agtaataaat ctctggaaca     1620
gatttggaat cacacgacct ggatggagtg ggacagagaa attaacaatt acacaagctt   1680
```

```
aatacactcc ttaattgaag aatcgcaaaa ccagcaagaa aagaatgaac aagaattatt    1740
ggaattagat aaatgggcaa gtttgtggaa ttggtttaac ataacaaatt ggctgtggta    1800
tataaaatta ttcataatga tagtaggagg cttggtaggt ttaagaatag tttttgctgt    1860
actttctata gtgaatagag ttaggcaggg atattcacca ttatcgtttc agacccacct    1920
cccaaccccg aggggacccg acaggcccga aggaatagaa gaagaaggtg gagagagaga    1980
cagagacaga tccattcgat tagtgaacgg atctcgacgg tatcgccttt aaaagaaaag    2040
gggggattgg ggggtacagt gcaggggaaa gaatagtaga cataatagca acagacatac    2100
aaactaaaga attacaaaaa caaattacaa aaattcaaaa ttttcgggtt tattacaggg    2160
acagcagaga tccagtttat cgataagctt gggagttccg cgttacataa cttacggtaa    2220
atggcccgcc tggctgaccg cccaacgacc cccgcccatt gacgtcaata atgacgtatg    2280
ttcccatagt aacgccaata gggactttcc attgacgtca atgggtggag tatttacggt    2340
aaactgccca cttggcagta catcaagtgt atcatatgcc aagtacgccc cctattgacg    2400
tcaatgacgg taaatggccc gcctggcatt atgcccagta catgacctta tgggactttc    2460
ctacttggca gtacatctac gtattagtca tcgctattac catggtgatg cggttttggc    2520
agtacatcaa tgggcgtgga tagcggtttg actcacgggg atttccaagt ctccacccca    2580
ttgacgtcaa tgggagtttg ttttggcacc aaaatcaacg ggactttcca aatgtcgta    2640 acaactccgc cccattgacg caaatgggcg gtaggcgtgt acggtgggag gtctatataa    2700
gcagagctcg tttagtgaac cgtcagatcg cctggagacg ccatccacgc tgttttgacc    2760
tccatagaag acaccgactc tactagagga tctatttccg gtgaattcgc caccatggcc    2820
tccctgctct cttctgtgg ggcctttat ctcctgggaa ccggttccat ggaagctgac    2880
atctaccaga ccccaagata ccttgttata gggacaggaa agaagatcac tctggaatgt    2940 tctcaaaacca tgggccatga caaaatgtac tggtatcaac aagatccagg aatggaacta    3000
cacctcatcc actattccta tggagttaat tccacagaga agggagatct ttcctctgag    3060
tcaacagtct ccagaataag gacggagcat tttcccctga ccctggagtc tgccaggccc    3120
tcacatacct ctcagtacct ctgtgccagc agtcggacgc ccaacattca gtacttcggc    3180
gccgggaccc ggctctcagt gctggaggac ctgaaaaacg tgttcccacc cgaggtcgct    3240
gtgtttgagc catcagaagc agagatctcc cacacccaaa aggccacact agtgtgcctg    3300
gccacaggct tctaccccga ccacgtggag ctgagctggt gggtgaatgg gaaggaggtg    3360
cacagtgggg tcagcacaga cccgcagccc tcaaggagc agcccgccct caatgactcc    3420
agatactgcc tgagcagccg cctgagggtc tcggccacct tctggcagaa ccccgcaac    3480 cacttccgct gtcaagtcca gttctacggg ctctcggaga tgacgagtg gacccaggat    3540 agggccaaac ctgtcaccca gatcgtcagc gccgaggcct ggggtagagc agactgtggc    3600
ttcacctccg agtcttacca gcaagggtc ctgtctgcca ccatcctcta tgagatcttg    3660
ctagggaagg ccaccttgta tgccgtgctg gtcagtgccc tcgtgctgat ggccatggtc    3720
aagagaaagg attccagagg cgggagcgga gccacgaact tctctctgtt aaagcaagca    3780
ggagacgtgg aagaaaaccc cggtcctatg aactcctctc tggactttct aattctgatc    3840
ttaatgtttg gaggaactag tggtcaacag ctgaatcaga gtcctcaatc tatgtttatc    3900
caggaaggag aagatgtctc catgaactgc acttcttcaa gcatatttaa cacctggcta    3960
tggtacaagc aggaacctgg ggaaggtcct gtcctcttga tagccttata taaggctggt    4020
```

```
gaattgacct caaatggaag actgactgct cagtttggta taaccagaaa ggacagcttc    4080
ctgaatatct cagcatccat acctagtgat gtaggcatct acttctgtgc tggcacatac    4140
cagaaagtta cctttggaac tggaacaaag ctccaagtca tcccaaatat ccagaaccct    4200
gaccctgccg tgtaccagct gagagactct aaatccagtg acaagtctgc atgcctattc    4260
accgattttg attctcaaac aaatgtgtca caaagtaagg attctgatgt gtatatcaca    4320
gacaaaactg tgctagacat gaggtctatg gacttcaaga gcaacagtgc tgtggcctgg    4380
agcaacaaat ctgactttgc atgtgcaaac gccttcaaca acagcattat tccagaagac    4440
accttcttcc ccagcccaga aagttcctgt gatgtcaagc tggtcgagaa agctttgaa    4500 acagatacga acctaaactt tcaaaacctg tcagtgattg ggttccgaat cctcctcctg    4560
aaagtggccg ggtttaatct gctcatgacg ctgcggctgt ggtccagctg actcgaggga    4620
tcccgcccct ctccctcccc ccccctaac gttactggcc gaagccgctt ggaataaggc    4680
cggtgtgcgt ttgtctatat gttatttcc accatattgc cgtctttgg caatgtgagg    4740 gcccggaaac ctggccctgt cttcttgacg agcattccta ggggtctttc ccctctcgcc    4800
aaaggaatgc aaggtctgtt gaatgtcgtg aaggaagcag ttcctctgga agcttcttga    4860
agacaaacaa cgtctgtagc gacccttgc aggcagcgga accccccacc tggcgacagg    4920
tgcctctgcg gccaaaagcc acgtgtataa gatacacctg caaaggcggc acaaccccag    4980
tgccacgttg tgagttggat agttgtggaa agagtcaaat ggctcacctc aagcgtattc    5040 aacaagggc tgaaggatgc ccagaaggta ccccattgta tgggatctga tctggggcct    5100
cggtgcacat gctttacatg tgtttagtcg aggttaaaaa acgtctaggc cccccgaacc    5160
acggggacgt ggttttcctt tgaaaaacac gatgataata tggtgagcaa gggcgaggag    5220
gataacatgg ccatcatcaa ggagttcatg cgcttcaagg tgcacatgga gggctccgtg    5280
aacggccacg agttcgagat cgagggcgag ggcgagggcc gcccctacga gggcacccag    5340
accgccaagc tgaaggtgac caaggtggc cccctgccct cgcctggga catcctgtcc    5400 cctcagttca tgtacggctc caaggcctac gtgaagcacc ccgccgacat ccccgactac    5460
ttgaagctgt ccttccccga gggcttcaag tgggagcgcg tgatgaactt cgaggacggc    5520
ggcgtggtga ccgtgaccca ggactcctcc ctgcaggacg gcgagttcat ctacaaggtg    5580
aagctgcgcg gcaccaactt cccctccgac ggccccgtaa tgcagaagaa gaccatgggc    5640
tgggaggcct cctccgagcg gatgtacccc gaggacggcg ccctgaaggg cgagatcaag    5700
cagaggctga agctgaagga cggcggccac tacgacgctg aggtcaagac cacctacaag    5760
gccaagaagc ccgtgcagct gcccggcgcc tacaacgtca acatcaagtt ggacatcacc    5820
tcccacaacg aggactacac catcgtggaa cagtacgaac gcgccgaggg ccgccactcc    5880
accggcggca tggacgagct gtacaagtga acgcgtctgg aacaagcttt ttccccgtat    5940 cccccaggt gtctgcaggc tcaaagagca gcgagaagcg ttcagaggaa agcgatcccg    6000
tgccaccttc cccgtgcccg ggctgtcccc gcacgctgcc ggctcgggga tgcgggggga    6060
gcgccggacc ggagcggagc cccgggcggc tcgctgctgc cccctagcgg gggagggacg    6120 taattcatc cctgggggct ttgggggggg gctgtcccg tgagctctta ctccctatca    6180
gtgatagaga acgtatgaag agtttactcc ctatcagtga tagagaacgt atgcagactt    6240
tactccctat cagtgataga gaacgtataa ggagtttact ccctatcagt gatagagaac    6300
gtatgaccag tttactccct atcagtgata gagaacgtat ctacagttta ctccctatca    6360
gtgatagaga acgtatatcc agtttactcc ctatcagtga tagagaacgt atgtcgaggt    6420
```

```
aggcgtgtac ggtgggcgcc tataaaagca gagctcgttt agtgaaccgt cagatcgcct    6480
ggagcaattc cacaacactt ttgtcttata cttatgctcg agggagtgca ggtggagact    6540
atctccccag gagacgggcg caccttcccc aagcgcggcc agacctgcgt ggtgcactac    6600
accgggatgc ttgaagatgg aaagaaagtt gattcctccc gggacagaaa caagcccttt    6660
aagtttatgc taggcaagca ggaggtgatc cgaggctggg aagaaggggt tgcccagatg    6720
agtgtgggtc agagagccaa actgactata tctccagatt atgcctatgg tgccactggg    6780
cacccaggca tcatcccacc acatgccact ctcgtcttcg atgtggagct tctaaaactg    6840
gaatctggcg gtggatccgg agtcgacgga tttggtgatg tcggtgctct tgagagtttg    6900
aggggaaatg cagatttggc ttacatcctg agcatggagc cctgtggcca ctgcctcatt    6960
atcaacaatg tgaacttctg ccgtgagtcc gggctccgca cccgcactgg ctccaacatc    7020
gactgtgaga agttgcggcg tcgcttctcc tcgctgcatt tcatggtgga ggtgaagggc    7080
gacctgactc caagaaaat ggtgctggct ttgctggagc tggcgcggca ggaccacggt    7140
gctctggact gctgcgtggt ggtcattctc tctcacggct gtcaggccag ccacctgcag    7200
ttcccagggg ctgtctacgg cacagatgga tgccctgtgt cggtcgagaa gattgtgaac    7260
atcttcaatg ggaccagctg ccccagcctg ggagggaagc ccaagctctt tttcatccag    7320
gcctgtggtg gggagcagaa agaccatggg tttgaggtgg cctccacttc ccctgaagac    7380
gagtcccctg gcagtaaccc cgagccagat gccacccgt tccaggaagg tttgaggacc    7440
ttcgaccagc tggacgccat atctagtttg cccacaccca gtgacatctt tgtgtcctac    7500
tctactttcc caggttttgt ttcctggagg gaccccaaga gtggctcctg gtacgttgag    7560
accctggacg acatctttga gcagtgggct cactctgaag acctgcagtc cctcctgctt    7620
agggtcgcta atgctgtttc ggtgaaaggg atttataaac agatgcctgg ttgctttaat    7680
ttcctccgga aaaacttttt ctttaaaaca tcagtcgact atccgtacga cgtaccagac    7740
tacgcactcg actaaaagct ttttccccgt atcccccag gtgtctgcag gctcaaagag    7800
cagcgagaag cgttcagagg aaagcgatcc cgtgccacct tccccgtgcc cgggctgtcc    7860
ccgcacgctg ccggctcggg gatgcggggg gagcgccgga ccggagcgga gccccgggcg    7920
gctcgctgct gcccctagc gggggaggga cgtaattaca tccctggggg ctttgggagg    7980
gggctgtccc cgtgagctca atcaacctct ggattacaaa atttgtgaaa gattgactgg    8040
tattcttaac tatgttgctc cttttacgct atgtggatac gctgctttaa tgcctttgta    8100
tcatgctatt gcttcccgta tggctttcat tttctcctcc ttgtataaat cctggttgct    8160
gtctctttat gaggagttgt ggcccgttgt caggcaacgt ggcgtggtgt gcactgtgtt    8220
tgctgacgca accccactg gttggggcat tgccaccacc tgtcagctcc tttccgggac    8280
tttcgctttc cccctcccta ttgccacggc ggaactcatc gccgcctgcc ttgcccgctg    8340
ctggacaggg gctcggctgt tgggcactga caattccgtg gtgttgtcgg ggaagctgac    8400 gtccttttcca tggctgctcg cctgtgttgc cacctggatt ctgcgcggga cgtccttctg    8460
ctacgtccct tcggccctca atccagcgga ccttccttcc cgcggcctgc tgccggctct    8520
gcggcctctt ccgcgtcttc gccttcgccc tcagacgagt cggatctccc tttgggccgc    8580
ctccccgcct ggaattaatt ctgcagtcga gacctagaaa aacatggagc aatcacaagt    8640
agcaatacag cagctaccaa tgctgattgt gcctggctag aagcacaaga ggaggaggag    8700
gtgggttttc cagtcacacc tcaggtacct ttaagaccaa tgacttacaa ggcagctgta    8760
```

```
gatcttagcc actttttaaa agaaaagagg ggactggaag ggctaattca ctcccaacga    8820
agacaagata tccttgatct gtggatctac cacacacaag gctacttccc tgattagcag    8880
aactacacac cagggccagg ggtcagatat ccactgacct ttggatggtg ctacaagcta    8940
gtaccagttg agccagataa ggtagaagag gccaataaag gagagaacac cagcttgtta    9000
caccctgtga gcctgcatgg gatggatgac ccggagagag aagtgttaga gtggaggttt    9060
gacagccgcc tagcatttca tcacgtggcc cgagagctgc atccggagta cttcaagaac    9120
tgctgatatc gagcttgcta caagggactt tccgctgggg actttccagg gaggcgtggc    9180
ctgggcggga ctggggagtg gcgagccctc agatcctgca tataagcagc tgcttttttgc    9240
ctgtactggg tctctctggt tagaccagat ctgagcctgg gagctctctg gctaactagg    9300
gaacccactg cttaagcctc aataaagctt gccttgagtg cttcaagtag tgtgtgcccg    9360
tctgttgtgt gactctggta actagagatc cctcagaccc ttttagtcag tgtggaaaat    9420
ctctagcagt agtagttcat gtcatcttat tattcagtat ttataacttg caaagaaatg    9480
aatatcagag agtgagaggc cttgacattg ctagcgttta ccgtcgacct ctagctagag    9540
cttggcgtaa tcatggtcat agctgttttc tgtgtgaaat tgttatccgc tcacaattcc    9600
acacaacata cgagccggaa gcataaagtg taaagcctgg ggtgcctaat gagtgagcta    9660
actcacatta attgcgttgc gctcactgcc cgctttccag tcgggaaacc tgtcgtgcca    9720
gctgcattaa tgaatcggcc aacgcgcggg gagaggcggt ttgcgtattg ggcgctcttc    9780
cgcttcctcg ctcactgact cgctgcgctc ggtcgttcgg ctgcggcgag cggtatcagc    9840
tcactcaaag gcggtaatac ggttatccac agaatcaggg gataacgcag gaaagaacat    9900
gtgagcaaaa ggccagcaaa aggccaggaa ccgtaaaaag gccgcgttgc tggcgttttt    9960
ccataggctc cgcccccctg acgagcatca caaaaatcga cgctcaagtc agaggtggcg   10020
aaacccgaca ggactataaa gataccaggc gtttccccct ggaagctccc tcgtgcgctc   10080
tcctgttccg accctgccgc ttaccggata cctgtccgcc tttctccctt cgggaagcgt   10140
ggcgctttct catagctcac gctgtaggta tctcagttcg gtgtaggtcg ttcgctccaa   10200
gctgggctgt gtgcacgaac ccccgttca gcccgaccgc tgcgccttat ccggtaacta   10260
tcgtcttgag tccaacccgg taagacacga cttatcgcca ctggcagcag ccactggtaa   10320
caggattagc agagcgaggt atgtaggcgg tgctacagag ttcttgaagt ggtggcctaa   10380
ctacggctac actagaagaa cagtatttgg tatctgcgct ctgctgaagc cagttacctt   10440
cggaaaaaga gttggtagct cttgatccgg caaacaaacc accgctggta gcggtggttt   10500
ttttgtttgc aagcagcaga ttacgcgcag aaaaaaagga tctcaagaag atcctttgat   10560
cttttctacg gggtctgacg ctcagtggaa cgaaaactca cgttaaggga ttttggtcat   10620
gagattatca aaaaggatct tcacctagat ccttttaaat taaaaatgaa gttttaaatc   10680
aatctaaagt atatatgagt aaacttggtc tgacagttac caatgcttaa tcagtgaggc   10740
acctatctca gcgatctgtc tatttcgttc atccatagtt gcctgactcc ccgtcgtgta   10800
gataactacg atacgggagg gcttaccatc tggccccagt gctgcaatga taccgcgaga   10860
cccacgctca ccggctccag atttatcagc aataaaccag ccagccggaa gggccgagcg   10920
cagaagtggt cctgcaactt tatccgcctc catccagtct attaattgtt gccgggaagc   10980
tagagtaagt agttcgccag ttaatagttt gcgcaacgtt gttgccattg ctacaggcat   11040
cgtggtgtca cgctcgtcgt ttggtatggc ttcattcagc tccggttccc aacgatcaag   11100
gcgagttaca tgatccccca tgttgtgcaa aaaagcggtt agctccttcg gtcctccgat   11160
```

```
cgttgtcaga agtaagttgg ccgcagtgtt atcactcatg gttatggcag cactgcataa    11220
ttctcttact gtcatgccat ccgtaagatg cttttctgtg actggtgagt actcaaccaa    11280
gtcattctga gaatagtgta tgcggcgacc gagttgctct tgcccggcgt caatacggga    11340
taataccgcg ccacatagca gaactttaaa agtgctcatc attggaaaac gttcttcggg    11400
gcgaaaactc tcaaggatct taccgctgtt gagatccagt tcgatgtaac ccactcgtgc    11460
acccaactga tcttcagcat cttttacttt caccagcgtt tctgggtgag caaaaacagg    11520
aaggcaaaat gccgcaaaaa agggaataag ggcgacacgg aaatgttgaa tactcatact    11580 cttcctttt caatattatt gaagcattta tcagggttat tgtctcatga gcggatacat    11640
atttgaatgt atttagaaaa ataaacaaat aggggttccg cgcacatttc cccgaaaagt    11700
gccacctgac gtcgacggat cgggagatca acttgtttat tgcagcttat aatggttaca    11760
aataaagcaa tagcatcaca aatttcacaa ataaagcatt ttttcactg cattctagtt    11820 gtggtttgtc caaactcatc aatgtatctt atcatgtctg gatcaactgg ataactcaag    11880
ctaaccaaaa tcatcccaaa cttcccaccc catacctat taccactgcc aattacctgt    11940
ggtttcattt actctaaacc tgtgattcct ctgaattatt ttcattttaa agaaattgta    12000
tttgttaaat atgtactaca aacttagtag t                                   12031

<210> SEQ ID NO 26
<211> LENGTH: 9961
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
tggaagggct aattcactcc caagaagac aagatatcct tgatctgtgg atctaccaca      60
cacaaggcta cttccctgat tagcagaact acacaccagg gccagggtc agatatccac     120 tgacctttgg atggtgctac aagctagtac cagttgagcc agataaggta gaagaggcca    180
ataaaggaga gaacaccagc ttgttacacc ctgtgagcct gcatgggatg gatgacccgg    240
agagagaagt gttagagtgg aggtttgaca gccgcctagc atttcatcac gtggcccgag    300
agctgcatcc ggagtacttc aagaactgct gatatcgagc ttgctacaag ggactttccg    360
ctggggactt tccagggagg cgtggcctgg gcgggactgg ggagtggcga gccctcagat    420
cctgcatata agcagctgct ttttgcctgt actgggtctc tctggttaga ccagatctga    480
gcctgggagc tctctggcta actagggaac ccactgctta agcctcaata aagcttgcct    540
tgagtgcttc aagtagtgtg tgcccgtctg ttgtgtgact ctggtaacta gagatccctc    600
agaccctttt agtcagtgtg gaaaatctct agcagtggcg cccgaacagg gacttgaaag    660
cgaaagggaa accagaggag ctctctcgac gcaggactcg gcttgctgaa gcgcgcacgg    720
caagaggcga gggcggcga ctggtgagta cgccaaaaat tttgactagc ggaggctaga    780
aggagagaga tgggtgcgag agcgtcagta ttaagcgggg gagaattaga tcgcgatggg    840
aaaaaattcg gttaaggcca gggggaaaga aaaatataa attaaaacat atagtatggg    900
caagcaggga gctagaacga ttcgcagtta atcctggcct gttagaaaca tcagaaggct    960
gtagacaaat actgggacag ctacaaccat cccttcagac aggatcagaa gaacttagat   1020
cattatataa tacagtagca accctctatt gtgtgcatca aaggatagag ataaagaca    1080 ccaaggaagc tttagacaag atagaggaag agcaaaacaa aagtaagacc accgcacagc   1140
```

```
aagcggccgg ccgctgatct tcagacctgg aggaggagat atgagggaca attggagaag    1200
tgaattatat aaatataaag tagtaaaaat tgaaccatta ggagtagcac ccaccaaggc    1260
aaagagaaga gtggtgcaga gagaaaaaag agcagtggga ataggagctt tgttccttgg    1320
gttcttggga gcagcaggaa gcactatggg cgcagcgtca atgacgctga cggtacaggc    1380
cagacaatta ttgtctggta tagtgcagca gcagaacaat ttgctgaggg ctattgaggc    1440
gcaacagcat ctgttgcaac tcacagtctg gggcatcaag cagctccagg caagaatcct    1500
ggctgtggaa agatacctaa aggatcaaca gctcctgggg atttggggtt gctctggaaa    1560
actcatttgc accactgctg tgccttggaa tgctagttgg agtaataaat ctctggaaca    1620
gatttggaat cacacgacct ggatggagtg ggacagagaa attaacaatt acacaagctt    1680
aatacactcc ttaattgaag aatcgcaaaa ccagcaagaa aagaatgaac aagaattatt    1740
ggaattagat aaatgggcaa gtttgtggaa ttggtttaac ataacaaatt ggctgtggta    1800
tataaaatta ttcataatga tagtaggagg cttggtaggt ttaagaatag tttttgctgt    1860
actttctata gtgaatagag ttaggcaggg atattcacca ttatcgtttc agacccacct    1920
cccaaccccg aggggacccg acaggcccga aggaatagaa gaagaaggtg gagagagaga    1980
cagagacaga tccattcgat tagtgaacgg atctcgacgg tatcgccttt aaaagaaaag    2040
gggggattgg ggggtacagt gcaggggaaa gaatagtaga cataatagca acagacatac    2100
aaactaaaga attacaaaaa caaattacaa aaattcaaaa ttttcgggtt tattacaggg    2160
acagcagaga tccagtttat cgataagctt gggagttccg cgttacataa cttacggtaa    2220
atggcccgcc tggctgaccg cccaacgacc cccgcccatt gacgtcaata atgacgtatg    2280
ttcccatagt aacgccaata gggactttcc attgacgtca atgggtggag tatttacggt    2340
aaactgccca cttggcagta catcaagtgt atcatatgcc aagtacgccc cctattgacg    2400
tcaatgacgg taaatggccc gcctggcatt atgcccagta catgacctta tgggactttc    2460
ctacttggca gtacatctac gtattagtca tcgctattac catggtgatg cggttttggc    2520
agtacatcaa tgggcgtgga tagcggtttg actcacgggg atttccaagt ctccacccca    2580
ttgacgtcaa tgggagtttg ttttggcacc aaaatcaacg ggactttcca aaatgtcgta    2640
acaactccgc cccattgacg caaatgggcg gtaggcgtgt acggtgggag gtctatataa    2700
gcagagctcg tttagtgaac cgtcagatcg cctggagacg ccatccacgc tgttttgacc    2760
tccatagaag acaccgactc tactagagga tctatttccg gtgaattcgc caccatgagc    2820
ctcgggctcc tgtgctgtgg ggcctttttct ctcctgtggg caggaccggt ggaagctgac    2880
atctaccaga ccccaagata ccttgttata gggacaggaa agaagatcac tctggaatgt    2940
tctcaaacca tgggccatga caaaatgtac tggtatcaac aagatccagg aatggaacta    3000
cacctcatcc actattccta tggagttaat tccacagaga agggagatct tcctctgag    3060 tcaacagtct ccagaataag gacgagcat tttcccctga ccctggagtc tgccaggccc    3120
tcacatacct ctcagtacct ctgtgccagc agtcggacgc ccaacattca gtacttcggc    3180
gccgggaccc ggctctcagt gctggaggac ctgaaaaacg tgttcccacc cgaactagtc    3240
gtgtttgagc catcagaagc agagatctcc cacacccaaa aggccacact ggtgtgcctg    3300
gccacaggct tctaccccga ccacgtggag ctgagctggt gggtgaatgg gaaggaggtg    3360
cacagtgggg tcagcacaga cccgcagccc ctcaaggagc agcccgccct caatgactcc    3420
agatactgcc tgagcagccg cctgagggtc tcggccacct tctggcagaa ccccgcaac    3480
```

-continued

```
cacttccgct gtcaagtcca gttctacggg ctctcggaga atgacgagtg gacccaggat    3540
agggccaaac ctgtcaccca gatcgtcagc gccgaggcct ggggtagagc agactgtggc    3600
ttcacctccg agtcttacca gcaaggggtc ctgtctgcca ccatcctcta tgagatcttg    3660
ctagggaagg ccaccttgta tgccgtgctg gtcagtgccc tcgtgctgat ggccatggtc    3720
aagagaaagg attccagagg cgggagcgga gccacgaact tctctctgtt aaagcaagca    3780
ggagacgtgg aagaaaaccc cggtcctatg acacgagtta gcttgctgtg ggcagtcgtg    3840
gtctccacct gtctcgagtc cggcatgggt caacagctga atcagagtcc tcaatctatg    3900
tttatccagg aaggagaaga tgtctccatg aactgcactt cttcaagcat atttaacacc    3960
tggctatggt acaagcagga acctggggaa ggtcctgtcc tcttgatagc cttatataag    4020
gctggtgaat tgacctcaaa tggaagactg actgctcagt ttggtataac cagaaaggac    4080
agcttcctga atatctcagc atccatacct agtgatgtag catctacttt ctgtgctggc    4140
acataccaga aagttacctt tggaactgga caaagctcc aagtcatccc aaatatccag    4200
aaccctgacc ctgccgtgta ccagctgaga gactctaaat ccagtgacaa gtctgtctgc    4260
ctattcaccg atttttgattc tcaaacaaat gtgtcacaaa gtaaggattc tgatgtgtat    4320
atcacagaca aaactgtgct agacatgagg tctatggact tcaagagcaa cagtgctgtg    4380
gcctggagca caaatctga cttttgcatgc gcaaacgcct tcaacaacag cattattcca    4440
gaagacacct tcttccccag cccagaaagt tcctgtgatg tcaagctggt cgagaaaagc    4500
tttgaaacag atacgaacct aaactttcaa aacctgtcag tgattgggtt ccgaatcctc    4560
ctcctgaaag tggccgggtt taatctgctc atgacgctgc ggctgtggtc cagctgactc    4620
gagggatccc gccccctctcc ctcccccccc cctaacgtta ctggccgaag ccgcttggaa    4680
taaggccggt gtgcgtttgt ctatatgtta ttttccacca tattgccgtc ttttggcaat    4740
gtgagggccc ggaaacctgg ccctgtcttc ttgacgagca ttcctagggg tctttcccct    4800
ctcgccaaag gaatgcaagg tctgttgaat gtcgtgaagg aagcagttcc tctgaagct    4860
tcttgaagac aaacaacgtc tgtagcgacc ctttgcaggc agcggaaccc cccacctggc    4920
gacaggtgcc tctgcggcca aaagccacgt gtataagata cacctgcaaa ggcggcacaa    4980
ccccagtgcc acgttgtgag ttggatagtt gtggaaagag tcaaatggct caccctcaagc    5040
gtattcaaca aggggctgaa ggatgcccag aaggtacccc attgtatggg atctgatctg    5100
gggcctcggt gcacatgctt tacatgtgtt tagtcgaggt taaaaaacgt ctaggccccc    5160
cgaaccacgg ggacgtggtt ttcctttgaa aaacacgatg ataatatggt gagcaagggc    5220
gaggaggata acatggccat catcaaggag ttcatgcgct tcaaggtgca catggagggc    5280
tccgtgaacg gccacgagtt cgagatcgag ggcgagggcg agggccgccc ctacgagggc    5340
acccagaccg ccaagctgaa ggtgaccaag ggtggccccc tgcccttcgc ctgggacatc    5400
ctgtcccctc agttcatgta cggctccaag gcctacgtga agcacccgc cgacatcccc    5460
gactacttga agctgtcctt cccccgagggc ttcaagtggg agcgcgtgat gaacttcgag    5520
gacggcggcg tggtgaccgt gacccaggac tcctccctgc aggacggcga gttcatctac    5580
aaggtgaagc tgcgcggcac caacttcccc tccgacggcc ccgtaatgca gaagaagacc    5640
atgggctggg aggcctcctc cgagcggatg taccccgagg acggcgccct gaagggcgag    5700
atcaagcaga ggctgaagct gaaggacggc ggccactacg acgctgaggt caagaccacc    5760
tacaaggcca agaagcccgt gcagctgccc ggcgcctaca acgtcaacat caagttggac    5820
atcacctccc acaacgagga ctacaccatc gtggaacagt acgaacgcgc cgagggccgc    5880
```

-continued

```
cactccaccg gcggcatgga cgagctgtac aagtgaacgc gtctggaaca atcaacctct    5940
ggattacaaa atttgtgaaa gattgactgg tattcttaac tatgttgctc cttttacgct    6000
atgtggatac gctgctttaa tgcctttgta tcatgctatt gcttcccgta tggctttcat    6060
tttctcctcc ttgtataaat cctgttgct gtctctttat gaggagttgt ggcccgttgt     6120
caggcaacgt ggcgtggtgt gcactgtgtt tgctgacgca accccactg gttgggcat      6180 tgccaccacc tgtcagctcc tttccgggac tttcgctttc ccctcccta ttgccacggc     6240 ggaactcatc gccgcctgcc ttgcccgctg ctggacaggg gctcggctgt gggcactga     6300 caattccgtg gtgttgtcgg ggaagctgac gtcctttcca tggctgctcg cctgtgttgc    6360
cacctggatt ctgcgcggga cgtccttctg ctacgtccct tcggccctca atccagcgga    6420
ccttccttcc cgcggcctgc tgccggctct gcggcctctt ccgcgtcttc gcttcgccc    6480 tcagacgagt cggatctccc tttgggccgc ctccccgcct ggaattaatt ctgcagtcga    6540
gacctagaaa aacatggagc aatcacaagt agcaatacag cagctaccaa tgctgattgt    6600
gcctggctag aagcacaaga ggaggaggag gtgggttttc cagtcacacc tcaggtacct    6660
ttaagaccaa tgacttacaa ggcagctgta gatcttagcc actttttaaa agaaaagagg    6720
ggactggaag ggctaattca ctcccaacga agacaagata tccttgatct gtggatctac    6780
cacacacaag gctacttccc tgattagcag aactacacac cagggccagg ggtcagatat    6840
ccactgacct ttggatggtg ctacaagcta gtaccagttg agccagataa ggtagaagag    6900
gccaataaag gagagaacac cagcttgtta caccctgtga gcctgcatgg gatggatgac    6960
ccggagagag aagtgttaga gtggaggttt gacagccgcc tagcatttca tcacgtggcc    7020
cgagagctgc atccggagta cttcaagaac tgctgatatc gagcttgcta caagggactt    7080
tccgctgggg actttccagg gaggcgtggc ctgggcggga ctggggagtg cgagccctc    7140 agatcctgca tataagcagc tgcttttgc ctgtactggg tctctctggt tagaccagat    7200
ctgagcctgg gagctctctg gctaactagg gaacccactg cttaagcctc aataaagctt    7260
gccttgagtg cttcaagtag tgtgtgcccg tctgttgtgt gactctggta actagagatc    7320
cctcagaccc ttttagtcag tgtggaaaat ctctagcagt agtagttcat gtcatcttat    7380
tattcagtat ttataacttg caaagaaatg aatatcagag agtgagaggc cttgacattg    7440
ctagcgttta ccgtcgacct ctagctagag cttggcgtaa tcatggtcat agctgtttcc    7500
tgtgtgaaat tgttatccgc tcacaattcc acacaacata cgagccggaa gcataaagtg    7560
taaagcctgg ggtgcctaat gagtgagcta actcacatta attgcgttgc gctcactgcc    7620
cgctttccag tcgggaaacc tgtcgtgcca gctgcattaa tgaatcggcc aacgcgcggg    7680
gagaggcggt ttgcgtattg ggcgctcttc cgcttcctcg ctcactgact cgctgcgctc    7740
ggtcgttcgg ctgcggcgag cggtatcagc tcactcaaag gcggtaatac ggttatccac    7800
agaatcaggg gataacgcag gaaagaacat gtgagcaaaa ggccagcaaa aggccaggaa    7860
ccgtaaaaag gccgcgttgc tggcgttttt ccataggctc cgcccccctg acgagcatca    7920
caaaaatcga cgctcaagtc agaggtggcg aaacccgaca ggactataaa gataccaggc    7980
gtttccccct ggaagctccc tcgtgcgctc tcctgttccg accctgccgc ttaccggata    8040
cctgtccgcc tttctccctt cgggaagcgt ggcgctttct catagctcac gctgtaggta    8100
tctcagttcg gtgtaggtcg ttcgctccaa gctgggctgt gtgcacgaac cccccgttca    8160
gcccgaccgc tgcgccttat ccggtaacta tcgtcttgag tccaacccgg taagacacga    8220
```

| | |
|---|---|
| cttatcgcca ctggcagcag ccactggtaa caggattagc agagcgaggt atgtaggcgg | 8280 |
| tgctacagag ttcttgaagt ggtggcctaa ctacggctac actagaagaa cagtatttgg | 8340 |
| tatctgcgct ctgctgaagc cagttacctt cggaaaaaga gttggtagct cttgatccgg | 8400 |
| caaacaaacc accgctggta gcggtggttt ttttgtttgc aagcagcaga ttacgcgcag | 8460 |
| aaaaaaagga tctcaagaag atcctttgat cttttctacg gggtctgacg ctcagtggaa | 8520 |
| cgaaaactca cgttaaggga ttttggtcat gagattatca aaaaggatct cacctagat | 8580 |
| cctttaaat taaaaatgaa gttttaaatc aatctaaagt atatatgagt aaacttggtc | 8640 |
| tgacagttac caatgcttaa tcagtgaggc acctatctca gcgatctgtc tatttcgttc | 8700 |
| atccatagtt gcctgactcc ccgtcgtgta gataactacg atacgggagg cttaccatc | 8760 |
| tggccccagt gctgcaatga taccgcgaga cccacgctca ccggctccag atttatcagc | 8820 |
| aataaaccag ccagccggaa gggccgagcg cagaagtggt cctgcaactt tatccgcctc | 8880 |
| catccagtct attaattgtt gccgggaagc tagagtaagt agttcgccag ttaatagttt | 8940 |
| gcgcaacgtt gttgccattg ctacaggcat cgtggtgtca cgctcgtcgt ttggtatggc | 9000 |
| ttcattcagc tccggttccc aacgatcaag gcgagttaca tgatccccca tgttgtgcaa | 9060 |
| aaaagcggtt agctccttcg gtcctccgat cgttgtcaga agtaagttgg ccgcagtgtt | 9120 |
| atcactcatg gttatggcag cactgcataa ttctcttact gtcatgccat ccgtaagatg | 9180 |
| cttttctgtg actggtgagt actcaaccaa gtcattctga atagtgta tgcggcgacc | 9240 |
| gagttgctct tgcccggcgt caatacggga taataccgcg ccacatagca gaactttaaa | 9300 |
| agtgctcatc attggaaaac gttcttcggg gcgaaaactc tcaaggatct taccgctgtt | 9360 |
| gagatccagt tcgatgtaac ccactcgtgc acccaactga tcttcagcat cttttacttt | 9420 |
| caccagcgtt tctgggtgag caaaaacagg aaggcaaaat gccgcaaaaa agggaataag | 9480 |
| ggcgacacgg aaatgttgaa tactcatact cttcctttt caatattatt gaagcattta | 9540 |
| tcagggttat tgtctcatga gcggatacat atttgaatgt atttagaaaa ataaacaaat | 9600 |
| aggggttccg cgcacatttc cccgaaaagt gccacctgac gtcgacggat cgggagatca | 9660 |
| acttgtttat tgcagcttat aatggttaca aataaagcaa tagcatcaca aatttcacaa | 9720 |
| ataaagcatt ttttcactg cattctagtt gtggtttgtc caaactcatc aatgtatctt | 9780 |
| atcatgtctg gatcaactgg ataactcaag ctaaccaaaa tcatcccaaa cttcccaccc | 9840 |
| catacctat taccactgcc aattacctgt ggtttcattt actctaaacc tgtgattcct | 9900 |
| ctgaattatt ttcattttaa agaaattgta tttgttaaat atgtactaca aacttagtag | 9960 |
| t | 9961 |

<210> SEQ ID NO 27
<211> LENGTH: 9955
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 27

| | |
|---|---|
| tggaagggct aattcactcc caagaagac aagatatcct tgatctgtgg atctaccaca | 60 |
| cacaaggcta cttccctgat tagcagaact acacaccagg gccagggtc agatatccac | 120 |
| tgacctttgg atggtgctac aagctagtac cagttgagcc agataaggta gaagaggcca | 180 |
| ataaaggaga gaacaccagc ttgttacacc ctgtgagcct gcatgggatg gatgacccgg | 240 |

```
agagagaagt gttagagtgg aggtttgaca gccgcctagc atttcatcac gtggcccgag      300
agctgcatcc ggagtacttc aagaactgct gatatcgagc ttgctacaag ggactttccg      360
ctggggactt tccagggagg cgtggcctgg gcgggactgg ggagtggcga gccctcagat      420
cctgcatata agcagctgct ttttgcctgt actgggtctc tctggttaga ccagatctga      480
gcctgggagc tctctggcta actagggaac ccactgctta agcctcaata aagcttgcct      540
tgagtgcttc aagtagtgtg tgcccgtctg ttgtgtgact ctggtaacta gagatccctc      600
agaccctttt agtcagtgtg gaaaatctct agcagtggcg cccgaacagg gacttgaaag      660
cgaaagggaa accagaggag ctctctcgac gcaggactcg gcttgctgaa gcgcgcacgg      720
caagaggcga ggggcggcga ctggtgagta cgccaaaaat tttgactagc ggaggctaga      780
aggagagaga tgggtgcgag agcgtcagta ttaagcgggg gagaattaga tcgcgatggg      840
aaaaaattcg gttaaggcca gggggaaaga aaaaatataa attaaaacat atagtatggg      900
caagcaggga gctagaacga ttcgcagtta atcctggcct gttagaaaca tcagaaggct      960
gtagacaaat actgggacag ctacaaccat cccttcagac aggatcagaa gaacttagat     1020
cattatataa tacagtagca accctctatt gtgtgcatca aaggatagag ataaaagaca     1080
ccaaggaagc tttagacaag atagaggaag agcaaaacaa aagtaagacc accgcacagc     1140
aagcggccgg ccgctgatct tcagacctgg aggaggagat atgagggaca attggagaag     1200
tgaattatat aaatataaag tagtaaaaat tgaaccatta ggagtagcac ccaccaaggc     1260
aaagagaaga gtggtgcaga gagaaaaaag agcagtggga ataggagctt tgttccttgg     1320
gttcttggga gcagcaggaa gcactatggg cgcagcgtca atgacgctga cggtacaggc     1380
cagacaatta ttgtctggta tagtgcagca gcagaacaat ttgctgaggg ctattgaggc     1440
gcaacagcat ctgttgcaac tcacagtctg gggcatcaag cagctccagg caagaatcct     1500
ggctgtggaa agatacctaa aggatcaaca gctcctgggg atttggggtt gctctggaaa     1560
actcatttgc accactgctg tgccttggaa tgctagttgg agtaataaat ctctggaaca     1620
gatttggaat cacacgacct ggatggagtg ggacagagaa attaacaatt acacaagctt     1680
aatacactcc ttaattgaag aatcgcaaaa ccagcaagaa aagaatgaac aagaattatt     1740
ggaattagat aaatgggcaa gtttgtggaa ttggtttaac ataacaaatt ggctgtggta     1800
tataaaatta ttcataatga tagtaggagg cttggtaggt ttaagaatag ttttgctgt      1860 actttctata gtgaatagag ttaggcaggg atattcacca ttatcgtttc agacccacct     1920
cccaaccccg aggggacccg acaggcccga aggaatagaa gaagaaggtg gagagagaga     1980
cagagacaga tccattcgat tagtgaacgg atctcgacgg tatcgccttt aaaagaaaag     2040
gggggattgg ggggtacagt gcaggggaaa gaatagtaga cataatagca acagacatac     2100
aaactaaaga attacaaaaa caaattacaa aaattcaaaa ttttcgggtt tattacaggg     2160
acagcagaga tccagtttat cgataagctt gggagttccg cgttacataa cttacggtaa     2220
atggcccgcc tggctgaccg cccaacgacc cccgcccatt gacgtcaata atgacgtatg     2280
ttcccatagt aacgccaata gggactttcc attgacgtca atgggtggag tatttacggt     2340
aaactgccca cttggcagta catcaagtgt atcatatgcc aagtacgccc cctattgacg     2400
tcaatgacgg taaatggccc gcctggcatt atgcccagta catgacctta tgggactttc     2460
ctacttggca gtacatctac gtattagtca tcgctattac catggtgatg cggttttggc     2520
agtacatcaa tgggcgtgga tagcggtttg actcacgggg atttccaagt ctccacccca     2580
ttgacgtcaa tgggagtttg ttttggcacc aaaatcaacg ggactttcca aatgtcgta       2640
```

-continued

```
acaactccgc cccattgacg caaatgggcg gtaggcgtgt acggtgggag gtctatataa    2700
gcagagctcg tttagtgaac cgtcagatcg cctggagacg ccatccacgc tgttttgacc    2760
tccatagaag acaccgactc tactagagga tctatttccg gtgaattcgc caccatggga    2820
cccaggctcc tcttctgggc actgcttttgt ctcctcggaa ccggtccggt tgaagctgac    2880
atctaccaga ccccaagata ccttgttata gggacaggaa agaagatcac tctggaatgt    2940
tctcaaacca tgggccatga caaaatgtac tggtatcaac aagatccagg aatgaaacta    3000
cacctcatcc actattccta tggagttaat ccacagagaa agggagatct ttcctctgag    3060
tcaacagtct ccagaataag gacgagcat tttcccctga ccctggagtc tgccaggccc    3120
tcacatacct ctcagtacct ctgtgccagc agtcggacgc ccaacattca gtacttcggc    3180
gccgggaccc ggctctcagt gctggaggac ctgaaaaacg tgttcccacc cgaggcggcc    3240
gcgtttgagc catcagaagc agagatctcc cacacccaaa aggccacact ggtgtgcctg    3300
gccacaggct tctaccccga ccacgtggag ctgagctggt gggtgaatgg gaaggaggtg    3360
cacagtgggg tcagcacaga cccgcagccc ctcaaggagc agcccgccct caatgactcc    3420
agatactgcc tgagcagccg cctgagggtc tcggccacct tctggcagaa ccccgcaac    3480
cacttccgct gtcaagtcca gttctacggg ctctcggaga atgacgagtg gacccaggat    3540
agggccaaac ctgtcaccca gatcgtcagc gccgaggcct ggggtagagc agactgtggc    3600
ttcacctccg agtcttacca gcaaggggtc ctgtctgcca ccatcctcta tgagatcttg    3660
ctagggaagg ccaccttgta tgccgtgctg gtcagtgccc tcgtgctgat ggccatggtc    3720
aagagaaagg attccagagg cgggagcgga gccacgaact tctctctgtt aaagcaagca    3780
ggagacgtgg aagaaaaccc cggtcctatg aactcctctc tggactttct aattctgatc    3840
ttaatgtttg gaggaactag tggtcaacag ctgaatcaga gtcctcaatc tatgtttatc    3900
caggaaggag aagatgtctc catgaactgc acttcttcaa gcatatttaa cacctggcta    3960
tggtacaagc aggaacctgg ggaaggtcct gtcctcttga tagccttata taaggctggt    4020
gaattgacct caaatggaag actgactgct cagtttggta taaccagaaa ggacagcttc    4080
ctgaatatct cagcatccat acctagtgat gtaggcatct acttctgtgc tggcacatac    4140
cagaaagtta cctttggaac tggaacaaag ctccaagtca tcccaaatat ccagaaccct    4200
gaccctgccg tgtaccagct gagagactct aaatccagtg acaagtctgc atgcctattc    4260
accgattttg attctcaaac aaatgtgtca caaagtaagg attctgatgt gtatatcaca    4320
gacaaaactg tgctagacat gaggtctatg gacttcaaga gcaacagtgc tgtggcctgg    4380
agcaacaaat ctgactttgc atgtgcaaac gccttcaaca acagcattat tccagaagac    4440
accttcttcc ccagcccaga aagttcctgt gatgtcaagc tggtcgagaa aagctttgaa    4500
acagatacga acctaaactt tcaaaacctg tcagtgattg ggttccgaat cctcctcctg    4560
aaagtggccg gttttaatct gctcatgacg ctgcggctgt ggtccagctg actgaggga    4620
tcccgcccct ctccctcccc ccccctaac gttactggcc gaagccgctt ggaataaggc    4680
cggtgtgcgt ttgtctatat gttattttcc accatattgc cgtcttttgg caatgtgagg    4740
gcccggaaac ctggccctgt cttccttgacg agcattccta ggggtctttc ccctctcgcc    4800
aaaggaatgc aaggtctgtt gaatgtcgtg aaggaagcag ttcctctgga agcttcttga    4860
agacaaacaa cgtctgtagc gaccctttgc aggcagcgga accccccacc tggcgacagg    4920
tgcctctgcg gccaaaagcc acgtgtataa gatacacctg caaaggcggc acaaccccag    4980
```

```
tgccacgttg tgagttggat agttgtggaa agagtcaaat ggctcacctc aagcgtattc    5040
aacaaggggc tgaaggatgc ccagaaggta ccccattgta tgggatctga tctggggcct    5100
cggtgcacat gctttacatg tgtttagtcg aggttaaaaa acgtctaggc cccccgaacc    5160
acggggacgt ggttttcctt tgaaaaacac gatgataata tggtgagcaa gggcgaggag    5220
gataacatgg ccatcatcaa ggagttcatg cgcttcaagg tgcacatgga gggctccgtg    5280
aacggccacg agttcgagat cgagggcgag ggcgagggcc gcccctacga gggcacccag    5340
accgccaagc tgaaggtgac caagggtggc cccctgccct cgcctggga catcctgtcc    5400 cctcagttca tgtacggctc caaggcctac gtgaagcacc ccgccgacat ccccgactac    5460
ttgaagctgt ccttccccga gggcttcaag tgggagcgcg tgatgaactt cgaggacggc    5520
ggcgtggtga ccgtgaccca ggactcctcc ctgcaggacg gcgagttcat ctacaaggtg    5580
aagctgcgcg gcaccaactt cccctccgac ggccccgtaa tgcagaagaa gaccatgggc    5640
tgggaggcct cctccgagcg gatgtacccc gaggacggcg ccctgaaggg cgagatcaag    5700
cagaggctga agctgaagga cggcggccac tacgacgctg aggtcaagac cacctacaag    5760
gccaagaagc ccgtgcagct gcccggcgcc tacaacgtca acatcaagtt ggacatcacc    5820
tcccacaacg aggactacac catcgtggaa cagtacgaac gcgccgaggg ccgccactcc    5880
accggcggca tggacgagct gtacaagtga acgcgtctgg aacaatcaac ctctggatta    5940
caaaatttgt gaaagattga ctggtattct taactatgtt gctcctttta cgctatgtgg    6000
atacgctgct ttaatgcctt tgtatcatgc tattgcttcc cgtatggctt tcatttttctc    6060 ctccttgtat aaatcctggt tgctgtctct ttatgaggag ttgtggcccg ttgtcaggca    6120
acgtggcgtg gtgtgcactg tgtttgctga cgcaaccccc actggttggg gcattgccac    6180
cacctgtcag ctccttttccg ggactttcgc tttccccctc cctattgcca cggcggaact    6240
catcgccgcc tgccttgccc gctgctggac aggggctcgg ctgttgggca ctgacaattc    6300
cgtggtgttg tcggggaagc tgacgtcctt ccatggctg ctcgcctgtg ttgccacctg    6360
gattctgcgc gggacgtcct tctgctacgt cccttcggcc ctcaatccag cggaccttcc    6420
ttcccgcggc ctgctgccgg ctctgcggcc tcttccgcgt cttcgccttc gccctcagac    6480
gagtcggatc tccctttggg ccgcctcccc gcctggaatt aattctgcag tcgagaccta    6540
gaaaaacatg gagcaatcac aagtagcaat acagcagcta ccaatgctga ttgtgcctgg    6600
ctagaagcac aagaggagga ggaggtgggt tttccagtca cacctcaggt acctttaaga    6660
ccaatgactt acaaggcagc tgtagatctt agccacttttt aaaagaaaaa gggggactg    6720 gaagggctaa ttcactccca acgaagacaa gatatccttg atctgtggat ctaccacaca    6780
caaggctact cccctgatta gcagaactac acaccagggc cagggatcag atatccactg    6840
acctttggat ggtgctacaa gctagtacca gttgagccag ataaggtaga agaggccaat    6900
aaaggagaga acaccagctt gttacaccct gtgagcctgc atgggatgga tgacccggag    6960
agagaagtgt tagagtggag gtttgacagc cgcctagcat ttcatcacgt ggcccgagag    7020
ctgcatccgg agtacttcaa gaactgctga tatcgagctt gctacaaggg actttccgct    7080
ggggactttc cagggaggcg tggcctgggc gggactgggg agtggcgagc cctcagatcc    7140
tgcatataag cagctgcttt ttgcctgtac tgggtctctc tggttagacc agatctgagc    7200
ctgggagctc tctggctaac tagggaaccc actgcttaag cctcaataaa gcttgccttg    7260
agtgcttcaa gtagtgtgtg cccgtctgtt gtgtgactct ggtaactaga gatccctcag    7320
acccttttag tcagtgtgga aaatctctag cagtagtagt tcatgtcatc ttattattca    7380
```

```
gtatttataa cttgcaaaga aatgaatatc agagagtgag aggcctttgac attgctagcg    7440
tttaccgtcg acctctagct agagcttggc gtaatcatgg tcatagctgt ttcctgtgtg    7500
aaattgttat ccgctcacaa ttccacacaa catacgagcc ggaagcataa agtgtaaagc    7560
ctggggtgcc taatgagtga gctaactcac attaattgcg ttgcgctcac tgcccgcttt    7620
ccagtcggga aacctgtcgt gccagctgca ttaatgaatc ggccaacgcg cggggagagg    7680
cggtttgcgt attgggcgct cttccgcttc ctcgctcact gactcgctgc gctcggtcgt    7740
tcggctgcgg cgagcggtat cagctcactc aaaggcggta atacggttat ccacagaatc    7800
aggggataac gcaggaaaga acatgtgagc aaaaggccag caaaaggcca ggaaccgtaa    7860
aaaggccgcg ttgctggcgt ttttccatag gctccgcccc cctgacgagc atcacaaaaa    7920
tcgacgctca agtcagaggt ggcgaaaccc gacaggacta taaagatacc aggcgtttcc    7980
ccctggaagc tccctcgtgc gctctcctgt tccgaccctg ccgcttaccg gatacctgtc    8040
cgcctttctc ccttcgggaa gcgtggcgct ttctcatagc tcacgctgta ggtatctcag    8100
ttcggtgtag gtcgttcgct ccaagctggg ctgtgtgcac gaaccccccg ttcagcccga    8160
ccgctgcgcc ttatccggta actatcgtct tgagtccaac ccggtaagac acgacttatc    8220
gccactggca gcagccactg gtaacaggat tagcagagcg aggtatgtag gcggtgctac    8280
agagttcttg aagtggtggc ctaactacgg ctacactaga agaacagtat ttggtatctg    8340
cgctctgctg aagccagtta ccttcggaaa aagagttggt agctcttgat ccggcaaaca    8400
aaccaccgct ggtagcggtg gtttttttgt ttgcaagcag cagattacgc gcagaaaaaa    8460
aggatctcaa gaagatcctt tgatcttttc tacggggtct gacgctcagt ggaacgaaaa    8520
ctcacgttaa gggattttgg tcatgagatt atcaaaaagg atcttcacct agatcctttt    8580
aaattaaaaa tgaagtttta atcaatcta aagtatatat gagtaaactt ggtctgacag    8640
ttaccaatgc ttaatcagtg aggcaccat ctcagcgatc tgtctatttc gttcatccat    8700
agttgcctga ctccccgtcg tgtagataac tacgatacgg gagggcttac catctggccc    8760
cagtgctgca atgataccgc gagacccacg ctcaccggct ccagatttat cagcaataaa    8820
ccagccagcc ggaagggccg agcgcagaag tggtcctgca actttatccg cctccatcca    8880
gtctattaat tgttgccggg aagctagagt aagtagttcg ccagttaata gtttgcgcaa    8940
cgttgttgcc attgctacag gcatcgtggt gtcacgctcg tcgtttggta tggcttcatt    9000
cagctccggt tcccaacgat caaggcgagt tacatgatcc cccatgttgt gcaaaaaagc    9060
ggttagctcc ttcggtcctc cgatcgttgt cagaagtaag ttggccgcag tgttatcact    9120
catggttatg gcagcactgc ataattctct tactgtcatg ccatccgtaa gatgcttttc    9180
tgtgactggt gagtactcaa ccaagtcatt ctgagaatag tgtatgcggc gaccgagttg    9240
ctcttgcccg gcgtcaatac gggataatac cgcgccacat agcagaactt taaaagtgct    9300
catcattgga aaacgttctt cggggcgaaa actctcaagg atcttaccgc tgttgagatc    9360
cagttcgatg taacccactc gtgcacccaa ctgatcttca gcatctttta ctttcaccag    9420
cgtttctggg tgagcaaaaa caggaaggca aaatgccgca aaaagggaa taagggcgac    9480
acggaaatgt tgaatactca tactcttcct ttttcaatat tattgaagca tttatcaggg    9540
ttattgtctc atgagcggat acatatttga atgtatttag aaaaataaac aatagggt    9600
tccgcgcaca tttccccgaa aagtgccacc tgacgtcgac ggatcgggag atcaacttgt    9660
ttattgcagc ttataatggt tacaaataaa gcaatagcat cacaaatttc acaaataaag    9720
```

-continued

| | |
|---|---|
| catttttttc actgcattct agttgtggtt tgtccaaact catcaatgta tcttatcatg | 9780 |
| tctggatcaa ctggataact caagctaacc aaaatcatcc caaacttccc accccatacc | 9840 |
| ctattaccac tgccaattac ctgtggtttc atttactcta aacctgtgat tcctctgaat | 9900 |
| tattttcatt ttaaagaaat tgtatttgtt aaatatgtac tacaaactta gtagt | 9955 |

<210> SEQ ID NO 28
<211> LENGTH: 9961
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 28

| | |
|---|---|
| tggaagggct aattcactcc caaagaagac aagatatcct tgatctgtgg atctaccaca | 60 |
| cacaaggcta cttccctgat tagcagaact acacaccagg gccagggggtc agatatccac | 120 |
| tgacctttgg atggtgctac aagctagtac cagttgagcc agataaggta gaagaggcca | 180 |
| ataaaggaga gaacaccagc ttgttacacc ctgtgagcct gcatgggatg gatgacccgg | 240 |
| agagagaagt gttagagtgg aggtttgaca gccgcctagc atttcatcac gtggcccgag | 300 |
| agctgcatcc ggagtacttc aagaactgct gatatcgagc ttgctacaag gactttccg | 360 |
| ctggggactt tccagggagg cgtggcctgg gcgggactgg ggagtggcga gccctcagat | 420 |
| cctgcatata agcagctgct ttttgcctgt actgggtctc tctggttaga ccagatctga | 480 |
| gcctgggagc tctctggcta actagggaac ccactgctta agcctcaata agcttgcct | 540 |
| tgagtgcttc aagtagtgtg tgcccgtctg ttgtgtgact ctggtaacta gagatccctc | 600 |
| agacccttt agtcagtgtg aaaatctct agcagtggcg cccgaacagg gacttgaaag | 660 |
| cgaaagggaa accagaggag ctctctcgac gcaggactcg gcttgctgaa gcgcgcacgg | 720 |
| caagaggcga ggggcggcga ctggtgagta cgccaaaaat tttgactagc ggaggctaga | 780 |
| aggagagaga tgggtgcgag agcgtcagta ttaagcgggg gagaattaga tcgcgatggg | 840 |
| aaaaaattcg gttaaggcca ggggggaaga aaaaatataa attaaaacat atagtatggg | 900 |
| caagcaggga gctagaacga ttcgcagtta atcctggcct gttagaaaca tcagaaggct | 960 |
| gtagacaaat actgggacag ctacaaccat cccttcagac aggatcagaa gaacttagat | 1020 |
| cattatataa tacagtagca accctctatt gtgtgcatca aaggatagag ataaaagaca | 1080 |
| ccaaggaagc tttagacaag atagaggaag agcaaaacaa aagtaagacc accgcacagc | 1140 |
| aagcggccgg ccgctgatct tcagacctgg aggaggagat atgagggaca attggagaag | 1200 |
| tgaattatat aaatataaag tagtaaaaat tgaaccatta ggagtagcac ccaccaaggc | 1260 |
| aaagagaaga gtggtgcaga gagaaaaaag agcagtggga ataggagctt tgttccttgg | 1320 |
| gttcttggga gcagcaggaa gcactatggg cgcagcgtca atgacgctga cggtacaggc | 1380 |
| cagacaatta ttgtctggta tagtgcagca gcagaacaat ttgctgaggg ctattgaggc | 1440 |
| gcaacagcat ctgttgcaac tcacagtctg ggcatcaag cagctccagg caagaatcct | 1500 |
| ggctgtggaa agatacctaa aggatcaaca gctcctgggg atttggggtt gctctggaaa | 1560 |
| actcatttgc accactgctg tgccttggaa tgctagttgg agtaataaat ctctggaaca | 1620 |
| gatttggaat cacacgacct ggatggagtg gacagagaa attaacaatt acacaagctt | 1680 |
| aatacactcc ttaattgaag aatcgcaaaa ccagcaagaa aagaatgaac aagaattatt | 1740 |
| ggaattagat aaatgggcaa gtttgtggaa ttggtttaac ataacaaatt ggctgtggta | 1800 |

```
tataaaatta ttcataatga tagtaggagg cttggtaggt ttaagaatag tttttgctgt   1860
actttctata gtgaatagag ttaggcaggg atattcacca ttatcgtttc agacccacct   1920
cccaaccccg aggggacccg acaggcccga aggaatagaa gaagaaggtg gagagagaga   1980
cagagacaga tccattcgat tagtgaacgg atctcgacgg tatcgccttt aaaagaaaag   2040
gggggattgg ggggtacagt gcaggggaaa gaatagtaga cataatagca acagacatac   2100
aaactaaaga attacaaaaa caaattacaa aaattcaaaa ttttcgggtt tattacaggg   2160
acagcagaga tccagtttat cgataagctt gggagttccg cgttacataa cttacggtaa   2220
atggcccgcc tggctgaccg cccaacgacc cccgcccatt gacgtcaata atgacgtatg   2280
ttcccatagt aacgccaata gggactttcc attgacgtca atgggtggag tatttacggt   2340
aaactgccca cttggcagta catcaagtgt atcatatgcc aagtacgccc cctattgacg   2400
tcaatgacgg taaatggccc gcctggcatt atgcccagta catgacctta tgggactttc   2460
ctacttggca gtacatctac gtattagtca tcgctattac catggtgatg cggttttggc   2520
agtacatcaa tgggcgtgga tagcggtttg actcacgggg atttccaagt ctccacccca   2580
ttgacgtcaa tgggagtttg ttttggcacc aaaatcaacg ggactttcca aatgtcgta   2640 acaactccgc cccattgacg caaatgggcg gtaggcgtgt acggtgggag gtctatataa   2700
gcagagctcg tttagtgaac cgtcagatcg cctggagacg ccatccacgc tgttttgacc   2760
tccatagaag acaccgactc tactagagga tctatttccg gtgaattcgc caccatgggc   2820
acaaggttgt tcttctatgt ggccctttgt ctcctgtgga ccggtcacat ggaagctgac   2880
atctaccaga ccccaagata ccttgttata gggacaggaa agaagatcac tctggaatgt   2940
tctcaaacca tgggccatga caaaatgtac tggtatcaac aagatccagg aatggaacta   3000
cacctcatcc actattccta tggagttaat tccacagaga agggagatct ttcctctgag   3060
tcaacagtct ccagaataag gacggagcat tttcccctga ccctggagtc tgccaggccc   3120
tcacataccT ctcagtacct ctgtgccagc agtcggacgc ccaacattca gtacttcggc   3180
gccgggaccc ggctctcagt gctggaggac ctgaaaaacg tgttcccacc cgaggtcgct   3240
gtgtttgagc catcagaagc agagatctcc cacacccaaa aggccacact agtgtgcctg   3300
gccacaggct tctaccccga ccacgtggag ctgagctggt gggtgaatgg gaaggaggtg   3360
cacagtgggg tcagcacaga cccgcagccc tcaaggagc agcccgccct caatgactcc   3420
agatactgcc tgagcagccg cctgagggtc tcggccacct tctggcagaa ccccgcaac   3480 cacttccgct gtcaagtcca gttctacggg ctctcggaga tgacgagtg gacccaggat   3540 agggccaaac ctgtcaccca gatcgtcagc gccgaggcct ggggtagagc agactgtggc   3600
ttcacctccg agtcttacca gcaagggtc ctgtctgcca ccatcctcta tgagatcttg   3660
ctagggaagg ccaccttgta tgccgtgctg gtcagtgccc tcgtgctgat ggccatggtc   3720
aagagaaagg attccagagg cgggagcgga gccacgaact tctctctgtt aaagcaagca   3780
ggagacgtgg aagaaaaccc cggtcctatg gcaggcattc gagctttatt tatgtacttg   3840
tggctgcagc tggactgggt ctcgagaggt caacagctga atcagagtcc tcaatctatg   3900
tttatccagg aaggagaaga tgtctccatg aactgcactt cttcaagcat atttaacacc   3960
tggctatggt acaagcagga acctgggaa ggtcctgtcc tcttgatagc cttatataag   4020
gctggtgaat tgacctcaaa tggaagactg actgctcagt ttggtataac cagaaaggac   4080
agcttcctga tatctcagc atccatacct agtgatgtag catctactt ctgtgctggc   4140 acataccaga aagttacctt tggaactgga acaaagctcc aagtcatccc aaatatccag   4200
```

```
aaccctgacc ctgccgtgta ccagctgaga gactctaaat ccagtgacaa gtctgtctgc    4260
ctattcaccg attttgattc tcaaacaaat gtgtcacaaa gtaaggattc tgatgtgtat    4320
atcacagaca aaactgtgct agacatgagg tctatggact tcaagagcaa cagtgcggcc    4380
gcctggagca acaaatctga ctttgcatgt gcaaacgcct tcaacaacag cattattcca    4440
gaagacacct tcttccccag cccagaaagt tcctgtgatg tcaagctggt cgagaaaagc    4500
tttgaaacag atacgaacct aaactttcaa aacctgtcag tgattgggtt ccgaatcctc    4560
ctcctgaaag tggccgggtt taatctgctc atgacgctgc ggctgtggtc cagctgactc    4620
gagggatccc gccctctcc ctcccccccc cctaacgtta ctggccgaag ccgcttggaa    4680
taaggccggt gtgcgtttgt ctatatgtta ttttccacca tattgccgtc ttttggcaat    4740
gtgagggccc ggaaacctgg ccctgtcttc ttgacgagca ttcctagggg tctttcccct    4800
ctcgccaaag gaatgcaagg tctgttgaat gtcgtgaagg aagcagttcc tctggaagct    4860
tcttgaagac aaacaacgtc tgtagcgacc ctttgcaggc agcggaaccc cccacctggc    4920
gacaggtgcc tctgcggcca aaagccacgt gtataagata cacctgcaaa ggcggcacaa    4980
ccccagtgcc acgttgtgag ttggatagtt gtggaaagag tcaaatggct cacctcaagc    5040
gtattcaaca aggggctgaa ggatgcccag aaggtacccc attgtatggg atctgatctg    5100
gggcctcggt gcacatgctt tacatgtgtt tagtcgaggt taaaaaacgt ctaggccccc    5160
cgaaccacgg ggacgtggtt ttcctttgaa aaacacgatg ataatatggt gagcaagggc    5220
gaggaggata acatggccat catcaaggag ttcatgcgct tcaaggtgca catggagggc    5280
tccgtgaacg gccacgagtt cgagatcgag ggcgagggcg agggccgccc ctacgagggc    5340
acccagaccg ccaagctgaa ggtgaccaag ggtggcccc tgcccttcgc ctgggacatc    5400
ctgtcccctc agttcatgta cggctccaag gcctacgtga agcaccccgc cgacatcccc    5460
gactacttga agctgtcctt ccccgagggc ttcaagtggg agcgcgtgat gaacttcgag    5520
gacggcggcg tggtgaccgt gacccaggac tcctccctgc aggacggcga gttcatctac    5580
aaggtgaagc tgcgcggcac caacttcccc tccgacggcc ccgtaatgca gaagaagacc    5640
atgggctggg aggcctcctc cgagcggatg taccccgagg acggcgccct gaagggcgag    5700
atcaagcaga ggctgaagct gaaggacggc ggccactacg acgctgaggt caagaccacc    5760
tacaaggcca agaagcccgt gcagctgccc ggcgcctaca acgtcaacat caagttggac    5820
atcacctccc acaacgagga ctacaccatc gtggaacagt acgaacgcgc cgagggccgc    5880
cactccaccg gcggcatgga cgagctgtac aagtgaacgc gtctggaaca atcaacctct    5940
ggattacaaa atttgtgaaa gattgactgg tattcttaac tatgttgctc cttttacgct    6000
atgtggatac gctgctttaa tgcctttgta tcatgctatt gcttcccgta tggctttcat    6060
tttctcctcc ttgtataaat cctggttgct gtctctttat gaggagttgt ggcccgttgt    6120
caggcaacgt ggcgtggtgt gcactgtgtt tgctgacgca accccactg gttgggcat    6180 tgccaccacc tgtcagctcc tttccgggac tttcgctttc ccctcccta ttgccacggc    6240 ggaactcatc gccgcctgcc ttgcccgctg ctggacaggg gctcggctgt tgggcactga    6300
caattccgtg gtgttgtcgg ggaagctgac gtcctttcca tggctgctcg cctgtgttgc    6360
cacctggatt ctgcgcggga cgtccttctg ctacgtccct tcggccctca atccagcgga    6420
ccttccttcc cgcggcctgc tgccggtctc gcggcctctt ccgcgtcttc gccttcgccc    6480
tcagacgagt cggatctccc tttgggccgc ctccccgcct ggaattaatt ctgcagtcga    6540
```

```
gacctagaaa aacatggagc aatcacaagt agcaatacag cagctaccaa tgctgattgt    6600
gcctggctag aagcacaaga ggaggaggag gtgggttttc cagtcacacc tcaggtacct    6660
ttaagaccaa tgacttacaa ggcagctgta gatcttagcc acttttaaa agaaaagagg    6720 ggactggaag ggctaattca ctcccaacga agacaagata tccttgatct gtggatctac    6780
cacacacaag gctacttccc tgattagcag aactacacac cagggccagg ggtcagatat    6840
ccactgacct ttggatggtg ctacaagcta gtaccagttg agccagataa ggtagaagag    6900
gccaataaag gagagaacac cagcttgtta caccctgtga gcctgcatgg gatggatgac    6960
ccggagagag aagtgttaga gtggaggttt gacagccgcc tagcatttca tcacgtggcc    7020
cgagagctgc atccggagta cttcaagaac tgctgatatc gagcttgcta caagggactt    7080
tccgctgggg actttccagg gaggcgtggc ctgggcggga ctgggagtg gcgagccctc    7140 agatcctgca tataagcagc tgcttttgc ctgtactggg tctctctggt tagaccagat    7200
ctgagcctgg gagctctctg gctaactagg gaacccactg cttaagcctc aataaagctt    7260
gccttgagtg cttcaagtag tgtgtgcccg tctgttgtgt gactctggta actagagatc    7320
cctcagaccc ttttagtcag tgtggaaaat ctctagcagt agtagttcat gtcatcttat    7380
tattcagtat ttataacttg caaagaaatg aatatcagag agtgagaggc cttgacattg    7440
ctagcgttta ccgtcgacct ctagctagag cttggcgtaa tcatggtcat agctgtttcc    7500
tgtgtgaaat tgttatccgc tcacaattcc acacaacata cgagccggaa gcataaagtg    7560
taaagcctgg ggtgcctaat gagtgagcta actcacatta attgcgttgc gctcactgcc    7620
cgctttccag tcgggaaacc tgtcgtgcca gctgcattaa tgaatcggcc aacgcgcggg    7680
gagaggcggt ttgcgtattg ggcgctcttc cgcttcctcg ctcactgact cgctgcgctc    7740
ggtcgttcgg ctgcggcgag cggtatcagc tcactcaaag gcggtaatac ggttatccac    7800
agaatcaggg gataacgcag gaaagaacat gtgagcaaaa ggccagcaaa aggccaggaa    7860
ccgtaaaaag gccgcgttgc tggcgttttt ccataggctc cgcccccctg acgagcatca    7920
caaaaatcga cgctcaagtc agaggtggcg aaacccgaca ggactataaa gataccaggc    7980
gtttccccct ggaagctccc tcgtgcgctc tcctgttccg accctgccgc ttaccggata    8040
cctgtccgcc tttctccctt cgggaagcgt ggcgctttct catagctcac gctgtaggta    8100
tctcagttcg gtgtaggtcg ttcgctccaa gctgggctgt gtgcacgaac cccccgttca    8160
gcccgaccgc tgcgccttat ccggtaacta tcgtcttgag tccaacccgg taagacacga    8220
cttatcgcca ctggcagcag ccactggtaa caggattagc agagcgaggt atgtaggcgg    8280
tgctacagag ttcttgaagt ggtggcctaa ctacggctac actagaagaa cagtatttgg    8340
tatctgcgct ctgctgaagc cagttacctt cggaaaaaga gttggtagct cttgatccgg    8400
caaacaaacc accgctggta gcggtggttt ttttgtttgc aagcagcaga ttacgcgcag    8460
aaaaaaagga tctcaagaag atcctttgat cttttctacg gggtctgacg ctcagtggaa    8520
cgaaaactca cgttaaggga ttttggtcat gagattatca aaaaggatct tcacctagat    8580
ccttttaaat taaaaatgaa gttttaaatc aatctaaagt atatatgagt aaacttggtc    8640
tgacagttac caatgcttaa tcagtgaggc acctatctca gcgatctgtc tatttcgttc    8700
atccatagtt gcctgactcc ccgtcgtgta gataactacg atacgggagg gcttaccatc    8760
tggccccagt gctgcaatga taccgcgaga cccacgctca ccggctccag atttatcagc    8820
aataaaccag ccagccggaa gggccgagcg cagaagtggt cctgcaactt tatccgcctc    8880
catccagtct attaattgtt gccgggaagc tagagtaagt agttcgccag ttaatagttt    8940
```

```
gcgcaacgtt gttgccattg ctacaggcat cgtggtgtca cgctcgtcgt ttggtatggc    9000
ttcattcagc tccggttccc aacgatcaag gcgagttaca tgatccccca tgttgtgcaa    9060
aaaagcggtt agctccttcg gtcctccgat cgttgtcaga agtaagttgg ccgcagtgtt    9120
atcactcatg gttatggcag cactgcataa ttctcttact gtcatgccat ccgtaagatg    9180
cttttctgtg actggtgagt actcaaccaa gtcattctga aatagtgta tgcggcgacc     9240 gagttgctct tgcccggcgt caatacggga taataccgcg ccacatagca gaactttaaa    9300
agtgctcatc attggaaaac gttcttcggg gcgaaaactc tcaaggatct taccgctgtt    9360
gagatccagt tcgatgtaac ccactcgtgc acccaactga tcttcagcat cttttacttt    9420
caccagcgtt tctgggtgag caaaaacagg aaggcaaaat gccgcaaaaa agggaataag    9480
ggcgacacgg aaatgttgaa tactcatact cttcctttt caatattatt gaagcattta     9540
tcagggttat tgtctcatga gcggatacat atttgaatgt atttagaaaa ataaacaaat    9600
aggggttccg cgcacatttc cccgaaaagt gccacctgac gtcgacggat cgggagatca    9660
acttgtttat tgcagcttat aatggttaca ataaagcaa tagcatcaca aatttcacaa    9720
ataaagcatt ttttcactg cattctagtt gtggtttgtc caaactcatc aatgtatctt    9780
atcatgtctg gatcaactgg ataactcaag ctaaccaaaa tcatcccaaa cttcccaccc    9840 catccctat taccactgcc aattacctgt ggtttcattt actctaaacc tgtgattcct     9900
ctgaattatt ttcattttaa agaaattgta tttgttaaat atgtactaca aacttagtag    9960
t                                                                    9961

<210> SEQ ID NO 29
<211> LENGTH: 9961
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
tggaagggct aattcactcc caaagaagac aagatatcct tgatctgtgg atctaccaca      60
cacaaggcta cttccctgat tagcagaact acacaccagg gccagggtc agatatccac      120 tgacctttgg atggtgctac aagctagtac cagttgagcc agataaggta gaagaggcca     180
ataaaggaga gaacaccagc ttgttacacc ctgtgagcct gcatgggatg gatgacccgg     240
agagagaagt gttagagtgg aggtttgaca gccgcctagc atttcatcac gtgcccgag     300 agctgcatcc ggagtacttc aagaactgct gatatcgagc ttgctacaag ggactttccg    360
ctggggactt tccagggagg cgtggcctgg gcgggactgg ggagtggcga gccctcagat    420
cctgcatata agcagctgct ttttgcctgt actgggtctc tctggttaga ccagatctga    480
gcctgggagc tctctggcta actagggaac ccactgctta agcctcaata agcttgcct    540 tgagtgcttc aagtagtgtg tgcccgtctg ttgtgtgact ctggtaacta gagatccctc    600 agacccttt agtcagtgtg gaaaatctct agcagtggcg cccgaacagg gacttgaaag     660
cgaaagggaa accagaggag ctctctcgac gcaggactcg gcttgctgaa gcgcgcacgg    720
caagaggcga ggggcggcga ctggtgagta cgccaaaaat tttgactagc ggaggctaga    780
aggagagaga tgggtgcgag agcgtcagta ttaagcgggg gagaattaga tcgcgatggg    840
aaaaaattcg gttaaggcca gggggaaaga aaaaatataa attaaaacat atagtatggg    900
caagcaggga gctagaacga ttcgcagtta atcctggcct gttagaaaca tcagaaggct    960
```

```
gtagacaaat actgggacag ctacaaccat cccttcagac aggatcagaa gaacttagat    1020
cattatataa tacagtagca accctctatt gtgtgcatca aaggatagag ataaaagaca    1080
ccaaggaagc tttagacaag atagaggaag agcaaaacaa aagtaagacc accgcacagc    1140
aagcggccgg ccgctgatct tcagacctgg aggaggagat atgagggaca attggagaag    1200
tgaattatat aaatataaag tagtaaaaat tgaaccatta ggagtagcac ccaccaaggc    1260
aaagagaaga gtggtgcaga gagaaaaaag agcagtggga ataggagctt tgttccttgg    1320
gttcttggga gcagcaggaa gcactatggg cgcagcgtca atgacgctga cggtacaggc    1380
cagacaatta ttgtctggta tagtgcagca gcagaacaat ttgctgaggg ctattgaggc    1440
gcaacagcat ctgttgcaac tcacagtctg gggcatcaag cagctccagg caagaatcct    1500
ggctgtggaa agatacctaa aggatcaaca gctcctgggg atttggggtt gctctggaaa    1560
actcatttgc accactgctg tgccttggaa tgctagttgg agtaataaat ctctggaaca    1620
gatttggaat cacacgacct ggatggagtg ggacagagaa attaacaatt acacaagctt    1680
aatacactcc ttaattgaag aatcgcaaaa ccagcaagaa aagaatgaac aagaattatt    1740
ggaattagat aaatgggcaa gtttgtggaa ttggtttaac ataacaaatt ggctgtggta    1800
tataaaatta ttcataatga tagtaggagg cttggtaggt ttaagaatag ttttgctgt    1860 actttctata gtgaatagag ttaggcaggg atattcacca ttatcgtttc agacccacct    1920
cccaaccccg aggggacccg acaggcccga aggaatagaa gaagaaggtg gagagagaga    1980
cagagacaga tccattcgat tagtgaacgg atctcgacgg tatcgccttt aaaagaaaag    2040
gggggattgg ggggtacagt gcaggggaaa gaatagtaga cataatagca acagacatac    2100
aaactaaaga attacaaaaa caaattacaa aaattcaaaa ttttcgggtt tattacaggg    2160
acagcagaga tccagtttat cgataagctt gggagttccg cgttacataa cttacggtaa    2220
atggcccgcc tggctgaccg cccaacgacc cccgcccatt gacgtcaata atgacgtatg    2280
ttcccatagt aacgccaata gggactttcc attgacgtca atgggtggag tatttacggt    2340
aaactgccca cttggcagta catcaagtgt atcatatgcc aagtacgccc cctattgacg    2400
tcaatgacgg taaatggccc gcctggcatt atgcccagta catgacctta tgggactttc    2460
ctacttggca gtacatctac gtattagtca tcgctattac catggtgatg cggttttggc    2520
agtacatcaa tgggcgtgga tagcggtttg actcacgggg atttccaagt ctccacccca    2580
ttgacgtcaa tgggagtttg ttttggcacc aaaatcaacg ggactttcca aaatgtcgta    2640
acaactccgc cccattgacg caaatgggcg gtaggcgtgt acggtgggag gtctatataa    2700
gcagagctcg tttagtgaac cgtcagatcg cctggagacg ccatccacgc tgttttgacc    2760
tccatagaag acaccgactc tactagagga tctatttccg gtgaattcgc accatggga    2820 atcaggctcc tgtgtcgtgt ggcctttgt ttcctggctg taggactagt agaagctgac    2880
atctaccaga ccccaagata ccttgttata gggacaggaa agaagatcac tctggaatgt    2940
tctcaaacca tgggccatga caaaatgtac tggtatcaac aagatccagg aatggaacta    3000
cacctcatcc actattccta tggagttaat tccacagaga agggagatct ttcctctgag    3060
tcaacagtct ccagaataag gacggagcat tttcccctga ccctggagtc tgccaggccc    3120
tcacatacct ctcagtacct ctgtgccagc agtcggacgc ccaacattca gtacttcggc    3180
gccgggaccc ggctctcagt gctggaggac ctgaaaaacg tgttcccacc cgaggtcgct    3240
gtgtttgagc catcagaagc agagatctcc cacacccaaa aggccacact ggcatgcctg    3300
```

```
gccacaggct tctaccccga ccacgtggag ctgagctggt gggtgaatgg gaaggaggtg    3360
cacagtgggg tcagcacaga cccgcagccc ctcaaggagc agcccgccct caatgactcc    3420
agatactgcc tgagcagccg cctgagggtc tcggccacct tctggcagaa cccccgcaac    3480
cacttccgct gtcaagtcca gttctacggg ctctcggaga atgacgagtg gacccaggat    3540
agggccaaac ctgtcaccca gatcgtcagc gccgaggcct ggggtagagc agactgtggc    3600
ttcacctccg agtcttacca gcaagggtc ctgtctgcca ccatcctcta tgagatcttg     3660
ctagggaagg ccaccttgta tgccgtgctg gtcagtgccc tcgtgctgat ggccatggtc    3720
aagagaaagg attccagagg cgggagcgga gccacgaact tctctctgtt aaagcaagca    3780
ggagacgtgg aagaaaaccc cggtcctatg acacgagtta gcttgctgtg ggcagtcgtg    3840
gtctccacct gtctcgagtc cggcatgggt caacagctga atcagagtcc tcaatctatg    3900
tttatccagg aaggagaaga tgtctccatg aactgcactt cttcaagcat atttaacacc    3960
tggctatggt acaagcagga acctgggaa ggtcctgtcc tcttgatagc cttatataag     4020
gctggtgaat tgacctcaaa tggaagactg actgctcagt ttggtataac cagaaaggac    4080
agcttcctga atatctcagc atccatacct agtgatgtag gcatctactt ctgtgctggc    4140
acataccaga agttaccctt tggaactgga acaaagctcc aagtcatccc aaatatccag    4200
aaccctgacc ctgccgtgta ccagctgaga gactctaaat ccagtgacaa gtctgtctgc    4260
ctattcaccg attttgattc tcaaacaaat gtgtcacaaa gtaaggattc tgatgtgtat    4320
atcacagaca aaactgtgct agacatgagg tctatggact tcaagagcaa cagtgcggcc    4380
gcctggagca acaaatctga cttttgcatgt gcaaacgcct tcaacaacag cattattcca    4440
gaagacacct tcttccccag cccagaaagt tcctgtgatg tcaagctggt cgagaaaagc    4500
tttgaaacag atacgaacct aaactttcaa aacctgtcag tgattgggtt ccgaatcctc    4560
ctcctgaaag tggccgggtt taatctgctc atgacgctgc ggctgtggtc cagctgactc    4620
gagggatccc gccctctcc ctccccccc cctaacgtta ctggccgaag ccgcttggaa      4680
taaggccggt gtgcgtttgt ctatatgtta ttttccacca tattgccgtc ttttggcaat    4740
gtgagggccc ggaaacctgg ccctgtcttc ttgacgagca ttcctagggg tctttcccct    4800
ctcgccaaag gaatgcaagg tctgttgaat gtcgtgaagg aagcagttcc tctggaagct    4860
tcttgaagac aaacaacgtc tgtagcgacc ctttgcaggc agcggaaccc cccacctggc    4920
gacaggtgcc tctgcggcca aaagccacgt gtataagata cacctgcaaa ggcggcacaa    4980 cccccagtgcc acgttgtgag ttggatagtt gtggaaagag tcaaatggct cacctcaagc   5040
gtattcaaca aggggctgaa ggatgcccag aaggtacccc attgtatggg atctgatctg    5100 gggcctcgt gcacatgctt tacatgtgtt tagtcgaggt taaaaaacgt ctaggccccc     5160
cgaaccacgg ggacgtggtt ttcctttgaa aaacacgatg ataatatggt gagcaagggc    5220
gaggaggata acatggccat catcaaggag ttcatgcgct tcaaggtgca catggagggc    5280
tccgtgaacg gccacgagtt cgagatcgag ggcgagggcg agggccgccc ctacgagggc    5340
acccagaccg ccaagctgaa ggtgaccaag ggtggccccc tgcccttcgc ctgggacatc    5400
ctgtcccctc agttcatgta cggctccaag gcctacgtga agcaccccgc cgacatcccc    5460
gactacttga agctgtcctt ccccgagggc ttcaagtggg agcgcgtgat gaacttcgag    5520
gacggcggcg tggtgaccgt gacccaggac tcctccctgc aggacggcga gttcatctac    5580
aaggtgaagc tgcgcggcac caacttcccc tccgacggcc ccgtaatgca gaagaagacc    5640
atgggctggg aggcctcctc cgagcggatg taccccgagg acggcgccct gaagggcgag    5700
```

-continued

```
atcaagcaga ggctgaagct gaaggacggc ggccactacg acgctgaggt caagaccacc    5760
tacaaggcca agaagcccgt gcagctgccc ggcgcctaca acgtcaacat caagttggac    5820
atcacctccc acaacgagga ctacaccatc gtggaacagt acgaacgcgc cgagggccgc    5880
cactccaccg gcggcatgga cgagctgtac aagtgaacgc gtctggaaca atcaacctct    5940
ggattacaaa atttgtgaaa gattgactgg tattcttaac tatgttgctc cttttacgct    6000
atgtggatac gctgctttaa tgcctttgta tcatgctatt gcttcccgta tggctttcat    6060
tttctcctcc ttgtataaat cctggttgct gtctctttat gaggagttgt ggcccgttgt    6120
caggcaacgt ggcgtggtgt gcactgtgtt tgctgacgca accccactg gttgggcat    6180 tgccaccacc tgtcagctcc tttccgggac tttcgctttc ccctcccta ttgccacggc    6240 ggaactcatc gccgcctgcc ttgcccgctg ctggacaggg gctcggctgt tgggcactga    6300
caattccgtg gtgttgtcgg ggaagctgac gtcctttcca tggctgctcg cctgtgttgc    6360
cacctggatt ctgcgcggga cgtccttctg ctacgtccct tcggccctca atccagcgga    6420
ccttccttcc cgcggcctgc tgccggctct gcggcctctt ccgcgtcttc gccttcgccc    6480
tcagacgagt cggatctccc tttgggccgc ctcccccgcct ggaattaatt ctgcagtcga    6540
gacctagaaa acatggagc aatcacaagt agcaatacag cagctaccaa tgctgattgt    6600
gcctggctag aagcacaaga ggaggaggag gtgggttttc cagtcacacc tcaggtacct    6660
ttaagaccaa tgacttacaa ggcagctgta gatcttagcc acttttaaa agaaaagagg    6720 ggactggaag ggctaattca ctcccaacga agacaagata tccttgatct gtggatctac    6780
cacacacaag gctacttccc tgattagcag aactacacac cagggccagg ggtcagatat    6840
ccactgacct ttggatggtg ctacaagcta gtaccagttg agccagataa ggtagaagag    6900
gccaataaag gagagaacac cagcttgtta caccctgtga gcctgcatgg gatggatgac    6960
ccggagagag aagtgttaga gtggaggttt gacagccgcc tagcatttca tcacgtggcc    7020
cgagagctgc atccggagta cttcaagaac tgctgatatc gagcttgcta caagggactt    7080
tccgctgggg actttccagg gaggcgtggc ctgggcggga ctgggagtg gcgagccctc    7140 agatcctgca tataagcagc tgcttttgc ctgtactggg tctctctggt tagaccagat    7200
ctgagcctgg gagctctctg gctaactagg gaacccactg cttaagcctc aataaagctt    7260
gccttgagtg cttcaagtag tgtgtgcccg tctgttgtgt gactctggta actagagatc    7320
cctcagaccc ttttagtcag tgtggaaaat ctctagcagt agtagttcat gtcatcttat    7380
tattcagtat ttataacttg caaagaaatg aatatcagag agtgagaggc cttgacattg    7440
ctagcgttta ccgtcgacct ctagctagag cttggcgtaa tcatggtcat agctgtttcc    7500
tgtgtgaaat tgttatccgc tcacaattcc acacaacata cgagccggaa gcataaagtg    7560
taaagcctgg ggtgcctaat gagtgagcta actcacatta attgcgttgc gctcactgcc    7620
cgctttccag tcgggaaacc tgtcgtgcca gctgcattaa tgaatcggcc aacgcgcggg    7680
gagaggcggt ttgcgtattg ggcgctcttc cgcttcctcg ctcactgact cgctgcgctc    7740
ggtcgttcgg ctgcggcgag cggtatcagc tcactcaaag gcggtaatac ggttatccac    7800
agaatcaggg gataacgcag gaaagaacat gtgagcaaaa ggccagcaaa aggccaggaa    7860
ccgtaaaaag gccgcgttgc tggcgttttt ccataggctc cgcccccctg acgagcatca    7920
caaaaatcga cgctcaagtc agaggtggcg aaacccgaca ggactataaa gataccaggc    7980
gtttccccct ggaagctccc tcgtgcgctc tcctgttccg accctgccgc ttaccggata    8040
```

| | |
|---|---|
| cctgtccgcc tttctcccctt cgggaagcgt ggcgctttct catagctcac gctgtaggta | 8100 |
| tctcagttcg gtgtaggtcg ttcgctccaa gctgggctgt gtgcacgaac ccccgttca | 8160 |
| gcccgaccgc tgcgccttat ccggtaacta tcgtcttgag tccaacccgg taagacacga | 8220 |
| cttatcgcca ctggcagcag ccactggtaa caggattagc agagcgaggt atgtaggcgg | 8280 |
| tgctacagag ttcttgaagt ggtggcctaa ctacggctac actagaagaa cagtatttgg | 8340 |
| tatctgcgct ctgctgaagc cagttacctt cggaaaaaga gttggtagct cttgatccgg | 8400 |
| caaacaaacc accgctggta gcggtggttt ttttgtttgc aagcagcaga ttacgcgcag | 8460 |
| aaaaaaagga tctcaagaag atcctttgat cttttctacg gggtctgacg ctcagtggaa | 8520 |
| cgaaaactca cgttaaggga ttttggtcat gagattatca aaaaggatct tcacctagat | 8580 |
| ccttttaaat taaaaatgaa gttttaaatc aatctaaagt atatatgagt aaacttggtc | 8640 |
| tgacagttac caatgcttaa tcagtgaggc acctatctca gcgatctgtc tatttcgttc | 8700 |
| atccatagtt gcctgactcc ccgtcgtgta gataactacg atacgggagg gcttaccatc | 8760 |
| tggccccagt gctgcaatga taccgcgaga cccacgctca ccggctccag atttatcagc | 8820 |
| aataaaccag ccagccggaa gggccgagcg cagaagtggt cctgcaactt tatccgcctc | 8880 |
| catccagtct attaattgtt gccgggaagc tagagtaagt agttcgccag ttaatagttt | 8940 |
| gcgcaacgtt gttgccattg ctacaggcat cgtggtgtca cgctcgtcgt ttggtatggc | 9000 |
| ttcattcagc tccggttccc aacgatcaag gcgagttaca tgatccccca tgttgtgcaa | 9060 |
| aaaagcggtt agctccttcg gtcctccgat cgttgtcaga agtaagttgg ccgcagtgtt | 9120 |
| atcactcatg gttatggcag cactgcataa ttctcttact gtcatgccat ccgtaagatg | 9180 |
| cttttctgtg actggtgagt actcaaccaa gtcattctga atagtgta tgcggcgacc | 9240 |
| gagttgctct tgcccggcgt caatacggga taataccgcg ccacatagca gaactttaaa | 9300 |
| agtgctcatc attggaaaac gttcttcggg gcgaaaactc tcaaggatct taccgctgtt | 9360 |
| gagatccagt tcgatgtaac ccactcgtgc acccaactga tcttcagcat cttttacttt | 9420 |
| caccagcgtt tctgggtgag caaaaacagg aaggcaaaat gccgcaaaaa agggaataag | 9480 |
| ggcgacacgg aaatgttgaa tactcatact cttccttttt caatattatt gaagcattta | 9540 |
| tcagggttat tgtctcatga gcggatacat atttgaatgt atttagaaaa ataaacaaat | 9600 |
| aggggttccg cgcacatttc cccgaaaagt gccacctgac gtcgacggat cgggagatca | 9660 |
| acttgtttat tgcagcttat aatggttaca ataaagcaa tagcatcaca atttcacaa | 9720 |
| ataaagcatt ttttcactg cattctagtt gtggtttgtc caaactcatc aatgtatctt | 9780 |
| atcatgtctg gatcaactgg ataactcaag ctaaccaaaa tcatcccaaa cttcccaccc | 9840 |
| cataccctat taccactgcc aattacctgt ggtttcattt actctaaacc tgtgattcct | 9900 |
| ctgaattatt ttcattttaa agaaattgta tttgttaaat atgtactaca aacttagtag | 9960 |
| t | 9961 |

<210> SEQ ID NO 30
<211> LENGTH: 9955
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 30

| | |
|---|---|
| tggaagggct aattcactcc caaagaagac aagatatcct tgatctgtgg atctaccaca | 60 |

```
cacaaggcta cttccctgat tagcagaact acacaccagg gccagggtc  agatatccac   120 tgacctttgg atggtgctac aagctagtac cagttgagcc agataaggta gaagaggcca   180
ataaaggaga gaacaccagc ttgttacacc ctgtgagcct gcatgggatg gatgacccgg   240
agagagaagt gttagagtgg aggtttgaca gccgcctagc atttcatcac gtggcccgag   300
agctgcatcc ggagtacttc aagaactgct gatatcgagc ttgctacaag ggactttccg   360
ctggggactt tccagggagg cgtggcctgg gcgggactgg ggagtggcga gccctcagat   420
cctgcatata agcagctgct ttttgcctgt actgggtctc tctggttaga ccagatctga   480
gcctgggagc tctctggcta actagggaac ccactgctta agcctcaata aagcttgcct   540
tgagtgcttc aagtagtgtg tgcccgtctg ttgtgtgact ctggtaacta gagatccctc   600
agaccctttt agtcagtgtg gaaaatctct agcagtggcg cccgaacagg gacttgaaag   660
cgaaagggaa accagaggag ctctctcgac gcaggactcg gcttgctgaa gcgcgcacgg   720
caagaggcga ggggcggcga ctggtgagta cgccaaaaat tttgactagc ggaggctaga   780
aggagagaga tgggtgcgag agcgtcagta ttaagcgggg gagaattaga tcgcgatggg   840
aaaaaattcg gttaaggcca ggggaaaga  aaaaatataa attaaaacat atagtatggg   900
caagcaggga gctagaacga ttcgcagtta atcctggcct gttagaaaca tcagaaggct   960
gtagacaaat actgggacag ctacaaccat cccttcagac aggatcagaa gaacttagat  1020
cattatataa tacagtagca accctctatt gtgtgcatca aaggatagag ataaaagaca  1080
ccaaggaagc tttagacaag atagaggaag agcaaaacaa aagtaagacc accgcacagc  1140
aagcggccgg ccgctgatct tcagacctgg aggaggagat atgagggaca attggagaag  1200
tgaattatat aaatataaag tagtaaaaat tgaaccatta ggagtagcac ccaccaaggc  1260
aaagagaaga gtggtgcaga gagaaaaaag agcagtggga ataggagctt tgttccttgg  1320
gttcttggga gcagcaggaa gcactatggg cgcagcgtca atgacgctga cggtacaggc  1380
cagacaatta ttgtctggta tagtgcagca gcagaacaat ttgctgaggg ctattgaggc  1440
gcaacagcat ctgttgcaac tcacagtctg gggcatcaag cagctccagg caagaatcct  1500
ggctgtggaa agatacctaa aggatcaaca gctcctgggg atttggggtt gctctggaaa  1560
actcatttgc accactgctg tgccttggaa tgctagttgg agtaataaat ctctggaaca  1620
gatttggaat cacacgacct ggatggagtg ggacagagaa attaacaatt acacaagctt  1680
aatacactcc ttaattgaag aatcgcaaaa ccagcaagaa aagaatgaac aagaattatt  1740
ggaattagat aaatgggcaa gtttgtggaa ttggtttaac ataacaaatt ggctgtggta  1800
tataaaatta ttcataatga tagtaggagg cttggtaggt ttaagaatag ttttgctgt  1860 actttctata gtgaatagag ttaggcaggg atattcacca ttatcgtttc agacccacct  1920
cccaaccccg aggggacccg acaggcccga aggaatagaa gaagaaggtg gagagagaga  1980
cagagacaga tccattcgat tagtgaacgg atctcgacgg tatcgccttt aaaagaaaag  2040
gggggattgg ggggtacagt gcaggggaaa gaatagtaga cataatagca acagacatac  2100
aaactaaaga attacaaaaa caaattacaa aaattcaaaa ttttcgggtt tattacaggg  2160
acagcagaga tccagtttat cgataagctt gggagttccg cgttacataa cttacggtaa  2220
atggcccgcc tggctgaccg cccaacgacc cccgcccatt gacgtcaata atgacgtatg  2280
ttcccatagt aacgccaata gggactttcc attgacgtca atgggtggag tatttacggt  2340
aaactgccca cttggcagta catcaagtgt atcatatgcc aagtacgccc cctattgacg  2400
tcaatgacgg taaatggccc gcctggcatt atgcccagta catgacctta tgggactttc  2460
```

```
ctacttggca gtacatctac gtattagtca tcgctattac catggtgatg cggttttggc   2520
agtacatcaa tgggcgtgga tagcggtttg actcacgggg atttccaagt ctccacccca   2580
ttgacgtcaa tgggagtttg ttttggcacc aaaatcaacg ggactttcca aaatgtcgta   2640
acaactccgc cccattgacg caaatgggcg gtaggcgtgt acggtgggag gtctatataa   2700
gcagagctcg tttagtgaac cgtcagatcg cctggagacg ccatccacgc tgttttgacc   2760
tccatagaag acaccgactc tactagagga tctatttccg gtgaattcgc caccatggcc   2820
tccctgctct tcttctgtgg ggccttttat ctcctgggaa ccggttccat ggaagctgac   2880
atctaccaga ccccaagata ccttgttata gggacaggaa agaagatcac tctggaatgt   2940
tctcaaacca tgggccatga caaaatgtac tggtatcaac aagatccagg aatggaacta   3000
cacctcatcc actattccta tggagttaat tccacagaga agggagatct ttcctctgag   3060
tcaacagtct ccagaataag gacggagcat tttcccctga ccctggagtc tgccaggccc   3120
tcacatacct ctcagtacct ctgtgccagc agtcggacgc ccaacattca gtacttcggc   3180
gccgggaccc ggctctcagt gctggaggac ctgaaaaacg tgttcccacc cgaggtcgct   3240
gtgtttgagc catcagaagc agagatctcc cacacccaaa aggccacact agtgtgcctg   3300
gccacaggct tctaccccga ccacgtggag ctgagctggt gggtgaatgg gaaggaggtg   3360
cacagtgggg tcagcacaga cccgcagccc tcaaggagc agcccgccct caatgactcc   3420
agatactgcc tgagcagccg cctgagggtc tcggccacct tctggcagaa cccccgcaac   3480
cacttccgct gtcaagtcca gttctacggg ctctcggaga atgacgagtg gacccaggat   3540
agggccaaac ctgtcaccca gatcgtcagc gccgaggcct ggggtagagc agactgtggc   3600
ttcacctccg agtcttacca gcaaggggtc ctgtctgcca ccatcctcta tgagatcttg   3660
ctagggaagg ccaccttgta tgccgtgctg gtcagtgccc tcgtgctgat ggccatggtc   3720
aagagaaagg attccagagg cgggagcgga gccacgaact tctctctgtt aaagcaagca   3780
ggagacgtgg aagaaaaccc cggtcctatg aactcctctc tggactttct aattctgatc   3840
ttaatgtttg gaggaactag tggtcaacag ctgaatcaga gtcctcaatc tatgtttatc   3900
caggaaggag aagatgtctc catgaactgc acttcttcaa gcatatttaa cacctggcta   3960
tggtacaagc aggaacctgg ggaaggtcct gtcctcttga tagccttata taaggctggt   4020
gaattgacct caaatggaag actgactgct cagtttggta taaccagaaa ggacagcttc   4080
ctgaatatct cagcatccat acctagtgat gtaggcatct acttctgtgc tggcacatac   4140
cagaaagtta cctttggaac tggaacaaag ctccaagtca tcccaaatat ccagaaccct   4200
gaccctgccg tgtaccagct gagagactct aaatccagtg acaagtctgc atgcctattc   4260
accgattttg attctcaaac aaatgtgtca caaagtaagg attctgatgt gtatatcaca   4320
gacaaaactg tgctagacat gaggtctatg gacttcaaga gcaacagtgc tgtggcctgg   4380
agcaacaaat ctgactttgc atgtgcaaac gccttcaaca acagcattat tccagaagac   4440
accttcttcc ccagcccaga aagttcctgt gatgtcaagc tggtcgagaa aagctttgaa   4500
acagatacga acctaaactt tcaaaacctg tcagtgattg ggttccgaat cctcctcctg   4560
aaagtggccg ggtttaatct gctcatgacg ctgcggctgt ggtccagctg actgaggga   4620 tcccgcccct ctccctcccc ccccctaac gttactggcc gaagccgctt ggaataaggc   4680
cggtgtgcgt ttgtctatat gttatttttcc accatattgc cgtcttttgg caatgtgagg   4740
gcccggaaac ctggccctgt cttcttgacg agcattccta ggggtctttc ccctctcgcc   4800
```

```
aaaggaatgc aaggtctgtt gaatgtcgtg aaggaagcag ttcctctgga agcttcttga    4860
agacaaacaa cgtctgtagc gacccctttgc aggcagcgga accccccacc tggcgacagg    4920
tgcctctgcg gccaaaagcc acgtgtataa gatacacctg caaggcggc acaaccccag    4980 tgccacgttg tgagttggat agttgtggaa agagtcaaat ggctcacctc aagcgtattc    5040 aacaagggc tgaaggatgc ccagaaggta ccccattgta tgggatctga tctggggcct    5100
cggtgcacat gctttacatg tgtttagtcg aggttaaaaa acgtctaggc cccccgaacc    5160
acggggacgt ggttttcctt tgaaaaacac gatgataata tggtgagcaa gggcgaggag    5220
gataacatgg ccatcatcaa ggagttcatg cgcttcaagg tgcacatgga gggctccgtg    5280
aacggccacg agttcgagat cgagggcgag ggcgagggcc gcccctacga gggcacccag    5340
accgccaagc tgaaggtgac caagggtggc cccctgccct cgcctggga catcctgtcc    5400 cctcagttca tgtacggctc caaggcctac gtgaagcacc ccgccgacat ccccgactac    5460
ttgaagctgt ccttccccga gggcttcaag tgggagcgcg tgatgaactt cgaggacggc    5520
ggcgtggtga ccgtgaccca ggactcctcc ctgcaggacg gcgagttcat ctacaaggtg    5580
aagctgcgcg gcaccaactt ccccctccgac ggccccgtaa tgcagaagaa gaccatgggc    5640
tgggaggcct cctccgagcg gatgtacccc gaggacggcg ccctgaaggg cgagatcaag    5700
cagaggctga agctgaagga cggcggccac tacgacgctg aggtcaagac cacctacaag    5760
gccaagaagc ccgtgcagct gcccggcgcc tacaacgtca acatcaagtt ggacatcacc    5820
tcccacaacg aggactacac catcgtggaa cagtacgaac gcgccgaggg ccgccactcc    5880
accggcggca tggacgagct gtacaagtga acgcgtctgg aacaatcaac ctctggatta    5940
caaaatttgt gaaagattga ctggtattct taactatgtt gctccttta cgctatgtgg    6000 atacgctgct ttaatgcctt tgtatcatgc tattgcttcc cgtatggctt tcattttctc    6060
ctccttgtat aaatcctggt tgctgtctct ttatgaggag ttgtggcccg ttgtcaggca    6120
acgtggcgtg gtgtgcactg tgtttgctga cgcaaccccc actggttggg gcattgccac    6180
cacctgtcag ctccttttccg ggactttcgc tttccccctc cctattgcca cggcggaact    6240
catcgccgcc tgccttgccc gctgctggac agggggctcgg ctgttgggca ctgacaattc    6300
cgtggtgttg tcggggaagc tgacgtcctt tccatggctg ctcgcctgtg ttgccacctg    6360
gattctgcgc gggacgtcct tctgctacgt cccttcggcc ctcaatccag cggaccttcc    6420
ttcccgcggc ctgctgccgg ctctgcggcc tcttccgcgt cttcgccttc gccctcagac    6480
gagtcggatc tccctttggg ccgcctcccc gcctggaatt aattctgcag tcgagaccta    6540
gaaaaacatg gagcaatcac aagtagcaat acagcagcta ccaatgctga ttgtgcctgg    6600
ctagaagcac aagaggagga ggaggtgggt tttccagtca cacctcaggt acctttaaga    6660
ccaatgactt acaaggcagc tgtagatctt agccacttttt taaaagaaaa gaggggactg    6720
gaagggctaa ttcactccca acgaagacaa gatatccttg atctgtggat ctaccacaca    6780
caaggctact tccctgatta gcagaactac acaccagggc caggggtcag atatccactg    6840
acctttggat ggtgctacaa gctagtacca gttgagccag ataaggtaga agaggccaat    6900
aaaggagaga acaccagctt gttacaccct gtgagcctgc atgggatgga tgacccggag    6960
agagaagtgt tagagtggag gtttgacagc cgcctagcat tcatcacgt ggcccgagag    7020 ctgcatccgg agtacttcaa gaactgctga tatcgagctt gctacaaggg actttccgct    7080
ggggactttc cagggaggcg tggcctgggc gggactgggg agtggcgagc cctcagatcc    7140
tgcatataag cagctgcttt ttgcctgtac tgggtctctc tggttagacc agatctgagc    7200
```

```
ctgggagctc tctggctaac tagggaaccc actgcttaag cctcaataaa gcttgccttg   7260
agtgcttcaa gtagtgtgtg cccgtctgtt gtgtgactct ggtaactaga gatccctcag   7320
acccttttag tcagtgtgga aaatctctag cagtagtagt tcatgtcatc ttattattca   7380
gtatttataa cttgcaaaga aatgaatatc agagagtgag aggccttgac attgctagcg   7440
tttaccgtcg acctctagct agagcttggc gtaatcatgg tcatagctgt ttcctgtgtg   7500
aaattgttat ccgctcacaa ttccacacaa catacgagcc ggaagcataa agtgtaaagc   7560
ctggggtgcc taatgagtga gctaactcac attaattgcg ttgcgctcac tgcccgcttt   7620
ccagtcggga acctgtcgt gccagctgca ttaatgaatc ggccaacgcg cggggagagg   7680
cggtttgcgt attgggcgct cttccgcttc ctcgctcact gactcgctgc gctcggtcgt   7740
tcggctgcgg cgagcggtat cagctcactc aaaggcggta atacggttat ccacagaatc   7800
aggggataac gcaggaaaga acatgtgagc aaaaggccag caaaaggcca ggaaccgtaa   7860
aaaggccgcg ttgctggcgt ttttccatag gctccgcccc cctgacgagc atcacaaaaa   7920
tcgacgctca agtcagaggt ggcgaaaccc gacaggacta taaagatacc aggcgtttcc   7980
ccctggaagc tccctcgtgc gctctcctgt tccgaccctg ccgcttaccg gatacctgtc   8040
cgcctttctc ccttcgggaa gcgtggcgct ttctcatagc tcacgctgta ggtatctcag   8100
ttcggtgtag gtcgttcgct ccaagctggg ctgtgtgcac gaaccccccg ttcagcccga   8160
ccgctgcgcc ttatccggta actatcgtct tgagtccaac ccggtaagac acgacttatc   8220
gccactggca gcagccactg gtaacaggat tagcagagcg aggtatgtag gcggtgctac   8280
agagttcttg aagtggtggc ctaactacgg ctacactaga agaacagtat ttggtatctg   8340
cgctctgctg aagccagtta ccttcggaaa aagagttggt agctcttgat ccggcaaaca   8400
aaccaccgct ggtagcggtg gttttttgt ttgcaagcag cagattacgc gcagaaaaaa   8460
aggatctcaa gaagatcctt tgatcttttc tacggggtct gacgctcagt ggaacgaaaa   8520
ctcacgttaa gggattttgg tcatgagatt atcaaaaagg atcttcacct agatcctttt   8580
aaattaaaaa tgaagtttta aatcaatcta agtatatat gagtaaactt ggtctgacag   8640
ttaccaatgc ttaatcagtg aggcacctat ctcagcgatc tgtctatttc gttcatccat   8700
agttgcctga ctccccgtcg tgtagataac tacgatacgg gagggcttac catctggccc   8760
cagtgctgca atgataccgc gagacccacg ctcaccggct ccagatttat cagcaataaa   8820
ccagccagcc ggaagggccg agcgcagaag tggtcctgca actttatccg cctccatcca   8880
gtctattaat tgttgccggg aagctagagt aagtagttcg ccagttaata gtttgcgcaa   8940
cgttgttgcc attgctacag gcatcgtggt gtcacgctcg tcgtttggta tggcttcatt   9000
cagctccggt tcccaacgat caaggcgagt tacatgatcc cccatgttgt gcaaaaaagc   9060
ggttagctcc ttcggtcctc cgatcgttgt cagaagtaag ttggccgcag tgttatcact   9120
catggttatg gcagcactgc ataattctct tactgtcatg ccatccgtaa gatgcttttc   9180
tgtgactggt gagtactcaa ccaagtcatt ctgagaatag tgtatgcggc gaccgagttg   9240
ctcttgcccg gcgtcaatac gggataatac cgcgccacat agcagaactt taaaagtgct   9300
catcattgga aaacgttctt cggggcgaaa actctcaagg atcttaccgc tgttgagatc   9360
cagttcgatg taacccactc gtgcacccaa ctgatcttca gcatctttta ctttcaccag   9420
cgtttctggg tgagcaaaaa caggaaggca aaatgccgca aaaaagggaa taagggcgac   9480
acggaaatgt tgaatactca tactcttcct ttttcaatat tattgaagca tttatcaggg   9540
```

-continued

```
ttattgtctc atgagcggat acatatttga atgtatttag aaaaataaac aaatagggt      9600 tccgcgcaca tttccccgaa aagtgccacc tgacgtcgac ggatcgggag atcaacttgt      9660
ttattgcagc ttataatggt tacaaataaa gcaatagcat cacaaatttc acaaataaag      9720 cattttttc actgcattct agttgtggtt tgtccaaact catcaatgta tcttatcatg       9780
tctggatcaa ctggataact caagctaacc aaaatcatcc caaacttccc accccatacc      9840
ctattaccac tgccaattac ctgtggtttc atttactcta aacctgtgat tcctctgaat      9900
tattttcatt ttaaagaaat tgtatttgtt aaatatgtac tacaaactta gtagt           9955
```

<210> SEQ ID NO 31
<211> LENGTH: 431
<212> TYPE: PRT
<213> ORGANISM: Homo sapiens

<400> SEQUENCE: 31

```
Met Pro Asn Pro Arg Pro Gly Lys Pro Ser Ala Pro Ser Leu Ala Leu
1               5                   10                  15

Gly Pro Ser Pro Gly Ala Ser Pro Ser Trp Arg Ala Ala Pro Lys Ala
            20                  25                  30

Ser Asp Leu Leu Gly Ala Arg Gly Pro Gly Thr Phe Gln Gly Arg
        35                  40                  45

Asp Leu Arg Gly Gly Ala His Ala Ser Ser Ser Leu Asn Pro Met
    50                  55                  60

Pro Pro Ser Gln Leu Gln Leu Pro Thr Leu Pro Leu Val Met Val Ala
65                  70                  75                  80

Pro Ser Gly Ala Arg Leu Gly Pro Leu Pro His Leu Gln Ala Leu Leu
                85                  90                  95

Gln Asp Arg Pro His Phe Met His Gln Leu Ser Thr Val Asp Ala His
            100                 105                 110

Ala Arg Thr Pro Val Leu Gln Val His Pro Leu Glu Ser Pro Ala Met
        115                 120                 125

Ile Ser Leu Thr Pro Pro Thr Thr Ala Thr Gly Val Phe Ser Leu Lys
    130                 135                 140

Ala Arg Pro Gly Leu Pro Pro Gly Ile Asn Val Ala Ser Leu Glu Trp
145                 150                 155                 160

Val Ser Arg Glu Pro Ala Leu Leu Cys Thr Phe Pro Asn Pro Ser Ala
                165                 170                 175

Pro Arg Lys Asp Ser Thr Leu Ser Ala Val Pro Gln Ser Ser Tyr Pro
            180                 185                 190

Leu Leu Ala Asn Gly Val Cys Lys Trp Pro Gly Cys Glu Lys Val Phe
        195                 200                 205

Glu Glu Pro Glu Asp Phe Leu Lys His Cys Gln Ala Asp His Leu Leu
    210                 215                 220

Asp Glu Lys Gly Arg Ala Gln Cys Leu Leu Gln Arg Glu Met Val Gln
225                 230                 235                 240

Ser Leu Glu Gln Gln Leu Val Leu Glu Lys Glu Lys Leu Ser Ala Met
                245                 250                 255

Gln Ala His Leu Ala Gly Lys Met Ala Leu Thr Lys Ala Ser Ser Val
            260                 265                 270

Ala Ser Ser Asp Lys Gly Ser Cys Cys Ile Val Ala Ala Gly Ser Gln
        275                 280                 285

Gly Pro Val Val Pro Ala Trp Ser Gly Pro Arg Glu Ala Pro Asp Ser
    290                 295                 300
```

```
Leu Phe Ala Val Arg Arg His Leu Trp Gly Ser His Gly Asn Ser Thr
305                 310                 315                 320

Phe Pro Glu Phe Leu His Asn Met Asp Tyr Phe Lys Phe His Asn Met
            325                 330                 335

Arg Pro Pro Phe Thr Tyr Ala Thr Leu Ile Arg Trp Ala Ile Leu Glu
            340                 345                 350

Ala Pro Glu Lys Gln Arg Thr Leu Asn Glu Ile Tyr His Trp Phe Thr
            355                 360                 365

Arg Met Phe Ala Phe Phe Arg Asn His Pro Ala Thr Trp Lys Asn Ala
        370                 375                 380

Ile Arg His Asn Leu Ser Leu His Lys Cys Phe Val Arg Val Glu Ser
385                 390                 395                 400

Glu Lys Gly Ala Val Trp Thr Val Asp Glu Leu Glu Phe Arg Lys Lys
                405                 410                 415

Arg Ser Gln Arg Pro Ser Arg Cys Ser Asn Pro Thr Pro Gly Pro
            420                 425                 430

<210> SEQ ID NO 32
<211> LENGTH: 825
<212> TYPE: PRT
<213> ORGANISM: Homo sapiens

<400> SEQUENCE: 32

Met Leu Asp Ile Cys Leu Glu Lys Arg Val Gly Thr Thr Leu Ala Ala
1               5                   10                  15

Pro Lys Cys Asn Ser Ser Thr Val Arg Phe Gln Gly Leu Ala Glu Gly
            20                  25                  30

Thr Lys Gly Thr Met Lys Met Asp Met Glu Asp Ala Asp Met Thr Leu
        35                  40                  45

Trp Thr Glu Ala Glu Phe Glu Glu Lys Cys Thr Tyr Ile Val Asn Asp
    50                  55                  60

His Pro Trp Asp Ser Gly Ala Asp Gly Gly Thr Ser Val Gln Ala Glu
65                  70                  75                  80

Ala Ser Leu Pro Arg Asn Leu Leu Phe Lys Tyr Ala Thr Asn Ser Glu
                85                  90                  95

Glu Val Ile Gly Val Met Ser Lys Glu Tyr Ile Pro Lys Gly Thr Arg
            100                 105                 110

Phe Gly Pro Leu Ile Gly Glu Ile Tyr Thr Asn Asp Thr Val Pro Lys
        115                 120                 125

Asn Ala Asn Arg Lys Tyr Phe Trp Arg Ile Tyr Ser Arg Gly Glu Leu
    130                 135                 140

His His Phe Ile Asp Gly Phe Asn Glu Glu Lys Ser Asn Trp Met Arg
145                 150                 155                 160

Tyr Val Asn Pro Ala His Ser Pro Arg Glu Gln Asn Leu Ala Ala Cys
                165                 170                 175

Gln Asn Gly Met Asn Ile Tyr Phe Tyr Thr Ile Lys Pro Ile Pro Ala
            180                 185                 190

Asn Gln Glu Leu Leu Val Trp Tyr Cys Arg Asp Phe Ala Glu Arg Leu
        195                 200                 205

His Tyr Pro Tyr Pro Gly Glu Leu Thr Met Met Asn Leu Thr Gln Thr
    210                 215                 220

Gln Ser Ser Leu Lys Gln Pro Ser Thr Glu Lys Asn Glu Leu Cys Pro
225                 230                 235                 240

Lys Asn Val Pro Lys Arg Glu Tyr Ser Val Lys Glu Ile Leu Lys Leu
                245                 250                 255
```

```
Asp Ser Asn Pro Ser Lys Gly Lys Asp Leu Tyr Arg Ser Asn Ile Ser
            260                 265                 270

Pro Leu Thr Ser Glu Lys Asp Leu Asp Asp Phe Arg Arg Gly Ser
        275                 280                 285

Pro Glu Met Pro Phe Tyr Pro Arg Val Val Tyr Pro Ile Arg Ala Pro
        290                 295                 300

Leu Pro Glu Asp Phe Leu Lys Ala Ser Leu Ala Tyr Gly Ile Glu Arg
305                 310                 315                 320

Pro Thr Tyr Ile Thr Arg Ser Pro Ile Pro Ser Ser Thr Thr Pro Ser
                325                 330                 335

Pro Ser Ala Arg Ser Ser Pro Asp Gln Ser Leu Lys Ser Ser Pro
            340                 345                 350

His Ser Ser Pro Gly Asn Thr Val Ser Pro Val Gly Pro Gly Ser Gln
            355                 360                 365

Glu His Arg Asp Ser Tyr Ala Tyr Leu Asn Ala Ser Tyr Gly Thr Glu
        370                 375                 380

Gly Leu Gly Ser Tyr Pro Gly Tyr Ala Pro Leu Pro His Leu Pro Pro
385                 390                 395                 400

Ala Phe Ile Pro Ser Tyr Asn Ala His Tyr Pro Lys Phe Leu Leu Pro
                405                 410                 415

Pro Tyr Gly Met Asn Cys Asn Gly Leu Ser Ala Val Ser Ser Met Asn
            420                 425                 430

Gly Ile Asn Asn Phe Gly Leu Phe Pro Arg Leu Cys Pro Val Tyr Ser
            435                 440                 445

Asn Leu Leu Gly Gly Ser Leu Pro His Pro Met Leu Asn Pro Thr
        450                 455                 460

Ser Leu Pro Ser Ser Leu Pro Ser Asp Gly Ala Arg Arg Leu Leu Gln
465                 470                 475                 480

Pro Glu His Pro Arg Glu Val Leu Val Pro Ala Pro His Ser Ala Phe
            485                 490                 495

Ser Phe Thr Gly Ala Ala Ala Ser Met Lys Asp Lys Ala Cys Ser Pro
        500                 505                 510

Thr Ser Gly Ser Pro Thr Ala Gly Thr Ala Ala Thr Ala Glu His Val
        515                 520                 525

Val Gln Pro Lys Ala Thr Ser Ala Ala Met Ala Ala Pro Ser Ser Asp
    530                 535                 540

Glu Ala Met Asn Leu Ile Lys Asn Lys Arg Asn Met Thr Gly Tyr Lys
545                 550                 555                 560

Thr Leu Pro Tyr Pro Leu Lys Lys Gln Asn Gly Lys Ile Lys Tyr Glu
            565                 570                 575

Cys Asn Val Cys Ala Lys Thr Phe Gly Gln Leu Ser Asn Leu Lys Val
            580                 585                 590

His Leu Arg Val His Ser Gly Glu Arg Pro Phe Lys Cys Gln Thr Cys
        595                 600                 605

Asn Lys Gly Phe Thr Gln Leu Ala His Leu Gln Lys His Tyr Leu Val
            610                 615                 620

His Thr Gly Glu Lys Pro His Glu Cys Gln Val Cys His Lys Arg Phe
625                 630                 635                 640

Ser Ser Thr Ser Asn Leu Lys Thr His Leu Arg Leu His Ser Gly Glu
                645                 650                 655

Lys Pro Tyr Gln Cys Lys Val Cys Pro Ala Lys Phe Thr Gln Phe Val
            660                 665                 670
```

His Leu Lys Leu His Lys Arg Leu His Thr Arg Glu Arg Pro His Lys
            675                 680                 685

Cys Ser Gln Cys His Lys Asn Tyr Ile His Leu Cys Ser Leu Lys Val
690                 695                 700

His Leu Lys Gly Asn Cys Ala Ala Pro Ala Pro Gly Leu Pro Leu
705                 710                 715                 720

Glu Asp Leu Thr Arg Ile Asn Glu Glu Ile Glu Lys Phe Asp Ile Ser
            725                 730                 735

Asp Asn Ala Asp Arg Leu Glu Asp Val Glu Asp Ile Ser Val Ile
            740                 745                 750

Ser Val Val Glu Lys Glu Ile Leu Ala Val Val Arg Lys Lys Glu
    755                 760                 765

Glu Thr Gly Leu Lys Val Ser Leu Gln Arg Asn Met Gly Asn Gly Leu
    770                 775                 780

Leu Ser Ser Gly Cys Ser Leu Tyr Glu Ser Ser Asp Leu Pro Leu Met
785                 790                 795                 800

Lys Leu Pro Pro Ser Asn Pro Leu Pro Leu Val Pro Lys Val Lys
                805                 810                 815

Gln Glu Thr Val Glu Pro Met Asp Pro
            820                 825

<210> SEQ ID NO 33
<211> LENGTH: 390
<212> TYPE: PRT
<213> ORGANISM: Homo sapiens

<400> SEQUENCE: 33

Met Pro Pro Ser Gly Leu Arg Leu Leu Leu Leu Leu Pro Leu Leu
1               5                   10                  15

Trp Leu Leu Val Leu Thr Pro Gly Arg Pro Ala Ala Gly Leu Ser Thr
                20                  25                  30

Cys Lys Thr Ile Asp Met Glu Leu Val Lys Arg Lys Arg Ile Glu Ala
            35                  40                  45

Ile Arg Gly Gln Ile Leu Ser Lys Leu Arg Leu Ala Ser Pro Pro Ser
50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Glu Pro Glu
                85                  90                  95

Pro Glu Pro Glu Ala Asp Tyr Tyr Ala Lys Glu Val Thr Arg Val Leu
            100                 105                 110

Met Val Glu Thr His Asn Glu Ile Tyr Asp Lys Phe Lys Gln Ser Thr
        115                 120                 125

His Ser Ile Tyr Met Phe Phe Asn Thr Ser Glu Leu Arg Glu Ala Val
    130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asp Ser
            180                 185                 190

Pro Glu Trp Leu Ser Phe Asp Val Thr Gly Val Val Arg Gln Trp Leu
        195                 200                 205

Ser Arg Gly Gly Glu Ile Glu Gly Phe Arg Leu Ser Ala His Cys Ser
    210                 215                 220

Cys Asp Ser Arg Asp Asn Thr Leu Gln Val Asp Ile Asn Gly Phe Thr
225                 230                 235                 240

Thr Gly Arg Arg Gly Asp Leu Ala Thr Ile His Gly Met Asn Arg Pro
            245                 250                 255

Phe Leu Leu Leu Met Ala Thr Pro Leu Glu Arg Ala Gln His Leu Gln
            260                 265                 270

Ser Ser Arg His Arg Arg Ala Leu Asp Thr Asn Tyr Cys Phe Ser Ser
        275                 280                 285

Thr Glu Lys Asn Cys Cys Val Arg Gln Leu Tyr Ile Asp Phe Arg Lys
    290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
            325                 330                 335

Ser Lys Val Leu Ala Leu Tyr Asn Gln His Asn Pro Gly Ala Ser Ala
        340                 345                 350

Ala Pro Cys Cys Val Pro Gln Ala Leu Glu Pro Leu Pro Ile Val Tyr
    355                 360                 365

Tyr Val Gly Arg Lys Pro Lys Val Glu Gln Leu Ser Asn Met Ile Val
370                 375                 380

Arg Ser Cys Lys Cys Ser
385                 390

<210> SEQ ID NO 34
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cgcagtagcg gtaaacggcg atgctgaagt crcmcagact cc                          42

<210> SEQ ID NO 35
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
cgcagtagcg gtaaacggcg atgcwgmtgt twcccagac                              39

<210> SEQ ID NO 36
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cgcagtagcg gtaaacggcg acactgragt yacscagaca cc                          42

<210> SEQ ID NO 37
<211> LENGTH: 39
<212> TYPE: DNA
<213> ORGANISM: Artificial Sequence
<220> FEATURE:

<223> OTHER INFORMATION: Description of Artificial Sequence: Synthetic
    primer

<400> SEQUENCE: 37
cgcagtagcg gtaaacggcg aggctggagt cachcaaas                              39

<210> SEQ ID NO 38
<211> LENGTH: 39
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 38
cgcagtagcg gtaaacggcg agcctggwgt casycagac                              39

<210> SEQ ID NO 39
<211> LENGTH: 38
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 39
cgcagtagcg gtaaacggcg gtgctggagt ykcccagw                               38

<210> SEQ ID NO 40
<211> LENGTH: 38
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 40
cgcagtagcg gtaaacggcg atgctgrrat cacccagr                               38

<210> SEQ ID NO 41
<211> LENGTH: 39
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 41
cgcagtagcg gtaaacggcg aagctgaagt tgcccagtc                              39

<210> SEQ ID NO 42
<211> LENGTH: 39
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 42
cgcagtagcg gtaaacggcg atgctggagt yatccagtc                              39

<210> SEQ ID NO 43
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 43
cgcagtagcg gtaaacggcg aagctggagt krytcagt                                   38

<210> SEQ ID NO 44
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
cgcagtagcg gtaaacggcg atgccatggt catccagaa                                  39

<210> SEQ ID NO 45
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
cgcagtagcg gtaaacggca atgccggcgt catgcagaa                                  39

<210> SEQ ID NO 46
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
cgcagtagcg gtaaacggcg atggtggaat cactcagtc                                  39

<210> SEQ ID NO 47
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
cgcagtagcg gtaaacggca gtgctgtcrt ctctcaama                                  39

<210> SEQ ID NO 48
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
cgcagtagcg gtaaacggcg aagctgacat ctaccagac                                  39

<210> SEQ ID NO 49
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 49
cgcagtagcg gtaaacggcg atgtgaaagt racccagarc yc                    42

<210> SEQ ID NO 50
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
cgcagtagcg gtaaacggca cactccaggc acagagata                        39

<210> SEQ ID NO 51
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
tgctaaaacg ctagctgctg gttcgtcgac caaggcagta tctggagtca ttgag      55

<210> SEQ ID NO 52
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
cgcagtagcg gtaaacggc                                              19

<210> SEQ ID NO 53
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ccagcagcta gcgttttagc aggacaaarc mttgascagc c                     41

<210> SEQ ID NO 54
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ccagcagcta gcgttttagc aaaggaccaa gtgtttcagc c                     41

<210> SEQ ID NO 55
<211> LENGTH: 41
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 55
ccagcagcta gcgttttagc agctcagtca gtgrcycagc c        41

<210> SEQ ID NO 56
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
ccagcagcta gcgttttagc agatgctaag accacmcagc c        41

<210> SEQ ID NO 57
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
ccagcagcta gcgttttagc aagaaaasaw stggagcaga gtc      43

<210> SEQ ID NO 58
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
ccagcagcta gcgttttagc aagccaaaag atagaacaga a        41

<210> SEQ ID NO 59
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
ccagcagcta gcgttttagc agaaaaccag gtggagcaca g        41

<210> SEQ ID NO 60
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
ccagcagcta gcgttttagc agcccagtck gtgasccagc w        41

<210> SEQ ID NO 61
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
ccagcagcta gcgttttagc aggaaattca gtgryccaga y       41

<210> SEQ ID NO 62
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
ccagcagcta gcgttttagc acagaaggag gtggagcagr atyc       44

<210> SEQ ID NO 63
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
ccagcagcta gcgttttagc aggagagart gtggrgcwgc a       41

<210> SEQ ID NO 64
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
ccagcagcta gcgttttagc agcccagaag rtwactcaar c       41

<210> SEQ ID NO 65
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
ccagcagcta gcgttttagc agcccagasa gtsactcagy c       41

<210> SEQ ID NO 66
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
ccagcagcta gcgttttagc aagtcaacag ggagaagagg a       41

<210> SEQ ID NO 67
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
ccagcagcta gcgttttagc aggagactcg gttacccaga c            41

<210> SEQ ID NO 68
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
ccagcagcta gcgttttagc aaaacaggag gtgacgcaga ktcc         44

<210> SEQ ID NO 69
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
ccagcagcta gcgttttagc aggccaacag aaggagaaaa g            41

<210> SEQ ID NO 70
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
ccagcagcta gcgttttagc agagctgaam gtggaacaaa r            41

<210> SEQ ID NO 71
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
ccagcagcta gcgttttagc aggacaacag gtaatgcaaa t            41

<210> SEQ ID NO 72
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
ccagcagcta gcgttttagc aacccagctg ctggagcaga g            41

<210> SEQ ID NO 73
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
ccagcagcta gcgttttagc aagtcaacag aagaatgatg a            41

<210> SEQ ID NO 74
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
ccagcagcta gcgttttagc acaacaacca gtgcagagtc c                          41

<210> SEQ ID NO 75
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
ccagcagcta gcgttttagc aggtcaacag ctgaatcaga g                          41

<210> SEQ ID NO 76
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
ccagcagcta gcgttttagc agaagacaag gtggtacaaa g                          41

<210> SEQ ID NO 77
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
ccagcagcta gcgttttagc aagcaattca gtcaagcaga c                          41

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
cgaccagctt gacatcacag                                                  20

<210> SEQ ID NO 79
<211> LENGTH: 9
<212> TYPE: PRT
<213> ORGANISM: Epstein-Barr virus

<400> SEQUENCE: 79

Phe Leu Arg Gly Arg Ala Tyr Gly Leu
1               5